US012461102B2

(12) United States Patent
Dempsey et al.

(10) Patent No.: US 12,461,102 B2
(45) Date of Patent: Nov. 4, 2025

(54) PRISTINE GRAPHENE BASED BIOSENSOR FOR BIOMARKER DETECTION AND RELATED CORE PARTICLES, MATERIALS COMPOSITIONS METHODS AND SYSTEMS

(71) Applicants: HAWKEYE BIO, LIMITED, Dublin (IE); THE UNIVERSITY OF KANSAS, Lawrence, KS (US); KANSAS STATE UNIVERSITY RESEARCH FOUNDATION, Manhattan, KS (US)

(72) Inventors: Paul W. Dempsey, Los Angeles, CA (US); Spencer Hantula, Long Beach, CA (US); Cristina-Mihaela Sandu Aparicio, Laguna Hills, CA (US); Stefan H. Bossmann, Kansas City, MO (US); Christopher M. Sorensen, Manhattan, KS (US); Obdulia Covarrubias-Zambrano, Lenexa, KS (US); Jose Covarrubias, Manhattan, KS (US)

(73) Assignees: HAWKEYE BIO, LIMITED, Dublin (IE); THE UNIVERSITY OF KANSAS, Lawrence, KS (US); KANSAS STATE UNIVERSITY RESEARCH FOUNDATION, Manhattan, KS (US)

( * ) Notice: Subject to any disclaimer, the term of this patent is extended or adjusted under 35 U.S.C. 154(b) by 0 days.

(21) Appl. No.: 18/051,422

(22) Filed: Oct. 31, 2022

(65) Prior Publication Data

US 2023/0258640 A1 Aug. 17, 2023

Related U.S. Application Data

(63) Continuation of application No. PCT/US2021/065573, filed on Dec. 29, 2021.

(60) Provisional application No. 63/131,972, filed on Dec. 30, 2020.

(51) Int. Cl.

| | |
|---|---|
| ***G01N 33/573*** | (2006.01) |
| ***G01N 33/533*** | (2006.01) |
| ***G01N 33/542*** | (2006.01) |
| ***G01N 33/543*** | (2006.01) |
| ***G01N 33/551*** | (2006.01) |

(52) U.S. Cl.

CPC ......... *G01N 33/573* (2013.01); *G01N 33/533* (2013.01); *G01N 33/542* (2013.01); *G01N 33/54346* (2013.01); *G01N 33/551* (2013.01)

(58) Field of Classification Search

CPC .. G01N 33/533; G01N 33/542; G01N 33/551; G01N 33/573

See application file for complete search history.

(56) References Cited

U.S. PATENT DOCUMENTS

| | | | |
|---|---|---|---|
| 4,708,861 A | 11/1987 | Popescu et al. | |
| 6,083,486 A | 7/2000 | Weissleder et al. | |
| 6,592,847 B1 | 7/2003 | Weissleder et al. | |
| 6,593,132 B1 | 7/2003 | Borgford | |
| 7,067,320 B2 | 6/2006 | Klimant | |
| 7,691,909 B2 | 4/2010 | Sorensen et al. | |
| 8,053,199 B2 | 11/2011 | Brasier et al. | |
| 8,877,951 B2 | 11/2014 | Wang et al. | |
| 8,947,656 B2 | 2/2015 | Cunningham et al. | |
| 8,969,027 B2 | 3/2015 | Bossmann et al. | |
| 9,216,154 B2 | 12/2015 | Bossmann et al. | |
| 9,440,857 B2 | 9/2016 | Sorensen et al. | |
| 9,682,155 B2 | 6/2017 | Bossmann et al. | |
| 9,731,034 B2 | 8/2017 | Bossmann et al. | |
| 10,173,898 B2 | 1/2019 | Blanford et al. | |
| 10,376,599 B2 | 8/2019 | Bossmann et al. | |
| 2002/0035082 A1 | 3/2002 | Grinstaff et al. | |
| 2004/0180094 A1 | 9/2004 | Joyce | |
| 2005/0123563 A1 | 6/2005 | Doranz et al. | |
| 2005/0239170 A1 | 10/2005 | Hedley et al. | |
| 2006/0286379 A1 | 12/2006 | Gao | |
| 2007/0116600 A1 | 5/2007 | Kochar et al. | |
| 2009/0098540 A1 | 4/2009 | Baeumner et al. | |
| 2009/0297689 A1 | 12/2009 | Edens et al. | |
| 2011/0014125 A1* | 1/2011 | Bossmann ......... | A61K 49/0036 977/773 |
| 2011/0223657 A1 | 9/2011 | Kaper et al. | |
| 2012/0107590 A1 | 5/2012 | Xu et al. | |
| 2012/0157824 A1 | 6/2012 | Bossmann et al. | |

(Continued)

FOREIGN PATENT DOCUMENTS

| | | |
|---|---|---|
| AU | 2009221976 A1 | 9/2009 |
| CA | 2717563 A1 | 9/2009 |

(Continued)

OTHER PUBLICATIONS

Phitsini Suvarnaphaet et al.,Graphenene-Based Materials for Biosensors: A Reveiew, Sensors, 17, 2161. (Year: 2017).*

(Continued)

*Primary Examiner* — Michael G. Hartley
*Assistant Examiner* — Jagadishwar R Samala
(74) *Attorney, Agent, or Firm* — Steinfl + Bruno LLP

(57) ABSTRACT

Provided herein are graphene biosensors and related core particles, compositions methods and systems in which more than one pristine graphene sheet is coated with a coating layer of an organic or inorganic material to provide a core graphene particle, to which detectable components comprising a detectable moiety and a peptide linkage are attached through binding of the peptide linkage.

30 Claims, 43 Drawing Sheets

Specification includes a Sequence Listing.

(56) References Cited

U.S. PATENT DOCUMENTS

| | | | |
|---|---|---|---|
| 2012/0263651 | A1 | 10/2012 | Widen et al. |
| 2013/0183702 | A1 | 7/2013 | Bossmann et al. |
| 2013/0323187 | A1 | 12/2013 | Fasel et al. |
| 2014/0335010 | A1 | 11/2014 | Sorensen et al. |
| 2014/0336514 | A1 | 11/2014 | Peyman |
| 2015/0119278 | A1 | 4/2015 | Goetzl |
| 2015/0132230 | A1 | 5/2015 | Bossmann et al. |
| 2015/0132785 | A1 | 5/2015 | Bossmann et al. |
| 2017/0212116 | A1 | 7/2017 | Braga et al. |
| 2017/0219548 | A1 | 8/2017 | Troyer et al. |
| 2018/0099057 | A1 | 4/2018 | Bossmann et al. |
| 2020/0300849 | A1 | 9/2020 | Motamedi et al. |
| 2024/0125800 | A1 | 4/2024 | Bossmann et al. |

FOREIGN PATENT DOCUMENTS

| | | | | |
|---|---|---|---|---|
| CN | 114981205 | A | 8/2022 | |
| EP | 1052293 | A1 | 11/2000 | |
| EP | 2260108 | A2 | 12/2010 | |
| EP | 2260108 | B1 | 9/2014 | |
| EP | 3358348 | A1 * | 8/2018 | ............ C01B 32/23 |
| JP | 2011517934 | A | 6/2011 | |
| JP | 2017501097 | A | 1/2017 | |
| JP | 2018533005 | A | 11/2018 | |
| JP | 2024509494 | A | 3/2024 | |
| KR | 100704548 | B1 | 4/2007 | |
| KR | 20140014443 | A | 2/2014 | |
| KR | 101421974 | B1 | 7/2014 | |
| KR | 20230115347 | A | 8/2023 | |
| KR | 102698801 | B1 | 8/2024 | |
| TW | 202238107 | A | 10/2022 | |
| WO | 02/00265 | A1 | 1/2002 | |
| WO | 02/41760 | A2 | 5/2002 | |
| WO | 02/102834 | A2 | 12/2002 | |
| WO | 2007/027640 | A2 | 3/2007 | |
| WO | 2007/107156 | A2 | 9/2007 | |
| WO | 2007/109364 | A2 | 9/2007 | |
| WO | 2008/127019 | A1 | 10/2008 | |
| WO | 2009/111470 | A2 | 9/2009 | |
| WO | 2009/111470 | A3 | 12/2009 | |
| WO | 2011/028698 | A2 | 3/2011 | |
| WO | 2012/050896 | A2 | 4/2012 | |
| WO | 2013/063047 | A1 | 5/2013 | |
| WO | 2014/090313 | A1 | 6/2014 | |
| WO | 2014/182169 | A2 | 11/2014 | |
| WO | 2015/084800 | A1 | 6/2015 | |
| WO | 2016/018798 | A1 | 2/2016 | |
| WO | 2016/149637 | A1 | 9/2016 | |
| WO | 2017/165800 | A2 | 9/2017 | |
| WO | 2020/051000 | A1 | 3/2020 | |
| WO | 2020/257229 | A2 | 12/2020 | |
| WO | 2022/015445 | A2 | 1/2022 | |
| WO | 2022/147171 | A1 | 7/2022 | |
| WO | 2022/147179 | A1 | 7/2022 | |
| WO | 2024/010609 | A1 | 1/2024 | |

OTHER PUBLICATIONS

Jong won Shim et al., Two-minute assembly of pristine large-area graphene based films, Nano Lett, 14, 1388-13989 (Year: 2014).*

Yue Lin et al.,Preparation of Pristine Graphene Sheets and Large-Area/Ultrathin Graphene Films for High Conducting and Transparent Applications, J Phys Chem, 117, 17237-17244. (Year: 2013).*

2nd Written Opinion (from International Preliminary Examining Authority) for International Application No. PCT/US2022/073477 filed on Jul. 6, 2022 on behalf of Hawkeye Bio, Limited. Mailed on Jun. 14, 2024. 7 pages.

Farber, C. et al., Complementarity of Raman and Infrared Spectroscopy for Structural Characterization of Plant Epicuticular Waxes. ACS Omega, Feb. 19, 2019, 4, 3700-3707.

Jagadeesh, P. et al., Advanced characterization techniques for nanostructured materials in biomedical applications. Advanced Industrial and Engineering Polymer Research, 2024, 7, 122-143.

Jayawardena, H.S. et al., Analytical Methods for Characterization of Nanomaterial Surfaces. Anal. Chem., Feb. 2, 2021, 93(4), 1889-1911. 47 pages.

Kapkiai, L.K. et al., Hybrid near-field scanning optical microscopy tips for live cell measurements. Applied Physics Letters, May 10, 2024, vol. 84, No. 19, 3750-3752.

Mahamuni, P.P. et al., Synthesis and characterization of zinc oxide nanoparticles by using polyol chemistry for their antimicrobial and antibiofilm activity. Biochemistry and Biophysics Reports. Dec. 12, 2018, 17, 71-80.

Notice of Allowance for KR Application No. 10-2023-7024768 filed on Dec. 29, 2021. Mailed on May 23, 2024. 6 pages.

Notice of Preliminary Rejection for KR Application No. 10-2023-7024768 filed on Dec. 29, 2021. Mailed on Nov. 27, 2023. 6 pages.

Notice of Reasons for Refusal for Japanese Application JP 2023-540759 filed Nov. 22, 2021. Mailed on Dec. 5, 2023. 8 pages.

Notice of Reasons for Refusal for Japanese Application JP 2023-540759 filed Nov. 22, 2021. Mailed on Jun. 4, 2024. 11 pages.

Schue, L. et al., Characterization methods dedicated to nanometer-thick hBN layers. 2D Materials, Dec. 1, 2016, 4, 015028. 12 pages.

Zhang, X. et al., Functionalized Nanoparticles for the Dispersion of Gas Hydrates in Slurry Flow. ACS Omega, Aug. 9, 2019, 4, 13496-13508.

Zhou, Q. et al., Real-space imaging with pattern recognition of a ligand-protected Ag374 nanocluster at sub-molecular resolution. Nature Communications, 2018, 9: 2948, 8 pages.

Adcock IM, Caramori G, Barnes PJ. Chronic Obstructive Pulmonary Disease and Lung Cancer: New Molecular Insights. Respiration. (Mar. 24, 2011); 81 :265-284.

Adem, S. et al. Giant magnetoresistive biosensors for real-time quantitative detection of protease activity. Sci Rep-uk 10, 7941 (2020). 10 pages.

Ahmed S, Bui M-PN, Abbas A. Paper-based chemical and biological sensors: Engineering aspects. Biosens Bioelectron. (Mar. 15, 2016); 77:249-263. doi: 10.1016/j.bios.2015.09.038. Abstract Only.

Ahn, S. R. et al. Peptide hormone sensors using human hormone receptor-carrying nanovesicles and graphene FETs. Sci Rep-uk 10, 388 (2020). 8 pages.

Ahrberg, Christian D. et al. "Polymerase chain reaction in microfluidic devices," Lab Chip, Sep. 6, 2016, pp. 3866-3884.

Ainavarapu, S.R.K., et al., "Contour length and refolding rate of a small protein controlled by engineered disulfide bonds". Biophysical Journal, Jan. 2007. 92(1): p. 225-233.

Akabas, M; Cohen, F; Finkelstein, A., Separation of the Osmotically Driven Fusion Event from Vesicle-Planar Membrane Attachment in a Model System for Exocytosis. J Cell Biol. (Mar. 1984), vol. 98, 1063-1071.

Allen and Cleland, Serum-induced leakage of liposome contents. Biochimica et Biophysica Acta, vol. 597 (1980) pp. 418-426.

Amini, A. P. et al. Multiscale profiling of protease activity in cancer. Nat Commun 13, 5745 (2022). 16 pages.

Backes, C., et al., Production and processing of graphene and related materials. 2D Mater., 2020. 7(2): p. 022001. 283 pages.

Bagsican, F. R. et al. Adsorption energy of oxygen molecules on graphene and two-dimensional tungsten disulfide. Sci Rep-uk 7, 1774 (2017). 10 pages.

Basel et al., "Protease-sensitive, polymer-caged liposomes: a method for making highly targeted liposomes using triggered release", ACS Nano, vol. 5, No. 3, pp. 2162-2175, Mar. 22, 2011 (Published On-line: Feb. 11, 2011).

Benedict Law, "Proteolysis: A Biological Process Adapted in Drug Delivery, Therapy, and Imaging," Bioconjugate Chemistry, (Mar. 9, 2009). 14 pages. DOI: 10.1021/bc800500a.

Bonnemain, Bruno, "Superparamagnetic Agents in Magnetic Resonance Imaging: Physicochemical Characteristics and Clinical Applications" Journal of Drug Targeting, vol. 6, No. 3, 167-174, (1998).

Cao, S., Li, Z., Zhao, J., Chen, M. & Ma, N. Rational Engineering a Multichannel Upconversion Sensor for Multiplex Detection of Matrix Metalloproteinase Activities. Acs Sensors, 3, 1522-1530 (Jul. 2018).

Castelaín, M., et al., "Effect of Click-Chemistry Approaches for Graphene Modification on the Electrical, Thermal, and Mechanical

(56) References Cited

OTHER PUBLICATIONS

Properties of Polyethylene/Graphene Nanocomposites". Macromolecules, Nov. 2013. 46(22): p. 8980-8987.
Abstact Only, Cazanave, S.C., Warren, A.D., Pacula, M., Touti, F., Zagorska, A., Gural, N., et al. Peptide-based urinary monitoring of fibrotic nonalcoholic steatohepatitis by mass-barcoded activity-based sensors. Science Translational Medicine 13(616): eabe8939. Oct. 20, 2021, 15 pages.
Chan, L. W. et al. Engineering synthetic breath biomarkers for respiratory disease. Nat Nanotechnol 15, 792-800 (2020). 14 pages.
Chen, H. et al. Detection of Matrilysin (MMP-7) Activity Using Polypeptide Functionalized Reduced Graphene Oxide Field-Effect Transistor Sensor. Anal Chem 88, 2994-2998 (Feb. 2016). 8 pages.
Covarrubias, J.J., "Rational Chemical Applications of Explosion-Graphene", Chemistry. 2021, Kansas State University: Manhattan, KS, USA. p. 110.
Cui, L., J. Wang, and M. Sun, Graphene Plasmon for Optoelectronics. Reviews in Physics, Feb. 9, 2021. 6: p. 100054. 20 pages.
Daina, A., O. Michielin, and V. Zoete, "iLOGP: a simple, robust, and efficient description of η-octanol/water partition coefficient for drug design using the GB/SA approach". Journal of chemical information and modeling, Dec. 2014. 54(12): p. 3284-3301. Abstract Only.
De Nicola, F., et al., "Wetting properties of graphene aerogels". Scientific Reports, 2020. 10(1): p. 1916. 7 pages.
Dekker, L.J.M., Burgers, P.C., Charif, H., Rijswijk, A.L.C.T.v., Titulaer, M.K., Jenster, G., et al. Differential expression of protease activity in serum samples of prostate carcinoma patients with metastases. Proteomics 10(12):2348-2358 (2010).
Dempsey, P.W., Aparicio, C.-M.S., Hantula, S., Covarrubias, J., Varghese, S., Neri, R., et al. Detection of early-stage lung cancer with an in vitro panel of activity-based biosensors to measure inflammatory protease enzymes. Journal of Clinical Oncology 40(16_ suppl):e20551-e20551 (2022).
Dhaubhadel, R., et al., "Aerosol gelation: Synthesis of a novel, lightweight, high specific surface area material". Aerosol science and technology, 2007. 41(8): p. 804-810.
DiTizio et al., Localized drug delivery using crosslinked gelatin gels containing liposomes: factors influencing liposome stability and drug release. Journal of Biomedical Materials Research, vol. 51, No. 1 (May 11, 2000) pp. 96-106.
Dixon, Christopher et al. "Printed Microfluidics," Adv. Funct. Mater. 2017, 1604824, 11 pages. wileyonlinelibrary.com.
Dudani, J. S., Ibrahim, M., Kirkpatrick, J., Warren, A. D. & Bhatia, S. N. Classification of prostate cancer using a protease activity nanosensor library. Proc National Acad Sci 115, 201805337 (2018). 6 pages.
Elegbede, Adekunle et al. "Mechanistic Studies of the Triggered Release of Liposomal Contents by Matrix Metalloproteinase-9," J. Am. Chem. Soc., 120 (32) 10633-10642, (Published online: Jul. 22, 2008).
Enzymes, MeSH Descriptor Data 2023. Website: meshb.nim.nih.gov/record/ui?ui=D004798.
Feng, L. et al. Detection of a Prognostic Indicator in Early-Stage Cancer Using Functionalized Graphene-Based Peptide Sensors. Adv Mater 24, 125-131 (2012).
Ferrari AC. Raman spectroscopy of graphene and graphite: Disorder, electron-phonon coupling, doping and nonadiabatic effects. Solid State Commun. 2007; 143(1-2):47-57. doi: 10.1016/j.ssc.2007.03.052.
Fujita, Yu "Extracellular vesicles in lung microenvironment and pathogenesis," Trends in Molecular Medicine, (Sep. 2015), vol. 21, No. 9, pp. 533-542.
Gallegos, Dustin et al., "Label-free biodetection using a smartphone" Lab Chip, vol. 13, (Apr. 3, 2013), pp. 2124-2132.
Ganesana, Mallikarjunarao et al. "Analytical Techniques in Neuroscience: Recent Advances in Imaging, Separation, and Electrochemical Methods," Anal. Chem., vol. 89, (Nov. 10, 2016), pp. 314-341.
Gu, Hongwei, "Synthesis and Cellular Uptake of Porphyrin Decorated Iron Oxide Nanoparticles—a Potential Candidate for Bimodal Anticancer Therapy," The Royal Society of Chemistry, Chem. Commun. 4270-4272; (Jul. 14, 2005).
Guler, O., et al., Production of graphene layer by liquid-phase exfoliation with low sonication power and sonication time from synthesized expanded graphite. Fullerenes, Nanotubes and Carbon Nanostructures, 2016. 24(2): p. 123-127.
Huang, Y. et al. Carbon nanotube-based multicolor fluorescent peptide probes for highly sensitive multiplex detection of cancer-related proteases. J Mater Chem B 1, 3470-3476 (2013).
International Preliminary Report on Patentability for International PCT Application No. PCT/US2021/065584 filed on Dec. 29, 2021, on behalf of Kansas State University Research Foundation et al. Mail Date: Jul. 13, 2023. 9 Pages.
Inui K, Wenger DA. Biochemical, immunological, and structural studies on a sphingolipid activator protein (SAP-1). Arch Biochem Biophys. Sep. 1984; 233(2): 556-64. Abstract Only. doi: 10.1016/0003-9861(84)90479-X.
Ivry, S.L., Meyer, N.O., Winter, M.B., Bohn, M.F., Knudsen, G.M., O'Donoghue, A.J., et al. Global substrate specificity profiling of post-translational modifying enzymes. Protein Sci 27(3):584-594 (2018).
Jung, Chu W. "Physical and Chemical Properties of Superparamagnetic Iron Oxide MR Contrast Agents: Ferumoxides, Ferumoxtran, Ferumoxsil," Magnetic Resonance Imaging, vol. 13, No. 5, 661-674, (1995).
Kalubowilage, M., Covarrubias-Zambrano, O., Malalasekera, A.P., Wendel, S.O., Wang, H., Yapa, A.S., et al. Early detection of pancreatic cancers in liquid biopsies by ultrasensitive fluorescence nanobiosensors. Nanomedicine: Nanotechnology, Biology and Medicine 14(6):1823-1832 (Aug. 2018). (Accepted Manuscript, 39 pages).
Katoch, J. et al. Structure of a Peptide Adsorbed on Graphene and Graphite. Nano Lett 12, 2342-2346 (2012).
Khatayevich, D. et al. Selective Detection of Target Proteins by Peptide-Enabled Graphene Biosensor. Small 10, No. 8, 1505-1513 (2014).
Kim, S. et al. Robust Magnetized Graphene Oxide Platform for In Situ Peptide Synthesis and FRET-Based Protease Detection. Sensors 20, 5275 (2020).
Kim, S.N., et al., "Preferential Binding of Peptides to Graphene Edges and Planes". J. Am. Chem. Soc., 2011. 133(37): p. 14480-14483. Abstract Only.
Kirkpatrick, J. D. et al. Urinary detection of lung cancer in mice via noninvasive pulmonary protease profiling. Sci. Transl. Med. 12, eaaw0262 (Apr. 2020). 11 pages.
Kudryashev, J. A., Madias, M. I., Kandell, R. M., Lin, Q. X. & Kwon, E. J. An Activity-Based Nanosensor for Minimally-Invasive Measurement of Protease Activity in Traumatic Brain Injury. Biorxiv 2022.12.26.521967 (2022) 39 pages. doi:10.1101/2022.12.26.521967.
Kwong, G. A. et al. Mass-encoded synthetic biomarkers for multiplexed urinary monitoring of disease. Nat Biotechnol., vol. 31, No. 1, 63-70 (Jan. 2013).
Lange, P., et al., "Evidence for graphene plasmons in the visible spectral range probed by molecules". arXiv:1404.6518, Condensed Matter, Nanoscale Physics, 2014.
Laurent et al., "Magnetic Iron Oxide Nanoparticles: Synthesis, Stabilization, Vectorization, PhysiochemicalCharacterizations, and Biological Applications," Chem. Rev, (2008), vol. 108, No. 6, 2064-2110.
Le, N. D. B. et al. Simple and Robust Polymer-based Sensor for Rapid Cancer Detection using Serum. Chem Commun (Camb) 55, 11458-11461 (2019). 5 pages.
Lee et al., Polymer-caged liposomes: a pH-responsive delivery system with high stability. Journal of American Chemical Society, vol. 129 (Published online Nov. 14, 2007) pp. 15096-15097.
Li, W., Y. Li, and K. Xu, "Azidated graphene: direct azidation from monolayers, click chemistry, and bulk production from graphite". Nano letters, 2020. 20(1): p. 534-539. Abstract Only.
Li, Y., Liu, W., Xu, Q., Hu, J. & Zhang, C. Construction of a sensitive protease sensor with DNA-peptide conjugates for single-molecule detection of multiple matrix metalloproteinases. Biosens Bioelectron 169, 112647 (Sep. 2020).

(56) References Cited

OTHER PUBLICATIONS

Loebach, D.V., "The relationship between particle size and molecular weight in emulsion polymerization", Chemical Engineering. 1975, Iowa State University: Ames, IA. p. 129.
Long, Kenneth D., "Smartphone instrument for portable enzyme-linked immunosorbent assays," Biomedical Optics Express, vol. 5, No. 11 (Oct. 1, 2014), 3792-3806.
Luong, D.X., et al., Gram-scale bottom-up flash graphene synthesis. Nature (London, U. K.). Jan. 2020. 577(7792): p. 647-651. Abstract Only.
Ma, M., et al., "Rational design, synthesis, and application of silica/graphene-based nanocomposite: A review". Mater. Des., 2021. 198: p. 109367.
Mackin, R. T. et al. Detection of Human Neutrophil Elastase by Fluorescent Peptide Sensors Conjugated to TEMPO-Oxidized Nanofibrillated Cellulose. Int J Mol Sci 23, 3101 (2022). 16 pages.
Mphahlele MJ, Agbo EN, Choong YS. Synthesis, Structure, Carbohydrate Enzyme Inhibition, Antioxidant Activity, In Silico Drug-Receptor Interactions and Drug-Like Profiling of the 5-Styryl-2-Aminochalcone Hybrids. Molecules. May 2021; 26(9):2692. 19 pages. doi: 10.3390/molecules26092692. PubMed PMID: 34064448.
Nuvoli, D., et al., "The production of concentrated dispersions of few-layer graphene by the direct exfoliation of graphite in organosilanes". Nanoscale Research Letters, 2012. 7(1): p. 1-7.
Paper for Sonarmed Air-Wave Health Economics in the adult ICU, (Mar. 24, 2011). 12 pages.
Papi, M. et al. Converting the personalized biomolecular corona of graphene oxide nanoflakes into a high-throughput diagnostic test for early cancer detection. Nanoscale 11, 15339-15346 (2019). 22 pages.
Patabadige, Damith E. "Integrating Optical Fiber Bridges in Microfluidic Devices to Create Multiple Excitation/ Detection Points for Single Cell Analysis," Analytical Chemistry, vol. 88, (Sep. 14, 2016), pp. 9920-9925.
Peng, Xian-Hong, "Targeted Magnetic Iron Oxide Nanoparticles for Tumor Imaging and Therapy," International Journal of Nanomedicine vol. 3 No. 3, 311-321; (2008(.
Perez, Manual J. "Use of Magnetic Nanoparticles as Nanosensors to Probe for Molecular Interactions," ChemBioChem vol. 5, 261-264; (2004).
Perez, Manuel J. "Peroxidase Substrate Nanosensors for MR Imaging" Nano Lett., vol. 4, No. 1, pp. 119-122 (Dec. 18, 2003).
Perez, Manuel J. "DNA-Based Magnetic Nanoparticle Assembly Acts as a Magnetic Relaxation Nanoswitch Allowing Screening of DNA-Cleaving Agents," JACS Communications, J. Am. Chem. Soc., vol. 124, No. 12, pp. 2856-2857 (Feb. 28, 2002).
Perez, Manuel J. "Magnetic Relaxation Switches Cable of Sensing Molecular Interactions," Nature Biotechnology, vol. 20, pp. 816-820 (Jul. 22, 2002).
Pinto I.F. et al. "The application of microbeads to microfluidic systems for enhanced detection and purification of biomolecules," Methods, (Dec. 8, 2016), 13 pages.
Puente, X.S., et al., "Human and mouse proteases: a comparative genomic approach". Nature Reviews Genetics, 2003. 4(7): p. 544-558.
Qian. Z. S. et al. A universal fluorescence sensing strategy based on biocompatible graphene quantum dots and graphene oxide for the detection of DNA. Nanoscale 6, 5671-5674 (2014).
Quagliarini, E., Santo, R. D., Pozzi, D. & Caracciolo, G. Protein corona-enabled serological tests for early stage cancer detection. Sensors Int 1, 100025 (Jul. 2020). 5 pages.
Rho, et al. Magnetic Nanosensor for Detection and Profiling of Erythrocyte-Derived Microvesicles. ACS Nano., 7(12): (Dec. 23, 2013), 11227-11233. 13 pages.
Roda, Aldo et al. "Smartphone-based biosensors: A critical review and perspectives," Trends in Analytical chemistry, (2016), vol. 79, pp. 317-325.
Sadeghi, Jalal "Out-of-plane integration of a multimode optical fiber for single particle/cell detection at multiple points on a microfluidic device with applications to particle/cell counting, velocimetry, size discrimination and the Analysis of single cell lysate injections," Lab on a Chip, (Nov. 24, 2016), 11 pages.
Salavagione, H.J., Chapter 16: Modification of graphene with polymers via addition chemistry, in Graphene Science Handbook: Mechanical and Chemical Properties, M. Allofkhazraei, Editor. 2016, 295-316, Institute of Polymer Science and Technology (CSIS) Madrid, Spain: Department of Polymer Physics, Elastomers, and Energy Application. 23 pages.
Sarkar, Nihar et al. "Matrix Metalloproteinase-Assisted Triggered Release of Liposomal Contents" Biocanjugate Chem., 19 (1), 57-64, (Published online Dec. 14, 2007).
Sarkar, S., E. Bekyarova, and R.C. Haddon, "Chemistry at the Dirac Point: Diels—Alder Reactivity of Graphene". Accounts of Chemical Research, 2012. 45(4): p. 673-682. Abstract Only.
Sarkar, S., et al., Diels—Alder "Chemistry of Graphite and Graphene: Graphene as Diene and Dienophile". Journal of the American Chemical Society, Mar. 2011. 133(10): p. 3324-3327. Abstract Only.
Shi, H. et al. A New Strategy Involving the Use of Peptides and Graphene Oxide for Fluorescence Turn-on Detection of Proteins. Sensors 18, 385 (2018). 12 pages.
Song, E. et al. A graphene oxide-based FRET sensor for rapid and sensitive detection of matrix metalloproteinase 2 in human serum sample. Biosens Bioelectron 47, 445-450 (2013).
Sorensen, C., "Light scattering by fractal aggregates: a review". Aerosol Science & Technology, 2001. 35(2): p. 648-687.
Soung, Young Hwa "Exosomes in Cancer Diagnostics," Cancers, vol. 9 (8), (Jan. 12, 2017), 11 pages.
Stanford, M.G., et al., "Flash Graphene Morphologies". ACS Nano, 2020. 14(10): p. 13691-13699. Abstract Only.
Strandvik, G. F. "Hypertonic Saline in Critical Care: A Review of the Literature and Guidelines for Use in Hypotensive States and Raised Intracranial Pressure," Journal of the Association of Anaesthetists of Great Britain and □ Ireland, 64, 990-1003, (2009).
Sun, Conroy, "Magnetic Nanoparticles in MR Imaging and Drug Delivery," Advanced Drug Delivery Reviews, vol. 60, 1252-1265, (Apr. 10, 2008).
Takamura, T. et al., Magnetic-Particle-Sensing Based Diagnostic Protocols and Applications. Sensors, (2015), 15, 12938-12998. Doi: 10.3390/s150612983.
Tan J-X, Wang X-Y, Su X-L, Li H-Y, Shi Y, Wang L, Ren G-S. Upregulation of HYAL1 expression in breast cancer promoted tumor cell proliferation, migration, invasion and angiogenesis. PLoS One. Jul. 2011; 6(7):e22836.9 pages. Retracted. doi: 10.1371/journal.pone.0022836.
Tehrani, Z. et al. Generic epitaxial graphene biosensors for ultrasensitive detection of cancer risk biomarker. 2d Mater 1, 025004 (2014). 20 pages.
Tite, T., Chiticaru, E. A., Burns, J. S. & Ioniţă, M. Impact of nano-morphology, lattice defects and conductivity on the performance of graphene based electrochemical biosensors. J Nanobiotechnol 17, 101 (2019). 22 pages.
Villanueva, J., Shaffer, D.R., Philip, J., Chaparro, C.A., Erdjument-Bromage, H., Olshen, A.B., et al. Differential exoprotease activities confer tumor-specific serum peptidome patterns. Journal of Clinical Investigation 116(1):271-284 (Jan. 2006).
Wang, C. et al. Ultrasensitive, high-throughput and multiple cancer biomarkers simultaneous detection in serum based on graphene oxide quantum dots integrated microfluidic biosensing platform. Anal Chim Acta 1178, 338791 (2021).
Wang et al., "Synthesis of Functionalized Bimagnetic Core/Shell Fe/Fe3O4 Nanoparticles for the Treatment of Cancer," Copyright American Chemical Society, Abstract from 44th Midwest Regional Meeting of the American Chemical Society, Iowa City, Iowa, United States, (Oct. 21-24, 2009) 1 page.
Wang, H. et al. Graphene Oxide-Peptide Conjugate as an Intracellular Protease Sensor for Caspase-3 Activation Imaging in Live Cells. Angewandte Chemie Int Ed 50, 7065-7069 (2011).
Wang, Xiao-Yang "Matrilysin-1 Mediates Bronchiolization of Alveoli, a Potential Premalignant Change in Lung Cancer," The American Journal of Pathology, vol. 175, No. 2, pp. 592-604, (Aug. 2009).
Wikipedia. Graphene. 2021 [cited Dec. 19, 2021]; Available from: https://en.wikipedia.org/wiki/Graphene#cite_note-geim2007-2. Downloaded from The Wayback Machine.

(56) References Cited

OTHER PUBLICATIONS

Wikipedia. Polymer. 2021 [cited Dec. 20, 2021]; Available from: https://en.wikipedia.org/wiki/Polymer. Downloaded through The Wayback Machine. 17 pages.
Woerner M, et al., Nanoarray-Surfaces by Reconstitution of the Porin MspA into Stabilized Long-Chain-Lipid-Monolayers at a Gold-Surface, (Jun. 23, 2016), Electroanalysis, vol. 18 No. 19-20, pp. 1859-1870. doi:10.1002/elan.200603636.
Wu, Y. et al. Multiple Biomarker Simultaneous Detection in Serum via a Nanomaterial-Functionalized Biosensor for Ovarian Tumor/Cancer Diagnosis. Micromachines 13, 2046 (2022). 11 pages.
Wu, Y., G. Li, and J.P. Camden, "Probing Nanoparticle Plasmons with Electron Energy Loss Spectroscopy". Chemical Reviews, Mar. 2018. 118(6): p. 2994-3031. Abstract Only.
Xu et al., Contributions of the MMP-2 collagen binding domain to gelatin cleavage: substrate binding via the collagen binding domain is required for hydrolysis of gelatin but not short peptides. Matrix Biology, vol. 23, No. 3 (Jun. 2004) pp. 171-181.
Yang, F. et al., Exosome separation using microfluidic systems: size-based, immunoaffinity-based and dynamic methodologies. Biotechnology Journal, (2017), 12, 1600699, 8 pages. DOI: 10.1002/biot.201600699.
Yang, KE et al. "Novel developments in mobile sensing based on the integration of microfluidic devices and smartphones," Lab Chip, vol. 16, (Feb. 8, 2016), pp. 943-958.
Yang, Y. et al., Paper-Based Microfluidic Devices: Emerging Themes and Applications. Analytical Chemistry, (Dec. 7, 2016), 89, 71-91. DOI: 10.101/acs.anlchem.6604581.
Yu, Hojeong, el. al. "Smartphone Fluorescence Spectroscopy" Analytical Chemistry, vol. 86, (Aug. 6, 2014), pp. 8805-8813.
Zhang, D. et al., Biosensors and bioelectronics on smartphone for portable biochemical detection. Biosensors and Bioelectronics, 75, (2016), 273-284.
Zhang, Y., Chen, X., Roozbahani, G. M. & Guan, X. Graphene oxide-based blosensing platform for rapid and sensitive detection of HIV-1 protease. Anal Bioanal Chem 410 (24), 6177-6185 (Sep. 2018). 19 pages.
Zhao Ming, "Magnetic Sensors for Protease Assays," Angew. Chem. Int. Ed. vol. 42, No. 12, pp. 1375-1378, (2003).
Zhao, "Systematic Analysis of Cell-Type Differences in the Epithelial Secretome Reveals Insights into the Pathogenesis of Respiratory Syncytial Virus-Induced Lower Respiratory Tract Infections", J Immunol. (Epub Mar. 3, 2017), 198(8):3345-3364.
Allen, T; and Cullis, P., "Drug Delivery Systems: Entering the Mainstream", Science. Mar. 19, 2004, vol. 303, 1818-1822.
American Cancer Society: How Chemotherapy Drugs Work. Downloaded Feb. 7, 2024. Website marked as Last Revised Nov. 22, 2019. 9 pages. cancer.org.
American Cancer Society: How Does Chemotherapy Work. Downloaded through The Wayback Machine for Jul. 25, 2008. Website marked as revised: Apr. 15, 2008. Website: www.cancer.org/docroot/ETO/content/ETO_1_4X_How_Does_Chemotherapy_Work.asp?sitearea=ETO (Jun. 21, 2008).
American Cancer Society: What Causes Side Effects. Downloaded through The Wayback Machine for Aug. 2, 2008. Website marked as revised: Dec. 9, 2005. Website: www.cancer.org/docroot/MBC/content/MBC_2_2X_What_Causes_Side_Effects.asp?sitearea=MBC (Jun. 21, 2008).
Badwal SPS, Giddey SS, Munnings C, Bhatt AI, Hollenkamp AF. Emerging electrochemical energy conversion and storage technologies. Frontiers in Chemistry (Lausanne, Switz). Sep. 24, 2014; vol. 2, Article 27:1-28. doi: 10.3389/fchem.2014.00079.
Bangham, AD.; Standish, M.M.; Watkins, J.C., Diffusion of Univalent lons across the Lamellae of Swollen Phospholipids. J. Mol. Biol. 1965, 13, 238-252.
Bangham et al. "Negative staining of phospholipids and their structural modification by surface-active agents as observed in the electron microscope," J. Mol. Biol. May 1964; 8:660-668.
Bangham, "Membrane models with phospholipids," Progr. Biophys. Mol. Biol. 1968, 18:29-95.
Barenholtz, Y; Amselem, S .; and Lichtenberg, D., A New Method for Preparation of Phospholipid Vesicles (Liposomes)—French Press. FEBS Letters, Mar. 1979, vol. 99, No. 1, pp. 210-214.
Bartlett, G.R., Phosphorus Assay in Column Chromatography, J Biol. Chem. Mar. 1959, vol. 234, No. 3, 466-468.
Basel MT, et al. Direct Observation of Gold Nanoparticle Assemblies with the Porin MspA on Mica. ACS Nano, 2009; vol. 3, No. 2:462-466.
Batzri, S.; and Korn, E.D. "BBA Report. BBA 71170. Single bilayer liposomes prepared without sonication". Biochim. Biophys. Acta. 1973, 298, 1015-1019.
Biedermann, F., W.M. Nau, and H.J. Schneider, "The Hydrophobic Effect Revisited-Studies with Supramolecular Complexes Imply High-Energy Water as a Noncovalent Driving Force". *Angewandte Chemie International Edition*, 2014. 53(42): p. 11158-11171. 15 pages.
Black, C.D.V.; and Gregoriadis, G., Intracellular Fate and Effect of Liposome-Entrapped Actinomycin D Injected in Rats. Biochem. Soc. Trans. 1976. 549th Meeting, Cambridge, vol. 2, pp. 869-871.
Bogenrieder, T; and Herlyn, M. "Axis of evil: molecular mechanisms of cancer metastasis," Oncogene. Sep. 29, 2003; 22(42):6524-36. doi: 10.1038/sj.onc.1206757.
Bracke KR, Demedts IK, Joos GF, Brusselle GG. CC-chemokine receptors in chronic obstructive pulmonary disease. Inflammation and Allergy: Drug Targets. 2007; 6:75-79.
Brennan and Nikaido, The Envelope of Mycobacteria, (1995), Annu Rev. Biochem. 64, 29-63.
Bruni, A; Toffano, G; Leon, A., Pharmacological effects of phosphatidylserine liposomes. Nature. Mar. 25, 1976, vol. 260, 331-333.
Byers DE, and Holtzman MJ. Alternatively activated macrophages and airway disease. Chest. 2011; 140 (3):768-774.
"CABS-flex 2.0", 5 pages. Downloaded Feb. 7, 2023. Website: biocomp.chem.uw.edu.pl/CABSflex/.
Capece, L., M. Arrar, A. E. Roitberg, S.-R. Yeh, M. A. Marti and D. A. Estrin, Substrate stereo specificity in tryptophan dioxygenase and indoleamine 2,3-dioxygenase. Proteins: Struct., Funct., Bioinf, 2010, 78, 2961-2972.
Castile, J.D.; Taylor, K.M.G., Factors affecting the size distribution of liposomes produced by freeze-thaw extrusion. Int. J Pharm. 1999, 188, 87-95.
Cederbaum, S. D.; H. Yu, W.W. Grody, R. M. Kern, P. Yoo and R. K. Iyer; Arginases I and II: do their functions overlap?, Mol Genet Metab, 2004, 81, Suppl 1, S38-44.
Charrois et al, "Rate of biodistribution of Stealth liposomes to tumor and skin: influence of liposome diameter and implications for toxicity and therapeutic activity," Biochem. Biophys. Acta, 1609, (2003), 102-108.
Chen et al., "Gold Nanoelectrodes of Varied Size: Transition to Molecule-Like Charging," *Science*, Jun. 26, 1998, vol. 280, 2098-2101.
Chen et al., "Quantized Capacitance Charging of Monolayer-Protected Au Clusters," *J. Phys. Chem. B*, 1998, vol. 102, No. 49, 9898-9907.
Cohen, F; Akabas, M; Finkelstein, A., Osmotic Swelling of Phospholipid Vesicles Causes Them to Fuse with a Planar Phospholipid Bilayer Membrane. Science. Jul. 30, 1982, vol. 217, 458-460.
Deamer, D.W.; and Bangham, A.D., "BBA Report. BBA 71267. Large Volume Liposomes by an Ether Vaporization Method", Biochim. Biophys. Acta. 1976, 443, 629-634.
Deamer, D.W., Preparation and Properties of Ether-Injection Liposomes. Annals NY. Acad. Sci. 1978, 308, 250-258.
Deng X, Smeets NMB, Sicard C, Wang J, Brennan JD, Filipe COM, Hoare T. Poly(oligoethylene glycol methacrylate) Dip-Coating: Turning Cellulose Paper into a Protein-Repellent Platform for Biosensors. J Am Chem Soc. Aug. 29, 2014; 136(37): 12852-12855. doi:10.1021/ja507372v.
Driscoll KE. Macrophage inflammatory proteins: Biology and role in pulmonary inflammation. Exp Lung Res. 1994; 20:473-490.
Duffy et al., "Urokinase-Plasminogen Activator, a New and Independent Prognostic Marker in Breast Cancer," Cancer Res, Nov. 1, 1990, 50, 6827-6829.

(56) References Cited

OTHER PUBLICATIONS

E. Diane Neerunjun, and Gregory Gregoriadis; Tumour Regression with Liposome-Entrapped Asparaginase: Some Immunological Advantages. Biochem Soc Trans Feb. 1, 1976; 4 (1): 133-134. doi: https://doi.org/10.1042/bst0040133.

Einstein, A; Uber die von der molekularkinetischen Theorie de Wurme geforderte Bewegung von in rehenden Flussigkeiten suspendierten Teilchen. Annalen der Physik. (1905), 17, 549-560. Original, plus google translation in English.

Ertel, A; Marangoni, A; Marsh, J; Hallett, F; Wood, J., Mechanical properties of vesicles. I. Coordinated analyses of osmotic swelling and lysis. Biophys J. Feb. 1993, vol. 64, 426-434.

Faller M, Niederweis M, and Schulz GE. The Structure of a Mycobacterial Outer-Membrane Channel. Science. Feb. 20, 2004; vol. 303(5661): 1189-1192.

Finklestein, A. and Cass, A. Effect of Cholesterol on the Water Permeability of Thin Lipid Membranes. Nature. Nov. 18, 1967, vol. 216, 717-718.

Fisher, J.F. and S. Mobashery, Recent advances in MMP inhibitor design. Cancer Metastasis Rev., 2006, 25, 115-136.

Forst D, Welte W, Wacker T, and Diederichs K. Structure of the sucrose-specific porin ScrY from *Salmonella typhimurium*and its complex with sucrose. Nat Struct Biol. Jan. 1998; vol. 5(1): 37-46.

Fricke, H, The Electric Capacity of Suspension with Special Reference to Blood. The Journal of General Physiology. V.9(2), Nov. 1925, pp. 137-152.

Gabizon, A; Sbmeeda, H; Horowitz, A; and Zalipsky, S. Tumor cell targeting of liposome-entrapped drugs with phospholipid-anchored folic acid-PEG conjugates. Adv Drug Delivery Rev 2004, 56, 1177-1192.

Gabizon, A; Shmeeda, H; and Zalipsky, S. Pros and Cons of the Lipsome Platform in Cancer Drug Targeting. J Liposome Res. 2006, 16, 175-183.

Gans, "Uber die Form ultramikroskopischer Goldteilchen", Annalen der Physik, *IV Folge*, 1912, 881-900. Original, plus English google translation.

Gao Y, Lam Avvy, Chan WCW. Automating Quantum Dot Barcode Assays Using Microfluidics and Magnetism for the Development of a Point-of-Care Device. ACS Appl Mater Interfaces. Feb. 25, 2013; 5:2853-2860.

Gelderman, K; Blok, V; Fleuren, G; Gortor, A. The Inhibitory Effect of CD46, CD55, and CD59 on Complement Activation After Immunotherapeutic Treatment of Cervical Carcinoma Cells with Monoclonal Antibodies or Bispecific Monoclonal Antibodies. Lab invest. Apr. 2002, vol. 82, No. 4, pp. 483-493.

Gregoriadis, G., & Ryman, B. E. (1971). Liposomes as carriers of enzymes or drugs: a new approach to the treatment of storage diseases. Biochemical journal, 124(5), 58P.

Gregoriadis, Gregory. Medical Progress: The Carrier Potential of Liposomes in Biology And Medicine (First of Two Parts). N. Engl. J. Med. Sep. 23, 1976, vol. 295 (13), 704-710.

H. M. Berman et al., "The Protein Data Bank." *Nucleic Acids Res.* 28, 235-242 (2000).

Hallett, F; Marsh, J; Nickel, B; Wood, J.; Mechanical Properties of Vesicles. Biophys J. Feb. 1993, vol. 64, 435-442.

Hamilton, R.L; Goerke, J.; Guo, L.S.S.; Williams, M.C.; Havel, R.J., Unilamellar liposomes made with the French pressure cell: a simple preparative and semiquantitative technique. J Lipid Res. 1980, vol. 21, 981-992.

Hazlehurst, L; Dalton, W. De Novo and Acquired Resistance to Antitumor Alkylating Agents. In Cancer Drug Discovery and Development: Cancer Drug Resistance. Teicher, B. Humana Press, Inc: Totowa, NJ, 2006; 377-389.

Higashi, S.L., et al., "Supramolecular architectures of nucleic acid/peptide hybrids".*International Journal of Molecular Sciences*, 2020. 21(24): 9458. 25 pages.

Hu et al., "Heat Dissipation of Au Particles in Aqueous Solution: Relaxation Time versus Size," J. Phys. Chem. B, 2002, vol. 106, No. 28, 7029-7033. Abstract Only. 1 page.

Huang, B., et al., "Recent advances and perspectives on supramolecular radical cages". *Chemical Science*, 2021. 12(41): p. 13648-13663.

Huang, C.; Mason, J.T.; Geometric packing constraints in egg phosphatidylcholine vesicles. Proc. Natl. Acad. Sci. USA. Jan. 1978, vol. 75, No. 1, pp. 308-310.

Huang, C. Studies on Phosphatidylcholine Vesicles. Formation and Physical Characteristics. Biochemistry. Jan. 1969, vol. 8, No. 1, 344-352.

Huff J.; Pavelenok, M.; Sukumaran, S.; Niedenveis, M. Functions of the Periplasmic Loop of the Porin MspA from *Mycobacterium segmatis*. J. Biol. Chem. Apr. 10, 2009, 284(15), 10223-10231.

Interview Summary including Office Action Appendix for U.S. Appl. No. 12/920,771, filed Sep. 2, 2010. Mailed on Aug. 23, 2013. 20 pages.

Journal of Clinical Oncology and Cancer Research, Allied Academics, 2024. "Guidelines for Authors". Downloaded from internet on Feb. 20, 2024.

Juliano, R. Á., & Stamp, D. (1975). The effect of particle size and charge on the clearance rates of liposomes and liposome encapsulated drugs. Biochemical and biophysical research communications, 63(3), 651-658.

Kasahara, M.; Hinckle, P.C. Reconstitution and Purification of the D-Glucose Transporter from Human Erythrocytes. J. Biol. Chem. Oct. 1977, vol. 252, No. 20, 7384-7390.

Kaye, S. Liposomes-Problems and promise as selective drug carriers. Cancer Treatment Reviews. 1981, 8, 27-50.

Kaye, S; Richardson, V. Potential of Liposomes as Drug-Carriers in Cancer Chemotherapy. Cancer Chemother Pharmacol. 1979, 3, 81-85.

Kimelburg, H.K.; Mayhew, E.; Papahadjopoulos, D. Distribution of Liposome-Entrapped Cations in Tumor-Bearing Mice. Life Sci. 1975, 17, 715-724.

Kinsky, Stephen C. Preparation of Liposomes and a Spectrophotometric Assay for Release of Trapped Glucose Marker. Meth. Enym. 1974, 32, 501-513.

Knoll, W., et al., "Streptavidin arrays as supramolecular architectures in surface-plasmon optical sensor formats." *Colloids and Surfaces A: Physicochemical and Engineering Aspects*, 2000. 161(1): p. 115-137.

Ko, J.; Park, H.; Heo, L.; Seok, C., GalaxyWEB server for protein structure prediction and refinement. Nucleic Acids Res, Published online May 30, 2012, 40 (Web Server issue), W294-W297.

Koslov, M.M.; Markin, V.S. A Theory of Osmotic Lysis of Lipid Vesicles. J Theor. Biol. 1984, 109, 17-39.

Lahav et al (2000). Photoelectrochemistry with Integrated Photosensitizer-Electron Acceptor and Au-Nanoparticle Arrays. *J. Am. Chem. Soc.*, vol. 122, pp. 11480-11487.

Liang J, Liu H, Huang C, Yao C, Fu Q, Li X, Cao D, Luo Z, Tang Y. Aggregated Silver Nanoparticles Based Surface-Enhanced Raman Scattering Enzyme Linked Immunosorbent Assay for Ultrasensitive Detection of Protein Biomarkers and Small Molecules.: Anal. Chem. Published online Apr. 30, 2015. 15 pages. DOI: 10.2021/acs.analchem.5b01011.

Lichtenberg, D.; Goni, F.; and Heerklotz, H. Detergent-resistant membranes should not be identified with membrane rafts. Trends in Biochemical Science. Aug. 2005, 30(8), 430-436.

Link, S. and El-Sayed, M.A., "Spectral Properties and Relaxation Dynamics of Surface Plasmon Electronic Oscillations in Gold and Silver Nanodots and Nanorods," J. Phys Chem B, (1999), vol. 103, No. 40, 8410-8426.

Liu et al, "Targeting of Tumor Cells by Cell Surface Urokinase Plasminogen Activator-dependent Anthrax Toxin," Journal of Biological Chemistry, May 2001, vol. 276, No. 21. 17976-17984.

Liu, J., et al., "Advances in Multicompartment Mesoporous Silica Micro/Nanoparticles for Theranostic Applications". *Annual Review of Chemical and Biomolecular Engineering*, 2018. 9: p. 389-411. 25 pages.

Liu, Z., S.K.M. Nalluri, and J.F. Stoddart, "Surveying macrocyclic chemistry: from flexible crown ethers to rigid cyclophanes". *Chemical Society Reviews*, 2017. 46(9): p. 2459-2478.

Loveland, B and Cebon, J., Cancer exploiting complement: a clue or an exception. Nature Immunology, (Nov. 2008), 9 (11). 1205-1206.

(56) References Cited

OTHER PUBLICATIONS

Magee, W. E., & Miller, O. V. (Feb. 11, 1972). Liposomes containing antiviral antibody can protect cells from virus infection. Nature, 235(5337), 339-341.
Markiewski, M; DeAngelis, R; Benencia, F; Ricklin—Lichtsteiner, S; Koutoulaki, A; Gerard, C; Coukos, F; Lambris, Modulation of the anti-turmor immune response by complement. J. Nat. Irnmunol. Nov. 2008, 9 (11), 1225-1235. 28 pages.
Mathai, J.; Tristam-Nagle, S.; Nagle, J.; and Zeidel, M. Structural Determinants of Water Permeability through the Lipid Membrane. J. Gen. Physiol. Jan. 2008, 131 (1), 69-76.
Matias et al. Cryo-Transmission Electron Microscopy of Frozen-Hydrated Sections of *Escherichia coli* and Pseudomonas aeruginosa. (Oct. 2003), J. Bacteriol. 185, No. 20, 6112-6118.
Mayer, LD.; Hope, M.J.; Cullis, P.R. Janoff, A.S., Solute distributions and trapping efficiencies observed in freeze-thawed multilamellar vesicles. Biochim. Biophys. Acta. 1985, 817, 193-196.
Mayhew, E.; Lazo, R.; Vail, W.J.; King, J.; Green, AM., Characterization of Liposomes Prepared Using a Microemulsifier, Biochim. Biophys. Acta. 1984, 775, 169-174.
McDougall, LN.; Dunnick, J.K.; Mcnamee, M.G., Distribution and Fate of Synthetic Lipid Vesicles in the Mouse: a Combined Radionuclide and Spin Label Study. Proc. Natl. Acad. Sci. USA, Sep. 1974, 71, No. 9, 3487-3491.
McLaughlin, C.K., G.D. Hamblin, and H.F. Sleiman, "Supramolecular DNA assembly". *Chemical Society Reviews*, 2011. 40(12): p. 5647-5656.
MilliporeSigma website, Life Science Products and Service Solutions, Downloaded Feb. 7, 2024. Website: www.sigmaaldrich.com/united-states.html.
MilliporeSigma website, Strategies for Deglycosylating N-Linked Glycans. Downloaded Feb. 7, 2024. Website: www.sigmaaldrich.com/US/en/technical-documents/technical-article/research-and-disease-areas/cell-signaling/endoglycosidases.
Moses, M; Brem, H; Langer, R., Advancing the field of drug delivery: Taking aim at cancer. Cancer Cell. Nov. 2003, 4, 337-341.
Munder M. Arginase: an emerging key player in the mammalian immune system. Br J Pharmacol. 2009; 158: 638-51.
NASA Publications Guide for Authors, NASA/SP-2005-7602 (Rev. 1). Jul. 2005. 57 pages.
National Geographic Style Manual, "Temperatures". Downloaded through the Wayback Machine for Feb. 1, 2022. 1 page. Website: sites.google.com/a/ngs.org/ngs-style-manual/.
Needham, D.: Nuim, R., Elastic deformation and failure of lipid bilayer membranes containing cholesterol. Biophys. J. Oct. 1990, 58, 997-1009.
Neron, B.; Menager, H.; Maufrais, C.; Joly, N.; Maupetit, J.; Letart, S.; Carrere, S.;Tuffery, P.; Letondal, C., Mobyle: a new full web bioinformatics framework. Bioinformatics 2009, 25 (22), 3005-3011.
Pakneshan, P.; Szyf, M.; Farias-Eisner, R.; Rabbani, S., Reversal of the Hypomethylation Status of Urokinase (uPA) Promoter Blocks Breast Cancer Growth and Metastasis. J. Biol. Chem. Jul. 2004, 279 (30), 31735-31744.
Papahadjopoulos, D; Allen, T; Gabizon, A; Mayhew, E; Mayhew, K; Huang, S; Lee, K; Woodle, M; Lasic, D; Redemann, C; Martin, F.; Sterically stabilized liposomes: Improvements in pharmacokinetics and antitumor therapeutic efficacy. Proc. Natl. Acad. Sci., Dec. 1991, 88, 11460-11464.
Park, J. and M. Yan, "Covalent functionalization of graphene with reactive intermediates". *Accounts of Chemical Research*, 2013. 46(1): p. 181-189.
Park, J; Benz, C; Martin, F.; Future Directions of Liposome- and Immunoliposome-Based Cancer Therapeutics. Seminars on Oncology 2004, 3I(S13), 196-205.
Payne, NJ.; Timmins, P.; Ambrose, C.V.; Ward, M.D.; Ridgeway, F. J.; Prolipsomes: A Novel Solution to an Old Problem. Journal of Pharm Sci. Apr. 1986, 75 (4), 325-329.
Pick, U.; Liposomes with a Large Trapping Capacity Prepared by Freezing and Thawing of Sonicated Phospholipid Mixtures. Arch Biochem. Biophys. Nov. 1981, 212 (1), 186-194.
Rahman, YE.; Wright, DJ.; Liposomes Containing Chelating Agents. J. Cell Biol. 1975, vol. 65, 112-122.
Rawicz, W.; Olbrich, K.; McIntosh, T.; Needham, D.; and Evans, E.; Effect of Chain Length and Unsaturation on Elasticity of Lipid bilayers. Biophys. J., Jul. 2000, 79, 328-339.
Rawlings, N.D., Barrett, A.J., Thomas, P.D., Huang, X., Bateman, A. & Finn, R.D. (Published Online Nov. 14, 2017) The MEROPS database of proteolytic enzymes, their substrates and inhibitors in 2017 and a comparison with peptidases in the Panther database. Nucleic Acids Res 46, D624-D632. Website: merops.sanger.ac.uk/.
RCSB Protein Data Bank (PDB). Website FAQ. Downloaded Feb. 23, 2024. Marked as Last Updated Apr. 10, 2023. 2 pages. Website: www.rcsb.org/pdb/home/home.do.
Reeves, J.P.; Dowben, R.M; Formation and Properties of Thin-walled Phospholipid Vesicles. J. Cell Physiol. 1969, 73, 49-60.
Riemer, et al. Colorimetric ferrozine-based assay for the quantitation of iron in cultured cells., Anal. Biochem. 2004, 331, 370-375.
Rutkowski, C.; \Villiams, L.; Haines, T.; and Cummins, H.; The Elasticity of Synthetic Phospholipid Vesicles Obtained by Photon Correlation Spectroscopy, Biochemistry. 1991, 30(23), 5688-5696.
Schuck, S.; Hansho, M.; Ek.ros, K.; Shevchenko, A.; and Simons, K.; Resistance of cell membranes to different detergents. PNAS. May 13, 2003, 100 (10), 5795-5800.
Sessa, et al. "Phospholipid spherules (liposomes) as a model for biological membranes," J. Lipid Res. May 1968; 9 (3):310-318.
Sharma, R; Kacevska, M; London, R; Clarke, S; Liddle, C; Robertson, G.; Downregulation of drug transport and metabolism in mice bearing extra-hepatic malignancies. Brit J Cancer. 2008, 98, 91-97.
Shen et al. In vitro cellular uptake and effects of Fe3O4 magnetic nanoparticles on Hela cells., Journal of Nanoscience and Nanotechnology 2009, 9, 2866-2871.
Shenoy, V; Vijay, I; Murthy, R. J.; Tumour targeting: biological factors and formulation advances in injectable lipid nanoparticles. Pharm Pharmacol. 2005, 57, 411-421.
Shetty, D., et al., "Can we beat the biotin-avidin pair?: cucurbit[7]uril-based ultrahigh affinity host-guest complexes and their applications". *Chemical Society Reviews*, 2015. 44(23): p. 8747-8761.
Shevchenko et al., Mass spectrometric sequencing of proteins silver-stained polyacrylamide gels. Anal. Chem. 68 (5) 850-858 (Mar. 1996).
Shin, W.-H.; Lee, G. R.; Heo, L.; Lee, H.; Seok, C., Prediction of Protein Structure and Interaction by Galaxy Protein Modeling Programs. BioDesign, Mar. 31, 2014, 2(1), 1-11.
Spindel, S., & Sapsford, K. E. (2014). Evaluation of optical detection platforms for multiplexed detection of proteins and the need for point-of-care biosensors for clinical use. Sensors, 14(12), 22313-22341.
Stewart, J.C.M. Colorimetric Determination of Phospholipids with Ammonium Ferrothiocyanate. Analytical Biochemistry. 104, 10-14 (1980).
Sun J. Photonics Based Strategies for Minimally Invasive Cancer Diagnosis Using Endogenous and Molecular Contrast. University Dissertation Abstracts Int 69 (48) 2465. 106 pages. (Aug. 2007).
Szoka, F.,Olson, F.; Hunt, C.A.; Vail, W.; Mayhev,, E.; Paphadjopoulos, D.; Preparation of Unilamellar Liposomes of Intermediate Size (0.1-0.2 um) by a Combination of Reverse Phase Evaporation and Extrusion Through Polycarbonate Membranes. Biochim. Biophys. Acta. 1980, 601, 559-571.
Tanaka, T., Taneda, K., Kobayashi, H., Okumura, K., Muranishi, S., & Sezaki, H. (1975). Application of liposomes to the pharmaceutical modification of the distribution characteristics of drugs in the rat. Chemical and Pharmaceutical Bulletin, 23(12), 3069-3074.
Taylor, A.E.; Miller, C.W.; On the Estimation of Phosphorus in Biological Material. J Biol. Chem. (1914), 37, 215-224.
The Laboratory of Theory of Biopolymers, website. Andrzej Kolinski Research Group, 1 page. Downloaded on Feb. 23, 2024. (Website: biocomp.chem.uw.edu.pl/).

(56) References Cited

OTHER PUBLICATIONS

The NCBI Style Guide, including Chapter 5. National Center for Biotechnology. Last updated: 2004. 57 pages. Website: www.ncbi.nlm.nih.gov/books/NBK995/.
Tomalia DA, Baker H, Dewald J, Hall M, Kallas G, Martin S, Roeck J, Ryder J, Smith P. A new class of polymers: starburst-dendritic macromolecules. Polymer Journal (Tokyo). 1985; 17 (1): 117-132. doi: 10.1295/polymj.17.117.
Uniprot, E9PJK1 E9PJK1_Human, Downloaded Feb. 7, 2024. 7 pages. Website: www.uniprot.org/uniprot/E9PJK1/entry.
UniProt, O00571 DDX3X_Human, Downloaded Feb. 7, 2024. 20 pages. Website: www.uniprot.org/uniprot/000571/entry.
UniProt, P01033 TIMP1_Human, Downloaded Feb. 7, 2024. 13 pages. Website: www.uniprot.org/uniprot/P01033/entry.
Uniprot, P05187 PPB1_Human, Downloaded Feb. 7, 2024. 14 pages. Website: www.uniprot.org/uniprot/P05187/entry.
UniProt, P54136 SYRC_Human, Downloaded Feb. 7, 2024. 15 pages. Website: www.uniprot.org/uniprot/P54136/entry.
UniProt, Q5T4S7 UBR4_Human, Downloaded Feb. 7, 2024. 15 pages. Downloaded Feb. 7, 2024. Website: www.uniprot.org/uniprot/Q5T4S7/entry.
UniProt, Q92882 OSTF1_Human, Downloaded Feb. 7, 2024. 11 pages. Website: www.uniprot.org/uniprot/Q92882/entry.
UniProt, Q969D9 TSLP_Human, Downloaded Feb. 7, 2024. 11 pages. Website: www.uniprot.org/uniprot/Q969D9/entry.
UniProtKB, Downloaded on Feb. 7, 2024. 2 pages. Website: www.uniprot.org/help/uniprotkb.
Wang et al., "Monodispersed Core-Shell Fe304@Au Nanoparticles," J. Phys Chem B, 2005, vol. 109, No. 46, 21593-21601.
Wang et al., "The Emerging Use of Quantum Dots in Analysis," Analytical Letters, 2007, 40, 1497-1520.
Wang, et al. "Supplementary Information: Synthesis and Calibration of Magnetic-Nanoparticle(Fe/Fe3/O4)-based Nanoplatforms for Highly Sensitive Fluorescence Detection of Cancer-Related Proteases." in Royal Society of Chemistry Journal "Photochemical & Photobiological Sciences" on Sep. 24, 2013. 11 pages. Doi: 10.1039/c3pp50260k.
Wang H. et al. Nanoplatforms for Highly Sensitive Fluorescence Detection of Cancer Related Proteases. Photochemical & Photobiological Sciences 13(2) 231-240, Feb. 2014.
Weinstein, John; Leserman, Lee.; Liposomes as Drug Carriers in Cancer Chemotherapy. Pharm. Therapy, 1984. 24, 207-233.
Zhang, B., et al., "Preparation of aramid nanofiber and its application in polymer reinforcement: A review". *Eur. Polym. J.*, 2020. 139: p. 109996. 10 pages.
Zhu, H., et al., "Supramolecular peptide constructed by molecular Lego allowing programmable self-assembly for photodynamic therapy". *Nature communications*, 2019. 10(1): p. 2412. 10 pages.
Zucker, S. et al., Critical appraisal of the use of matrix metalloproteinase inhibitors in cancer treatment. Oncogene (Dec. 27, 2000) 19 (56), 6642-6650. Doi:10/1038/sj.on.1204097.
Abernethy, "The Historical and Current Interest in Coumarin", Journal of Chemical Education, Sep. 1969, vol. 46, No. 9, 561-568.
Andreasen et al., "The Urokinase-Type Plasminogen Activator System in Cancer Metastasis: A Review," Int J. Cancer, 1997, 72, 1-22.
Bailey, R. et al., "Alloyed Semiconductor Quantum Dots: Tuning the Optical Properties without Changing the Particle Size," *J. Am. Chem. Soc.*, 2003, vol. 125, No. 23, 7100-7106.
Balivada et aL, "A/C magnetic hyperthermia of melanoma mediated by iron(0)/iron oxide core/shell magnetic nanoparticles: a mouse study," *BMC Cancer*, Mar. 2010, vol. 10, No. 1, 119. 10 pages.
Biju et al., "Semiconductor quantum dots and metal nanoparticles: syntheses, optical properties, and biological applications," Analytical and Bioanalytical Chemistry, 2008, 391, 2469-2495.
Boatman et al., "A Safer, Easier, Faster Synthesis for CdSe Quantum Dot Nanocrystals," *Journal of Chemical Education*, Nov. 2005, vol. 82, No. 11, 1697-1699.
Bossmann, "6. Nanoparticles for hyperthermia treatment of cancer," *Fabrication and Bio-Application of Functionalized Nanomaterials*, 2009, 171-206.
Bremer et al, "Optical Imaging of Spontaneous Breast Tumors Using Protease Sensing 'Smart' Optical Probes," Investigative Radiology, Jun. 2005, vol. 40, No. 6, 321-327.
Cai et al., "Nanoplatforms for Targeted Molecular Imaging in Living Subjects", *Small*, vol. 3, Issue 11, 2007, pp. 1840-1854.
Chan et al., "Luminescent quantum dots for multiplexed biological detection and imaging," *Current Opinion in Biotechnology*, 2002, vol. 13, 40-46.
Chang E. et al. Protease Activated Quantum Dot Probes. Biochemical and Biophysical Research Communications 334:1317-1321, 2005.
Chang et al, "Protease-activated quantum dot probes," *Biochemical and Biophysical Research Communications*, 2005, vol. 334, No. 4, 1317-1321.
Chang et al, "Protease-Activated Quantum Dot Probes," Biophotonics and New Therapy Frontiers, Proc. of SPIE. vol. 6191, (2006), 61911E-1-61911E-10. 10 pages.
Charrois et al., "Drug release rate influences the pharmokinetics, biodistribution, therapeutic activity, and toxicity of pegylated liposomal doxorubicin formations in murine breast cancer," Biochimica et Biophysica Acta 1663, 2004, 167-177.
Chau et al. (2008). Incorporation of a matrix metalloproteinase-sensitive substrate into self-assembling peptides—A model for biofunctional scaffolds. *Biomaterials*, vol. 29, pp. 1713-1719.
Chen et al., "A new temperature- and pH-responsive copolymer for possible use in protein conjugation," *Macromol. Chem. Phys* , 1995, 196, 1251-1259.
Chen et al., "Chitosan/b-lactoglobulin core-shell nanoparticles as nutraceutical carriers," *Biomaterials*, May 10, 2005, vol. 26, Issue 30, 6041-6053. Abstract Only. 2 pages.
Choi et al. "Renal clearance of quantum dots," Nature Biotechnology, Oct. 2007, vol. 25, No. 10, 1165-1170.
Crozier et al., "Experimental measurement of the dispersion relations of the surface plasmon modes of metal nanoparticle chains," *Optics Express*, Dec. 2007, vol. 15, No. 26, 17482-17493.
Dabbousi et al, "(CdSe)ZnS Core-Shell Quantum Dots: Synthesis and Characterization of a Size Series of Highly Luminescent Nanocrystallites," J. Phys. Chem. B, 1997, vol. 101, No. 46, 9463-9475.
Dahal et al., "Synthesis of Water-Soluble Iron-Gold Alloy Nanoparticles," *Chemistry of Materials*, 2008, vol. 20, No. 20, 6389-6395.
Dictionary meaning Chromophore Luminophore Viologen. 2012. 1 page.
Duffy, "Proteases as Prognostic Markers in Cancer," Clinical Cancer Research, Apr. 1996, vol. 2, 613-618.
Duffy, "Urokinase-type plasminogen activator: a potent marker of metastatic potential in human cancers," Biochemical Society Transactions, 2002, vol. 30, Part 2, 207-210.
Duhamel, "Pyrene fluorescence to study polymeric systems," Molecular Interfacial Phenomena of Polymers and Biopolymers, 2005, vol. 7, 214-221.
Elliott et al., "Gold nanoshell thermal confinement of conformal laser thermal therapyin liver metastasis," Proceedings of SPIE, 2008, 6865 (Nanoscale Imaging, Sensing. and Actuation for Biomedical Applications V), 68650Q/1-68650Q/8. 8 pages.
Eustis et al., "Aspect Ratio Dependence of the Enhanced Fluorescence Intensity of Gold Nanorods: Experimental and Simulation Study," *J Phys. Chem. B*, 2005, vol. 109, No. 34, 16350-16356.
Fagadar-Cosma et al., "Combinatorial Synthesis and Characterization of New Asymmetric Porphyrins as Potential Photosensitizers in Photodynamic Therapy," Combinatorial Chemistry & High, Throughput Screening, 2007, vol. 10, No. 6, 466-472.
Fallahpour, "The Higher Oligopyridines and their Metal Complexes," Current Organic Synthesis, 2006, vol. 3, No. 1, 19-39.
Farrer et al, "Highly Efficient Multiphoton-Absorption-Induced Luminescence from Gold Nanoparticles," *Nano Letters*, 2005, vol. 5, No. 6, 1139-1142.

(56) References Cited

OTHER PUBLICATIONS

Fisher et al, "Emission Intensity Dependence and Single-Exponential Behavior in Single Colloidal Quantum Dot Fluorescence Lifetimes," J. Phys. Chem. B, 2004, vol. 108, No. 1, 143-148.
Foekens et al, "The Urokinase System of Plasminogen Activation and Prognosis in 2780 Breast Cancer Patients," Cancer Res., 60, 2000, 636-643. 19 pages. (Website: cancerres.aacrjournals.org/content/60/3/636.full).
Fukami et al., "Study for usefulness of Indocyanine green as an infrared marker," *Biomarkers and Biological Spectral Imaging*, Proceedings of SPIE, 2001, vol. 4259, 157-162.
Garcia et al, "Biological and Clinical Significance of Cathepsin D in Breast Cancer Metastasis," *Stem Cells*, 1996, vol. 14, 642-650.
Geier et al., "Boundary effects of molecular diffusion in nanoporous materials: A pulsed field gradient nuclear magnetic resonance study", *Journal of Chemical Physics*, Jan. 2004, vol. 120, No. 1, 367-373.
Green, "The Organometallic Synthesis of Bifunctional Core/Shell Nanoparticles," *Small*, vol. 1, No. 7, 2005, 684-686.
Gunnarsson et al., "Confined Plasmons in Nanofabricated Single Silver Particle Pairs: Experimental Observations of Strong Interparticle Interactions," *J. Phys. Chem. B.*, 2005, vol. 109, No. 3, 1079-1087.
Hall et al., "Enhanced Invasion of Hormone Refractory Prostate Cancer Cell Through Hepatocyle Growth Factor (HGF) Induction of Urokinase-Type Plasminogen Activator (u-PA)", *The Prostate*, 2004, vol. 59, pp. 167-176.
Hamelin et al, "The Static Dielectric Constant of Liquid Water Between 274 and 418 K Near the Saturated Vapor Pressure," *International Journal of Thermophysics*, 1998, vol. 19, No. 5, 1359-1380.
Hao et al. "Electromagnetic fields around silver nanoparticles and dimers," Journal of Chemical Physics. Jan. 2004, vol. 120, No. 1, pp. 357-366.
Hergert and Wriedt, Eds., "Mie Theory 1908-2008: Present developments and interdisciplinary aspects of light scattering," *Universitat Bremen*, Bremen 2008, pp. 1-112.
Hu et al., "Gold nanostructures: engineering their plasmonic properties for biomedical applications," *Chem. Soc. Rev.*, 2006, 35, 1084-1094.
Huang et al, "Gold nanoparticles: interesting optical properties and recent applications in cancer diagnostics and therapy," *Nanomedicine 2.5*, Oct. 2007, 681-693. 13 pages.
Hutter et al, "Exploitation of Localized Surface Plasmon Resonance," AdvancedMaterials, Oct. 2004. vol. 16, No. 19, pp. 1686-1706.
International Preliminary Report on Patentability for PCT/US2021/065573 filed on Dec. 29, 2021 on behalf of Hawkeye Bio, Limited. Mail Date: Apr. 14, 2023. 6 pages.
International Search Report and Written Opinion for International Application No. PCT/US2022/073477 filed on Jul. 6, 2022 on behalf of Hawkeye Bio, Limited. Mailed on Mar. 2, 2023. 14 pages.
Ito et al., "Tumor regression by combined immunotherapy and hyperthermia using magnetic nanoparticles in an experimental subcutaneous murine melanoma," Cancer Sci, Mar. 2003, vol. 94, No. 3, 308-313.
Jackson et al., "From homoligand-to mixed-ligand-monolayer-protected metal nanoparticles: a scanning tunneling microscopy investigation," *Journal of the American Chemical Society*, 2006, vol. 128, Issue 34, 11135-11149. Abstract Only. 2 pages.
Jain et al., "Calculated Absorption and Scattering Properties of Gold Nanoparticles of Different Size, Shape, and Composition: Applications in Biological Imaging and Biomedicine." *J. Phys. Chem. B*, 2006, vol. 110, No. 14, 7238-7248.
Jain et al., "Universal Scaling of Plasmon Coupling in Metal Nanostructures: Extension from Particle Pairs to Nanoshells," *Nano Letters*, 2007, vol. 7, No. 9, 2854-2858.
Jain et al., "Surface Plasmon Coupling and Its Universal Size Scaling in Metal Nanostructures of Complex Geometry: Elongated Particle Pairs and Nanosphere Trimers," *J. Phys. Chem. C.*, 2008, vol. 112, No. 13, 4954-4960.
Jares-Erijman et al, "Imaging molecular interactions in living cells by FRET microscopy," *Current Opinion in Chemical Biology*, 2006, vol. 10, 409-416.
Johansson et al., "Matrix metalloproteinases in tumor invasion." Cellular and MolecularLife Sciences, 2000, 57, 5-15.
Jones et al. "Solvent Effects on Emission Yield and Lifetime for Coumarin Laser Dyes. Requirements for a Rotatory Decay Mechanism." J Phys. Chem., vol. 89, No. 2, 1985, 294-300.
Kalita et al, "Optical and Electronic Properties of Metal and Semiconductor Nanostructures," Nanoscale Materials in Chemistry, Second Edition, Edited by Klabunde and Richards, 2009, John Wiley & Sons, Inc., Chapter 16, 535-572.
Kelly et al., "The Optical Properties of Metal Nanoparticles: The Influence of Size, Shape, and Dielectric Environment", *J Phys Chem. B*, 2003. vol. 107, No. 3, 668-677.
Khasigov, P; Podobed, O; Gracheva, T; Salbiev, K; Grachev, S; Berezov, T., Role of Matrix Metalloproteinases and Their Inhibitors in Tumor Invasion and Metastasis. Biochemistry (Moscow), 2002, vol. 68, No. 7, pp. 711-717.
Kim, et al., "Chip-Based Protease Assay Using Fluorescence Resonance Energy Transfer Between Quantum Dots and Fluorophores," Biochip Journal, Dec. 2007, vol. 1, No. 4, pp. 228-233.
Kim et al, "Type-II Quantum Dots: CdTe/CdSe{Core/Shell) and CdSe/ZnTe(Core/Shell) Heterostructures," *J. Am. Chem. Soc*, 2003, vol. 125, No. 38, 11466-11467.
Kircher et al. "Ratio imaging of enzyme activity using dual wavelength optical reporters", Molecular Imaging, MIT Press, US, vol. 1, No. 2, 1, pp. 89-95, Apr. 2002.
Kjaergaard et al., "Structure and ligand interactions of the urokinase receptor (uPAR)," Frontiers in Bioscience, May 2008, 13, 5441-5461.
Kondon et al., "Origin of Size-Dependent Energy Transfer from Photoexcited CdSe Quantum Dots to Gold Nanoparticles," J. Phys Chem. C, 2008, vol. 112, No. 17, 6695-6699.
Koole et al., "Time-Dependent Photoluminescence Spectroscopy as a Tool to Measure the Ligand Exchange Kinetics on a Quantum Dot Surface," *ACS Nano*, 2008, vol. 2, No. 8, 1703-1714.
Kostova., "Synthetic and Natural Coumarins as Antioxidants", Mini-Reviews in Medicinal Chemistry, 2006, vol. 6, No. 4, 365-374.
Kulakovich et al., "Enhanced Luminescence of CdSe Quantum Dots on Gold Colloids," Nano Lett, 2002, vol. 2, No. 12, 1449-1452.
Kumaraswamy et al., "Fluoresent-conjugated polymer superquenching facilitates highly sensitive detection of proteases," The National Academy of Sciences of the USA, 2004, vol. 101, No. 20, 7511-7515. 18 pages.
Lakowicz, "Review: Radiative Decay Engineering: Biophysical and Biomedical Applications," Analytical Biochemistry, 2001, 298, 1-24.
Law et al. Feb. 2008. Structural Modification of Protease Inducible Preprogrammed Nanofiber Precursor. *Biomacromolecules*, vol. 9, No. 2, pp. 421-425.
"What is a Particle" from Particle Engineering Research Center at the University of Florida. Downloaded on Oct. 2, 2014. 5 pages. (Website: perc.ufl.edu/particle.asp).
Leatherdale et al., "On the Absorption Cross Section of CdSe Nanocrystal Quantum Dots," Journal of Physical Chemistry B, 2002, vol. 106, No. 31, 7619-7622.
Leaym et al. "Synthesis of Water-Soluble Highly Charged and Methylene-Bridged Resorcin[4]arenes," Synthesis, 2008, No. 6, 932-942.
Lee et al., "Biological Imaging of HEK293 Cells Expressing PLCγ1 Using Surface-Enhanced Raman Microscopy," Anal. Chem., 2007, vol. 79, No. 3, 916-922.
Lee et al, "Gold and Silver Nanoparticles in Sensing and Imaging: Sensitivity of Plasmon Response to Size, Shape, and Metal Composition," *J Phys Chem. B*, 2006, vol. 110, No. 39, 19220-19225.
Li et al. Sep. 23, 2003. Large-Scale Synthesis of Nearly Monodisperse CdSe/CdS Core/Shell Nanocrystals Using Air-Stable Reagents via

(56) References Cited

OTHER PUBLICATIONS

Successive Ion Layer Adsorption and Reaction. J. Am. Chem. Soc., vol. 125, No. 41, pp. 12567-12575.
Liao et al., "Biomedical applications of plasmon resonant metal nanoparticles," *Nanomedicine*, 2006, 1, 201-208. 13 pages.
Link et al., Alloy Formation of Gold-Silver Nanoparticles and the Dependence of the Plasmon Absorption on Their Composition, *J Phys Chem. B*, 1999, vol. 103, No. 18. 3529-3533.
Liu et al., "A nanoplasmonic molecular ruler for measuring nuclease activity and DNA footprinting," *Nature Nanotechnology*, Oct. 2006, vol. 1, 47-52.
Lopez Arbeloa et al, "Photophysics of amino-aromatic laser dyes," Trends in Photochemistry & Photobiology, 1994, vol. 3, No. 1, pp. 145-155.
Meijer et aL, "Effect of restraint and injection methods on heart rate and body temperature in mice," Laboratory Animals, 2006, 40, 382-391.
Miguel et al., "Comparative analysis of the $^1$H NMR relaxation enhancement produced by iron oxide and core-shell iron-iron oxide nanoparticles," *Magnetic Resonance Imaging*, 2007, vol. 25, Issue 10, 1437-1441. Abstract Only. 1 page.
Mohamed et al., "The 'lightening' gold nanorods: fluorescence enhancement of over a million compared to the gold metal," *Chemical Physics Letters* 317, Feb. 2000, 517-523.
Mulet et al, "Nanoscale radiative heat transfer between a small particle and a plane surface," Applied Physics Letters, May 2001, vol. 78, No. 19, 2931-2933.
Mulvaney, "Surface Plasmon Spectroscopy of Nanosized Metal Particles," Langmuir, 1996, vol. 12, No. 3, 788-800.
Murov et al., "Handbook of Photochemistry: Second Edition, Revised and Expanded," *Marcel Dekker, Inc.*, New York, Basel, Hong Kong, 1993, p. 27. 3 pages.
Murray et al, "Synthesis and Characterization of Nearly Monodisperse CdE (E=S, Se, Te) *Semiconductor Nanocrystallites*," J. Am. Chem. Soc. 1993. vol. 115, No. 19. 8706-8715.
Nau, Werner M. et al. "Substrate-Selective Supramolecular Tandem Assays: Monitoring Enzyme Inhibition of Arginase and Diamine Oxidase by Fluorescent Dye Displacement from Calixarene and Cucurbituril Macrocycles," *J. Am. Chem Soc*. 2009, May 22, 2009, 131, pp. 11558-11570.
Odom et al., "How Gold Nanoparticles Have Stayed in the Light: The 3M's Principle," *ACS Nano*, 2008, vol. 2. No. 4, 612-616.
Oldenburg et al., "Infrared extinction properties of gold nanoshells," *Applied Physics Letters*, Nov. 1999, vol. 75, No. 19, 2897-2899.
Ottaviani et al., "Phase Separation of Poly(N-isopropylacrylamide) in Mixtures of Water and Methanol: A Spectroscopic Study of the Phase-Transition Process with a Polymer Tagged with a Fluorescent Dye and a Spin Label," Helvetica Chimica Acta, 2001, vol. 84, 2476-2492.
Park et al, "Fabrication of Magnetic Core@Shell Fe Oxide@Au Nanoparticles for Interfacial Bioactivity and Bio-separation," *Langmuir*, 2007, vol. 23, No. 17, 9050-9056.
Patterson, "Fluorescent Proteins for Cell Biology," Methods in Molecular Biology, 2007, Chapter 5, 411: Reporter Genes: A Practical Guide, 47-80.
Paul, "Ruthenium, osmium and rhodium complexes of polypyridyl ligands: Metal-promoted activities, stereochemical aspects and electrochemical properties," Proceedings Indian Academy of Sciences. (Chemical Sciences), Aug. 2002, vol. 114, No. 4, 269-276.
Periasamy and Day. Eds., "Book Review: Molecular Imaging, FRET Microscopy and Spectroscopy," Journal of Biomedical Optics, Nov./Dec. 2006, vol. 11, No. 6, 069901-1-069901-2. 2 pages.
Pham et al. 2004. Developing a Peptide-Based Near-Infrared Molecular Probe for Protease Sensing. *Bioconjugate Chem.*, vol. 15, pp. 1403-1407.
Pilotte, L. et al. "Reversal of tumoral immune resistance by inhibition of tryptophan 2,3-dioxygense", Natl. Acad. Sci. U.S. A., Feb. 2012, vol. 109, No. 7, pp. 2497-2502.
Pinchuk et al., "Optical properties of metallic nanoparticles: influence of interface effects and interband transitions," *Surface Science* 557, 2004, 269-280.
Plech et al., "Laser-induced heating and melting of gold nanoparticles studied by time-resolved x-ray scattering," Physical Review B, 2004, 70, 195423-1-195423-7. 7 pages.
Ponce et al. "Hyperthermia mediated liposomal drug delivery," International Journal of Hyperthermia, 2006, vol. 22, No. 3, 205-213.
Pons et al., "On the Quenching of Semiconductor Quantum Dot Photoluminescence by Proximal Gold Nanoparticies," *Nano Letters*, 2007, vol. 7, No. 10, 3157-3164.
Prasad et al; "Digestive Ripening of Thiolated Gold Nanoparticles: The Effect of Alkyl Chain Length," *Langmuir*, 2002, vol. 18, No. 20, 7515-7520.
Protasenko et al., "Demonstration of a Low-Cost, Single-Molecule Capable, Multimode Opticial Microscope," *Chem. Educator*, 2005, vol. 10, No. 4, 269-282.
Qin, H., et al., "Chemical amination via cycloaddition of graphene for use in a glucose sensor". *Journal of nanoscience and nanotechnology*, 2016. vol. 16, No. 5: p. 5034-5037.
Reinhard et al., "Calibration of Dynamic Molecular Rulers Based on Plasmon Coupling between Gold Nanoparticles," *Nano Letters*, 2005, vol. 5, No. 11, 2246-2252.
Reinhard et al., "Use of plasmon coupling to reveal the dynamics of DNA bending and cleavage by single EcoRV restriction enzymes," *PNAS*, Feb. 2007, vol. 104, No. 8, 2667-2672.
Rochford et al. Mar. 27, 2007.Tetrachelate Porphyrin Chromophores for Metal Oxide Semiconductor Sensitization: Effect of the Spacer Length and Anchoring Group Position. *J. Am. Chem. Soc.*, vol. 129, No. 15, pp. 4655-4665.
Roux et al, "Polymer based pH-sensitive carriers as a means to improve the cytoplasmic delivery of drugs," *International Journal of Pharmaceutics*, 2002, 242, 25-36.
Russier-Antoine et al., "Wavelength dependence of the hyper Rayleigh scattering response from gold nanoparticles," *Journal of Chemical Physics*, Jun. 2004, vol. 120, No. 22, 10748-10752.
Samarakoon et al., "Early Detection of Cancer through Matrix Metalloproteinases," Copyright American Chemical Society, Abstract from 44th Midwest Regional Meeting of the American Chemical Society, Iowa City, Iowa, United States, Oct. 21-24, 2009. 1 Page.
Samarakoon et al, "Test of An in-Vivo Sensor for Urokinase Using Fluorescence Microscopy." Copyright American Chemical Society, Abstract from 44th Midwest Regional Meeting of tile American Chemical Society, Iowa City, Iowa, United States, Oct. 21-24, 2009. 1 page.
Schellenberger et al., "Protease-Specific Nanosensors for Magnetic Resonance Imaging," *Bioconjugate Chem., American Chemical Society*, Dec. 17, 2008, No. 19, No. 12, 2440-2445.
Schild et al, "Cononsolvency in Mixed Aqueous Solutions of Poly(N-isopropylacrylamide)," *Macromolecules*, 1991, vol. 24, No. 4, 948-952.
Schmid et al., "Nanoparticulated Gold: Syntheses, Structures, Electronics, and Reactivities," *Eur. J. Inorg. Chem.*, 2003. 3081-3098.
Seegers et al. High-Throughput Fluorescence-Based Screening Assays for Tryptophan-Catabolizing Enzymes. J Biomol Screen (Oct. 2014) vol. 19, No. 9, pp. 1266-1274, 9 pages.
Shinkai et al., "Functional Magnetic Particles for Medical Application," J. Biosci. Bioeng, 2002, vol. 94, No. 6, 606-613.
Simoes et al, "On the formulation of pH-sensitive liposomes with long circulation times", Adv. Drug. Deliv. Reviews, 56, 2004, 947-965.
Sounderya et al.2008. Use of Core/Shell Structured Nanoparticles for Biomedical Applications. *Recent Patents on Biomedical Engineering* 2008, vol. 1, No. 1, Jan. 2008, pp. 34-42.
Steinfeld, "Quenching of Fluorescence in Small Molecules," Accounts of Chemical Research, Sep. 1970, vol. 3, 313-320.
Sun et al, "Theoretical Study on Gold-Coated Iron Oxide Nanostructure: Magnetism and Bioselectivity for Amino Acids," J. Phys. Chem. C, 2007, vol. 111, No. 11, 4159-4163.
Tiefenauer, "Magnetic Nanoparticles as Contrast Agents for Medical Diagnosis," Nanotechnology in Biology and Medicine, 2007, Chapter 29, 29-1 to 29-20. 11 pages.

(56) References Cited

OTHER PUBLICATIONS

Tomek, P. et al. "Formation of an N-formylkynurenine-derived fluorophore and its use for measuring indoleamine 2,3-dioxygenase 1 activity", Anal. Bioanal. Chem., 2013, 405, 2515-2524.
Torchilin, "Multifunctional nanocarriers," Advanced Drug Delivery Reviews, 2006, 58, 1532-1555.
Turk et al., "Determination of protease cleavage site motifs using mixture-based oriented peptide libraries," Nature Biotechnology, Jul. 2001, vol. 19, 661-667.
Vail et al.,"Pegylated Liposomal Doxorubicin: Proof of Principle Using Preclinical Animal Models and Pharmacokinetic Studies," Seminars in Oncology, 2004, 31, (Suppl. 13), 16-35.
Wang et al., Particle-based detection of DNA hybridization using electrochemical stripping measurements of an iron tracer, *Analytica Chimica Acta*, Apr. 15, 2003, vol. 482, No. 2, 149-155.
Wang et al., "Synthesis of 'Light Switches for Urokinase Activity' Using Consensus (Cleavage) Sequences Between Bimagnetic Core/Shell Fe/Fe304 Nanoparticles and a Porphyrin," Copyright American Chemical Society, Abstract from 44th Midwest Regional Meeting of the American Chemical Society, Iowa City, Iowa, United States, Oct. 21-24, 2009. 1 page.
Warnecke et al, "Synthesis, Cleavage Profile, and Antitumor Efficacy of an Albumin-Binding Prodrug of Methotrexate that is Cleaved by Plasmin and Cathepsin B," Arch. Pharm. Chem. Life Sci., 2007, 340, 389-395.
Website: www.coumarins.com, printed main screen from website on Dec. 6, 2010, 1 page.
Weinmann, "History of the Development and Applications of Coumarin and Coumarin-related Compounds." Coumarins: Biology, Applications and Mode of Action, 1997, John Wiley & Sons Ltd., Chapter 1, pp. 1-22.
Willets et al, "Localized Surface Plasmon Resonance Spectroscopy and Sensing," *Annu. Rev. Phys. Chem.*, 2007, vol. 58, 267-297.
Wiltschi et al., "Binding assays with artificial tethered membranes using surface plasmon resonance," *Methods* 39, 2006, 134-146.
Winkler et al, "Quantum Dots: An Experiment for Physical or Materials Chemistry," *Journal of Chemical Education*, Nov. 2005, vol. 82, No. 11, 1700-1702.
Winnik et al., "Cononsolvency of Poly(N-isopropylacrylamide): A Look at Spin-Labeled Polymers in Mixtures of Water and Tetrahydrofuran," Macromolecules, 1993, vol. 26, No. 17, 4577-4585.
Winnik et al., "Cononsolvency of Poly(N-isopropylacrylamide) in Mixed Water-Methanol Solutions: A Look at Spin-Labeled Polymers," Macromolecules, 1992, vol. 25, No. 22, 6007-6017.
Woerner M, et al. Characterization of nanostructured surfaces generated by reconstitution of the Porin MspA from *Mycobacterium smegmatis*. Small. 2007; 3(6): 1084-1097. doi:10.1002/smll.200600559.
Xia, Z. et al., "Multiplex Detection of Protease Activity with Quantum Dot Nanosensors Prepared by Intein-Mediated Specific Bioconjugation," *Analytical Chemistry*, vol. 80, No. 22, Nov. 15, 2008, 8649-8655.
Yasuda et al, "Characterization of New Fluorogenic Substrates for the Rapid and Sensitive Assay of Cathepsin E and 7 Cathepsin D," Journal of Biochemistry, 1999, vol. 125, No. 6, 1137-1143.
Yasuda, Yoshiyuki, et al. A new selective substrate for cathepsin E based on the cleavage site sequence of alpha2-macroglobulin. Biological Chemistry (Mar. 2005), 386(3), 299-305.
Yun et al., "Nanometal Surface Energy Transfer in Optical Rulers, Breaking the FRET Barrier," *J. Am. Chem. Soc.*, 2005, vol. 127, No. 9, 3115-3119.
Zeng et at. "Fe/Fe oxide nanocomposite particles with large specific absorption rate for hyperthermia," *Applied Physics Letters*, Jun. 7, 2007, vol. 90, No. 23, 233112-1 to 233112-3. 4 pages.
Zhang et al., "Surfactant-Mediated Self-Assembly of Au Nanoparticles and Their Related Conversion to Complex Mesoporous Structures," *Langmuir*, 2008, vol. 24, No. 8, 3740-3746.
Zhong et al., "Synthesis and Assembly of Alloy and Core-Shell Nanoparticles for Sensor Applications," *Polymer Preprints*; 2006, 47(2), 941-942.
2nd Written Opinion for PCT/US2021/065573 filed on Dec. 29, 2021 on behalf of Hawkeye Bio, Limited Mail Date: Dec. 12, 2022 6 pages.
Decision to Grant a European patent pursuant to Article 97(1) EPC, dated Aug. 21, 2014, for EP Application No. 09718303.2 filed Mar. 3, 2009 on behalf of Kansas State University Research Foundation. 2 pages.
Examination Report dated Mar. 11, 2016 for Indian Application 6080/CHENP/2010 filed Sep. 27, 2010. 4 pages.
Extended European Search Report dated Aug. 26, 2011, for EP Application No. 09718303.2 filed Mar. 3, 2009 on behalf of Kansas State University Research Foundation. 10 pages.
International Preliminary Report on Patentability dated Mar. 6, 2012, in corresponding PCT application PCT/US2021/047301 filed on Aug. 31, 2010. 8 pages.
International Preliminary Report on Patentability dated Sep. 7, 2010, in corresponding PCT application PCT/US2009/035875 filed on Mar. 3, 2009. 7 pages.
International Preliminary Report on Patentability for International PCT Application No. PCT/US2011/053711, filed on Sep. 28, 2011, on behalf of Kansas State University Research Foundation, Mailed on Apr. 2, 2013, 7 pages.
International Preliminary Report on Patentability for International PCT Application No. PCT/US2016/023188, filed on Mar. 18, 2016, on behalf of Kansas State University Research Foundation, Mailed on Sep. 19, 2017, 13 pages.
International Preliminary Report on Patentability for International PCT Application No. PCT/US2017/024070 filed on Mar. 24, 2017, on behalf of The Board of Regents of the University of Texas System et al., Mailed on Sep. 25, 2018, 11 Pages.
International Search Report and Written Opinion dated Oct. 21, 2009, in corresponding PCT application PCT/US2009/035875 filed on Mar. 3, 2009/ 11 pages.
International Search Report and Written Opinion for International PCT Application No. PCT/US2011/053711, filed on Sep. 28, 2011, on behalf of Kansas State University Research Foundation, Mailed on Apr. 24, 2012, 11 pages.
International Search Report and Written Opinion for International PCT Application No. PCT/US2016/023188, filed on Mar. 18, 2016, on behalf of Kansas State University Research Foundation, Mailed on Jul. 1, 2016, 16 pages.
International Search Report and Written Opinion for International PCT Application No. PCT/US2017/024070 filed on Mar. 24, 2017, on behalf of The Board of Regents of the University of Texas System et al., Mailed on Dec. 15, 2017, 16 Pages.
International Search Report and Written Opinion for International PCT Application No. PCT/US2021/065584 filed on Dec. 29, 2021, on behalf of Kansas State University Research Foundation et al. Mail Date: Apr. 29, 2022. 15 Pages.
International Search Report and Written Opinion for PCT/US2021/065573 filed on Dec. 29, 2021 on behalf of Hawkeye Bio, Limited Mail Date: Apr. 26, 2022 14 pages.
Amna B. et al., "Click chemistry: a fascinating method of connecting organic groups" *Organic Communications*, vol. 14:2, Apr. 2021, pp. 97-120.
Bian, T., R. Chang, and P.T. Leung, "Forster resonance energy transfer between molecules in the vicinity of graphene-coated nanoparticles". *Plasmonics*, 2016. 11(5): p. 1239-1246.
Blume, J.E., et al., "Rapid, deep and precise profiling of the plasma proteome with multi-nanoparticle protein corona". *Nature communications*, 2020. 11(1): p. 3662; including Supplementary Reporting Summary. 17 pages.
Boens et al.. "Fluorescence Lifetime Standards for Time and Frequency Domain Fluorescence Spectroscopy," *Anal. Chem.*, vol. 79, No. 5, 2007, 2137-2149.
Cernat A. et al., "Click chemistry on azide-functionalized graphene oxide" *Electrochemistry Communications*, vol. 98, (2019), pp. 23-27.

(56) References Cited

OTHER PUBLICATIONS

Communication pursuant to Article 94(3) EPC dated Dec. 9, 2013, for EP Application No. 09718303.2 filed Mar. 3, 2009 on behalf of Kansas State University Research Foundation. 4 pages.
Communication pursuant to Article 94(3) EPC dated Oct. 23, 2012, for EP Application No. 09718303.2 filed Mar. 3, 2009 on behalf of Kansas State University Research Foundation. 6 pages.
The European Search Report dated Apr. 24, 2013 from the corresponding EP 10814356 application, filed from PCT/US2010047301 on Mar. 28, 2012 claiming priority date of Sep. 2, 2009. 12 pages.
The International Search Report and Written Opinion dated May 25, 2011 in the corresponding PCT/US2010/047301 filed on Aug. 31, 2010. 12 pages.
The Patent Examination Report No. 1, dated Sep. 20, 2013 in the corresponding Australian Patent Application No. 2009221976 filed on Mar. 3, 2009. 4 pages.
Dahl et al., "Toward Greener Nanosynthesis: Chem. Rev", vol. 107, No. 6, 2007, 2228-2269.
Daina A, et al. , "SwissADME: a free web tool to evaluate pharmacokinetics, drug-likeness and medicinal chemistry friendliness of small molecules". *Sci Rep*. 2017; 7:42717. 13 pages.
Dani et al., "MspA Porin-Gold Nanoparticle Assemblies: Enhanced Binding through a Controlled Cysteine Mutation," *Nano Lett*, 2007. 9 pages.
Declaration Under 37 C.F.R 1.132 by Dr. Stefan Bossmann filed on Dec. 27, 2012. 4 pages.
Denis P. A. "Organic Chemistry of Graphene: The Diels-Alder Reaction" *Chemistry, A European Journal*, vol. 19, 2013, pp. 15719-15725.
Eastoe et al, "Recent advances in nanoparticle synthesis with reversed micelles," *Advances in Colloid and Interface Science*, 128-130, 2006, 5-15.
*EBI*. MEROPS—the Peptidase Database, Release 12.4. 2021; 1 page. The MEROPS website and database are run by Neil D. Rawlings. Available from: website: www.ebi.ac.uk/merops/.
Fang M. "Covalent polymer functionalization of graphene nanosheets and mechanical properties of composites" Journal of Materials Chemistry, vol. 19, 2009, pp. 7098-7105.
Farivar, F., et al., "Highly Water Dispersible Functionalized Graphene by Thermal Thiol-Ene Click Chemistry". *Materials*, 2021. 14(11): 2830. 11 pages.
Final Office Action dated May 30, 2013, in U.S. Appl. No. 12/920,771, filed Sep. 2, 2010. 14 pages.
Gendron, R., et al., "Inhibition of the activities of matrix metalloproteinases 2, 8, and 9 by chlorhexidine". *Clinical Diagnostic Laboratory Immunology*, May 1999. 6(3): p. 437-439.
Gregoriadis, G., & Allison, A. C. (Sep. 1974). Entrapment of proteins in liposomes prevents allergic reactions in pre-immunised mice. FEBS letters, 45(1-2), 71-74.
Gregoriadis, G., & Ryman, B. E. (1972). Fate of protein-containing liposomes injected into rats: An approach to the treatment of storage diseases. European journal of biochemistry, 24(3), 485-491.
Gregoriadis, G., & Ryman, B. E. (1972). Lysosomal localization of β-fructofuranosidase-containing liposomes injected into rats. Some implications in the treatment of genetic disorders. Biochemical Journal, 129(1), 123-133.
Gregoriadis, G., Putman, D., Louis, L., & Neerunjun, D. (1974). Comparative effect and fate of non-entrapped and liposome-entrapped neuraminidase injected into rats. Biochemical Journal, 140(2), 323-330. 10 pages.
Han et al, "Hyperthermia-Induced Antitumor Activity of Thermosensitive Polymer Modified Temperature-Sensitive Liposomes." *Journal of Pharmaceutical Sciences*, vol. 95, No. 9, Sep. 2006, 1909-1917.
Han W. et al., "Water compatible supramolecular polymers: recent progress" *Chem Soc Rev*, 2021, vol. 50, pp. 10025-10043.
Hossain et al, "Novel Peptides Bearing Pyrene and Coumarin Units with or without B-Cyclodextrin in Their Side Chains Exhibit Intramolecular Fluorescence Resonance Energy Transfer," *J. Am Chem. Soc.*, vol. 125, No. 37, 2003, 11178-11179.
Hunt A. et al., "Modulation of the band gap of graphene oxide: The role of AA-stacking", Carbon, vol. 66, 2014, pp. 539-546.
Invitation pursuant to Rule 63(1) EPC dated Feb. 7, 2011, for EP Application No. 09718303.2 filed Mar. 3, 2009 on behalf of Kansas State University Research Foundation. 2 pages.
Jain et al. "On the Universal Scaling Behavior of the Distance Decay of Plasmon Coupling in Metal Nanoparticle Pairs: A Plasmon Ruler Equation," Nano Lett. vol. 7, No. 7, 2007, 2080-2088.
Juris et al., "Ru(II) Polypyridine Complexes: Photophysics, Photochemistry, Electrochemistry, and Chemiluminescence," *Coordination Chemistry Reviews*. 84, 1988, 85-277.
Kalubowilage M. et al., "Early detection of pancreatic cancers in liquid biopsies by ultrasensitive fluorescence Nanobiosensors", *Nanomedicine*, Accepted date Apr. 24, 2018, 39 pages.
Kasi A. et al., "Early detection of pancreatic cancers by novel nanobiosensor-based protease biomarkers using hierarchical decision structure." *Journal of Clinical Oncology*, vol. 39 No. 15, May 28, 2021, pp. 1-3. (Abstract Only).
Kontos, C. K. et al, Kallikrein-related peptidases (KLKs): a gene family of novel cancer biomarkers', *Clinical Chemistry and Laboratory Medicine* (*CCLM*), vol. 50, No. 11, 2012, pp. 1877-1891. 15 Pages. Website: doi.org/10.1515/cclm-2012-0247.
Krieg E. "Supramolecular Polymers in Aqueous Media" *Chemical Reviews*, vol. 116, Jan. 4, 2016, pp. 2414-2477.
Li, J., et al., "Click and patterned functionalization of graphene by Diels-Alder reaction". *Journal of the American Chemical Society*, 2016. 138(24): p. 7448-7451.
Lohse et al., "Monitoring receptor signaling by intramolecular FRET," *Current Opinion in Pharmacology*, 7, 2007, 547-553.
Macdiarmid, "Synthetic Metals": A Novel Role For Organic Polymers (Nobel Lecture), Chemistry in New Zealand, Sep. 2001, 8-17, Copyright The Nobel Foundation, 2001 (originally published in Angew. Chem. Int Ed., 2001. 40, 2581).
Malalasekera, et al., A nanobiosensor for detection of arginase activity, Nanomedicine: Nanotechnology, Biology, and Medicine, (2016). 30 pages. DOI: 10.1016/j.nano.2016.08.014.
Maye et al., "Synthesis, Processing, Assembly and Activation of Core-Shell Structured Gold Nanoparticle Catalysts," Gold Bulletin, 36/3, 2003, 75-82.
McDougall, I. R., Dunnick, J. K., Goris, M. L., & Kriss, J. P. (1975). In vivo distribution of vesicles loaded with radiopharmaceuticals: a study of different routes of administration. Journal of Nuclear Medicine: Official Publication, Society of Nuclear Medicine, 16(6), 488-491.
Meraz-Cruz, N., et al., "Thermal stability of human matrix metalloproteinases". *Heliyon*, 2020. 6(5): p. e03865. 7 pages.
Mitschke J. et al., "The role of proteases in epithelial-to-mesenchymal cell transitions in cancer" *Cancer and Metastasis Reviews*, Sep. 3, 2019, pp. 1-14.
Moghimi, "2: Passive Targeting of Solid Tumors: Pathophysiological Principles and Physicochemical Aspects of Delivery Systems," Nanotechnology for Cancer Therapy, 11-18, Pub CRC Press, Ed. Amiji M., (2006).
Mulks, M. H. et al, 'IgA proteases of two distinct specificities are released by Neisseria meningitidis', *J. Exp. Med.*, vol. 152, Nov. 1980. pp. 1442-1447. 6 Pages.
Nad et al, "Photophysical Properties of Coumarin-152 and Coumarin-481 Dyes: Unusual Behavior in Nonpolar and in Higher Polarity Solvents," *J Phys Chem A*, vol. 107, No. 24, 2003, 4808-4816.
Namvari M. et al., "Sweet graphene I: Toward hydrophilic graphene nanosheets via click grafting alkyne-saccharides onto azide-functionalized graphene oxide" *Carbohydrate Research*, Jun. 11, 2014, pp. 1-20.
National Cancer Institute: What is Cancer, Cancer Statistics. http://www.cancer.gov/cancertopics/what-is-cancer, Updated: Oct. 11, 2021, Retrieved Feb. 26, 2023, 10 pages.
Nepal, A., et al., "One-step synthesis of graphene via catalyst-free gas-phase hydrocarbon detonation". *Nanotechnology*, 2013. 24(24): p. 245602.; including Supplementary Information. 36 pages.
Non-Final Office Action dated Jul. 15, 2014, in U.S. Appl. No. 12/920,771, filed Sep. 2, 2010. 21 pages.
Non-Final Office Action dated Sep. 27, 2012, in U.S. Appl. No. 12/920,771, filed Sep. 2, 2010. 48 pages.

(56) References Cited

OTHER PUBLICATIONS

Non-Final Office Action filed Jan. 26, 2015 for U.S. Appl. No. 14/605,039 on behalf of Kansas State University Research Foundation. Mail date: Oct. 12, 2016. 40 pages.
Non-Final Office Action filed Jan. 26, 2015 for U.S. Appl. No. 14/605,083 on behalf of Kansas State University Research Foundation. Mail date: Oct. 27, 2016. 41 pages.
Non-Final Office Action filed Mar. 13, 2013 for U.S. Appl. No. 13/800,456 on behalf of Kansas State University Research Foundation. Mail date: Aug. 21, 2014. 16 pages.
Non-Final Office Action filed Mar. 13, 2013 for U.S. Appl. No. 13/800,456 on behalf of Kansas State University Research Foundation. Mail date: Mar. 10, 2015. 10 pages.
Non-Final Office Action for U.S. Appl. No. 15/559,543, filed Sep. 19, 2017 on behalf of Kansas State University Research Foundation. Mail date: Sep. 20, 2018. 7 pages.
Non-Final Office Action for U.S. Appl. No. 16/088,407, filed Sep. 25, 2018, on behalf of The Board of Regents of the University of Texas System et al., Mail Date: May 11, 2022, 26 pages.
Non-Final Office Action for U.S. Appl. No. 16/088,407, filed Sep. 25, 2018, on behalf of The Board of Regents of the University of Texas System et al., Mail Date: Nov. 25, 2022, 16 pages.
Notice of Acceptance, dated Feb. 18, 2014, for Australian Patent Application No. AU20090221976, filed on Mar. 3, 2009. 2 pages.
Notice of Allowance for U.S. Appl. No. 12/920,771, filed Sep. 2, 2010 on behalf of Kansas State University Research Foundation Mail Date: Oct. 24, 2014 13 pages.
Notice of Allowance for U.S. Appl. No. 13/800,456, filed Mar. 13, 2013 on behalf of Kansas State University Research Foundation. Mail date: Sep. 9, 2015. 7 pages.
Notice of Allowance for U.S. Appl. No. 14/605,039, filed Jan. 26, 2015 on behalf of Kansas State University Research Foundation. Mail date: Feb. 22, 2017. 5 pages.
Notice of Allowance for U.S. Appl. No. 14/605,083, filed Jan. 26, 2015 on behalf of Kansas State University Research Foundation. Mail date: Apr. 17, 2017. 11 pages.
Notice of Allowance for U.S. Appl. No. 15/559,543, filed Sep. 19, 2017 on behalf of Kansas State University Research Foundation. Mail date: Apr. 1, 2019. 7 pages.
Notice of Reasons for Refusal for Japanese Application JP 2010-549817 filed Mar. 3, 2009, issued Jan. 14, 2014. 7 pages.
P05109-S10A8_Human. UniProt. (n.d.). Retrieved Feb. 25, 2023, from https://www.uniprot.org/uniprotkb/P05109/entry, 1 page.
P05231-IL6_Human, UniProt. (n.d.). Retrieved Feb. 25, 2023, from http://www.uniprot.org/uniprot/P05231, 1 page.
P78556-CCL20_Human. UniProt. (n.d.). Retrieved Feb. 25, 2023, from http://www.uniprot.org/uniprot/P78556, 1 page.
Pasinszki T. et al., "Synthesis and Application of Zero-Valent Iron Nanoparticles in Water Treatment, Environmental Remediation, Catalysis, and Their Biological Effects" *Nanomaterials*, May 9, 2020, 10, 917. pp. 1-37.
Patel S. "A critical review on serine protease: Key immune manipulator and pathology mediator" *Allergol Immunopathol*, Feb. 2017, vol. 45(6), pp. 579-591.
Q01638-ILRL1_Human, (n.d.). Retrieved Feb. 25, 2023, from http://www.uniprot.org/uniprot/Q01638, 1 page.
Restriction Requirement filed Mar. 13, 2013 for U.S. Appl. No. 13/800,456 on behalf of Kansas State University Research Foundation. Mail date: Jun. 25, 2014. 11 pages.
Restriction Requirement for U.S. Appl. No. 12/920,771, filed Sep. 2, 2010 on behalf of Kansas State University Research Foundation. Mail Date: Mar. 19, 2012. 9 pages.
Restriction Requirement for U.S. Appl. No. 13/393,472, filed Feb. 29, 2012 on behalf of Kansas State University Research Foundation Mail Date: Jan. 6, 2015 19 pages.
Restriction Requirement for U.S. Appl. No. 15/559,543, filed Sep. 19, 2017 on behalf of Kansas State University Research Foundation. Mail date: Jul. 12, 2018. 6 pages.
Restriction Requirement for U.S. Appl. No. 16/088,407, filed Sep. 25, 2018, on behalf of The Board of Regents of the University of Texas System et al., Mail Date: Feb. 11, 2022, 5 pages.
Rogach, "Binary Superlattices of Nanoparticles: Self-Assembly Leads to 'Metamaterials.'" *Angew. Chem. Int*, 43, 2004, 148-149.
Sandhya, M., et al., "Ultrasonication an intensifying tool for preparation of stable nanofluids and study the time influence on distinct properties of graphene nanofluids—A systematic overview". *Ultrasonics Sonochemistry*, 2021. 73: p. 105479. 16 pages.
Sarmanova Olga E. et al: "A method for optical imaging and monitoring of the excretion of fluorescent nanocomposites from the body using artificial neural networks", *Nanomedicine: Nanotechnology, Biology, and Medicine, Elsevier*, Amsterdam, NL, vol. 14, No. 4, Apr. 12, 2018 (Apr. 12, 2018) , pp. 1371-1380.
Segal, A. W., Wills, E. J., Richmond, J. E., Slavin, G., Black, C. D. V., & Gregoriadis, G. (1974). Morphological observations on the cellular and subcellular destination of intravenously administered liposomes. British Journal of Experimental Pathology, 55(4), 320-327. 14 pages.
Sen et al., "Surface energy transfer from rhodamine 6G to gold nanoparticles: A spectroscopic ruler," *Appl. Phys. Lett.*, 91, 2007, 043104-1-043104-3. 3 pages.
Stoeva et al., Gram-Scale Synthesis of Monodisperse Gold Colloids by the Solvated Metal Atom Dispersion Method and Digestive Ripening and Their Organization into Two-and Three-Dimensional Structures, *J. Am. Chem. Soc.*, vol. 124, No. 10, 2002, 2305-2311.
Strom, T.A., et al., "Nitrene addition to exfoliated graphene: a one-step route to highly functionalized graphene. Chemical communications", 2010. 46(23): p. 4097-4099.; including Supplementary Information. 13 pages.
Tian J. et al., "Pegylated folate an peptide-decorated graphene oxide nanovehicle for in vivo targeted delivery of anticancer drugs and therapeutic self-monitoring", *Biosensors and Bioelectronics*, vol. 80, 2016, pp. 519-524
Turk et al., "Cysteine cathepsins (proteases)—On the main stage of cancer?" Cancer Cell. vol. 5, Issue 5, May 2004, pp. 409-410.
Tyson et al., "Long-Range Resonance Energy Transfer to [Ru(bpy)3]2+ ," *J. Phys. Chem.*, vol. 104, No. 13, 2000, 2919-2924.
Udukala D. N. et al., "Early breast cancer screening using iron/iron oxide-based nanoplatforms with sub-femtomolar limits of detection" *Beilstein Journal of Nanotechnology*, Mar. 2016, vol. 7, pp. 364-373.
Udukala D. N. et al., "Early detection of non-small cell lung cancer in liquid biopsies by ultrasensitive protease activity analysis" *Journal of Cancer Metastasis Treatment*, Jul. 2020, vol. 6, pp. 1-13.
Wang, et al., Magnetic-fe/fe3O4-nanoparticle-bound SN38 as carboxylesterase-clevable prodrug for the delivery to tumors within moncytes/macrophages, Beilstein Journal of Nanotechnology, Jun. 13, 2012, 3, 444-455. Doi: 10.3762/bjnano3.51.
Wang H. et al., "Nanoplatforms for highly sensitive fluorescence detection of cancer-related proteases" *Photochemical & Photobiological Sciences*, Sep. 2013, pp. 1-10; including Supplementary Information. 23 pages.
Weili W. et al., "Chiral detection using reusable fluorescent amylose-functionalized graphene", *Chemical Science*, vol. 2, No. 10, 2011, pp. 2050-2056.
Wright J. P. et al., "Synthesis of turbostratic nanoscale graphene via chamber detonation of oxygen/acetylene mixtures" *Nano Select*, 2021, pp. 1-15.
Yang X. et al., "Organic/inorganic supramolecular nano-systems based on host/guest interactions" *Coordination Chemistry Reviews*, vol. 428, 2021, 213609. 15 pages.
Zhang Y. et al., "Joint Entropy-Assisted Graphene Oxide-Based Multiplexing Biosensing Platform for Simultaneous Detection of Multiple Proteases" *Analytical Chemistry*, Oct. 2020, 8 pages.
Zhao X. "Molecular defect-containing bilayer graphene exhibiting brightened luminescence" *Science Advances*, vol. 6, Feb. 28, 2020, pp. 1-6.
Zhou, J., et al., "Two-dimensional nanomaterials for Förster resonance energy transfer-based sensing applications". *Nanophotonics*, 2020. 9(7): p. 1855-1875.

(56) References Cited

OTHER PUBLICATIONS

Abbas, G. et al. Electrostatic Gating of Monolayer Graphene by Concentrated Aqueous Electrolytes. The Journal of Physical Chemistry Letters, (2023), 14, 4281-4288.
Covarrubias-Zambrano, O. et al. Few-Layer Graphene-Based Optical Nanobiosensors for the Early-Stage Detection of Ovarian Cancer Using Liquid Biopsy and an Active Learning Strategy., Cells, 14, 375. (Mar. 4, 2025). 17 pages. Special Issue of Nanofluidics, Nanopores, and Nanomaterials for Understanding Biology.
Gao Y. et al. Interplay of graphene-DNA interactions: Unveiling sensing potential of graphene materials. Appl Phys Rev. (Mar. 2024), 11(1). 63 pages. DOI: 10.1063/5.0171364.
Georgakilas, V. et al. Functionalization of Graphene: Covalent and Non-Covalent. Approaches, Derivatives and Application. Chem. Rev., Sep. 25, 2012, 112, 6156-6214.
International Preliminary Report on Patentability for International Application No. PCT/US2022/073477 filed on Jul. 6, 2022 on behalf of Hawkeye Bio, Limited. Mailed on Sep. 9, 2024. 8 pages.
Koh, B. et al. Multi-omics profiling with untargeted proteomics for blood-bases early detections of lung cancer. medRxiv. 27 pages. Posted Jan. 4, 2024. Doi.org/10/1101/2024.01.03.24300798.
Kumar, Y. B. et al. Chapter 7: Reversible and irreversible functionalization of graphene, Theoretical and Computational Chemistry, vol. 21, (2022), 33 pages.
Montoya Mira, J.L., et al. Early detection of pancreatic cancer by a high-throughput protease-activated nanosensor assay. Sci. Transl. Med., Feb. 12, 2025. 17, eadq3110. 15 pages.
Montoya Mira, J.L., et al. Supplementary Materials for: Early detection of pancreatic cancer by a high-throughput protease-activated nanosensor assay. Sci. Transl. Med., Feb. 12, 2025. 17, eadq3110. 28 pages.
Padavic-Callaghan, K. The superconductivity of layered graphene is surprisingly strange. NewScientist, Feb. 5, 2025. www.newscientist.com/article/2466930-the-superconductivity-of-layered-graphene-is-surprisingly-strange/.
Shahriari, S. et al. Graphene and Graphene Oxide as a Support for Biolmolecules in the Development of Biosensors. Nanotechnology, Science and Applications, Nov. 16, 2021. 14. 197-220.
Wittmann, S. et al. Dielectric Surface Charge Engineering for Electrostatic Doping of Graphene, Applied Electronic Materials, (Apr. 21, 2020), 2, 1235-1242.

* cited by examiner

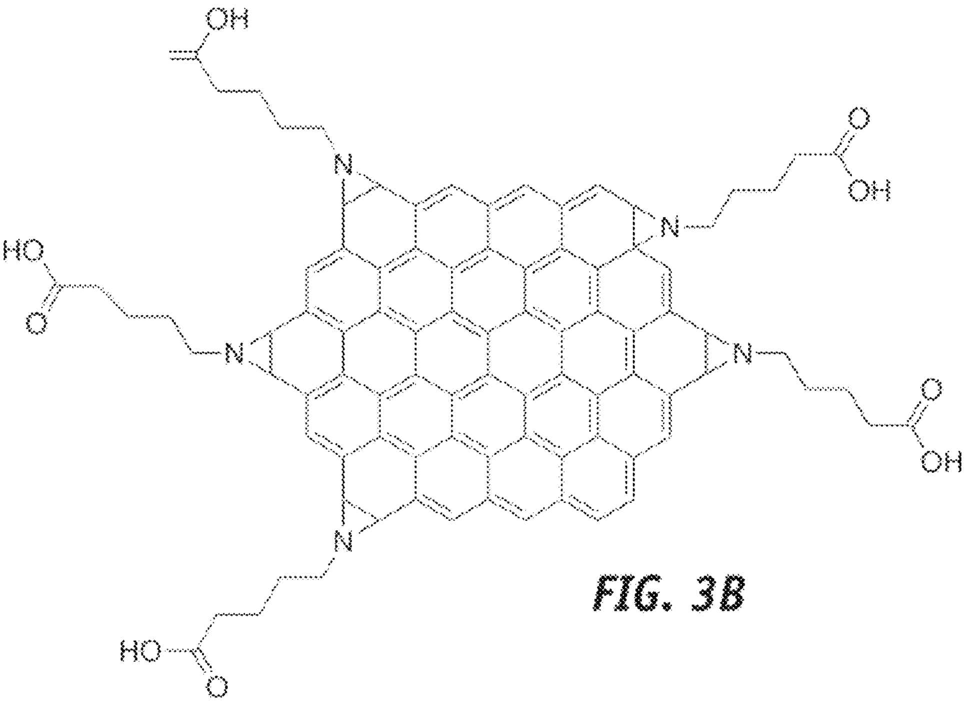
FIG. 3B
FIG. 3C
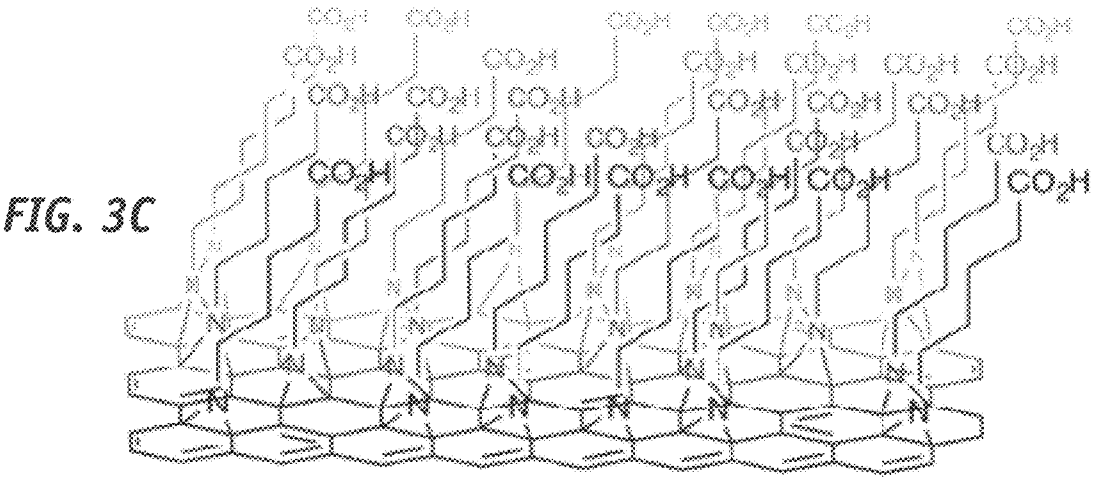
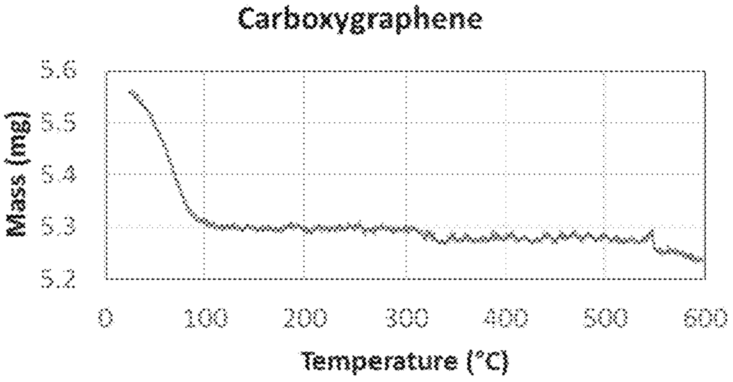
FIG. 3D

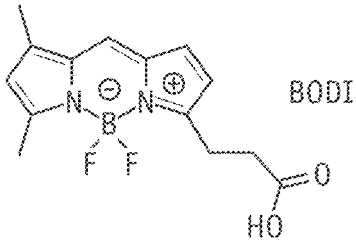
BODIPY FL
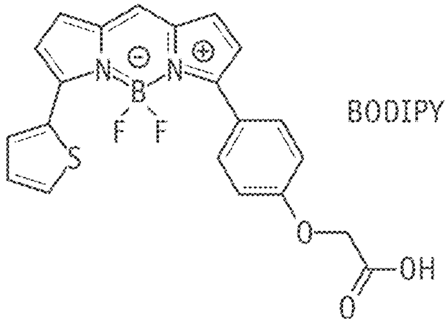
BODIPY TR
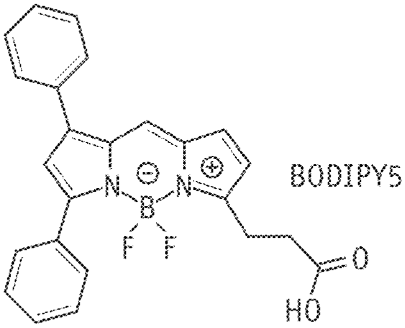
BODIPY530/550
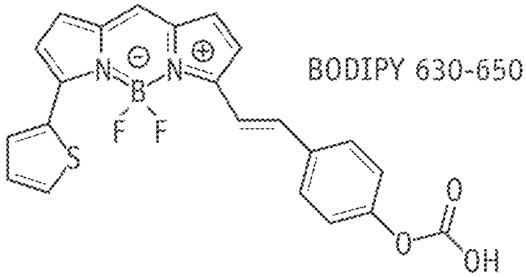
BODIPY 630-650
FIG. 6C
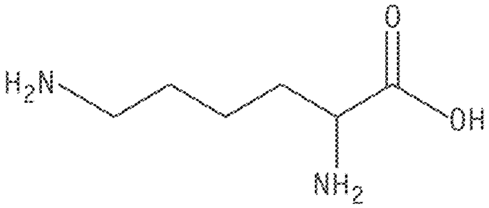
lysine
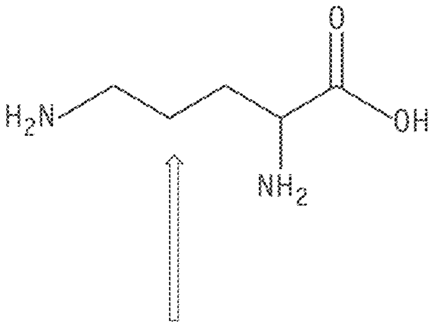
ornithine
Spacer
FIG. 7

| Before incubation (425 nm) | | | | | | | |
|---|---|---|---|---|---|---|---|
| | 1.00E-11 | 5.00E-12 | 1.00E-12 | 1.00E-13 | 1.00E-14 | 1.00E-15 | M |
| Serum A | 257.5 | 90 | 71 | 96 | 17 | 10.5 | |
| AC | 13 | | | | | | |
| Blank | 3 | | | | | | |

| After 60 min incubation (425 nm) | | | | | | | |
|---|---|---|---|---|---|---|---|
| | 1.00E-11 | 5.00E-12 | 1.00E-12 | 1.00E-13 | 1.00E-14 | 1.00E-15 | M |
| Serum A | 1697.500 | 988.000 | 907 | 420.000 | 35.500 | 17 | |
| AC | 16.2 | | | | | | |
| Blank | 0 | | | | | | |

| Buffer | Buffer | pH | MgCl2 | CaCl2 | ZnCl2 | NaCl | Other |
|---|---|---|---|---|---|---|---|
| 1 | 25μM Hepes | 7.2 | 10μM | 10μM | 10μM | | |
| 2 | 1 x PBS | 7.33 | 10μM | 10μM | 10μM | 155mM | |
| 3 | 0.1 x PBS | 7.39 | 10μM | 10μM | 10μM | 15.5mM | |
| 4 | 2.5mM Tris | 7.18 | 10μM | 10μM | 10μM | | |
| 5 | 250μM Tris | 7.25 | 10μM | 10μM | 10μM | | |
| 6 | 250μM Tris | 7.19 | 10μM | 10μM | 10μM | 50mM | |
| 7 | 5mM MES | 7.23 | 10μM | 10μM | 10μM | | |
| 8 | 5mM MES | 7.2 | 10μM | 10μM | 10μM | 30mM | |
| 9 | 5mM MES | 7.22 | 10μM | 10μM | 10μM | 154mM | |
| 10 | 5mM MES | 7.2 | 10μM | 10μM | 10μM | | 5% DMSO |
| 11 | 5mM MES | 7.2 | 10μM | 10μM | 10μM | | 10% DMSO |

| Sample | Drying protocol | Total Weight Loss (wt%) |
|---|---|---|
| **Lot120120** | 24 hr ambient | 28.8 |
| **CG1.0** | 24 hr ambient | 7.97 |
| **CG1.2** | 24 hr 50°C + desiccant | 5.63 |
| **CG1.3** | 10min 50°C, 48 hr + desiccant | 2.47 |
| **CG1.4** | 50°C oven 24 hr | 1.4 |

| Step | Dispersion | Graphene | Bromovaleric Acid | Sodium Azide | EDC | DMAP | PEI | Peptide |
|---|---|---|---|---|---|---|---|---|
| **KSU protocol** | | | | | | | | |
| **CG1.0** | Stir bar | 2.0g Graphene | 0.5g/g Graphene | 0.18g/g Graphene | | | | |
| **CGP-102** | Stir bar | 0.5g CG1.0 | | | 264 mg/g CG | 261 mg/g CG | 540 mg/g CG | |
| **NE-100** | 1 min water bath | 103mg CGP102 | | | 101.9mg/g CGP | 107mg/g GCP | | 67.9mg/g CGP |
| **HEB Protocol** | | | | | | | | |
| **CG1.2** | 10min Probe pulse | 0.85g Graphene | 1.0g/g Graphene | 0.36g/g Graphene | | | | |
| **CGP-103** | 15 min water bath | 0.25g CG1.2 | | | 252 mg/g CG | 252 mg/g CG | 500 mg/g CG | |
| **NE-101** | 10 min water bath | 50.7 mg CGP-103 | | | 108mg/g CGP | 114mg/g CGP | | 69mg/g CGP |
| **HEB Protocol** | | | | | | | | |
| **CG1.3** | 20min Probe pulse | 0.5g Graphene | 2.0g/g Graphene | 0.72g/g Graphene | | | | |
| **CGP104** | 15 min water bath | 0.26g CG1.3 | | | 243 mg/g | 247 mg/g | 500 mg/g | |
| **NE 102** | 10 min water bath | 54.2mg CGP-104 | | | 105mg/g CGP | 111mg/g CGP | | 65mg/g CGP |

*FIG. 28*

| | C | H | O | N |
|---|---|---|---|---|
| Graphene -Lot 1 | 98.82% | <0.5% | <0.5% | <0.5% |
| **Graphene -Lot 2** | 98.78% | <0.5% | <0.5% | <0.5% |
| **CG KSU*** | 94.22% | 1.79% | 2.82% | 1.17% |
| **CG1.0** | 92.30% | 1.36% | 3.50% | — |
| **CGP102** | 76.00% | 3.55% | 7.33% | 10.03% |
| **CG1.0** | 97.7% | 0.93% | <0.5% | — |
| **CG1.2** | 86.55% | 0.88% | 1.62% | — |
| **CG1.3** | 97.53% | 0.7% | 0.68% | — |
| **CG1.4** | 98.49% | 0.57% | <0.5% | — |

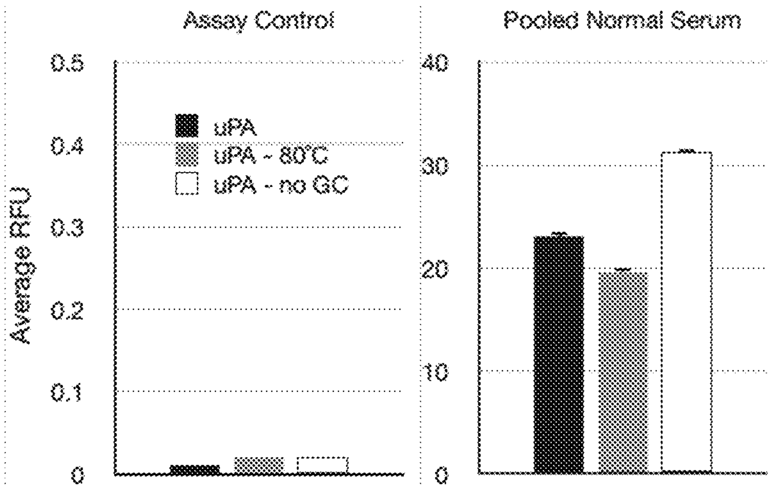
Figure 32
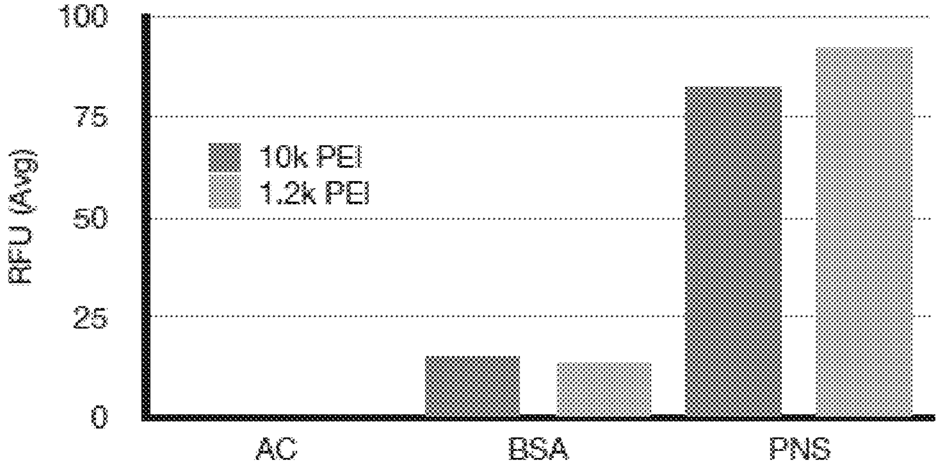
Figure 33
| 0.03 mg/mL MMP1 solution in water | |
|---|---|
| DLS | 713.30 nm |
| PDI | 0.147 |
| Zeta potential | +4.36 mV |
Figure 34

B

| B. | MMP1-G-PEI | MMP1-G-TEG3amine |
|---|---|---|
| Time (min) | Assay Control | Assay Control |
| 0 | 7 | 5 |
| 15 | 22 | 6 |
| 30 | 29 | 9 |
| 45 | 29 | 6 |
| 60 | 19 | 12 |

| | | MMP1 | MMP2 | MMP3 | MMP7 | MMP9 | MMP10 | MMP11 | MMP12 | MMP13 |
|---|---|---|---|---|---|---|---|---|---|---|
| EU 351 | LC | 1.1 | 0.7 | 0.4 | 0.6 | 0.4 | 2.4 | 1.4 | 1.4 | 1.0 |
| n=256 | non-LC | 1.5 | 1.1 | 0.6 | 1.0 | 0.6 | 4.1 | 2.2 | 1.9 | 1.4 |
| US SST-18 | LC | 1.1 | 0.6 | 0.5 | 0.7 | 0.4 | 2.1 | 1.2 | 0.9 | 1.0 |
| n=175 | non-LC | 1.7 | 0.7 | 0.6 | 1.1 | 0.5 | 3.9 | 2.1 | 2.0 | 1.7 |

| | | MMP13 | MMP15 | CTSB | CTSD | CTSE | CTSH | CTSK | NE | uPA | ARG |
|---|---|---|---|---|---|---|---|---|---|---|---|
| EU 351 | LC | 1.0 | 1.1 | 0.3 | 1.4 | 1.1 | 0.6 | 1.8 | 1.5 | 3.1 | 0.6 |
| n=256 | non-LC | 1.4 | 1.8 | 0.5 | 2.3 | 1.2 | 1.0 | 2.9 | 2.4 | 4.8 | 0.9 |
| US SST-18 | LC | 1.0 | 0.7 | 0.3 | 2.5 | 1.4 | 0.7 | 2.5 | 3.5 | 2.2 | 0.4 |
| n=175 | non-LC | 1.7 | 1.1 | 0.5 | 3.9 | 1.5 | 1.0 | 4.3 | 5.7 | 3.7 | 0.5 |

| EU n=256 | MMP1 | MMP2 | MMP3 | MMP7 | MMP9 | MMP10 | MMP11 | MMP12 | MMP13 |
|---|---|---|---|---|---|---|---|---|---|
| t-test p-value | 5.4E-11 | 2.8E-24 | 2.6E-13 | 4.0E-17 | 5.0E-21 | 2.6E-26 | 9.8E-21 | 3.9E-11 | 2.2E-14 |

| EU n=256 | MMP15 | CTSB | CTSD | CTSE | CTSH | CTSK | NE | uPA | ARG |
|---|---|---|---|---|---|---|---|---|---|
| t-test p-value | 1.4E-22 | 3.1E-14 | 4.3E-22 | 1.0E-03 | 5.6E-21 | 2.9E-20 | 1.5E-20 | 5.9E-21 | 2.4E-24 |

| US n=175 | MMP1 | MMP2 | MMP3 | MMP7 | MMP9 | MMP10 | MMP11 | MMP12 | MMP13 |
|---|---|---|---|---|---|---|---|---|---|
| t-test p-value | 1.1E-17 | 4.2E-15 | 6.3E-10 | 1.6E-14 | 1.4E-05 | 9.4E-26 | 4.9E-25 | 8.2E-23 | 6.8E-21 |

| US n=175 | MMP15 | CTSB | CTSD | CTSE | CTSH | CTSK | NE | uPA | ARG |
|---|---|---|---|---|---|---|---|---|---|
| t-test p-value | 2.0E-20 | 4.1E-13 | 1.3E-20 | 2.9E-07 | 3.0E-16 | 1.6E-34 | 2.6E-27 | 3.7E-29 | 2.6E-06 |

a)

A. NE
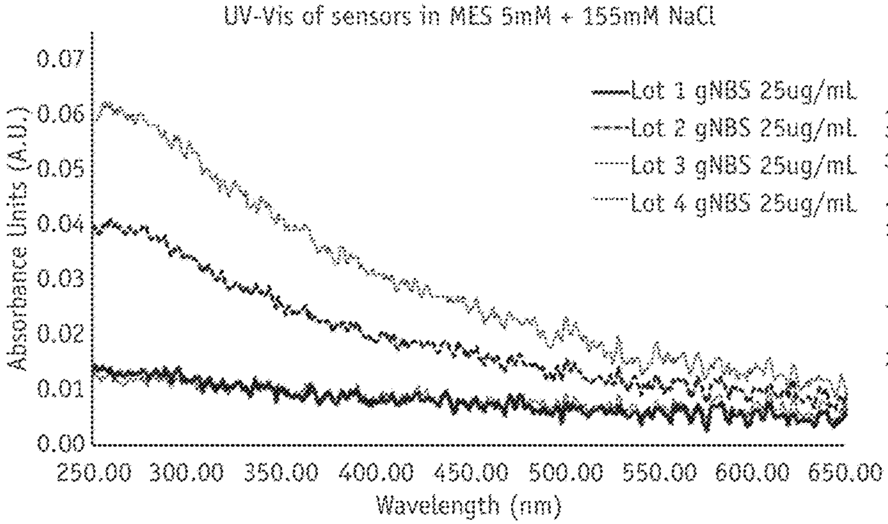
B. MMP15
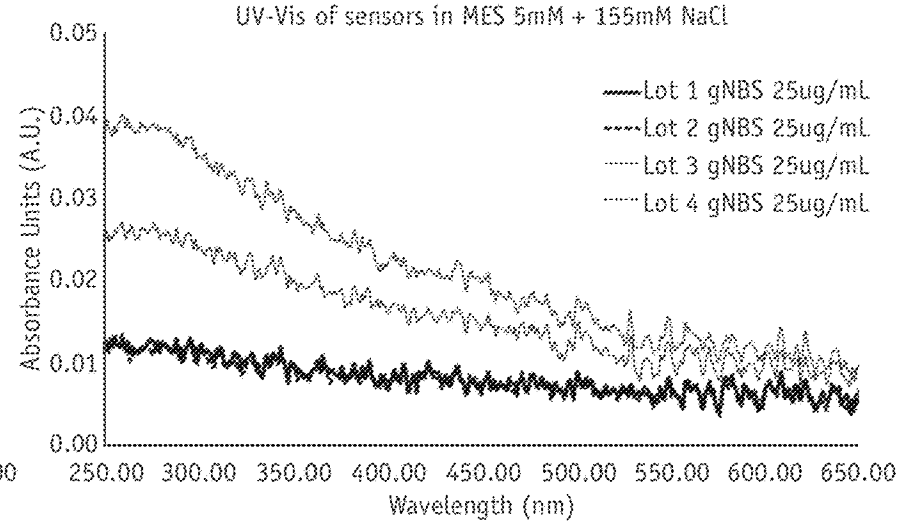
Table of Absorbance efficiency at 270nm per mg/mL
| Units: $OD_{270}$/mg/mL | Lot 1 | Lot 2 | Lot 3 | Lot 4 |
|---|---|---|---|---|
| **NE gNBS** | 0.93 | 2.63 | 1.23 | 4.84 |
| **MMP15 gNBS** | 0.94 | 0.82 | 3.03 | 3.16 |
*FIG. 55*

| MMP15 | Wavelength | Parameter | FeNBS 300ug/mL | Lot 1 25ug/mL | Lot 2 25ug/mL | Lot 3 25ug/mL | Lot 4 25ug/mL |
|---|---|---|---|---|---|---|---|
| MMP15 | 270nm | OD at 270nm | -66% | -19% | -2% | -48% | -13% |
| MMP15 | 650nm | OD at 650nm | -84% | -43% | 2% | -49% | -9% |
| NE | 270nm | OD at 270nm | -66% | -9% | -7% | -35% | -13% |
| NE | 650nm | OD at 650nm | -79% | -27% | -6% | -44% | -10% |

Figure 58

SEQUENCE LISTING

```
Sequence total quantity: 133
SEQ ID NO: 1            moltype = AA  length = 7
FEATURE                 Location/Qualifiers
REGION                  1..7
                        note = Synthetic supramolecular recognition sequence
source                  1..7
                        mol_type = protein
                        organism = synthetic construct
SEQUENCE: 1
CQEQFWW                                                                  7

SEQ ID NO: 2            moltype = AA  length = 13
FEATURE                 Location/Qualifiers
REGION                  1..13
                        note = Synthetic supramolecular recognition sequence
source                  1..13
                        mol_type = protein
                        organism = synthetic construct
SEQUENCE: 2
PYFPRGSSYQ GWN                                                           13

SEQ ID NO: 3            moltype = AA  length = 6
FEATURE                 Location/Qualifiers
REGION                  1..6
                        note = Synthetic supramolecular recognition sequence
source                  1..6
                        mol_type = protein
                        organism = synthetic construct
SEQUENCE: 3
CCIQNQ                                                                   6

SEQ ID NO: 4            moltype = AA  length = 8
FEATURE                 Location/Qualifiers
REGION                  1..8
                        note = Synthetic supramolecular recognition sequence
source                  1..8
                        mol_type = protein
                        organism = synthetic construct
SEQUENCE: 4
AWYQPQFE                                                                 8

SEQ ID NO: 5            moltype = AA  length = 6
FEATURE                 Location/Qualifiers
REGION                  1..6
                        note = Synthetic supramolecular recognition sequence
source                  1..6
                        mol_type = protein
                        organism = synthetic construct
SEQUENCE: 5
EQQKRN                                                                   6

SEQ ID NO: 6            moltype = AA  length = 8
FEATURE                 Location/Qualifiers
REGION                  1..8
                        note = Synthetic supramolecular recognition sequence
source                  1..8
                        mol_type = protein
                        organism = synthetic construct
SEQUENCE: 6
CNHGKFYC                                                                 8

SEQ ID NO: 7            moltype = AA  length = 8
FEATURE                 Location/Qualifiers
REGION                  1..8
                        note = Synthetic supramolecular recognition sequence
```

-continued

```
source                1..8
                      mol_type = protein
                      organism = synthetic construct
SEQUENCE: 7
NIYCNIAY                                                           8

SEQ ID NO: 8          moltype = AA  length = 8
FEATURE               Location/Qualifiers
REGION                1..8
                      note = Synthetic supramolecular recognition sequence
source                1..8
                      mol_type = protein
                      organism = synthetic construct
SEQUENCE: 8
KAYRWEFI                                                           8

SEQ ID NO: 9          moltype = AA  length = 9
FEATURE               Location/Qualifiers
REGION                1..9
                      note = Synthetic supramolecular recognition sequence
source                1..9
                      mol_type = protein
                      organism = synthetic construct
SEQUENCE: 9
IQNSGAPCH                                                          9

SEQ ID NO: 10         moltype = AA  length = 10
FEATURE               Location/Qualifiers
REGION                1..10
                      note = Synthetic supramolecular recognition sequence
source                1..10
                      mol_type = protein
                      organism = synthetic construct
SEQUENCE: 10
WQEAKNANQM                                                         10

SEQ ID NO: 11         moltype = AA  length = 8
FEATURE               Location/Qualifiers
REGION                1..8
                      note = Synthetic supramolecular recognition sequence
source                1..8
                      mol_type = protein
                      organism = synthetic construct
SEQUENCE: 11
RHQKTYSF                                                           8

SEQ ID NO: 12         moltype = AA  length = 10
FEATURE               Location/Qualifiers
REGION                1..10
                      note = Synthetic supramolecular recognition sequence
VARIANT               1
source                1..10
                      mol_type = protein
                      organism = synthetic construct
SEQUENCE: 12
XLPPHWAGAL                                                         10

SEQ ID NO: 13         moltype = AA  length = 10
FEATURE               Location/Qualifiers
REGION                1..10
                      note = Synthetic supramolecular recognition sequence
VARIANT               1
source                1..10
                      mol_type = protein
                      organism = synthetic construct
SEQUENCE: 13
XLPPHWAFAL                                                         10

SEQ ID NO: 14         moltype = AA  length = 28
FEATURE               Location/Qualifiers
REGION                1..28
                      note = Synthetic supramolecular recognition sequence
source                1..28
                      mol_type = protein
                      organism = synthetic construct
SEQUENCE: 14
LTELEKALNS IIDVYHKYSL IKGNFHAV                                     28

SEQ ID NO: 15         moltype = AA  length = 30
```

-continued

```
FEATURE                 Location/Qualifiers
REGION                  1..30
                        note = Synthetic supramolecular recognition sequence
source                  1..30
                        mol_type = protein
                        organism = synthetic construct
SEQUENCE: 15
GESMNFSDVF DSSEDYFVSV NTSYYSVDSE                                   30

SEQ ID NO: 16           moltype = AA  length = 12
FEATURE                 Location/Qualifiers
REGION                  1..12
                        note = Synthetic supramolecular recognition sequence
source                  1..12
                        mol_type = protein
                        organism = synthetic construct
SEQUENCE: 16
GTQWWVVCQQ FG                                                      12

SEQ ID NO: 17           moltype = AA  length = 10
FEATURE                 Location/Qualifiers
REGION                  1..10
                        note = Synthetic supramolecular recognition sequence
source                  1..10
                        mol_type = protein
                        organism = synthetic construct
SEQUENCE: 17
PGHWSDWSPS                                                         10

SEQ ID NO: 18           moltype = AA  length = 28
FEATURE                 Location/Qualifiers
REGION                  1..28
                        note = Synthetic supramolecular recognition sequence
source                  1..28
                        mol_type = protein
                        organism = synthetic construct
SEQUENCE: 18
YFPEPVTVSG AGTFPAVLGS GQPPGKGL                                     28

SEQ ID NO: 19           moltype = AA  length = 25
FEATURE                 Location/Qualifiers
REGION                  1..25
                        note = Synthetic supramolecular recognition sequence
source                  1..25
                        mol_type = protein
                        organism = synthetic construct
SEQUENCE: 19
TAVYYCANRA GWGMGDYWGQ GTQVT                                        25

SEQ ID NO: 20           moltype = AA  length = 16
FEATURE                 Location/Qualifiers
REGION                  1..16
                        note = Synthetic supramolecular recognition sequence
source                  1..16
                        mol_type = protein
                        organism = synthetic construct
SEQUENCE: 20
TASNYGAGYS TNDRHS                                                  16

SEQ ID NO: 21           moltype = AA  length = 10
FEATURE                 Location/Qualifiers
REGION                  1..10
                        note = Synthetic supramolecular recognition sequence
source                  1..10
                        mol_type = protein
                        organism = synthetic construct
SEQUENCE: 21
NRPAQAWMLG                                                         10

SEQ ID NO: 22           moltype = AA  length = 20
FEATURE                 Location/Qualifiers
REGION                  1..20
                        note = Synthetic supramolecular recognition sequence
source                  1..20
                        mol_type = protein
                        organism = synthetic construct
SEQUENCE: 22
AVYYCQQNNE DPRTFGGGTK                                              20
```

-continued

```
SEQ ID NO: 23           moltype = AA  length = 13
FEATURE                 Location/Qualifiers
REGION                  1..13
                        note = Synthetic supramolecular recognition sequence
source                  1..13
                        mol_type = protein
                        organism = synthetic construct
SEQUENCE: 23
AGDGYYPYAM DNW                                                      13

SEQ ID NO: 24           moltype = AA  length = 13
FEATURE                 Location/Qualifiers
REGION                  1..13
                        note = Synthetic supramolecular recognition sequence
source                  1..13
                        mol_type = protein
                        organism = synthetic construct
SEQUENCE: 24
GWLPFGFILI SAG                                                      13

SEQ ID NO: 25           moltype = AA  length = 11
FEATURE                 Location/Qualifiers
REGION                  1..11
                        note = Synthetic supramolecular recognition sequence
source                  1..11
                        mol_type = protein
                        organism = synthetic construct
SEQUENCE: 25
YQQKPGQPPK L                                                        11

SEQ ID NO: 26           moltype = AA  length = 29
FEATURE                 Location/Qualifiers
REGION                  1..29
                        note = Synthetic supramolecular recognition sequence
source                  1..29
                        mol_type = protein
                        organism = synthetic construct
SEQUENCE: 26
SVNWIRQPPG KALEWLAMIW GDGKIVYNS                                     29

SEQ ID NO: 27           moltype = AA  length = 10
FEATURE                 Location/Qualifiers
REGION                  1..10
                        note = Synthetic supramolecular recognition sequence
source                  1..10
                        mol_type = protein
                        organism = synthetic construct
SEQUENCE: 27
WLPFGFILIS                                                          10

SEQ ID NO: 28           moltype = AA  length = 14
FEATURE                 Location/Qualifiers
REGION                  1..14
                        note = Synthetic supramolecular recognition sequence
source                  1..14
                        mol_type = protein
                        organism = synthetic construct
SEQUENCE: 28
TYYCQQWSGY PYTF                                                     14

SEQ ID NO: 29           moltype = AA  length = 13
FEATURE                 Location/Qualifiers
REGION                  1..13
                        note = Synthetic supramolecular recognition sequence
source                  1..13
                        mol_type = protein
                        organism = synthetic construct
SEQUENCE: 29
SHFPYSQYQF WKN                                                      13

SEQ ID NO: 30           moltype = AA  length = 35
FEATURE                 Location/Qualifiers
REGION                  1..35
                        note = Synthetic supramolecular recognition sequence
source                  1..35
                        mol_type = protein
                        organism = synthetic construct
SEQUENCE: 30
DMSDTNWWKG TSKGRTGLIP SNYVAEQAES IDNPL                              35
```

-continued

```
SEQ ID NO: 31           moltype = AA  length = 17
FEATURE                 Location/Qualifiers
REGION                  1..17
                        note = Synthetic supramolecular recognition sequence
source                  1..17
                        mol_type = protein
                        organism = synthetic construct
SEQUENCE: 31
IAGKLQSAGS ALWTDQL                                                  17

SEQ ID NO: 32           moltype = AA  length = 19
FEATURE                 Location/Qualifiers
REGION                  1..19
                        note = Synthetic supramolecular recognition sequence
source                  1..19
                        mol_type = protein
                        organism = synthetic construct
SEQUENCE: 32
SSPKHVRFSW HQDAVTVTC                                                19

SEQ ID NO: 33           moltype = AA  length = 10
FEATURE                 Location/Qualifiers
REGION                  1..10
                        note = Synthetic supramolecular recognition sequence
source                  1..10
                        mol_type = protein
                        organism = synthetic construct
SEQUENCE: 33
AKCCPCQQWW                                                          10

SEQ ID NO: 34           moltype = AA  length = 15
FEATURE                 Location/Qualifiers
REGION                  1..15
                        note = Synthetic supramolecular recognition sequence
source                  1..15
                        mol_type = protein
                        organism = synthetic construct
SEQUENCE: 34
VQEFYKDTYN KLKTK                                                    15

SEQ ID NO: 35           moltype = AA  length = 16
FEATURE                 Location/Qualifiers
REGION                  1..16
                        note = Synthetic supramolecular recognition sequence
source                  1..16
                        mol_type = protein
                        organism = synthetic construct
SEQUENCE: 35
LNNHTASILN RMQANF                                                   16

SEQ ID NO: 36           moltype = AA  length = 19
FEATURE                 Location/Qualifiers
REGION                  1..19
                        note = Synthetic supramolecular recognition sequence
source                  1..19
                        mol_type = protein
                        organism = synthetic construct
SEQUENCE: 36
VGIYILIAVG AVMMFVGFK                                                19

SEQ ID NO: 37           moltype = AA  length = 18
FEATURE                 Location/Qualifiers
REGION                  1..18
                        note = Synthetic supramolecular recognition sequence
source                  1..18
                        mol_type = protein
                        organism = synthetic construct
SEQUENCE: 37
NERNINITKD LLDLLVAH                                                 18

SEQ ID NO: 38           moltype = AA  length = 16
FEATURE                 Location/Qualifiers
REGION                  1..16
                        note = Synthetic supramolecular recognition sequence
source                  1..16
                        mol_type = protein
                        organism = synthetic construct
SEQUENCE: 38
```

-continued

```
DINWVKQRPG QGLEWI                                                   16

SEQ ID NO: 39          moltype = AA  length = 16
FEATURE                Location/Qualifiers
REGION                 1..16
                       note = Synthetic supramolecular recognition sequence
source                 1..16
                       mol_type = protein
                       organism = synthetic construct
SEQUENCE: 39
VLLQGKNPDI TKAWKL                                                   16

SEQ ID NO: 40          moltype = AA  length = 16
FEATURE                Location/Qualifiers
REGION                 1..16
                       note = Synthetic supramolecular recognition sequence
source                 1..16
                       mol_type = protein
                       organism = synthetic construct
SEQUENCE: 40
NLSRSRWFDF PFTREE                                                   16

SEQ ID NO: 41          moltype = AA  length = 8
FEATURE                Location/Qualifiers
REGION                 1..8
                       note = Synthetic protease consensus sequence
source                 1..8
                       mol_type = protein
                       organism = synthetic construct
SEQUENCE: 41
LAQAVVSS                                                            8

SEQ ID NO: 42          moltype = AA  length = 8
FEATURE                Location/Qualifiers
REGION                 1..8
                       note = Synthetic protease consensus sequence
source                 1..8
                       mol_type = protein
                       organism = synthetic construct
SEQUENCE: 42
GSQHIRAE                                                            8

SEQ ID NO: 43          moltype = AA  length = 12
FEATURE                Location/Qualifiers
REGION                 1..12
                       note = Synthetic protease consensus sequence
source                 1..12
                       mol_type = protein
                       organism = synthetic construct
SEQUENCE: 43
SLLKSRMVPN FN                                                       12

SEQ ID NO: 44          moltype = AA  length = 8
FEATURE                Location/Qualifiers
REGION                 1..8
                       note = Synthetic protease consensus sequence
source                 1..8
                       mol_type = protein
                       organism = synthetic construct
SEQUENCE: 44
GDSGLGRA                                                            8

SEQ ID NO: 45          moltype = AA  length = 8
FEATURE                Location/Qualifiers
REGION                 1..8
                       note = Synthetic protease consensus sequence
source                 1..8
                       mol_type = protein
                       organism = synthetic construct
SEQUENCE: 45
EVALVALK                                                            8

SEQ ID NO: 46          moltype = AA  length = 8
FEATURE                Location/Qualifiers
REGION                 1..8
                       note = Synthetic protease consensus sequence
source                 1..8
                       mol_type = protein
                       organism = synthetic construct
```

-continued

```
SEQUENCE: 46
LGLEGANL                                                    8

SEQ ID NO: 47          moltype = AA  length = 8
FEATURE                Location/Qualifiers
REGION                 1..8
                       note = Synthetic protease consensus sequence
source                 1..8
                       mol_type = protein
                       organism = synthetic construct
SEQUENCE: 47
AALGSAPG                                                    8

SEQ ID NO: 48          moltype = AA  length = 12
FEATURE                Location/Qualifiers
REGION                 1..12
                       note = Synthetic protease consensus sequence
source                 1..12
                       mol_type = protein
                       organism = synthetic construct
SEQUENCE: 48
SLLIFRSWAN FN                                               12

SEQ ID NO: 49          moltype = AA  length = 8
FEATURE                Location/Qualifiers
REGION                 1..8
                       note = Synthetic protease consensus sequence
source                 1..8
                       mol_type = protein
                       organism = synthetic construct
SEQUENCE: 49
VEPNSLEE                                                    8

SEQ ID NO: 50          moltype = AA  length = 8
FEATURE                Location/Qualifiers
REGION                 1..8
                       note = Synthetic protease consensus sequence
source                 1..8
                       mol_type = protein
                       organism = synthetic construct
SEQUENCE: 50
GEPLSLLP                                                    8

SEQ ID NO: 51          moltype = AA  length = 8
FEATURE                Location/Qualifiers
REGION                 1..8
                       note = Synthetic protease consensus sequence
source                 1..8
                       mol_type = protein
                       organism = synthetic construct
SEQUENCE: 51
IPVSLRSG                                                    8

SEQ ID NO: 52          moltype = AA  length = 8
FEATURE                Location/Qualifiers
REGION                 1..8
                       note = Synthetic protease consensus sequence
source                 1..8
                       mol_type = protein
                       organism = synthetic construct
SEQUENCE: 52
RPFSMIMG                                                    8

SEQ ID NO: 53          moltype = AA  length = 8
FEATURE                Location/Qualifiers
REGION                 1..8
                       note = Synthetic protease consensus sequence
source                 1..8
                       mol_type = protein
                       organism = synthetic construct
SEQUENCE: 53
VPLSLTMG                                                    8

SEQ ID NO: 54          moltype = AA  length = 8
FEATURE                Location/Qualifiers
REGION                 1..8
                       note = Synthetic protease consensus sequence
source                 1..8
                       mol_type = protein
```

```
                        organism = synthetic construct
SEQUENCE: 54
GPSGLRGA                                                    8

SEQ ID NO: 55           moltype = AA  length = 8
FEATURE                 Location/Qualifiers
REGION                  1..8
                        note = Synthetic protease consensus sequence
source                  1..8
                        mol_type = protein
                        organism = synthetic construct
SEQUENCE: 55
VPLSLYSG                                                    8

SEQ ID NO: 56           moltype = AA  length = 8
FEATURE                 Location/Qualifiers
REGION                  1..8
                        note = Synthetic protease consensus sequence
source                  1..8
                        mol_type = protein
                        organism = synthetic construct
SEQUENCE: 56
GAANLVRG                                                    8

SEQ ID NO: 57           moltype = AA  length = 9
FEATURE                 Location/Qualifiers
REGION                  1..9
                        note = Synthetic protease consensus sequence
source                  1..9
                        mol_type = protein
                        organism = synthetic construct
SEQUENCE: 57
GVPLSLTMG                                                   9

SEQ ID NO: 58           moltype = AA  length = 11
FEATURE                 Location/Qualifiers
REGION                  1..11
                        note = Synthetic protease consensus sequence
source                  1..11
                        mol_type = protein
                        organism = synthetic construct
SEQUENCE: 58
PQGLAGQRGI V                                                11

SEQ ID NO: 59           moltype = AA  length = 8
FEATURE                 Location/Qualifiers
REGION                  1..8
                        note = Synthetic protease consensus sequence
source                  1..8
                        mol_type = protein
                        organism = synthetic construct
SEQUENCE: 59
GPAGLRLA                                                    8

SEQ ID NO: 60           moltype = AA  length = 11
FEATURE                 Location/Qualifiers
REGION                  1..11
                        note = Synthetic enzyme consensus sequence
source                  1..11
                        mol_type = protein
                        organism = synthetic construct
SEQUENCE: 60
RDIYAAPFFR K                                                11

SEQ ID NO: 61           moltype = AA  length = 14
FEATURE                 Location/Qualifiers
REGION                  1..14
                        note = Synthetic enzyme consensus sequence
source                  1..14
                        mol_type = protein
                        organism = synthetic construct
SEQUENCE: 61
AMERRRTSAA RRSY                                             14

SEQ ID NO: 62           moltype = AA  length = 13
FEATURE                 Location/Qualifiers
REGION                  1..13
                        note = Synthetic enzyme consensus sequence
source                  1..13
```

-continued

```
                          mol_type = protein
                          organism = synthetic construct
SEQUENCE: 62
KARAAVSPQK RKA                                                             13

SEQ ID NO: 63             moltype = AA  length = 16
FEATURE                   Location/Qualifiers
REGION                    1..16
                          note = Synthetic enzyme consensus sequence
source                    1..16
                          mol_type = protein
                          organism = synthetic construct
SEQUENCE: 63
RARKRRLSAP PLASGD                                                          16

SEQ ID NO: 64             moltype = AA  length = 15
FEATURE                   Location/Qualifiers
REGION                    1..15
                          note = Synthetic enzyme consensus sequence
source                    1..15
                          mol_type = protein
                          organism = synthetic construct
SEQUENCE: 64
AKAGPPLSPR PPHVH                                                           15

SEQ ID NO: 65             moltype = AA  length = 15
FEATURE                   Location/Qualifiers
REGION                    1..15
                          note = Synthetic enzyme consensus sequence
source                    1..15
                          mol_type = protein
                          organism = synthetic construct
SEQUENCE: 65
DLFIPDNYLK MKPAP                                                           15

SEQ ID NO: 66             moltype = AA  length = 15
FEATURE                   Location/Qualifiers
REGION                    1..15
                          note = Synthetic enzyme consensus sequence
source                    1..15
                          mol_type = protein
                          organism = synthetic construct
SEQUENCE: 66
AELDPEDSMD MDMAP                                                           15

SEQ ID NO: 67             moltype = AA  length = 15
FEATURE                   Location/Qualifiers
REGION                    1..15
                          note = Synthetic enzyme consensus sequence
source                    1..15
                          mol_type = protein
                          organism = synthetic construct
SEQUENCE: 67
EDEAEELSDE DEELK                                                           15

SEQ ID NO: 68             moltype = AA  length = 15
FEATURE                   Location/Qualifiers
REGION                    1..15
                          note = Synthetic enzyme consensus sequence
source                    1..15
                          mol_type = protein
                          organism = synthetic construct
SEQUENCE: 68
AAGPAPLSPV PPVVH                                                           15

SEQ ID NO: 69             moltype = AA  length = 16
FEATURE                   Location/Qualifiers
REGION                    1..16
                          note = Synthetic enzyme consensus sequence
source                    1..16
                          mol_type = protein
                          organism = synthetic construct
SEQUENCE: 69
DASRPPPLSP LPSPRA                                                          16

SEQ ID NO: 70             moltype = AA  length = 9
FEATURE                   Location/Qualifiers
REGION                    1..9
                          note = Synthetic arginase consensus sequence
```

```
source                  1..9
                        mol_type = protein
                        organism = synthetic construct
SEQUENCE: 70
GRRRRRRRG                                                         9

SEQ ID NO: 71           moltype = AA  length = 17
FEATURE                 Location/Qualifiers
REGION                  1..17
                        note = Synthetic supramolecular recognition sequence
source                  1..17
                        mol_type = protein
                        organism = synthetic construct
SEQUENCE: 71
AISGSGGSTY YANSVLG                                                17

SEQ ID NO: 72           moltype = AA  length = 20
FEATURE                 Location/Qualifiers
REGION                  1..20
                        note = Synthetic supramolecular recognition sequence
source                  1..20
                        mol_type = protein
                        organism = synthetic construct
SEQUENCE: 72
TNLGILHSMV ARAVGNNTQG                                             20

SEQ ID NO: 73           moltype = AA  length = 17
FEATURE                 Location/Qualifiers
REGION                  1..17
                        note = Synthetic supramolecular recognition sequence
source                  1..17
                        mol_type = protein
                        organism = synthetic construct
SEQUENCE: 73
GIITYALSGG EIKILAG                                                17

SEQ ID NO: 74           moltype = AA  length = 8
FEATURE                 Location/Qualifiers
REGION                  1..8
                        note = Synthetic protease consensus sequence
source                  1..8
                        mol_type = protein
                        organism = synthetic construct
SEQUENCE: 74
SAVLLEAT                                                          8

SEQ ID NO: 75           moltype = AA  length = 8
FEATURE                 Location/Qualifiers
REGION                  1..8
                        note = Synthetic protease consensus sequence
source                  1..8
                        mol_type = protein
                        organism = synthetic construct
SEQUENCE: 75
SQNYPIVQ                                                          8

SEQ ID NO: 76           moltype = AA  length = 12
FEATURE                 Location/Qualifiers
REGION                  1..12
                        note = Synthetic arginase consensus sequence
source                  1..12
                        mol_type = protein
                        organism = synthetic construct
SEQUENCE: 76
GRRRRRRRGS SS                                                     12

SEQ ID NO: 77           moltype = AA  length = 24
FEATURE                 Location/Qualifiers
REGION                  1..24
                        note = Synthetic supramolecular recognition sequence
source                  1..24
                        mol_type = protein
                        organism = synthetic construct
SEQUENCE: 77
AVYYCQQNNE DPRTFGGGTK SSSG                                        24

SEQ ID NO: 78           moltype = AA  length = 21
FEATURE                 Location/Qualifiers
REGION                  1..21
```

-continued

```
                      note = Synthetic supramolecular recognition sequence
source                1..21
                      mol_type = protein
                      organism = synthetic construct
SEQUENCE: 78
QFVKDLLLHL KKLFREGRFN G                                              21

SEQ ID NO: 79         moltype = AA  length = 21
FEATURE               Location/Qualifiers
REGION                1..21
                      note = Synthetic supramolecular recognition sequence
source                1..21
                      mol_type = protein
                      organism = synthetic construct
SEQUENCE: 79
QFVKDSLLHL KKLFREGRFN G                                              21

SEQ ID NO: 80         moltype = AA  length = 21
FEATURE               Location/Qualifiers
REGION                1..21
                      note = Synthetic supramolecular recognition sequence
source                1..21
                      mol_type = protein
                      organism = synthetic construct
SEQUENCE: 80
QFVKDSLLHL SKLFREGRFN G                                              21

SEQ ID NO: 81         moltype = AA  length = 21
FEATURE               Location/Qualifiers
REGION                1..21
                      note = Synthetic supramolecular recognition sequence
source                1..21
                      mol_type = protein
                      organism = synthetic construct
SEQUENCE: 81
QFVKDSLLHL SKLFRESRFN G                                              21

SEQ ID NO: 82         moltype = AA  length = 8
FEATURE               Location/Qualifiers
REGION                1..8
                      note = Synthetic enzyme consensus sequence
source                1..8
                      mol_type = protein
                      organism = synthetic construct
SEQUENCE: 82
NVLHSWAV                                                             8

SEQ ID NO: 83         moltype = AA  length = 8
FEATURE               Location/Qualifiers
REGION                1..8
                      note = Synthetic enzyme consensus sequence
source                1..8
                      mol_type = protein
                      organism = synthetic construct
SEQUENCE: 83
ALQARPGP                                                             8

SEQ ID NO: 84         moltype = AA  length = 12
FEATURE               Location/Qualifiers
REGION                1..12
                      note = Synthetic enzyme consensus sequence
source                1..12
                      mol_type = protein
                      organism = synthetic construct
SEQUENCE: 84
SGVVIATVIV IT                                                        12

SEQ ID NO: 85         moltype = AA  length = 8
FEATURE               Location/Qualifiers
REGION                1..8
                      note = Synthetic enzyme consensus sequence
source                1..8
                      mol_type = protein
                      organism = synthetic construct
SEQUENCE: 85
RSARGLKG                                                             8

SEQ ID NO: 86         moltype = AA  length = 8
FEATURE               Location/Qualifiers
```

-continued

```
REGION                 1..8
                       note = Synthetic enzyme consensus sequence
source                 1..8
                       mol_type = protein
                       organism = synthetic construct
SEQUENCE: 86
RQSRIVFG                                                            8

SEQ ID NO: 87          moltype = AA  length = 8
FEATURE                Location/Qualifiers
REGION                 1..8
                       note = Synthetic enzyme consensus sequence
source                 1..8
                       mol_type = protein
                       organism = synthetic construct
SEQUENCE: 87
GEPVSGLP                                                            8

SEQ ID NO: 88          moltype = AA  length = 8
FEATURE                Location/Qualifiers
REGION                 1..8
                       note = Synthetic enzyme consensus sequence
source                 1..8
                       mol_type = protein
                       organism = synthetic construct
SEQUENCE: 88
VPMSMRGG                                                            8

SEQ ID NO: 89          moltype = AA  length = 8
FEATURE                Location/Qualifiers
REGION                 1..8
                       note = Synthetic enzyme consensus sequence
source                 1..8
                       mol_type = protein
                       organism = synthetic construct
SEQUENCE: 89
EPYHLMAL                                                            8

SEQ ID NO: 90          moltype = AA  length = 8
FEATURE                Location/Qualifiers
REGION                 1..8
                       note = Synthetic enzyme consensus sequence
source                 1..8
                       mol_type = protein
                       organism = synthetic construct
SEQUENCE: 90
RPLSLQTG                                                            8

SEQ ID NO: 91          moltype = AA  length = 8
FEATURE                Location/Qualifiers
REGION                 1..8
                       note = Synthetic enzyme consensus sequence
source                 1..8
                       mol_type = protein
                       organism = synthetic construct
SEQUENCE: 91
GPKNLKAP                                                            8

SEQ ID NO: 92          moltype = AA  length = 8
FEATURE                Location/Qualifiers
REGION                 1..8
                       note = Synthetic enzyme consensus sequence
source                 1..8
                       mol_type = protein
                       organism = synthetic construct
SEQUENCE: 92
GPANLVAP                                                            8

SEQ ID NO: 93          moltype = AA  length = 8
FEATURE                Location/Qualifiers
REGION                 1..8
                       note = Synthetic enzyme consensus sequence
source                 1..8
                       mol_type = protein
                       organism = synthetic construct
SEQUENCE: 93
LPQGLRTE                                                            8

SEQ ID NO: 94          moltype = AA  length = 8
```

-continued

```
FEATURE                Location/Qualifiers
REGION                 1..8
                       note = Synthetic enzyme consensus sequence
source                 1..8
                       mol_type = protein
                       organism = synthetic construct
SEQUENCE: 94
LPQKSQHG                                                                    8

SEQ ID NO: 95          moltype = AA  length = 8
FEATURE                Location/Qualifiers
REGION                 1..8
                       note = Synthetic enzyme consensus sequence
source                 1..8
                       mol_type = protein
                       organism = synthetic construct
SEQUENCE: 95
LYYVSLSP                                                                    8

SEQ ID NO: 96          moltype = AA  length = 8
FEATURE                Location/Qualifiers
REGION                 1..8
                       note = Synthetic enzyme consensus sequence
source                 1..8
                       mol_type = protein
                       organism = synthetic construct
SEQUENCE: 96
SYYVSLSP                                                                    8

SEQ ID NO: 97          moltype = AA  length = 7
FEATURE                Location/Qualifiers
REGION                 1..7
                       note = Synthetic enzyme consensus sequence
source                 1..7
                       mol_type = protein
                       organism = synthetic construct
SEQUENCE: 97
RRRRRRR                                                                     7

SEQ ID NO: 98          moltype = AA  length = 8
FEATURE                Location/Qualifiers
REGION                 1..8
                       note = Synthetic enzyme consensus sequence
source                 1..8
                       mol_type = protein
                       organism = synthetic construct
SEQUENCE: 98
EAFRSTGA                                                                    8

SEQ ID NO: 99          moltype = AA  length = 8
FEATURE                Location/Qualifiers
REGION                 1..8
                       note = Synthetic enzyme consensus sequence
source                 1..8
                       mol_type = protein
                       organism = synthetic construct
SEQUENCE: 99
GTSRSAGG                                                                    8

SEQ ID NO: 100         moltype = AA  length = 8
FEATURE                Location/Qualifiers
REGION                 1..8
                       note = Synthetic enzyme consensus sequence
source                 1..8
                       mol_type = protein
                       organism = synthetic construct
SEQUENCE: 100
YRFRILGG                                                                    8

SEQ ID NO: 101         moltype = AA  length = 8
FEATURE                Location/Qualifiers
REGION                 1..8
                       note = Synthetic enzyme consensus sequence
source                 1..8
                       mol_type = protein
                       organism = synthetic construct
SEQUENCE: 101
IESKINGG                                                                    8
```

-continued

```
SEQ ID NO: 102          moltype = AA  length = 8
FEATURE                 Location/Qualifiers
REGION                  1..8
                        note = Synthetic enzyme consensus sequence
source                  1..8
                        mol_type = protein
                        organism = synthetic construct
SEQUENCE: 102
VRSRIVKG                                                                    8

SEQ ID NO: 103          moltype = AA  length = 8
FEATURE                 Location/Qualifiers
REGION                  1..8
                        note = Synthetic enzyme consensus sequence
source                  1..8
                        mol_type = protein
                        organism = synthetic construct
SEQUENCE: 103
TQPRIVGG                                                                    8

SEQ ID NO: 104          moltype = AA  length = 8
FEATURE                 Location/Qualifiers
REGION                  1..8
                        note = Synthetic enzyme consensus sequence
source                  1..8
                        mol_type = protein
                        organism = synthetic construct
SEQUENCE: 104
ALGRKLVG                                                                    8

SEQ ID NO: 105          moltype = AA  length = 8
FEATURE                 Location/Qualifiers
REGION                  1..8
                        note = Synthetic enzyme consensus sequence
source                  1..8
                        mol_type = protein
                        organism = synthetic construct
SEQUENCE: 105
STPPTPSP                                                                    8

SEQ ID NO: 106          moltype = AA  length = 8
FEATURE                 Location/Qualifiers
REGION                  1..8
                        note = Synthetic enzyme consensus sequence
source                  1..8
                        mol_type = protein
                        organism = synthetic construct
SEQUENCE: 106
VKAASLGK                                                                    8

SEQ ID NO: 107          moltype = AA  length = 10
FEATURE                 Location/Qualifiers
REGION                  1..10
                        note = Synthetic enzyme consensus sequence
source                  1..10
                        mol_type = protein
                        organism = synthetic construct
SEQUENCE: 107
TCCATCATCC                                                                  10

SEQ ID NO: 108          moltype = AA  length = 8
FEATURE                 Location/Qualifiers
REGION                  1..8
                        note = synthetic polypeptide
source                  1..8
                        mol_type = protein
                        organism = synthetic construct
SEQUENCE: 108
GLAGLVGP                                                                    8

SEQ ID NO: 109          moltype = AA  length = 4
FEATURE                 Location/Qualifiers
REGION                  1..4
                        note = synthetic polypeptide
source                  1..4
                        mol_type = protein
                        organism = synthetic construct
SEQUENCE: 109
DAFK                                                                        4
```

```
SEQ ID NO: 110          moltype = AA  length = 8
FEATURE                 Location/Qualifiers
REGION                  1..8
                        note = synthetic polypeptide
source                  1..8
                        mol_type = protein
                        organism = synthetic construct
SEQUENCE: 110
TSEEIRGG                                                            8

SEQ ID NO: 111          moltype = AA  length = 12
FEATURE                 Location/Qualifiers
REGION                  1..12
                        note = synthetic polypeptide
source                  1..12
                        mol_type = protein
                        organism = synthetic construct
SEQUENCE: 111
SLLIFRSWAN FN                                                       12

SEQ ID NO: 112          moltype = AA  length = 10
FEATURE                 Location/Qualifiers
REGION                  1..10
                        note = synthetic polypeptide
source                  1..10
                        mol_type = protein
                        organism = synthetic construct
SEQUENCE: 112
SGKPILFFRL                                                          10

SEQ ID NO: 113          moltype = AA  length = 11
FEATURE                 Location/Qualifiers
REGION                  1..11
                        note = synthetic polypeptide
source                  1..11
                        mol_type = protein
                        organism = synthetic construct
SEQUENCE: 113
SGSPAFLAKN R                                                        11

SEQ ID NO: 114          moltype = AA  length = 10
FEATURE                 Location/Qualifiers
REGION                  1..10
                        note = synthetic polypeptide
source                  1..10
                        mol_type = protein
                        organism = synthetic construct
SEQUENCE: 114
SGKPIIFFRL                                                          10

SEQ ID NO: 115          moltype = AA  length = 8
FEATURE                 Location/Qualifiers
REGION                  1..8
                        note = synthetic polypeptide
source                  1..8
                        mol_type = protein
                        organism = synthetic construct
SEQUENCE: 115
GAFRMCAG                                                            8

SEQ ID NO: 116          moltype = AA  length = 8
FEATURE                 Location/Qualifiers
REGION                  1..8
                        note = synthetic polypeptide
source                  1..8
                        mol_type = protein
                        organism = synthetic construct
SEQUENCE: 116
EFVRSPTP                                                            8

SEQ ID NO: 117          moltype = AA  length = 8
FEATURE                 Location/Qualifiers
REGION                  1..8
                        note = synthetic polypeptide
source                  1..8
                        mol_type = protein
                        organism = synthetic construct
SEQUENCE: 117
```

-continued

```
QFVRSPSG                                                    8

SEQ ID NO: 118          moltype = AA  length = 8
FEATURE                 Location/Qualifiers
REGION                  1..8
                        note = synthetic polypeptide
source                  1..8
                        mol_type = protein
                        organism = synthetic construct
SEQUENCE: 118
AKLKAENN                                                    8

SEQ ID NO: 119          moltype = AA  length = 8
FEATURE                 Location/Qualifiers
REGION                  1..8
                        note = synthetic polypeptide
source                  1..8
                        mol_type = protein
                        organism = synthetic construct
SEQUENCE: 119
EGLGQAGN                                                    8

SEQ ID NO: 120          moltype = AA  length = 8
FEATURE                 Location/Qualifiers
REGION                  1..8
                        note = synthetic polypeptide
source                  1..8
                        mol_type = protein
                        organism = synthetic construct
SEQUENCE: 120
GKKGAVGE                                                    8

SEQ ID NO: 121          moltype = AA  length = 8
FEATURE                 Location/Qualifiers
REGION                  1..8
                        note = synthetic polypeptide
source                  1..8
                        mol_type = protein
                        organism = synthetic construct
SEQUENCE: 121
GFFFWALG                                                    8

SEQ ID NO: 122          moltype = AA  length = 8
FEATURE                 Location/Qualifiers
REGION                  1..8
                        note = synthetic polypeptide
source                  1..8
                        mol_type = protein
                        organism = synthetic construct
SEQUENCE: 122
GPLGMLSQ                                                    8

SEQ ID NO: 123          moltype = AA  length = 13
FEATURE                 Location/Qualifiers
REGION                  1..13
                        note = synthetic polypeptide
source                  1..13
                        mol_type = protein
                        organism = synthetic construct
SEQUENCE: 123
GAGVPMSMRG GAG                                              13

SEQ ID NO: 124          moltype = AA  length = 8
FEATURE                 Location/Qualifiers
REGION                  1..8
                        note = synthetic polypeptide
source                  1..8
                        mol_type = protein
                        organism = synthetic construct
SEQUENCE: 124
GPSGLQTG                                                    8

SEQ ID NO: 125          moltype = AA  length = 11
FEATURE                 Location/Qualifiers
REGION                  1..11
                        note = synthetic polypeptide
source                  1..11
                        mol_type = protein
                        organism = synthetic construct
```

-continued

```
SEQUENCE: 125
PQGLAGQRGI V                                              11

SEQ ID NO: 126          moltype = AA  length = 12
FEATURE                 Location/Qualifiers
REGION                  1..12
                        note = synthetic polypeptide
source                  1..12
                        mol_type = protein
                        organism = synthetic construct
SEQUENCE: 126
GPQGLAGQRG IV                                             12

SEQ ID NO: 127          moltype = AA  length = 8
FEATURE                 Location/Qualifiers
REGION                  1..8
                        note = synthetic polypeptide
source                  1..8
                        mol_type = protein
                        organism = synthetic construct
SEQUENCE: 127
IPESLRAG                                                  8

SEQ ID NO: 128          moltype = AA  length = 8
FEATURE                 Location/Qualifiers
REGION                  1..8
                        note = synthetic polypeptide
source                  1..8
                        mol_type = protein
                        organism = synthetic construct
SEQUENCE: 128
ESDASQTG                                                  8

SEQ ID NO: 129          moltype = AA  length = 6
FEATURE                 Location/Qualifiers
REGION                  1..6
                        note = synthetic polypeptide
source                  1..6
                        mol_type = protein
                        organism = synthetic construct
SEQUENCE: 129
SGASAC                                                    6

SEQ ID NO: 130          moltype = AA  length = 5
FEATURE                 Location/Qualifiers
REGION                  1..5
                        note = synthetic polypeptide
source                  1..5
                        mol_type = protein
                        organism = synthetic construct
SEQUENCE: 130
SGRSA                                                     5

SEQ ID NO: 131          moltype = AA  length = 23
FEATURE                 Location/Qualifiers
REGION                  1..23
                        note = synthetic eptide
source                  1..23
                        mol_type = protein
                        organism = synthetic construct
SEQUENCE: 131
KGTSKGRTGL IPSNYVAEQA EAG                                 23

SEQ ID NO: 132          moltype = AA  length = 13
FEATURE                 Location/Qualifiers
REGION                  1..13
                        note = synthetic peptide
source                  1..13
                        mol_type = protein
                        organism = synthetic construct
SEQUENCE: 132
GAGVPLSLYS GAG                                            13

SEQ ID NO: 133          moltype = AA  length = 12
FEATURE                 Location/Qualifiers
REGION                  1..12
                        note = Synthetic peptide
source                  1..12
                        mol_type = protein
```

-continued

```
                    organism = synthetic construct
SEQUENCE: 133
GAGRRRRRRR AG                                                    12
```

PRISTINE GRAPHENE BASED BIOSENSOR FOR BIOMARKER DETECTION AND RELATED CORE PARTICLES, MATERIALS COMPOSITIONS METHODS AND SYSTEMS

CROSS-REFERENCE TO RELATED APPLICATION

The present application is a continuation of International Application PCT/US2021/065573 entitled "PRISTINE GRAPHENE BASED BIOSENSOR FOR BIOMARKER DETECTION AND RELATED CORE PARTICLES, MATERIALS COMPOSITIONS METHODS AND SYSTEMS" filed on Dec. 29, 2021, which, in turn, claims priority to U.S. Provisional Application No. 63/131,972 entitled "PRISTINE GRAPHENE BASED NANOBIOSENSOR FOR BIOMARKER DETECTION" filed on Dec. 30, 2020, the contents of which are incorporated herein by reference in their entirety.

STATEMENT OF GOVERNMENT GRANT

This invention was made with Government support under grant number 2032751 awarded by the National Science Foundation. The Government has certain rights in the invention.

INCORPORATION BY REFERENCE STATEMENT FOR SEQUENCE LISTING

Further, the computer readable form of the sequence listing of the XML file P2672-USBC-2023-02-17-Sequence Listing_ST26 created on Feb. 17, 2023, and having size 169,363 bytes measured on Windows Server 2019 Datacenter is incorporated herein by reference in its entirety.

FIELD

The present disclosure relates to biomarkers' detection and related biosensor. In particular the present disclosure relates to pristine graphene biosensors for biomarker detection and related core particles, materials compositions methods and systems.

BACKGROUND

Detection of biomarkers is central to many fields of investigations such as medical field and basic biological research.

In particular, detection of biomarkers is key to acquiring understanding of a several biological events in various organisms including occurrence of various conditions from cancer to viral infections to additional events such as blood-clotting and inflammation.

Despite progress made in the field, robust, reproducible detection of biomarkers in samples at nanomolar or lower concentrations in particular in connection with conditions remains challenging.

SUMMARY

The present disclosure related to graphene-based biosensors (herein also graphene biosensor or biosensor) and related core particles, materials, compositions methods and systems, which are so stable in a sample in the sense of the disclosure which in several embodiments allow detection of biomarkers at picomolar or femtomolar concentrations with high reproducibility and signal to noise ratio as will be understood by a skilled person.

According to a first aspect a graphene core particle is described. The graphene core particle comprises more than one pristine graphene nanosheets coated by a coating layer of an organic and/or inorganic compound having a solubility in water of 1% by weight at 25 degree C. In the graphene core particle the more than one pristine graphene nanosheets and/or the organic and/or inorganic compound of the coating layer are configured to present a functional group capable of binding a corresponding functional group in an aqueous solution.

According to a second aspect a biosensor is described configured to detect a target biomarker. The biosensor comprises: a graphene core particle of the disclosure, and a detectable moiety capable of emitting a fluorescent signal, the detectable moiety attached to the core particle through a peptide linkage comprising a recognition sequence specific for a target biomarker.

In the biosensor, the coating layer and the peptide linkage are configured to set a quenching distance between the graphene nanosheets and the detectable moiety wherein the graphene nanosheet quenches the fluorescent signal of the detectable moiety.

In the biosensor, the peptide linkage is further configured to set, upon recognition by the target biomarker of the recognition sequence, an emitting distance between the graphene nanosheets and the detectable moiety wherein the graphene nanosheet does not quench the fluorescent signal of the detectable moiety.

In the biosensor, the target biomarker specific peptide linkage and the detectable moiety thus form a target specific detectable component configured to emit a detectable fluorescent signal upon modification of the peptide linkage by the target biomarker.

According to a third aspect a multiplex biosensor is described, comprising: a core particle of the disclosure and a plurality of target specific detectable components attached to the graphene core particle. In the multiplex biosensor each target specific detectable component is formed by a detectable moiety capable of emitting a fluorescent signal in an excited state, and having an excitation spectrum and an emission spectrum, the detectable moiety attached to a peptide linkage comprising a recognition sequence specific for a target biomarker.

In each target specific detectable component the peptide linkage is configured to provide in combination with the coating layer of the core particle, a quenching distance between the detectable moiety and the graphene sheet core particle wherein the graphene nanosheet quenches the fluorescent signal of the detectable moiety.

In the biosensor, the recognition sequence for the target biomarker of each detectable component is configured to specifically detect a target biomarker and the plurality of detectable components is selected to specifically detect a plurality of different target biomarkers.

In the plurality of target specific detectable components of the biosensor, each detectable moiety has an excitation spectrum having a minimized overlap with the emission spectrum of another detectable moiety of the plurality of target specific detectable components.

According to a fourth aspect a composition is described comprising one or more graphene core particles and/or one or more biosensors herein described in combination with a suitable auxiliary agent such as a vehicle diluent, excipient or the like. In some embodiments, the composition is a pharmaceutical composition and the auxiliary agent is a pharmaceutically accepted auxiliary agent. In embodiments where the composition comprises two or more graphene biosensors presenting two or more detectable components specific for different target biomarkers the excitation spectrum of each detectable moieties of the two or more detectable components has a minimized overlap with the emission spectrum of another detectable moiety of the two or more detectable components.

According to a fifth aspect a method and a system are described for making a core particle herein described. The method comprises providing a pristine graphene nanosheet having a graphene surface; and coating the graphene surface with a layer of an organic and/or inorganic molecules.

The system for making a core particle herein described, comprises pristine graphene nanosheets having a graphene surface and reagents to chemically transform, the graphene surface to provide pristine graphene nanosheets coated with a coating layer.

According to a sixth aspect a method and a system are described for making a biosensor herein described. The method comprises providing a core particle herein described and attaching to the graphene surface a detectable moiety through a peptide linkage.

The system for making a biosensor herein described comprises a pristine graphene nanosheet having a graphene surface, a peptide linkage, a detectable moiety and reagents for attaching the detectable moiety to the graphene surface through the peptide linkage. In the system for making a biosensor herein described the components are comprised in a configuration for simultaneous combined or sequential use in the method of making a biosensor herein described.

According to a seventh aspect a method and a system are described for detecting the activity of a biomarker in a biological sample. The method comprises: contacting a biological sample with any biosensor according to the present disclosure to create a reaction solution; and detecting a change in the reaction solution.

The system comprises a biosensor herein described and reagents for simultaneous combined or sequential use in a method of detection the activity of a biomarker in a biological sample herein described.

According to an eighth aspect a method and system are described for multiplexed detection of the activity of a plurality of biomarker in a biological sample. The method comprises: contacting a biological sample with a multiplex biosensor according to the present disclosure configured to present detectable components specific for the plurality of the biomarkers, the contacting performed to create a reaction solution; and detecting a change in said reaction solution. In addition, or in the alternative, the method can comprise contacting the biological sample with multiple biosensor each presenting a peptide linkage specific for one biomarker of the plurality of the biomarkers.

The system for multiplexed detection of the activity of a plurality of biomarker in a biological sample comprises a multiplex biosensor herein described and/or biosensor each presenting a peptide linkage specific for one biomarker of the plurality of the biomarkers as well as optionally a plurality of and reagents for simultaneous combined or sequential use in a method of detection the activity of a biomarker in a biological sample herein described According to a ninth aspect in methods and systems for detection of a target biomarker the detecting is preceded by a heating of the sample and/or of the testing solution. In particular, it has been found unexpectedly that pretreating sera and/or running the protease assay at selected temperatures improve signal to noise using separate and additive mechanisms.

Biosensors and related graphene core particles, materials, compositions methods and systems herein described provide in several embodiments graphene based biosensor highly stable in an aqueous sample. which can maintain a percentage of at least 95% particles in suspension with a change in colloidal stability of ~24% or less at OD650 for months.

Biosensors and related core particles, materials, compositions methods and systems herein described allow in several embodiments detection of a biomarker at picomolar or femtomolar concentrations with high reproducibility which in some embodiments a coefficient of variation in detected signal between different manufactured lots or batches of less than 10%.

Biosensors and related core particles, materials, compositions methods and systems herein described allow in several embodiments detection of a biomarker at picomolar or femtomolar concentrations in an aqueous solution with a signal to noise ratio of 25 or higher across multiple sensors as will be understood by a skilled person upon reading of the present disclosure.

Biosensors and related core particles, materials, compositions methods and systems herein described allow in several embodiments detection of a multiple biomarker in an aqueous sample with high multiplex ability with a number different detectable components up to 10 in the UV/Vis spectrum or up to 50 the entire electromagnetic spectrum, presented on a same graphene particle or within a same solution as will be understood by a skilled person upon reading of the present disclosure.

Biosensors and related core particles, materials, compositions methods and systems herein described allow in several embodiments production of robust biosensor that can be dispersed in aqueous forms, dried and be redispersed for up to 10 cycles of dispersion. Accordingly, biosensor of the disclosure can be comprised in compositions and systems in a dry form as will be understood by a skilled person.

Biosensors and related core particles, materials, compositions methods and systems herein described can be used in connection with various applications wherein reproducible detection of one or more biomarkers is desired, in particular when present at very low concentrations, such as picomolar or femtomolar concentrations. For example biosensors and related core particles, materials, compositions methods and systems herein described can be used in medical and diagnostics applications for visualization of the onset of disease pathologies, and responses to drug treatments and therapy facilitating development of diagnostic and therapeutic cellular agents, as well as for visualization of biological events, such as cellular signaling, homeostasis, cellular migration, responses to external stimuli such as temperature and pH, among other advantages identifiable by a skilled person.

Additional exemplary applications include uses of the biosensors and related core particles, materials, compositions methods and systems herein described in several fields including basic biology research, applied biology, bio-engineering, aetiology, medical research, medical diagnostics, therapeutics, in drug research and to develop diagnostic and therapeutic approaches and tools and in additional fields identifiable by a skilled person upon reading of the present disclosure.

The details of one or more embodiments of the disclosure are set forth in the accompanying drawings and the description below. Other features, objects, and advantages will be apparent from the description and drawings, and from the claims.

BRIEF DESCRIPTION OF THE DRAWINGS

The accompanying drawings, which are incorporated into and constitute a part of this specification, illustrate one or more embodiments of the present disclosure and, together with the detailed description and example sections, serve to explain the principles and implementations of the disclosure. Exemplary embodiments of the present disclosure will become more fully understood from the detailed description and the accompanying drawings, wherein:

FIG. 3B shows an exemplary structure of a single nanosheet of carboxygraphene (CG).

FIG. 3C shows a side-view illustration of the structure of an exemplary carboxygraphene top layer showing high density distribution of carboxylic acid groups across the surface.

FIG. 3D shows Differential Thermogravimetry (DTA) of synthesized carboxygraphene 20 under $N_2$.

FIG. 6C shows four exemplary BODIPY dyes with no or only a minimal overlap between the excitation and absorption spectra, and in particular BODIPY FL, BODIPY TR, BODIPY 530550, and BODIPY 630650.

FIG. 7 shows a schematic representation of lysine and ornithine as possible spacers for biosensor.

FIG. 13A shows a chart in which the left bars of each pair of bars indicates the initial fluorescence signal detected after adding MMP1 in serum before incubation; right bars of each pair of bars show fluorescence signal detected after 60 min. incubation at 37° C. AC (assay control) is the biosensor solution mixed with buffer alone, while blank is the buffer alone; these represent the background signal, or fluorescence signal that is measured from the buffer and biosensors alone.

FIG. 28 shows a table reporting the formulation for biosensor manufacture HEB Lot NE100, HEB Lot NE 101 and HEB Lot NE 102 with increasing dispersion efforts.

FIG. 32 shows charts reporting the results of experiments directed to the preparation of gNBS without carboxylation step. uPA gNBS were assembled by attaching PEI to a carboxygraphene backbone (uPA) or directly to a graphene backbone using EDC chemistry, or reacted with PEI without EDC but heating to 80° C. uPA-TCPP was subsequently added to all three backbones and the resulting gNBS stimulated with pooled normal sera (Pool Normal Serum) or buffer (Assay Control) for 90 min at 45° C. before being measured on a VarioSkan Lux at 421/653 nm.

FIG. 33 shows a chart reporting the results of rapid conjugation of PEI without previous carboxylation. uPA gNBS were prepared by activating 1.2 k or 10 k PEI with Azidoacetic acid NHS ester and coupling it to graphene at 80° C. Activity of the resulting sensors was assessed by stimulating with buffer, 50 mg/mL BSA or pooled normal sera.

FIG. 34 shows a table reporting DLS and zeta potential results for MMP1 G-TEG3amine biosensor.

FIG. 55 shows charts illustrating an example impact of dispersal and solvent removal on absorbance efficiency of gNBS. Working solutions of gNBS were prepared in 5 mM MES pH 7.4 with 155 mM NaCl at a concentration of 25 μg/mL. The absorption across 250 nm to 650 nm was measured for each lot reflecting two lots with no sonication (Lots 1 and 2) and two lots prepared with 1 hr sonication (Lots 3 and 4) and solvent removal (Lot 4). Data are presented as spectra or absorbance efficiency at OD270. In particular, FIG. 54 Panel A indicates the change in absorbance efficiency for NE biosensor across 250 nm to 650 nm. FIG. 54 Panel B shows the change is absorbance efficiency for MMP15 biosensor across 250 nm to 650 nm. The table highlights the increase in absorbance efficiency at $OD_{270}$ across 4 lots of each biosensor.

FIG. 58 shows charts illustrating exemplary colloidal stability of gNBS sensors. Working solutions of gNBS were prepared in 5 mM MES ph 7.4 with 155 mM NaCl at 25 μg/mL. The absorption at 250 nm to 650 nm was measured for each lot upon vortexing the solution. The samples were left to sit for 1 hour at room temperature. A second sample was measured after 60 min. The data represent the fold change in Absorbance from time 0. The different samples reflect two gNBS lots with no sonication (Lots 1 and 2) and two lots prepared with 1 hr sonication (Lots 3 and 4) and solvent removal (Lot 4). FeNBS (300 μg/mL) are included for comparison. Lot 2 had large gNBS particles that did not remain in suspension at all underestimating the colloidal stability.

DETAILED DESCRIPTION

Figure 1:
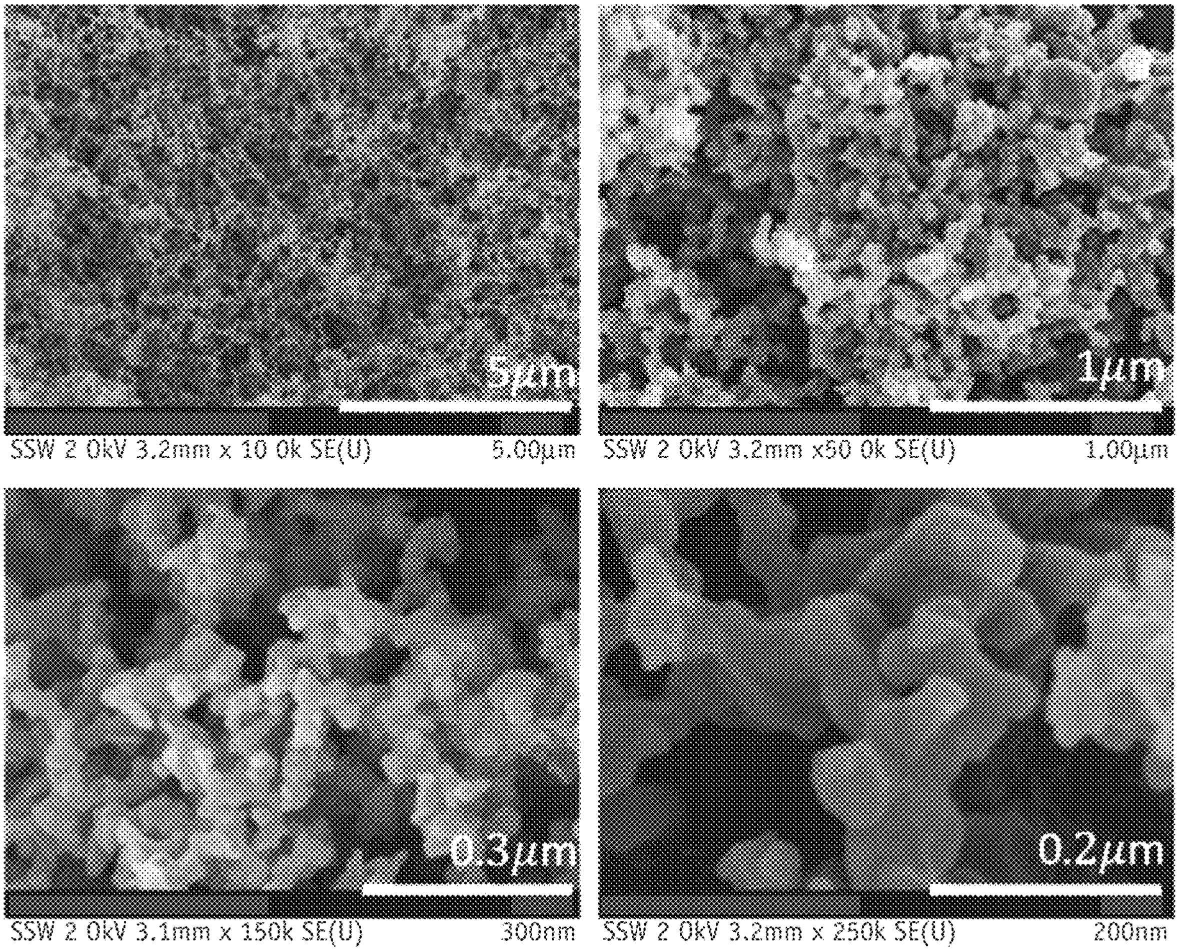
FIG. 1 shows SEM (Scanning Electron Microscopy) of explosion graphene from [1].

The present disclosure relates to graphene-based biosensors and related core particles, materials, compositions, methods and systems for assays for noninvasive detection and quantification of various biological markers.

The term "graphene" as used herein indicates an allotrope of carbon consisting of a single layer of atoms arranged in a two-dimensional honeycomb lattice nanostructure. The name is derived from "graphite" and the suffix -ene, reflecting the fact that the graphite allotrope of carbon contains numerous double bonds. In particular, graphene refers in the sense of the disclosure to a single layer of at least 1000 carbon atoms in sp2 hybridization that are arranged in a hexagonal manner. A graphene aggregate or graphene particle as used herein exchangeable, refers to at least two layers of graphene stacked over one another.

Accordingly, graphene in the sense of the disclosure comprises at least 98% carbon atoms organized in sheets. In a graphene sheet each atom is connected to its three nearest neighbors by a σ-bond, and contributes one electron to a conduction band that extends over the whole sheet. ([3]) (see schematics and properties discussed in Example 1 and Example 2).

In graphene in the sense of the disclosure, a typical apparent static contact angle $\theta^*$ of a typical graphene surface is $\theta^*=150\pm15°$, which is borderline super-hydrophobic ($\theta^*\geq150°$). Based on this finding and the fact that graphene consists mostly only of carbon (at least 99±1%), it is well established that graphene is among the most hydrophobic materials known. Therefore, it's dispersibility in water is $<1\times10^{-8}$ mg per milliliter. [4].

Graphene absorbs light in the UV, visible and near-IR region with absorption coefficients that exceeds graphite[5]. Accordingly, graphene in the sense of the disclosure is a material configured to absorbs light of all visible wavelengths. ([3]) Stacked graphene features light absorption over the entire wavelength range from far UV to mid-IR (100 to 1500 nm) [6]. For explosion graphene (5-7 layers), we found absorption coefficients alpha >5,000 ml mg-1 m−1 at 660 nm, which is in excellent agreement with the literature [7]. In general, graphene from various sources has absorption coefficients alpha from 1,000 to 5,000 at 660 nm.

In graphene in the sense of the disclosure, direct excitation occurs at deep/far ultraviolet, and surface plasmons of graphene in the visible range are of various intensity, direct excitation and surface plasmon of graphene are not capable of effectively exciting most detectable moiety capable of emit a fluorescent signal in an excited state (such as fluorescent dyes or particles). This indication applies to the entire visible range of the electromagnetic spectrum (400 to 730 nm) as will be understood by a skilled person. [6]

Graphene in the sense of the disclosure comprises pristine graphene (graphene in its original, pure, unoxidized form) as well as graphene in an oxidized or surface-modified form, (surface-modified) graphene and additional graphene forms identifiable by a skilled person.

Pristine graphene can be identified by techniques identifiable by a skilled person such as XRD (layer distance), TEM and SEM (morphology), RAMAN (layer distance and turbostratic properties, if present), and FTIR (lack of signature organic functional groups, with the exception of carbon-carbon double bond and aromatic overtones). In particular, FTIR and RAMAN spectra can be used to identify pristine graphene over surface-only oxidized or chemically modified graphene as the related spectra will change in view of the oxidation/chemical modification of the graphene surface as will understood by a skilled person. XRD, TEM, SEM, RAMAN, FTIR can be used to identify pristine graphene over oxidation/chemical modification that destroys the layer structure of graphene, in view of the changes in the related spectra also identifiable by a skilled person. Additionally, in all cases elementary analysis will confirm that the graphene material is >98% carbon as will be understood by a skilled person.

In embodiments herein described pristine graphene in the sense of the disclosure can be used as a component of a graphene core particle herein described in which more than one pristine graphene sheet forms a graphene particle which is coated with a coating material configured for attachment of a detectable component specific for a target biomarker. The term "particle" or "particulate" as used herein indicates a portion of matter with distinct physical or chemical properties, such as size volume, density, or mass. Exemplary particle of various materials are described in U.S. Provisional Patent Application Ser. No. 63/132,058, filed Dec. 30, 2020, entitled "Optical Nanobiosensors for Rapid Identification of Lung Conditions" filed on Dec. 30, 2020 and to corresponding PCT application No. PCT/US2021/065584 entitled "Nanosensors For Rapid Identification of Lung Conditions" filed on Dec. 29, 2021 with the disclosure of each of which is incorporated by reference in its entirety.

Particle in the sense of the disclosure have a size from 1 to 5000 nanometers. In particular, a particle in the sense of the disclosure can have a size from 1 to 250 nanometer, and size from 50 to 150 nm in a nanoscopic mesoscopic/system. Size as used herein is a maximum physical length of any two points of a particle. In a particle in the sense of the disclosure, the size of the particle refers to the longest distance between any two points of the particle. For example, an irregularly shaped graphene particle has a size that is the longest between any two carbons on the irregularly shaped graphene particle. In a spherically shaped particle, the size of the particle is the diameter of the spherically shaped particle.

In a graphene particle of the disclosure the mass distribution of the graphene particles can be detected by centrifugation and measurement of the time required for sedimentation and additional techniques identifiable by a skilled person. The actual size of the graphene particles in air (or N2, Ar) and a suitable hydrophobic solvent (e.g. chloroform) can be determined by means of Dynamic Light Scattering (DLS). The surface charge of the particles can be determined by means of Zeta Potential Measurements.

A graphene particle can have layers arranged in AB, or Bernal-stacked form, where half of the atoms lie directly over the center of a hexagon in the lower graphene sheet, and half of the atoms lie over an atom. A graphene particle can also have layers arranged in in the AA form, in which the layers are exactly aligned in which each carbon atom in one layer is disposed exactly over another carbon atom of an adjacent layer of graphene. In turbostratic particles (AA and AB stacking) the individual layers can move with respect to each other as will be understood by a skilled person.

In a graphene core particle of the present disclosure comprises pristine graphene sheets aggregated via van der Waals stacking in configurations comprising more than one graphene layer.

A "sheet" or "layer" in the sense of the disclosure indicates a two-dimensional nanostructure with thickness in a scale ranging from 1 to 150 nm. A single layer of carbon atoms with hexagonal lattices of a graphene material is 0.34 nm as will be understood by a skilled person. Since a single layer of graphene absorbs a 2.3% of incident light, allowing around 97.7% to pass through, inclusion of 2 or more sheets in the graphene core particle of the disclosure allows enhanced light absorption (blackness) which arises from the electronic interaction of stacked graphene layers in particular when the stacked graphene layers are organized in few layer graphene.

The term "few layer graphene" as used herein indicates a number of graphene layer ranging from about 2 to about 100 graphene sheets, preferably 3 to 50 graphene sheets, and even more preferably 5 to 25 sheets. In a few layer graphene as disclosed herein the lowest number of layers is 2, the maximum number of stacked graphene layers is 100 and the interlayer distance in graphene is 0.348±0.003 nm, compared to 0.337 nm in graphite. [8]. The lower bound for the largest diameter of the stacked graphene flakes is 10 nm, the upper bound is 5,000 nm.

The number of nanosheets in a graphene particle in the sense of the disclosure can be detected by means of Transmission Electron Microscopy (TEM), X-ray diffraction (XRD), Raman spectroscopy and additional techniques identifiable by a skilled person.

In a graphene particle of the disclosure the graphene nanosheets typically have a size ranging from about 20 to about 500 nm (e.g. 200 nm or 150 nm size detected through Transmission Electron Microscopy (TEM) images), where the "size" refers to the maximum point to point distance in the graphene core particle (e.g., diameter in the case of spherical particles, or a diagonal distance in a rectangular shape).

In preferred embodiments, a graphene particle of the disclosure is a few layer graphene particle having 2 to 100 graphene sheet to allow light absorbance properties which enables efficient quenching of a fluorescent signal emitted by a detectable moiety of the disclosure as will be understood by a skilled person upon reading of the present disclosure.

In preferred embodiments of the disclosure, the graphene particle has a further a size of 900 nm or less, preferably, 500 nam or less, more preferably, 350 nm or less and even more preferably between 50 nm and 250 nm to allow formation of a stable core particle of the disclosure in combination with a coating material and detection of target biomarker in picomolar or even femtomolar concentrations.

In particular, pristine graphene sheets forming a graphene particle herein described can be provided according to methods and techniques identifiable by a skilled person.

For example, pristine graphene can be generated via explosion of acetylene/oxygen mixtures in an explosion chamber. The graphene nanosheets so generated aggregate in the gas phase and form aerogels, which can be harvested according to approaches identifiable by a skilled person to provide graphene also identified as Detonation graphene or Explosion Graphene.

Pristine graphene can also be obtained from graphite via oxidative exfoliation. According to a related method graphite is oxidized under chemically very harsh conditions (e.g. Hummers Methods) and heat, yielding oxidized single layer graphene (named graphene oxide). Graphene oxide is then reduced to few layer pristine graphene using hydrazine or other reductants according to approaches identifiable by a skilled person. [9]

Pristine graphene can also be obtained by performing flash synthesis. Accordingly, Organic materials can be transformed into few layer graphene by applying direct currents according to approaches identifiable by a skilled person to obtained flash graphene. [10, 11]

Pristine graphene can also be obtained through CVD (chemical vapor deposition) which generates graphene monolayers on substrates (not suitable for sensitive optical biosensors) according to approaches identifiable by a skilled person to provide CVD graphene.[9]

In some embodiments of graphene core particles herein described, pristine graphene starting materials are preferably prepared using detonation-synthesized graphene or flash synthesized graphene which can be prepared with processes and approaches identifiable by a skilled person (see e.g. [12], [8], [13], [14] incorporated by reference herein in their entirety).

Preparation of detonation sized graphene entails, inter alia, a one-step process involving the controlled detonation of carbon-containing material(s) as a solid, liquid, or gas, with an oxidizing agent or source of oxygen (e.g., $O_2$, $N_2O$, NO) in a reaction vessel at relatively high temperatures to produce pristine graphene nanosheets and ramified fractal aggregates of these nanosheets without the use of catalytic materials. In general, the reaction vessel is loaded with the desired amount of reactants and a spark is used to achieve detonation of the materials. An aerosol is produced which often undergoes gelation to form an aerosol gel comprising graphene particles. ([15] and ([16]).

In a scaled-up approach, the apparatus comprises a reaction chamber, a vacuum source operably connected with the reaction chamber, and an ignition assembly. The reaction chamber is operably coupled with a source of a carbon-containing material and a source of an oxidizer. The vacuum source is operable to selectively evacuate at least a portion of the contents of the reaction chamber, especially following generation of the particulate materials. The ignition assembly is also operably connected to the reaction chamber and configured to initiate combustion of a quantity of the carbon-containing material and a quantity of the oxidizer delivered to the reaction chamber from their respective sources. The ignition assembly comprises a pair of electrodes that are operable to generate an ionizing arc therebetween, each electrode is contained within a respective cassette that is removably received within the ignition assembly. A scaled-up apparatus and synthesis process for mass production of pristine graphene is described in co-pending U.S. Ser. No. 63/039,087, filed Jun. 15, 2020 and corresponding PCT/US2021/037321, filed Jun. 15, 2021, each incorporated by reference herein.

Exemplary carbon-containing materials to use for the reaction include, carbon-rich precursors, gases, gas mixtures, powders, aerosols, and other injectable materials. The carbon-containing material may comprise a single material or compound, or a mixture of carbon-containing compounds. Examples include coal, petroleum coke, biochar, carbon black, biowaste (e.g., food or agricultural waste products), biomass or organic waste (e.g., cellulosic materials, grasses, etc.). It will be appreciated that higher carbon content materials are particularly preferred. The starting material can include any hydrocarbon compound, and in particular a saturated or unsaturated $C1-C_{12}$ hydrocarbon compound, with highly saturated C1-C12 hydrocarbons being particularly preferred. In particular embodiments, preferred hydrocarbon materials include acetylene, ethylene, toluene, butadiene, and/or isoprene. The temperature and/or pressure parameters can be adjusted according to the selected material.

In one or more embodiments, the combustion reaction occurs at a temperature of at least 3000 K, at least 3500 K, or at least 4000 K. In particular embodiments, the combustion reaction occurs at a temperature of between about 3000 K to about 5000 K, between about 3500 K to about 4500K, or about 4000 K. It has been discovered that the combustion of the carbon-containing materials and oxidizer at these temperatures favors the formation of highly ordered graphene particulates as opposed to graphitic soot. Inert gaseous materials such as helium, neon, argon, or nitrogen can be included in the reaction mixture charged into the reaction vessel to assist with temperature control during combustion, if necessary. Also, in certain embodiments, especially in embodiments in which the combustion reaction is a detonation, the combustion of the reaction mixture proceeds very quickly. Detonation typically involves a supersonic exothermic front that accelerates through a medium and eventually drives a shock front propagating directly in front of it. In certain embodiments, the combustion has a duration of between about 5 to about 100 ms, between about 10 to about 75 ms, or between about 20 to about 50 ms.

The ratio of oxidizing agent to carbon-containing material present in the reaction vessel prior to detonation can contribute to the characteristics of the graphene particulates formed upon detonation of the reaction mixture. In certain embodiments, the molar ratio of oxidizing agent to carbon-containing material is 1.5 or less, preferably 1.0 or less, even more preferably 0.5 or less. In particular embodiments, the ratio of oxidizing agent to carbon-containing material is from about 0.1 to about 1.5, from about 0.18 to about 1.2, from about 0.18 to about 1.0, or from about 0.18 to about 0.8, or from about 0.18 to about 0.5. The process permits the bulk synthesis or large quantities of graphene in excellent purities. For preferred purposes of creating graphene nanosheet particulates of the desired size ranges herein, the ratio of oxidizing agent to carbon-containing material is preferably from about 0.2 to about 0.5, with about 0.3, 0.35, or 0.4 being particularly preferred ratios. Preferred particulates of pristine graphene will range from about 20 to about 500 nm in size with approximately 150 nm+/−20 nm being a target size range. Notably, it is not necessary for the biosensor of the disclosure that the resulting particulates be monodisperse. Rather, polydisperse graphene particulate mixtures can be easily used to prepare the biosensors. In fact, according to light scattering experiments the graphene aggregates feature super-aggregate fractal morphology with a fractal dimension of Df=2.5±0.1 on micron scales composed of smaller aggregates with fractal dimensions of $D_f$=1.8±0.1. This behavior has previously not observed for metal, metal-oxide, metal/metal oxide, or semiconductor particles in (nano)biosensors.

Alternative approaches for synthesizing pristine graphene include flash graphene (PCT/US2019/047967, filed Aug. 23, 2019, WIPO publication WO2020/051000, incorporated by reference herein), which uses flash Joule heating of various carbon-based materials or other carbon sources, such as coal, petroleum coke, biochar, carbon black, food waste, rubber tires, and mixed plastic waste to convert the material to graphene. The carbon source is lightly compressed in a reaction vessel between two electrodes, and a high voltage discharge from a capacitor bank brings the carbon source material in the reaction vessel to at least 3000 K in less than 100 ms. The process converts the amorphous carbon in the carbon source into flash graphene. Yields in this process depend heavily on the carbon content of the starting material. In some embodiments, the carbon source material may be mixed with carbon black or another similar conductive material to improve the conductivity of the material. In some embodiments, the flash graphene has an average particle size of less than 20 nm. In some embodiments, the flash graphene is produced in the form of larger, but thin sheets of average size of 0.5 to 1.2 μm. Such thin sheets may be suitable for alternative sensors where graphene nanosheets in single layers are deposited onto a solid surface, instead of used in particulate form.

The pristine graphene that results from these new synthesis processes can adopt various morphologies, but preferably is in the form of ramified fractal aggregates, nanosheets, crystalline flakes, nanoplatelets and platelet chains, as single or multilayer graphene, and can be generally characterized macroscopically as a fluffy or fuzzy black powder or particulate material of high purity (>98.5% carbon).

The particulates can be observed under an electron microscope as thin monolayers entangled with each other with overlapped edges, or more ordered stacking of nanosheets comprising or consisting of two to three layers, but potentially up to 25 layers, potentially up to 10 layers, for example 2 to 25 layers, and even more preferably about 5 to about 10 layers (with overall sizes ranging from 20 nm to 500 nm).

Thus, references herein to "pristine" graphene are used specifically to denote the highly pure graphene produced by high temperature (e.g., ~>3000K) conversion of a carbon source into graphene (e.g., rapid heating or combustion of amorphous carbon into detonation graphene, flash graphene, etc.) as compared to graphene made via organic synthesis, chemical-vapor deposition, or exfoliation from graphite. In other words, the pristine graphene is preferably essentially free of graphite or graphite oxide. As such, the pristine graphene is highly pure meaning that it is essentially free (less than 0.5% w/w, preferably less than 0.1% w/w) of foreign substances and impurities, with a carbon content of at least about 98.5%, and preferably at least 99% (and conversely an oxygen content of less than 1%). A discussion of detection of detonation graphene with Transmission Electron Microscopy (TEM) is provided in Example 21 and related FIGS. 19A and 19B which show exemplary TEM images of pristine detonation graphene.

In some embodiments relates to biosensors based upon pristine graphene nanosheet particles and related core particles, materials comprise detonation graphene preferably 0.25, 0.30, or 0.35).

In some most preferred embodiments the graphene nanosheet particulate comprises an aggregate of graphene in fractal form.

The term "fractal" as used herein in connection with an object indicates an object that displays a property known as self-similarity, i.e. a geometric shape that can be reduced to smaller parts, with each smaller part being a reduced copy of the whole. A fractal dimension is a statistical quantity that describes how a fractal appears to fill space. [17]

Accordingly, typically, stacked few layer graphene features in fractal form have fractal dimensions between Df=2.5±0.3 (upper bound) and Df=1.8±0.4 (lower bound) as will be understood by a skilled person [8] (see also Example 1).

The fractal nature of graphene vs. other nanomaterials used in biosensors can be ascertain by light scattering methods such as SEM (Scanning Electron Microscopy) [18], and additional techniques identifiable by a skilled person, such as light-scattering methods[19]] (see also Example 1)

In graphene core particles herein described, more than one graphene nanosheets are coated with a coating layer of an organic and/or inorganic material. Accordingly, in order to allow coating, the graphene nanosheets are functionalized or derivatized to present a functional group on the surface capable of binding corresponding functional group presented on organic and/or inorganic material to allow formation of the coating layer.

The term "functional group" as used herein indicates specific groups of atoms within a molecular structure that are responsible for a characteristic chemical reaction of that structure. Exemplary functional groups include hydrocarbons, groups containing double or triple bonds, groups containing halogen, groups containing oxygen, groups containing nitrogen and groups containing phosphorus and sulfur all identifiable by a skilled person.

The term "corresponding" used in connection with elements such as functional groups identify two or more elements capable of reacting one with another under appropriate conditions. Typically, a reaction between corresponding moieties and in particular functional groups, results in binding of the two elements.

The term "bind", "binding", "conjugation" as used herein indicates an attractive interaction between two elements which results in a stable association of the element in which the elements are in close proximity to each other. If each element is comprised in a molecule the result of binding is typically formation of a molecular complex. Attractive interactions in the sense of the present disclosure includes both non-covalent binding and, covalent binding. Covalent binding indicates a form of chemical bonding that is characterized by the sharing of pairs of electrons between atoms, or between atoms and other covalent bonds. For example, attraction-to-repulsion stability that forms between atoms when they share electrons is known as covalent bonding. Covalent bonding includes many kinds of interaction, including σ-bonding, π-bonding, metal to non-metal bonding, agostic interactions, and three-center two-electron bonds. Non-covalent binding as used herein indicates a type of chemical bond, such as protein protein interaction, that does not involve the sharing of pairs of electrons, but rather involves more dispersed variations of electromagnetic interactions. Non-covalent bonding includes ionic bonds, hydrophobic interactions, electrostatic interactions, hydrogen bonds, and dipole-dipole bonds. Electrostatic interactions include association between two oppositely charged entities.

Exemplary pairs functional groups and the corresponding coupling chemistry are shown in the following Schemes (I) to (IX).

Scheme (I)

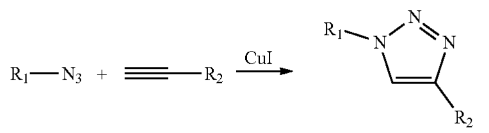

Scheme (II)

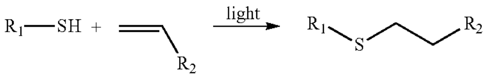

Scheme (III)

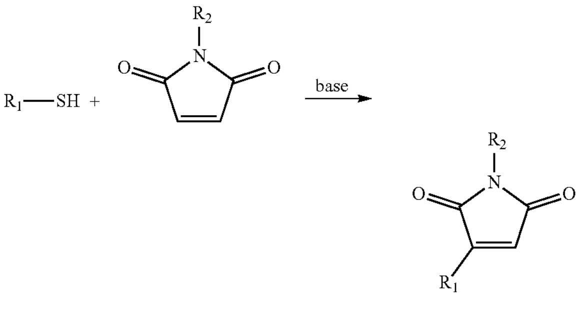

Scheme (IV)

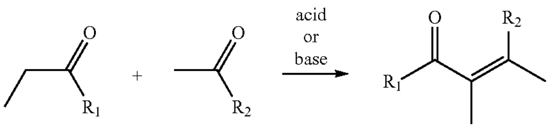

Scheme (V)

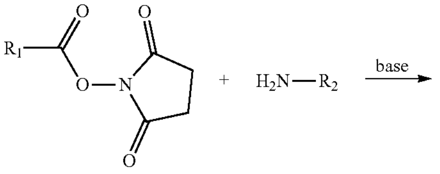

-continued

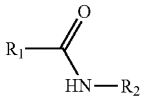

Scheme (VI)

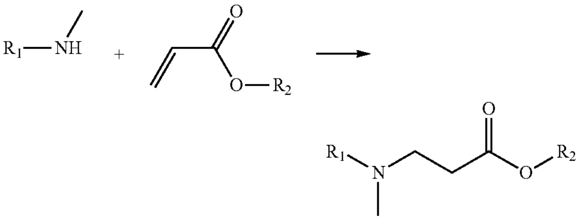

Scheme (VII)

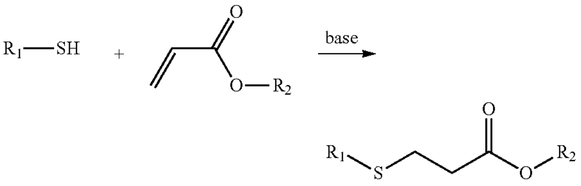

Scheme (VIII)

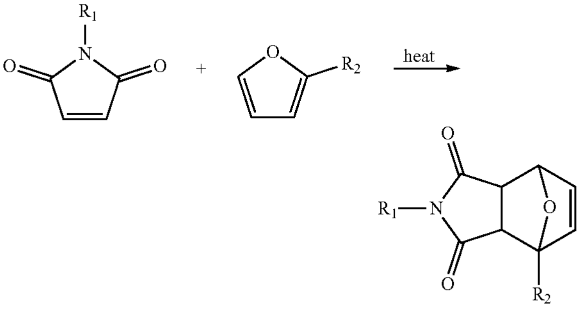

Scheme (IX)

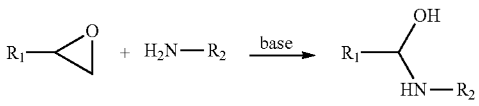

Additional pairs of corresponding functional groups in the sense of the disclosure will be identifiable by a skilled person.

In embodiments herein described, the pristine graphene nanosheet particulates obtained with methods described herein can be functionalized with a suitable functional group as described herein to facilitate preparation of derivative compounds suitable for use as the core particle for the biosensors. Graphene can be functionalized using a chemical modification of organic groups via covalent functionalization. Another approach involves a Fenton oxidation process described in detail in PCT/US2020/038055, filed Jun. 17, 2020, incorporated by reference herein. In this process, the surface of stacked graphene is oxidized utilizing ferrous sulfate and hydrogen peroxide as oxidants, resulting in creating >95% of carboxylic acid functions at the surface. All other possible functional groups, such as hydroxides, aldehydes, ketones, or oxiranes are present at <5%.

The methods generally comprise reacting pristine graphene particulates with hydrogen peroxide in an aqueous reaction solution at low pH (<5.0) in the presence of a source of iron. The reaction solution is agitated or stirred for a period of time to react hydroperoxyl radicals generated in the reaction solution with the graphene particulates to oxidize the outer surface of the pristine graphene particulates in solution and yield graphene/graphene oxide particulates. The resulting graphene/graphene oxide particulate comprise a graphene core with a thin graphene oxide surface coating or shell that can be readily modified via various reactions.

In a particular embodiment, a preferred graphene derivative having a high density of surface —COOH groups, referred to herein as "carboxygraphene" can be synthesized using pristine graphene and surface functionalization based upon cycloaddition of nitrene which yields a stable azirane anchor. In a particular process, pristine graphene nanoparticulates are dispersed in a suitable organic polar solvent system, such as anhydrous dimethylformamide (DMF), dimethylacetamide (DMA), dimethyl sulfoxide (DMSO), acetone, acetonitrile, or chloroform, at room temperature. After the dispersion is complete, carboxylic acids with a primary or secondary halogen (e.g., chloroacetic acid, 3-iodopropionic acids, 4-bromo-butyric acid, 4-bromovaleric acid, 5-bromovaleric acid, etc.) are added, followed by the addition of anhydrous hydrazoic acid, or its azide derivatives, such as anhydrous sodium azide ($NaN_3$), lithium azide, and/or potassium azide. The temperature of the reaction solution is then slowly increased (~1° C./minute) to about 80° C. Between 20° C. and 40° C., a nucleophilic substitution reaction ($S_N$) occurs, in which an organic azide and solvent-soluble sodium halogenide are formed. The organic azide releases dinitrogen ($N_2$) and forms a nitrene intermediate at temperatures above ~50° C. Nitrenes feature 6 instead of 8 electrons in the outer shell of nitrogen. This reactive intermediate undergoes a cycloaddition with a II-II double bond at the surface of the graphene honeycomb lattice to form a stable azirane anchor (three-membered C—N—C ring). The azirane-cycloaddition offers the opportunity to add a tailored amount of carboxylic acids to the surface of graphene without compromising the optical and electrical properties of the graphene itself. In this case, a high density of carboxylic acid groups can be added across the surface of the graphene nanosheet particulates for further functionalization and/or interaction with a water-soluble polymer coating (see Examples 2 to 9).

In some embodiments additional functional modifications of graphene can be described to allow further reaction and formation of a coating layer according to the disclosure. In this connection, Although aliphatic linkages are used for functionalization herein, aromatic reactions are also described in the literature for chemical amination of graphene surfaces. ([20] incorporated by reference herein (see Example 10).

Moreover, additional modifications could be carried out to decrease the surface charge of the graphene making it suitable for binding cationic polymers in lieu of or in addition to the functionalizations described above as will be understood by a skilled person upon reading of the disclosure.

In graphene core particles herein described the graphene nanosheets are coated with a coating layer of an organic and/or inorganic material.

The term "coating layer" as used herein indicates a sheet, quantity, or thickness of a material covering a surface or body. In particular a coating layer in the sense of the disclosure indicates a thickness of an organic and/or inorganic material covering the surface of a graphene particle. In a graphene core particle of the disclosure the coating layer has two major functions: a) permit the dispersion of graphene in aqueous buffers and b) maintaining a distance of attached detectable moiety of disclosure of <20 nm to facilitate effective quenching in their tethered state.

In particular in embodiments herein described a coating layer is applied of a hydrophilic organic and/or inorganic compound having a solubility in water of 1% by weight at 25 degree C.

The term "organic compound" as used herein indicates any chemical compounds that contain carbon-hydrogen bonds and the ability to facilitate and/or accept hydrogen bonds from water. All or part of the hydrogen atoms in an organic compound can be substituted by other atoms.

The term "inorganic compound" as used herein indicates a chemical to any chemical substance that does not contains C—H bond. Typically an inorganic compound that features at least one element that heavier than fluorine In particular, an organic and/or inorganic compound suitable to provide biosensors herein described a solubility in water of at least 10 grams per liter $H_2O$ and is able to be covalently linked to, or in water electrostatically stably attached to, the graphene as described herein as will be understood by a skilled person.

In some embodiments, an organic and/or inorganic compound suitable to provide biosensors herein described feature a consensus log P (or c Log P)<0.

A c Log P value in the sense of the disclosure refers to the logarithm of its partition coefficient between n-octanol and water log(Coctanol/Cwater) as is known by a person skilled in the art. High lipophilicity corresponds to a high c Log P value. Organic molecules of coatings of the present disclosure can be configured with a combination of moieties and/or substituents to have specific c log P values as will be understood by a skilled person upon reading of the present disclosure.

Coating material according to the present disclosure are expected to have a range of c Log P between 1 and −2.5 preferably from 0 to −2.

In some embodiments the inorganic compounds comprise mesoporous silica, mesoporous silazanes, aluminum oxide, tin oxide, titanium dioxide, zirconium dioxide, oxides of lanthanides. Alkoxide and alkoxy-amine, and amine-precursors (e.g. $Si(NH—CH_3)_4$; $Si(O—CH_2—CH_3)_3(CH_2—CH_2—CH_2—NH_2)$; $M(O—CH_2—CH_3)_4$ with M=Si, Sn, Ti, Zn; or $M(O—CH_2—CH_3)_3$ with (M=Al or lanthanide(III) cations) react with hydroxyl groups, carboxylic acids, or oxirene rings at the surface of graphene or chemically modified graphene to for stable O-metal bonds. This is followed by hydrolysis of the alkoxy, alkoxy-amine, and amine-bonds around the graphene-attached metals, resulting in semiconductor-oxides and metal-oxides layers surrounding graphene. [21]

In particular, in some embodiments the inorganic compound can be a mesoporous silica which is a form of silica having pores with diameters between 2 and 50 nm. Mesoporous silica can be prepared with starting material, for example, of tetraethyl orthosilicate (TEOS) or (3-mercaptopropyl)trimethoxysilane, often abbreviated to MPTMS. In an exemplary process, the silica precursors will be deposited in tetrahydrofuran/water mixtures (THF/H2O: 99:1 to 95:5 percent by weight) by stirring at room temperature for 24 h, following by centrifugation at 5,000 RPM for 10 min., redispersing in $H_2O$, followed by collection by means of centrifugation (5,000 RPM for 15 min.). The thickness of the mesoporous silica layers around (stacked) graphene will be determined by the weight ratio between TEOS or MPTMS and graphene (0.001/1.0 to 0.1/1) as will be understood by a skilled person.

In embodiments, where the inorganic compound is a mesoporous silica functionalization of the silica surface featuring polar Si—OH groups (silanol) can be achieved, for example, by one of the following steps:

Silyl ether formation: Si—OH+X—R→Si—O—R+HX, X=halogen), followed by organic chemistry. For that purpose, the organic group R gas to contain a polar functional group.

Tethering the C-terminal end of a peptide sequence or a carboxylic ester group in its side chain to an amine group contained in the coating by means of a stable amide bond.

Reacting the mesoporous silica layer (or metal oxide layer) around graphene with $SiCl_4$, $SiHCl_3$, $SiH_2Cl_2$ or $Si(CH_3)_2Cl_2$, and subsequent chemisorption of the N-terminal end of a peptide to the Si—Cl groups on the surface. This can also be achieved by reacting a polar hydroxyl, thiol, or carboxylic acid group.

Polar Si—Cl groups on the surface can react with $NaN_3$ (sodium azide) to form silicon-azides, which undergo click reactions.

In some embodiments the organic compounds comprise aliphatic amines, aromatic amines, oligoethylene glycols, aliphatic oligoamines, ethylene oligoimines, aliphatic carboxylic acids, aromatic carboxylic acids, aliphatic alcohols, aliphatic sulfonic acids, aromatic sulfonic acids, and combinations thereof.

In some embodiments an inorganic and/or organic compound forming the coating layer comprises one or more polymers. The term "polymers" as used herein indicates a substance or material consisting of very large molecules, or macromolecules, composed of many repeating subunits. Polymers can be organic or inorganic, synthetic and natural and are usually created via polymerization of many small molecules, known as monomers. Their consequently large molecular mass, relative to small molecule compounds, produces unique physical properties including toughness, high elasticity, viscoelasticity, and a tendency to form amorphous and semicrystalline structures rather than crystals as will be understood by a skilled person [22])

In one or more embodiments, the coating organic polymer can be represented by Formula (I).

Formula (I)

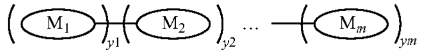

wherein M1 to Mm are polymerized monomeric moieties formed by a same or different polymerizable organic monomers, wherein m ranges from 1 to 10 and y1, y2 to ym are each independently 1 to 1,000.

In particular, exemplary polymerizable organic monomers comprise aziridine propylene oxide, ethylene glycol, acrylic acid, methacrylic acid, 2-hydroxyethyl methacrylate, methacrylamide, N-iso-propylacrylamide, 2-hydroxypropyl methacrylate, N-vinylpyrrolidone, 2-vinylpyridine, 2-vinylpyridine N-oxide, 2-ethyl-2-oxazoline.

Accordingly, in one or more embodiments, one or more water-soluble organic polymers can then be added to the surface of the graphene derivative (e.g., carboxygraphene). Examples for suitable water-soluble polymers of Formula (I) include polyethyleneimine, polycaprolactone, polyethylene glycol, polyvinyl alcohol, polyvinylpyrrolidone, (meth) acrylate- and (meth)acrylamide polymers, polystyrene-carboxylic acid, polystyrene-amine, as well as natural biopolymers (e.g., dextran, pullulan, chitosan, alginate, cellulose, and hyaluronic acid) as well as mixtures or co-polymers thereof.

In some embodiments, the polymers comprise or consist of homopolymers such as polyethyleneimine, polycaprolactone, polyvinyl alcohol, polyglycolate, polyvinylpyrrolidone, (meth)acrylate- and (meth)acrylamide polymers, polystyrene-carboxylic acid, polystyrene-amine, polystyrene-sulfonic acid, dextran, pullulan, chitosan, alginate, cellulose, and hyaluronic acid, and mixtures or co-polymers thereof.

In some embodiments, the polymer comprise or consist of block copolymers. In those embodiments when block copolymers are being used, hydrophobic polymers, such as polystyrene, polyisobutylenes, polyvinylchloride, polyethylene, polypropylene and additional can be components of block copolymers as long as the block co-polymer features a consensus log P<0, or a solubility in water of $>1.0\times10^3$ grams per liter $H_2O$.[23] Hydrophobic polymers are expected to be adsorbed on the surface of pristine graphene, whereas their hydrophilic component will mediate water-dispersibility. In some of those embodiments, where the surface charge of -graphene is positive (zeta potential=+60 mV) such as in explosion graphene, [1, 8] this allows the combination of hydrophobic and charge attraction when negatively charged polymers, such as polystyrene-sulfonic acid are used in block copolymers of polystyrene and additional organic co-polymers identifiable by a skilled person.

In some embodiments wherein, hydrophobic-hydrophilic block copolymers are used, the block copolymers will be dissolved in a solvent that also disperses graphene well (e.g. dimethylformamide (DMF)). Under continuing sonication, $H_2O$ is added to the mixture, forcing the hydrophobic end of the block-copolymer to bind to graphene. This bond is strengthened due to the presence of negatively charged groups in the hydrophobic-hydrophilic block copolymers as will be understood by a skilled person.

In some embodiments, preferred organic polymers comprise one or more of polyethyleneimine, polycaprolactone, polyethylene glycol, polyvinyl alcohol, polyvinylpyrrolidone, (meth)acrylate- and (meth)acrylamide polymers, as well as polystyrene-carboxylic acid and polystyrene-amine. Other preferred coatings are chemically modified oligoethylene glycols, and oligoimines, and starburst dendrimers.

In some embodiments the graphene particles can be coated with a monolayer of water-soluble organic molecules, for instance oligoethylene glycols, which can be tethered to the surface of graphene (see Example 32).

Aliphatic oligoimines, aliphatic thioethers, starburst dendrimers, water-soluble peptides (other than consensus sequences), carbohydrates (e.g. galactose, glucose, mannose, fructose, sialic acid, hyaluronic acid, dextran, glycan-like Gb3 trisaccharides, galabiose). Note that all carbohydrates can be aminated in various positions.

In some embodiments the graphene particles can be coated by an inorganic water-soluble shell (for instance a mesoporous silica nanolayer). Preferred are mesoporous silica, mesoporous aminosilica and titanium dioxide.

In graphene core particles of the disclosure, one or more organic and/or inorganic compounds are reacted with a functional group presented on the surface of the graphene nanosheets (e.g. a carboxylic group see Examples 3 to 9) to form a thin and tight layer of polymer around the graphene aggregates (as opposed to a thick layer or halo). (see Example 30, Example 32, Example 35). [24]

In embodiment of the disclosure, graphene core particles comprising more than one pristine graphene nanosheets coated by a coating layer of an organic and/or inorganic compound having a solubility in water of 1% by weight at 25 degree C. has been surprisingly be found to be stable in an aqueous solution and capable of attaching a detectable component specific for a target biomarker.

It has been surprising found that graphene particle with the above features exhibit a stability in aqueous solutions which can exceeds 20 or even 30 days. Additionally, it has been found that depending on the concentration, possible sedimentation of graphene particles so coated can be addressed by dispersing the particles e.g. through sonication so that a solution can be obtained comprising more than 95% of particles as will be understood by a skilled person.

In particular, the biosensor as described are chemically stable and physically stable in a buffer suspension defined by a decrease of equal to or less than 20%, preferably equal to or less than 10%, and more preferably equal to or less than 1% over 30 days in the light absorption of the detectable moiety in the buffer suspension.

The term "stable" and "stability" as used herein indicate chemical stability as well as colloidal stability.

The term "chemical stability" as used herein refers to the preservation of chemical identity of a biosensor. As a skilled person would understand, biosensor as described herein comprises chemical bonds that connect each component of the biosensor together, including graphene, coating material, peptide, and detectable moiety. It is further to be understand that each of graphene, coating material, peptide, and detectable moiety comprises chemical bonding that connects atoms together to form the graphene, coating material, peptide, and detectable moiety. A preservation of chemical identity of a biosensor is mean that none of the chemical bonds that make up the biosensor is not broken and no new chemical bond is formed. Such chemical integrity can be ascertained by measurements including but not limited to elemental analysis, UV-vis absorption spectroscopy, magnetic resonance spectroscopy, RAMAN spectroscopy, IR spectroscopy, and fluorescence spectroscopy.

The term "colloidal stability" as used herein refers to the preservation of physical state of a colloidal suspension of a biosensor. colloidal stability depends on several types of interactions including Van der Walls and electrostatic interactions (classical Derjaguin-Landau-Verwey-Overbeek (DLVO) theory), steric interactions (e.g. polymer adsorption), and hydrophobic effect. Electrophoretic light scattering (ELS) is a common technique used to evaluate the potential of dispersion to remain stable. ELS allows measuring zeta-potential of a dispersion, which provides information about electrostatic interactions and, by extrapolation, to their tendency to agglomerate. The zeta-potential is considered to be a reliable indicator of dispersion stability, but several parameters such as steric effects, sedimentation, or hydrophobic effects, will also have a strong influence.

In some embodiments, herein described core graphene particles and related biosensor are chemically stable and physical stable in a buffer suspension defined by a decrease of equal to or less than 20%, preferably 10%, and more preferably equal to or less than 1% over 30 days in the light absorption of the detectable moiety in the buffer suspension.

Accordingly, in embodiments herein described a stable graphene core particle of the disclosure refers to a graphene particle which when included in suspension in an aqueous solution, result in a solution in which at least 95% particles remain in suspension with a change in colloidal stability of ~24% or less at OD650.

In particular, data have been obtained reflecting changes of colloidal stability are 26% or less, with subranges. 22% and 25% averaging 24% settling reflecting the worst performance of 4 lots of nanobiosensors according to the disclosure. In one representative embodiment, the stability of graphene at 60 min measured at OD650 showed a 9% and 10% decrease in absolute colloidal stability for NE and MMP15 nanobiosensors (see Lot 4 in Example 40). It is therefore expected less than 10% decrease in colloidal stability in an aqueous solution of graphene biosensors of the disclosure according to preferred embodiments.

In particular, in preferred embodiments herein described, a stable graphene core particle of the disclosure, comprise one or more organic and/or inorganic compounds reacted to form a coating layer of 1-20 nm thickness with a packing density of at least $2.40\pm0.05\times10^{-5}$ mol/g, preferably up to $6.0\pm0.5\times10^{-4}$ mol/g.

Accordingly, in preferred stable graphene core particle of the disclosure the minimal geometric extension of the attached coating layer is 0.45 nm and can go up to 20 nm and the coating layer overs at least 50%, preferably at least 85% and more preferably at least 90%. Most preferably, a monolayer of polymer is formed around the graphene, preferably fully encapsulating the graphene nanosheets therein. In most preferred embodiments, the graphene particle has a size from 10 nm to 5000 nm preferably from 150 to 500 nm on average as determined using scanning electron microscopy and digital light scattering measurements In those embodiments, stability of the graphene core particles can be in terms of months and even years with examples of graphene particles and related biosensors stable in aqueous solution for more than 12 months as will be understood by a skilled person upon reading of the present disclosure.

The determination of surface coverage is performed by comparing the BET surface. The Brunauer-Emmett-Teller (BET) theory aims to explain the physical adsorption of gas molecules on a solid surface and serves as the basis for an important analysis technique for the measurement of the specific surface area of materials. It measures the adsorption of N2 onto graphene at 77K. The result of this measurement is the size of the accessible surface (here: $150\pm40$ $m^2/g$). From titration experiments with polar headgroups (acids or based), we determine the average density of surface groups. Dynamic Light scattering is used to measure the size of the polymers that will be attached, as well as the size of graphene+layer+polymer. Depending on the chemical nature of surface coating and polymer, the zeta potential of the surface is continuously changing until complete surface coverage is achieved.

In some embodiments herein described graphene core particle of the disclosure are combined with detectable components to provide a graphene biosensor herein described. In particular, the graphene biosensor herein described comprises a detectable moiety attached to the graphene core particle through a peptide linkage comprising a recognition sequence specific for a target biomarker.

The term "biomarker" as used herein indicates a biological molecule found in a biological environment that is associated with a biological event. In particular a biomarker can be associated to occurrence of physiological events (biological events, associated with the normal functions of living organisms and their parts) or with modification of physiological conditions and in particular occurrence of sign of a normal or abnormal process, or of a condition.

The term "condition" as used herein with respect to a living organism indicates a physical status of the body of the living organism individual (as a whole or as one or more of its parts), that does not conform to a standard physical status associated with a state of complete physical, mental and social well-being for the individual. Conditions herein described include but are not limited to disorders and diseases wherein the term "disorder" indicates a condition of the living individual that is associated to a functional abnormality of the body or of any of its parts, and the term "disease" indicates a condition of the living individual that impairs normal functioning of the body or of any of its parts and is typically manifested by distinguishing signs and symptoms.

Accordingly in embodiments herein described target biomarkers can be selected that are associated to a condition of an individual for diagnostic purpose and/or to see how well the body responds to a treatment for a condition.

Target biomarker of the disclosure are also molecule configured to interact with peptide linkages to modify the related conformation. In some embodiments, the target biomarkers are protein configured for specific interaction with peptide recognition sequences.

The term "protein" as used herein indicates a polypeptide with secondary, tertiary, and possibly quaternary structure. The protein's secondary, tertiary, and quaternary structure can occur on a variety of length scales (tenths of A to nm) and time scales (ns to s), so that in various instances the secondary, tertiary and possibly quaternary structures are dynamic and not perfectly rigid.

The term "polypeptide" as used herein indicates a polymer composed of two or more amino acid monomers and/or analogs thereof wherein the portion formed by the alpha carbon, the amine group and the carboxyl group of the amino acids in the polymer forms the backbone of the polymer. As used herein the term "amino acid", "amino acid monomer", or "amino acid residue" refers to any of the naturally occurring amino acids, any non-naturally occurring amino acids, and any artificial amino acids, including both D and L optical isomers of all amino acid subsets. In particular, amino acid refers to organic compounds composed of amine (—NH2) and carboxylic acid (—COOH), and a side-chain specific to each amino acid connected to an alpha carbon. Different amino acids have different side chains and have distinctive characteristics, such as charge, polarity, aromaticity, reduction potential, hydrophobicity, and pKa. Amino acids can be covalently linked to forma polymer through peptide bonds by reactions between the amine group of a first amino acid and the carboxylic acid group of a second amino acid.

The term "polypeptide" includes amino acid polymers of any length including full length proteins, as well as analogs and fragments thereof. The polypeptide provides the primary structure of a protein wherein the term "primary structure" of a protein refers to the sequence of amino acids in the polypeptide chain covalently linked to form the polypeptide polymer. A protein "sequence" indicates the order of the amino acids that form the primary structure. Covalent bonds between amino acids within the primary structure can include peptide bonds or disulfide bonds. Polypeptides in the sense of the present disclosure are usually composed of a linear chain of amino acid residues covalently linked by peptide bond. The two ends of the linear polypeptide chain encompassing the terminal residues and the adjacent segment are referred to as the carboxyl terminus (C-terminus) and the amino terminus (N-terminus) based on the nature of the free group on each extremity.

Depending on their size, peptides may be classified as oligopeptides (2-20 residues) and polypeptides (>20 residues). Proteins typically consist of polypeptide chains exceeding 50 residues in length. [25] The average lengths of peptides can be estimated to 0.35 to 0.40 nm per amino acid, depending on the 2D structure of the peptide (alpha-helix or amorphous). [25] Note that peptides forming beta-sheets are not suitable for the design of biosensors, because their release kinetics upon enzymatic cleavage is very slow. A peptide of 50 amino acids has a length of 17.5 to 20 nm, depending on its 2D structure. It should also be noted that non-natural amino acids can be used in these peptides, either for anchoring the peptide to the surface of graphene or graphene-attached organic or inorganic shells, or for the attachment of the fluorophore (organic dye or nanostructure).

As used herein the term "amino acid", "amino acid monomer", or "amino acid residue" refers to organic compounds composed of amine and carboxylic acid functional groups, along with a side-chain specific to each amino acid. In particular, alpha- or α-amino acid refers to organic compounds composed of amine (—NH2) and carboxylic acid (—COOH), and a side-chain specific to each amino acid connected to an alpha carbon. Different amino acids have different side chains and have distinctive characteristics, such as charge, polarity, aromaticity, reduction potential, hydrophobicity, and pKa. Amino acids can be covalently linked to form a polymer through peptide bonds by reactions between the amine group of a first amino acid and the carboxylic acid group of a second amino acid. Amino acid in the sense of the disclosure refers to any of the twenty naturally occurring amino acids, non-natural amino acids, and includes both D an L optical isomers.

In preferred embodiments, target biomarker are proteins with a length >50 amino acids such as enzymes and chemokines/cytokine). Some of these enzymes have coenzymes and co-factors, which consist of heterocycles binding metals (for instance all matrix metalloproteinases). Some of these proteins are posttranslationally modified and are attached to sugars or lipids as will be understood by a skilled person.

In additional embodiments, target biomarkers can comprise many inorganic and organic molecules that are capable of changing the conformation of a peptide linkage or cleating the peptide linkage. The term "conformation" as used herein in connection with peptides or proteins is defined as the arrangement in space of its constituent atoms which determine the protein structure (the three dimensional arrangement of atoms in a polypeptide) and the protein overall shape of the molecule. The term "cleavage" as used herein in connection with compounds and peptides indicates a breaking of a chemical bond and/or a chemical reaction that involves a breaking of a chemical bond. Cleavage of a peptide linkage typically results in the enzymatic hydrolysis of a peptide bond in the linkage and in the breaking of the linkage down into smaller peptide moieties as will be understood by a skilled person.

A method to identify an organic and/or inorganic biomarker configured to interact with peptide linkages to modify the conformation of the peptide or to cleave a peptide linkage can be performed by computationally modeling the tertiary structure of a peptide linkage to provide a computationally modeled peptide linkage computationally modeling the tertiary structure of a candidate organic or inorganic biomarker to provide a computationally modeled candidate organic or inorganic biomarker determining the target site of interaction of the computationally modeled peptide linkage and computationally modeled candidate organic or inorganic biomarker determining changes in the computationally modeled peptide linkage following interaction candidate organic or inorganic biomarker in the target site of interaction selecting the computationally modeled peptide linkage and organic or inorganic target biomarker when the determined change is a change in the conformation of the peptide linkage or a cleavage of the peptide linkage In addition or in the alternative the method to identify organic and/or inorganic biomarker configured to interact with peptide linkages the method can comprise Contacting the candidate organic and/or inorganic biomarker with the peptide linkage for a time and under conditions allowing interaction between the candidate organic and/or inorganic compound and the peptide linkage; and Detecting a change in conformation of the peptide linkage and/or cleavage of the peptide linkage, the detecting performed following the contacting to provide a detecting result; and Selecting the organic and/or inorganic biomarker when the detecting result is a detected change in the conformation of the peptide linkage or a detected cleavage of the peptide linkage thus providing the identified organic and/or inorganic biomarker.

A biosensor of the disclosure can then be configured to detect the target compound by attaching the peptide linkage to a detectable moiety and to a graphene core particle of the disclosure selected to have a coating layer of a thickness selected to have the detectable moiety at a quenching distance of 20 nm or less with respect to the graphene particle following the attaching. In particular if the target compound has a detected change in the conformation of the peptide linkage resulting in an increase in the length of the peptide linkage, the coating layer is configured so that in the biosensor provided following the attaching the detectable moiety is at an emitting distance following the increase in the length of the peptide linkage, as will be understood by a skilled person upon reading of the disclosure. The functionality of the biosensor so built can then be tested as will be understood by a skilled person For example identification of protein biomarker and corresponding supramolecular recognition sequences was performed according to the following procedure:

1) The primary structure of the target was retrieved from a data bank (e.g., UniProtKB or Protein Data Bank).
2) The tertiary structure of the target was determined and then refined utilizing proteins structure predicting software, such as the GalaxyWEB protein structure prediction cluster, developed by Dr. Seok at the Computational Biology Lab, Seoul National University, Korea.
3) The primary structure of a monoclonal antibody (MAB) fragment against the target was retrieved from a data source (e.g. Protein Data Bank, SciFinder, or information provided by the vendors of antibodies). A tertiary structure was generated using Galaxy-WEB.
4) A docking procedure between the target and antibody chain is simulated using the Mobyle platform developed by the Institute Pasteur Biology IT Center, Paris, France. This procedure reveals the "true" epitope of the target.
5) A final "site finder" procedure is then performed on the Mobyle platform docking the epitope of the target to the improved structure of the antibody(Ab) fragment. This structure reveals the peptide sequence of the Ab fragment that is actually responsible for binding to the target in the example of protein protein interaction.

F)

In addition or in the alternative to the exemplary method for identification of protein biomarker and corresponding supramolecular recognition sequences, a final "site finder" procedure is then performed on the Mobyle platform docking the protease epitope of the target to the improved structure of the protease enzyme active site. This structure reveals the peptide sequence of the active site that is actually responsible for binding to the target.

In addition or in the alternative to the exemplary method for identification of protein biomarker and corresponding supramolecular recognition sequences cleavage sites and sequences for protease targeting can be identified from available sites such as MEROPS (a peptidase database).

In the exemplary method for identification of protein biomarker and corresponding supramolecular recognition sequence, if the supramolecular recognition sequence was linear, it was synthesized and used as a recognition sequence for the nanosensors. It is was not linear, of if the LOD of the resulting nanobiosensor was not at least $10^{-14}$ M, the in silico procedure was repeated using the structural information from another mAb.

In some exemplary embodiments, many organic molecules can also interact with a protein such as an enzymes which are capable to interact with a peptide and change its conformation. In this regard all enzyme inhibitors can change the conformation of a protein which it binds. Exemplary enzyme inhibitors include nonpeptidic HIV-1 protease inhibitor tipranavir, diisopropylfluorophosphate (DFP), anticancer drug methotrexate, penicillin G as inhibitor for *Streptomyces* transpeptidase.

In some exemplary embodiments, the interaction between a target biomarker and a peptide linkage can result in cleavage of the peptide linkage. In particular, in some embodiments the target biomarker comprises be a protease. Exemplary protease includes Serine proteases, Cysteine, Threonine proteases, Aspartic proteases, Glutamic proteases, Metalloproteases, and Asparagine peptide lyases. In general, all known 553 proteases of the human genome are of potential interest (21 aspartic, 143 cysteine, 186 metallo, 176 serine and 27 threonine proteases), as well as their analogues in rodent models can be detected with a biosensor of the disclosure as will be understood by a skilled person [26].

In some embodiments, the target biomarker comprises enzymes performing post-translational modifications of peptides, which change their biophysical properties (dynamic, effective lengths, etc.). Examples are arginase (converting arginine to ornithine) and all groups of enzymes attaching or removing any chemical group to a size chain of a peptide. Examples include enzymes capable of (de)phosphorylation (kinases, phosphatases), glycosylating enzymes (N-glycosylation,)-glycosylation, glypiation, C-glycosylation, and phosphoglycosylation), ubiquination, S-nitrosylation, methylaton, N-acetylation, and Lipidation (C-terminal glycosyl phosphatidylinositol (GPI)) anchor, N-terminal myristoylation, S-myristoylation, S-prenylation).

In some embodiments, the target biomarker comprises proteins (e.g. cytokines/chemokines) capable of binding tailored oligopeptides. The binding events change the biophysical properties of the peptides (dynamic, effective lengths, etc. Exemplary biomarker that can be detected comprise all cytokines, chemokines, signalling peptides (e.g. pro-inflammatory factors, anti-inflammatory factors, growth-factors) and hormones are of interest as will be understood by a skilled person.

In embodiments herein described peptides linkage that are part of detectable components of graphene biosensors of the disclosure are selected to bind specifically to a target biomarker of interest as will be understood by a skilled person.

The wording "specific" "specifically" or "specificity" as used herein with reference to the binding of a first molecule to second molecule refers to the recognition, contact and formation of a stable complex between the first molecule and the second molecule, together with substantially less to no recognition, contact and formation of a stable complex between each of the first molecule and the second molecule with other molecules that may be present. Exemplary specific bindings are antibody-antigen interaction, cellular receptor-ligand interactions, polynucleotide hybridization, enzyme substrate interactions and additional interactions identifiable by a skilled person. The wording "specific" "specifically" or "specificity" as used herein with reference to a computer supported tool, such as a software indicates a tool capable of identifying a target sequence (such as the one of a marker herein described) among a group of sequences e.g. within a database following alignment of the target sequence with the sequences of the database. Exemplary software configured to specifically detect target sequences comprise Primer-3, PerlPrimer and PrimerBlast. simultaneously measure multiple analytes in a single experiment.

In some embodiment, the recognition sequence can be a supramolecular recognition sequence or consensus sequence for the target protein, which means that the linkage recognition has specificity (i.e., contains a selective binding site) for the target protein). Thus, it will be appreciated that the recognition sequences avoid non-specific binding motifs. Further, the oligopeptide linkage can be "cleavable," or it can be "non-cleavable." Recognition sequences described herein are preferably cleavable for rapid diagnosis.

In embodiments of graphene nanobiosensor of the disclosure peptide linkages can include any variety of recognition sequences or consensus sequences for the biomarker of interest, which means that the linkage sequence has specificity for (i.e., contains a selective binding and/or cleavage site for) the target biomarker. Thus, it will be appreciated that the linkage sequences avoid non-specific binding motifs. The peptide linkages are typically short, linear oligopeptides that position the detectable moiety within suitable proximity of the graphene carrier particle for quenching. In particular embodiments, the peptide linkages can be less than 100 amino acid residues in length, preferably less than 75 amino acid residues in length, more preferably 50 amino acid residues or less. In most preferred embodiments the peptide linkages will be shorter and have less than 50 amino acid residues in length, more preferably less than 30 amino acid residues in length even more preferably 20 amino acid residues or less.

For example, in a graphene biosensor of the disclosure a peptide linkage can range from 4 to 50 amino acid residues, more preferably from 4 to 30 amino acid residues and even more preferably 10 to 20 amino acid residues. As used herein, references to "specific interactions" or "specificity" in connection with recognition intended to differentiate the recognition sequences from non-specific binding or reactions between molecules and means that the set of specific target biomarkers for which the oligopeptide sequence can interact is limited, and in some cases even exclusive, such that neither binding nor enzymatic cleavage occurs at an appreciable rate or frequency with any other molecule except for the target biomarker.

In particular, in embodiments herein described specificity of a peptide linkage for a target biomarkers result to minimal interactions of the peptide linkage for a biomarker different from the specific biomarker targeted by the peptide linkage as will be understood by a skilled person.

The biosensors can be configured to target a wide variety of biomarkers, depending upon the selected recognition sequence. Examples include numerous enzymes including proteases, kinases, arginases, cytokines/chemokines, dioxygenases (e.g., indoleamine 2,3-dioxygenase 1, and/or tryptophan 2,3-dioxygenase), esterases, and the like, which can then be correlated to a particular health status in the sample being tested. For example, such biomarkers can be indicators of cancer or precancerous cellular activity, bacterial activity, inflammation, etc. and are known in the literature. In one or more embodiments, the recognition sequence comprises, consists essentially, or even consists of a "consensus sequence," which refers to an enzyme substrate (peptide sequence) that undergoes enzymatic cleavage in the presence of the target analyte (e.g. protease, esterase, etc.). Such consensus sequences are described, for example, in U.S. Pat. Nos. 8,969,027 and 9,216,154, U.S. Publication No. 2017/0219548, each incorporated by reference herein to the extent not inconsistent with the present disclosure. The relevant consensus sequences are provided in the table of this disclosure. The guiding paradigm is that for very proteases a consensus sequence can be designed in-silico that will be cleaved faster by its target protease than by any other protease.

In one or more embodiments, the recognition sequence comprises, consists essentially, or even consists of a recognition sequence for detection of enzymatic posttranslational modification as described, for example, in WO 2016/149637, filed Mar. 18, 2016, incorporated by reference herein to the extent not inconsistent with the present disclosure. In this embodiment, arginine in GR7G is converted to ornithine GO7G, thus changing the dynamics and geometric extension of the peptide, which enables fluorescence detection in optical Fe/$Fe_3O_4$ nanobiosensors. Other posttranslational enzymes that were detected areindeolamine-2,3-dioxygenase and tryptophan 2,3-dioxygenase as will be understood by a skilled person.

In the presence of a target biomarker such as a target enzyme, the enzyme modifies the recognition sequence (without cleavage), and more particularly modifies both the primary structure (amino acid residues and metabolic products) and the secondary structure of the recognition sequence. Such "modification" or "posttranslational modification" as used herein, refers to conversion or transformation of the amino acid residues (and particularly the side chains) in the substrate sequence to a different form and/or different residue. This, in turn, extends, "unfolds," or "unravels" the secondary structure and/or increases and/or decreases the mobility of the recognition sequence. In one or more embodiments, the recognition sequence comprises, consists essentially, or even consists of a supramolecular recognition sequence to detect physical binding without chemical modification or enzymatic cleavage. In particular, the target protein binds to the supramolecular recognition sequence linearly, such that the initial folded secondary structure, such as an alpha-helix and/or beta-sheet structure, is modified and linearly extends or unfolds. In each instance, interaction of the target analyte (e.g., protein, enzyme, etc.) with the recognition sequence gives rise to a detectable change in the biosensor, which is indicative of the presence of the target analyte.

In one or more embodiments, the recognition sequence comprises, consists essentially, or even consists of a recognition sequence for a biomarker of inflammation, infection, and/or bacterial activity as described, for example, in WO2016/018798, filed Jul. 27, 2015, incorporated by reference herein to the extent not inconsistent with the present disclosure. In some of those embodiments, target biomarkers can be enzymes indicative of inflammation, infection, and/or bacterial activity such as MMP-8, MMP-9, MMP-11, MMP-14, and neutrophil elastase in comparison to MMP-1, MMP-2, MMP-3, MMP-7, MMP-12, and MMP-13. Other enzymes target biomarker that are considered partially indicative of inflammation, infection, and/or bacterial activity were Cathepsins-B, -D, -E, -K, and -L and urokinase plasminogen activator as will be understood by a skilled person.

In general, enzymes such as proteases and/or esterases are exemplary biomarkers indicative of inflammation, infection, and/or bacterial activity. The recognition sequence is selected to be cleavable by a protease or esterase either specifically (e.g., using a consensus sequence cleavable only by a target protease) or generally (e.g., using sequences cleavable by any protease or esterase). Upon cleavage of the linkage, the particles are released from one another, giving rise to the spectral change that can be detected in the system.

The recognition sequence is typically provided as part of an oligopeptide linkage between the detectable moiety and the pristine graphene carrier particle. Suitable oligopeptide linkages will comprise (consist essentially or even consist of) the recognition sequence for the target biomarker, typically along with a terminal carboxylic acid group (C-terminus), and a terminal amine group (N-terminus). The oligopeptide can also comprise a thiol group at the C terminus, and a carboxylic acid group at the N terminus. In some embodiments, the oligopeptide linker comprises a hydrophilic region of at least 10 amino acids N-terminal to the recognition sequence, and a linking region C-terminal to the recognition sequence, wherein the C-terminal linking region comprises a thiol reactive group at its terminus. In some embodiments, the C-terminus of the oligopeptide comprises a cysteine residue, lysine, or aspartate. In some embodiments, the N-terminal hydrophilic region of the oligopeptide has an excess positive or negative charge at a ratio of about 1:1. The N-terminal hydrophilic region can also comprise amino acid residues capable of forming hydrogen bonds with each other.

In some embodiments, the C-terminal and N-terminal linking regions can consist of virtually any amino acid sequence that is non-cleavable (e.g., not a recognition sequence): (X)~-[Recognition Sequence]-$(X)_m$, where X is any amino acid (that in sequence does not result in a cleavage sequence), and each of n and m are less than 5.

In some embodiments, the recognition sequences can include one or more spacer residues on the N- and/or C-terminal ends. For example, between 1 and 10 amino acids (any amino acids, naturally and non-naturally, L- and D-, or combinations thereof) can be used at one or both ends as spacers to further extend the oligopeptide chain length depending upon the detectable moieties selected. Examples include N-terminal sequences such as GAG- and C-terminal sequences such as -AG.

Depending upon the target biomarker, a desired recognition sequence can be selected and synthesized. It will be appreciated that various sequences are also available in the literature or can be determine through in silico binding studies.

Exemplary recognition sequences are listed in the table below with their relevant biomarker. In some cases, a proposed cleavage point is indicated by the "-". Variants of the listed sequences are also contemplated

TABLE 1

Consensus and Recognition Sequences

| Biomarker | Consensus and Recognition Sequences | SEQ ID NO: |
|---|---|---|
| ADAM 17 | LAQA-VVSS | 41 |
| ADAM 33 | GSQH-IRAE | 42 |
| Cathepsin B | SLLKSR-MVPNFN | 43 |
| | GLAG-LVGP | 108 |
| | DAFK | 109 |
| Cathepsin C | TSEE-IRGG | 110 |
| Cathepsin D | GDSG-LGRA | 44 |
| | SLLIFRSWANFN | 111 |
| | SGKPILFFRL | 112 |
| Cathepsin E | EVAL-VALK | 45 |
| | SGSPAFLAKNR | 113 |
| | SGKPIIFFRL | 114 |
| Cathepsin F | GAFR-MCAG | 115 |
| Cathepsin H | EFVR-SPTP | 116 |
| | QFVR-SPSG | 117 |
| Cathepsin K | LGLE-GANL | 46 |
| | AKLK-AENN | 118 |

TABLE 1-continued

Consensus and Recognition Sequences

| Biomarker | Consensus and Recognition Sequences | SEQ ID NO: |
|---|---|---|
| Cathepsin L | AALG-SAPG | 47 |
| | SGVVIA-TVIVIT | 84 |
| | SLLIFR-SWANFN | 48 |
| Cathepsin S | EGLG-QAGN | 119 |
| Cathepsin W | GKKG-AVGE | 120 |
| Cathepsin Z | GFFF-WALG | 121 |
| Granzyme B | VEPN-SLEE | 49 |
| Neutrophil elastase | GEPL-SLLP | 50 |
| | GEPV-SGLP | 87 |
| Gelatinase (bacterial) | GPLGMLSQ | 122 |
| MMP 1 | IPVS-LRSG | 51 |
| | VPMS-MRGG | 88 |
| | GAGVPMS-MRGGAG | 123 |
| MMP 2 | IPVS-LRSG | 51 |
| MMP 3 | RPFS-MIMG | 52 |
| MMP 7 | VPLS-LTMG | 53 |
| MMP 8 | GPSG-LRGA | 54 |
| MMP 9 | VPLS-LYSG | 55 |
| MMP10 | GPSG-LQTG | 124 |
| MMP 11 | GAAN-LVRG | 56 |
| MMP 12 | GVPLS-LTMG | 57 |
| | GPKA-LGLA | 58 |
| MMP 13 | PQGLA-GORGIV | 125 |
| | GPQGLA-GQRGIV | 126 |
| MMP 14 (MT1-MMP) | GPAG-LRLA | 59 |
| | IPES-LRAG | 127 |
| MMP15 | ESDA-SQTG | 128 |
| ALK | RDIYAAPFFRK | 60 |
| AURKB | AMERRRTSAARRSY | 61 |
| CDK2 | KARAAVSPQKRKA | 62 |
| PKD2 | RARKRRLSAPPLASGD | 63 |
| MAPK1 | AKAGPPLSPRPPHVH | 64 |
| JAK2 | DLFIPDNYLKMKPAP | 65 |
| PLK1 | AELDPEDSMDMDMAP | 66 |
| PLK3 | EDEAEELSDEDEELK | 67 |
| ERK1/MAPK3 | AAGPAPLSPVPPVVH | 68 |
| JunK2/MAPK9 | DASRPPPLSPLPSPRA | 69 |
| ARG I/II | GYRFR-ILGGG | 70 |
| UPA | SGA-SAC | 129 |
| | SGRSA | 130 |
| CCL 2 | CQEQFWW | 1 |

TABLE 1-continued

| Consensus and Recognition Sequences | | |
|---|---|---|
| Biomarker | Consensus and Recognition Sequences | SEQ ID NO: |
| MCP-1[a] | PYFPRGSSYQGWN | 2 |
| CCL 3 | CCIQNQ | 3 |
| CCL 4 | AWYQPQFE | 4 |
| CCL 21 | EQQKRN | 5 |
| CXCL 2 | CNHGKFYC | 6 |
| CXCL 5 | NIYCNIAY | 7 |
| CXCL 8 (IL-8) | KAYRWEFI | 8 |
| CXCL 9 | IQNSGAPCH | 9 |
| HSP 27 | WQEAKNANQM | 10 |
| HSP 70 | RHQKTYSF | 11 |
| HSP 90 | XLPPHWAGAL | 12 |
| MIF | XLPPHWAFAL | 13 |
| Calprotectin | LTELEKALNSIIDVYHKYSLIKGNFHAV | 14 |
| CCL20[b] | GESMNFSDVFDSSEDYFVSVNTSYYSVDSE | 15 |
| | GTQWWVVCQQFG | 16 |
| GCSF[c] | PGHWSDWSPS | 17 |
| IL-6 | YFPEPVTVSGAGTFPAVLGSGQPPGKGL | 18 |
| | TAVYYCANRAGWGMGDYWGQGTQVT | 19 |
| | TASNYGAGYSTNDRHS | 20 |
| | NRPAQAWMLG | 21 |
| IL-13 | AVYYCQQNNEDPRTFGGGTK | 22 |
| | AGDGYYPYAMDNW | 23 |
| | GWLPFGFILISAG | 24 |
| | YQQKPGQPPKL | 25 |
| | SVNWIRQPPGKALEWLAMIWGDGKIVYNS | 26 |
| | WLPFGFILIS | 27 |
| IL1RL1[d] | TYYCQQWSGYPYTF | 28 |
| MIP-1[e] | SHFPYSQYQFWKN | 29 |
| OSTF1[f] | DMSDTNWWKGTSKGRTGLIPSNYVAEQAESIDNPL | 30 |
| | KGTSKGRTGLIPSNYVAEQAEAG | 131 |
| TIMP-1[g] | IAGKLQSAGSALWTDQL | 31 |
| TSLP[h] | SSPKHVRFSWHQDAVTVTC | 32 |
| | AKCCPCQQWW | 33 |

[a]Monocyte Chemoattractant Protein-1;
[b]Chemokine (C-C motif) ligand 20 (CCL20) or liver activation regulated chemokine (LARC) or Macrophage Inflammatory Protein-3 (MIP3A);
[c]Granulocyte colony-stimulating factor;
[d]Interleukin-1-receptor-like type 1;
[e]Macrophage Inflammatory Protein;
[f]Osteoclast Stimulating Factor-1;
[g]Metalloproteinase Inhibitor 1;
[h]Thymic stromal lymphopoietin.

In one or more embodiments, the nanosensors can be configured with recognition sequences specific for cytokines detection. In those embodiments, the oligopeptide linkage comprises a linear supramolecular recognition sequence (i.e., paratope) for the receptor/binding site of the cytokine of interest. In the presence of the cytokine, stretching of the tether during cytokine binding leads to a signal change (e.g., fluorescence increase) from the attached detectable particle, which can be detected. The nanosensors can measure cytokine concentrations. Exemplary supramolecular recognition sequences are listed in Table 2 below.

TABLE 2

Supramolecular Recognition Sequences for the Detection of Protein Targets

| | Recognition Sequence(s) | SEQ ID NO: | Accession No. | LOD* Moles/L |
|---|---|---|---|---|
| Cytokine/Chemokine Targets | | | | |
| CCL 2 | CQEQFWW | 1 | P13500 | $10^{-14}$ |
| MCP-1[a] | PYFPRGSSYQGWN | 2 | P13500 | $10^{-15}$ |
| CCL 3 | CCIQNQ | 3 | P10147 | $10^{-15}$ |
| CCL 4 | AWYQPQFE | 4 | P13236 | $10^{-14}$ |
| CCL 21 | EQQKRN | 5 | O00585 | $10^{-15}$ |
| CXCL 2 | CNHGKFYC | 6 | P19875 | $10^{-14}$ |
| CXCL 5 | NIYCNIAY | 7 | P42830 | $10^{-13}$ |
| CXCL 8 (IL-8) | KAYRWEFI | 8 | P10145 | $10^{-16}$ |
| CXCL 9 | IQNSGAPCH | 9 | Q07325 | $10^{-15}$ |
| HSP 27 | WQEAKNANQM | 10 | Q5S1U1 | $10^{-15}$ |
| HSP 70 | RHQKTYSF | 11 | P0DMV8 | $10^{-15}$ |
| HSP 90 | XLPPHWAGAL | 12 | P02829 | $10^{-15}$ |
| MIF | XLPPHWAFAL | 13 | P14174 | $10^{-15}$ |
| Calprotectin | LTELEKALNSIIDVYHKYSLIKGNFHAV | 14 | S100A9 | $10^{-14}$ |
| CCL20[b] | GESMNFSDVFDSSEDYFVSVNTSYYSVDSE<br>GTQWWVVCQQFG | 15<br>16 | P78556 | $10^{-15}$ |
| GCSF[c] | PGHWSDWSPS | 17 | P09919 | $10^{-15}$ |
| IL-6 | YFPEPVTVSGAGTFPAVLGSGQPPGKGL<br>TAVYYCANRAGWGMGDYWGQGTQVT<br>TASNYGAGYSTNDRHS<br>NRPAQAWMLG | 18<br>19<br>20<br>21 | P05231 | $10^{-16}$ |
| IL-13 | AVYYCQQNNEDPRTFGGGTK<br>AGDGYYPYAMDNW<br>GWLPFGFILISAG<br>YQQKPGQPPKL<br>SVNWIRQPPGKALEWLAMIWGDGKIVYNS<br>WLPFGFILIS | 22<br>23<br>24<br>25<br>26<br>27 | P35225 | $10^{-15}$ |
| IL1RL1[d] | TYYCQQWSGYPYTF | 28 | P14778 | $10^{-15}$ |
| MIP-1[e] | SHFPYSQYQFWKN | 29 | Q9BPZ7 | $10^{-15}$ |
| OSTF1[f] | DMSDTNWWKGTSKGRTGLIPSNYVAEQAE<br>SIDNPL | 30 | Q92882 | $10^{-15}$ |
| TIMP-1[g] | IAGKLQSAGSALWTDQL | 31 | P01033 | $10^{-12}$ |
| TSLP[h] | SSPKHVRFSWHQDAVTVTC<br>AKCCPCQQWW | 32<br>33 | Q960D9 | $10^{-14}$ |
| Peptide Aptamers-Exosome surface markers | | | | |
| CD-9[i] | VQEFYKDTYNKLKTK | 34 | P21926 | $10^{-14}$ |
| CD-63[i] | LNNHTASILNRMQANF | 35 | P08962 | $10^{-14}$ |
| CD-81[i] | VGIYILIAVGAVMMFVGFK | 36 | P60033 | $10^{-15}$ |
| Exosome content analysis-markers of lung inflammation | | | | |
| O00571[j] | NERNINITKDLLDLLVAH | 37 | O00571 | $10^{-14}$ |
| P05187[k] | DINWVKQRPGQGLEWI | 38 | P05187 | $10^{-15}$ |

TABLE 2-continued

| Supramolecular Recognition Sequences for the Detection of Protein Targets | | | | |
|---|---|---|---|---|
| | Recognition Sequence(s) | SEQ ID NO: | Accession No. | LOD* Moles/L |
| P54136[l] | VLLQGKNPDITKAWKL | 39 | P54136 | $10^{-15}$ |
| Q5T4S7[m] | NLSRSRWFDFPFTREE | 40 | Q5T4S7 | $10^{-14}$ |

[a]Monocyte Chemoattractant Protein-1;
[b]Chemokine (C-C motif) ligand 20 (CCL20) or liver activation regulated chemokine (LARC) or Macrophage Inflammatory Protein-3 (MIP3A);
cGranulocyte colony-stimulating factor;
[d]Interleukin-1-receptor-like type 1;
[e]Macrophage Inflammatory Protein;
[f]Osteoclast Stimulating Factor-1;
[g]Metalloproteinase Inhibitor 1;
[h]Thymic stromal lymphopoietin;
[i]CD: Cluster of Differentiation;
[j]ATP-dependent RNA helicase DDX3X (from human bronchial airway epithelial cells);
[k]Alkaline phosphatase, placental type, phosphatase PPB1;
[l]Arginine-tRNA ligase, cytoplasmic;
[m]E3 ubiquitin-protein ligase UBR4 (small airway epithelial cells);
*Estimated limit of detection (LOD).

In some embodiments, the supramolecular recognition sequences can include one or more spacer residues on the N- and/or C-terminal ends. For example, between 1 and 10 amino acids (any amino acids, naturally and non-naturally, L- and D-, or combinations thereof) can be used at one or both ends as spacers. Examples include N-terminal sequences such as GAG- and C-terminal sequences such as -AG.

In some embodiments, any other linear peptide sequence of suitable length (e.g., at least 10 amino acid residues) can be used for the supramolecular recognition sequences, with the exception of sequences featuring consensus motifs. If synthesized on a peptide synthesizer, peptide sequences up to about 25 amino acid residues can be used, whereas sequence synthesized in an organism (e.g., *E. coli*) can be up to about 300 amino acid residues in length. Any designed sequence should to be checked for the presence of cleavage sequences, utilizing a data bank, such as MEROPS.

In some embodiments, peptide-aptamers for targeting CD9, CD63, and CD81, which are generally accepted surface markers of exosomes have also been developed. They are capable of binding to the exosomes and permit their isolation directly from collected biospecimens using the nanosensors without prior (ultra)centrifugation. The combined use of CD9, CD63, and CD81 will ensure that virtually all exosomes occurring from the sample, such as from airway cells, will be trapped. After treatment with a lysis buffer, the cargo of the captured exosomes can then be analyzed. Analysis of exosomes presents another existing aspect of the technology. Exosomes occurring from small airway epithelial cells and bronchial airway epithelial cells differ significantly in their proteasomes (including the tetraspanin content (CD9, CD 63, CD81) in their outer membranes.

In some embodiments, the biosensor of the disclosure show flexibility to adapt the underlying nanosensor structure by modifying the particles, oligopeptide linkages, and the like to suit the sensor technology available, and likewise, using a variety of sensor technologies for detecting additional targets. For example, a nanosensor can be prepared for detecting protease activity, in which graphene core particle of the disclosure are used in connection with the peptide linkages and moieties described in U.S. Pat. No. 8,969,027 as will be understood by a skilled person.

In some embodiments, Enzyme consensus sequences that can also be used in nanosensors in combination with one or more above include those in Table 3 below, where the cleavage point is indicated by the "-".

TABLE 3

| Enzyme | Consensus Sequence | SEQ ID NO: | Accession No. |
|---|---|---|---|
| ADAM 17 | LAQA-VVSS | 41 | P78536 |
| ADAM 33 | GSQH-IRAE | 42 | Q9BZ11 |
| Cathepsin B | SLLKSR-MVPNFN | 43 | P07858 |
| Cathepsin D | GDSG-LGRA | 44 | P07339 |
| Cathepsin E | EVAL-VALK | 45 | P14091 |
| Cathepsin G | NVLH-SWAV | 82 | |
| Cathepsin H | ALQA-RPGP | 83 | |
| Cathepsin K | LGLE-GANL | 46 | P43235 |
| Cathepsin L | AALG-SAPG | 47 | P07711 |

TABLE 3-continued

| Enzyme | Consensus Sequence | SEQ ID NO: | Accession No. |
|---|---|---|---|
| Cathepsin L | SGVVIA-TVIVIT | 84 | |
| Cathepsin S | SLLIFR-SWANFN | 48 | P25774 |
| Granzyme B | VEPN-SLEE | 49 | P10144 |
| Human airway trypsin-like peptidase (HAT) | RSAR-GLKG | 85 | |
| TMPRSS2 (Epitheliasin, transmembrane protease, serine 2) | RQSR-IVFG | 86 | |
| NE | GEPL-SLLP | 50 | P08246 |
| NE | GEPV-SGLP | 87 | |
| MMP 1 | IPVS-LRSG | 51 | P03956 |
| MMP 1 | VPMS-MRGG | 88 | |
| MMP 2 | IPVS-LRSG | 51 | P08253 |
| MMP 3 | RPFS-MIMG | 52 | P08254 |
| MMP 7 | VPLS-LTMG | 53 | P09237 |
| MMP 8 | GPSG-LRGA | 54 | P22894 |
| MMP8 | EPYH-LMAL | 89 | |
| MMP 9 | VPLS-LYSG | 55 | P14780 |
| MMP10 | RPLS-LQTG | 90 | |
| MMP 11 | GAAN-LVRG | 56 | P24347 |
| MMP 12 | GVPLS-LTMG | 57 | P34960 |
| MMP 12 | GPKN-LKAP | 91 | |
| MMP 12 | GPAN-LVAP | 92 | |
| MMP 13 | PQGLA-GQRGIV | 58 | P33435 |
| MMP 14 | GPAG-LRLA | 59 | P50281 |
| MMP 14 | LPQG-LRTE | 93 | |
| MMP15 | LPQK-SQHG | 94 | |
| ALK | RDIYAAPFFRK | 60 | Q9UM73 |
| AURKB | AMERRRTSAARRSY | 61 | Q96GD4 |
| CDK2 | KARAAVSPQKRKA | 62 | P24941 |
| PKD2 | RARKRRLSAPPLASGD | 63 | Q504Y2 |
| MAPK1 | AKAGPPLSPRPPHVH | 64 | P28482 |
| JAK2 | DLFIPDNYLKMKPAP | 65 | O60674 |
| PLK1 | AELDPEDSMDMDMAP | 66 | P53350 |
| PLK3 | EDEAEELSDEDEELK | 67 | Q9H4B4 |
| ERK1/MAPK3 | AAGPAPLSPVPPVVH | 68 | P27361 |
| JunK2/MAPK9 | DASRPPPLSPLPSPRA | 69 | P45984 |
| Proteinase 3 (PR3) | LYYV-SLSP | 95 | |

TABLE 3-continued

| Enzyme | Consensus Sequence | SEQ ID NO: | Accession No. |
|---|---|---|---|
| Proteinase 3 (myeloblastin) | SYYV-SLSP | 96 | |
| ARG I/II | GRRRRRRRG | 70 | P05089 (ARG1) P78540 (ARG2) |
| | GAGRRRRRRRAG | 133 | |
| ARG II | RRRRRRR | 97 | |
| KLK-1 | EAFR-STGA | 98 | |
| KLK-2 | GTSR-SAGG | 99 | |
| KLK-5 | YRFR-ILGG | 100 | |
| KLK-12 | LESK-INGG | 101 | |
| KLK-13 | VRSR-IVKG | 102 | |
| KLK-14 | TQPR-IVGG | 103 | |
| KLK-15 | ALGR-KLVG | 104 | |
| Streptococcus pneumoniae IgA1 protease | STPP-TPSP | 105 | |
| Mycosin Protease MycP1 | VKAA-SLGK | 106 | |
| Rv2869c (Mycobacterium tuberculosis)-like peptidase (RIP-1) | TCCA-TCAT-CC | 107 | |

In some embodiments, the consensus sequences of a peptide linkage can include an N-terminal spacer (e.g., GAG, GAA, GAP) and a C-terminal spacer (e.g., GA, AG, or EG).

In graphene biosensor of the disclosure the peptide linkages are used to attach detectable moieties or labels to the graphene core particle.

The term "attach" or "attached" as used herein, refers to connecting or uniting by a bond, link, force or tie in order to keep two or more components together, which encompasses either direct or indirect attachment where, for example, a first molecule is directly bound to a second molecule or material, or one or more intermediate molecules are disposed between the first molecule and the second molecule or material.

The terms "detect" or "detection" as used herein indicates the determination of the existence, presence or fact of a target in a limited portion of space, including but not limited to a sample, a reaction mixture, a molecular complex and a substrate. The "detect" or "detection" as used herein can comprise determination of chemical and/or biological properties of the target, including but not limited to ability to interact, and in particular bind, other compounds, ability to activate another compound and additional properties identifiable by a skilled person upon reading of the present disclosure. The detection can be quantitative or qualitative. A detection is "qualitative" when it refers, relates to, or involves identification of a quality or kind of the target or signal in terms of relative abundance to another target or signal, which is not quantified. A detection is "quantitative" when it refers, relates to, or involves the measurement of quantity or amount of the target or signal (also referred as quantitation), which includes but is not limited to any analysis designed to determine the amounts or proportions of the target or signal. A quantitative detection in the sense of the disclosure comprises detection performed semi-quantitatively, above/below a certain amount of target biomarker as will be understood by a skilled person.

The term "detectable moiety" or "label" as used herein refer to a molecule capable of detection, including but not limited to radioactive isotopes, fluorophores, chemiluminescent dyes, chromophores, enzymes, enzymes substrates, enzyme cofactors, enzyme inhibitors, dyes, metal ions, particles, metal sols, ligands (such as biotin, avidin, streptavidin or haptens) and the like. As a consequence, the wording "labeling signal" as used herein indicates the signal emitted from the label that allows detection of the label, including but not limited to radioactivity, fluorescence, chemoluminescence, production of a compound in outcome of an enzymatic reaction and the like.

In embodiments herein described detectable moiety is capable of emitting a fluorescent signal. The term fluorescent signal indicates a longer wavelength light signal emitted by a compound capable of being electronically excited by a light source of shorter wavelength.

Exemplary detectable labels a compound capable of being excited by a light source and emit a fluorescent signal include detectable particles that generate a detectable signal (e.g., optical or spectroscopic), such as fluorescence or color change, which can be perceived visually or measured with an appropriate instrument. Chromophore/luminophores suitable for use in the inventive assays include any organic or inorganic dyes, fluorophores, phosphors, light absorbing particles (e.g., Au, Ag, Pt, Pd), combinations thereof, or the non-magnetic metalated complexes thereof. Preferably, the selected chromophore/luminophores are smaller than the graphene carrier particle, and typically will have a particle size (maximum edge-to-edge dimension, i.e., diameter) of less than about 20 nm.

Suitable organic dyes are selected from the group consisting of coumarins, pyrene, cyanines, benzenes, N-methylcarbazole, erythrosin B, N-acetyl-L-tryptophanamide, 2,5-diphenyloxazole, rubrene, and N-(3-sulfopropyl)acridinium. Specific examples of preferred coumarins include 7-aminocoumarin, 7-dialkylamino coumarin, and coumarin 153. Examples of preferred benzenes include 1,4-bis(5-phenyloxazol-2-yl)benzene and 1,4-diphenylbenzene. Examples of preferred cyanines include oxacyanines, thiacyanines, indocyanins, merocyanines, and carbocyanines. Other exemplary cyanines include ECL Plus, ECF, C3-Oxacyanine, C3-Thiacyanine Dye (EtOH), C3-Thiacyanine Dye (PrOH), C5-Indocyanine, C5-Oxacyanine, C5-Thiacyanine, C7-Indocyanine, C7-Oxacyanine, CypHer5, Dye-33, cyanines (Cy7, Cy7.5, Cy5.0, Cy5.5, Cy3Cy5 ET, Cy3B, Cy3.0, Cy3.5, Cy2), CBQCA, NIR1, NIR2, NIR3, NIR4, NIR820, SNIR1, SNIR2, SNIR4, Merocyanine 540, Pinacyanol-Iodide, 1,1-Diethyl-4,4-carbocyanine iodide, Stains All, Dye-1041, or Dye-304, as well as all BODIPY dyes.

Cyanine dyes can be attached in a variety of configurations, ideally using a peptide linkage that is shorter than the Förster-radius of the cyanine dye (5-6 nm for Cy3.0 and Cy3.5, 6-7 nm for Cy5.0 and Cy5.5, and approx. 7 nm for Cy7 and Cy7.5). The maximal length of the tether, consisting of any spacers (~2.84 nm) and not more than 12 amino acid residues in the cleavage sequences (up to 4 nm) indicates that shorter cleavage sequences (uPA and MMP's) are suitable for use with Cy3.x and Cy5.x dyes, whereas the cathepsins are preferably linked to Cy5.x and Cy.7.x dyes to permit optimal quenching of the tethered cyanine dyes. For all of the cyanines, their emission maxima are red-shifted with respect to the autofluorescence of human urine. Multiple cyanines can be linked to a single particle to create oligoplexing nanoplatforms, to measure the activity of up to four enzymes simultaneously. All four dyes in the UVA or blue region of the electromagnetic spectrum can be excited simultaneously, or each dye can be excited individually. All cyanine dyes have an excitation maximum, which is blue-shifted by 20-25 nm with respect to their emission maximum (typical for fluorescent singlet states). Exemplary emission spectra of: NS-Cy3.0 ($\lambda$ex=538, $\lambda$em=560), NS-Cy5.5 ($\lambda$ex=639, $\lambda$em=660), NS-Cy7.0 ($\lambda$ex=740, $\lambda$em=760) and NS-Cy7.5 ($\lambda$ex=808, $\lambda$em=830).

Suitable inorganic dyes are selected from the group consisting of metalated and non-metalated porphyrins, phthalocyanines, chlorins (e.g., chlorophyll A and B), and metalated chromophores. Preferred porphyrins are selected from the group consisting of tetra carboxy-phenyl-porphyrin (TCPP) and Zn-TCPP. Preferred metalated chromophores are selected from the group consisting of ruthenium polypyridyl complexes, osmium polypyridyl complexes, rhodium polypyridyl complexes, 3-(1-methylbenzoimidazol-2-yl)-7-(diethylamino)-coumarin complexes of iridium(III), and 3-(benzothiazol-2-yl)-7-(diethylamino)-coumarin complexes with iridium(III).

Suitable fluorophores and phosphophores are selected from the group consisting of phosphorescent dyes, fluoresceines, rhodamines (e.g., rhodamine B, rhodamine 6G), and anthracenes (e.g., 9-cyanoanthracene, 9,10-diphenylanthracene, 1-Chloro-9,10-bis(phenyl-ethynyl)anthracene).

The broad UV/Vis absorption spectrum of graphene and derivatives permits the attachment of multiple detectable labels with respective (different) recognition sequence to target more than one biomarker at a time. In order to function, there should be no or only a minimal overlap between the excitation and absorption spectra of the co-attached detectable labels, thus minimizing FRET between the particles and/or interference of respective signals. Whereas, principally, any combination of fluorescent dyes can be envisioned, BODIPY dyes are especially suitable, because they feature small Stokes-shifts (the distance between the maxima of lowest excitation and fluorescent bands). An example for this strategy is the parallel use of BODIPY FL (505$\lambda$ex/513$\lambda$em), BODIPY 530550 (534$\lambda$ex/554$\lambda$em), BODIPY TR (589$\lambda$ex/617$\lambda$em), and BODIPY 630650 (646$\lambda$ex/660$\lambda$em) connected via respective (different) sequences to monitor the activity of four biomarkers independently with a single biosensor. Exemplary BODIPY dyes are shown discussed in Example 7.

Alternatively, cyanine dyes 2, 3, 5, and 7 are another possible combination. However, cyanine dyes have much larger Foerster radii and may interfere with each other, even when diluted.

Fluorescent quantum dots and fluorescent particles can also be used. A quantum dot is a semiconductor composed of atoms from groups II-VI or III-V elements of the periodic table (e.g., CdSe, CdTe, InP). The optical properties of quantum dots can be manipulated by synthesizing a (usually stabilizing) shell. Such quantum dots are known as core-shell quantum dots (e.g., CdSe/ZnS, InP/ZnS, InP/CdSe). Quantum dots of the same material, but with different sizes, can emit light of different colors. Their brightness is attributed to the quantization of energy levels due to confinement of an electron in all three spatial dimensions. In a bulk semiconductor, an electron-hole pair is bound within the Bohr exciton radius, which is characteristic for each type of semiconductor. A quantum dot is smaller than the Bohr exciton radius, which causes the appearance of discrete energy levels. The band gap, $\Delta E$, between the valance and conduction band of the semiconductor is a function of the nanocrystal's size and shape. Quantum dots feature slightly lower luminescence quantum yields than traditional organic fluorophores, but they have much larger absorption cross-sections and very low rates of photobleaching. Molar extinction coefficients of quantum dots are about $10^5$-$10^6$ $M^{-1}cm^{-1}$, which is 10-100 times larger than organic dyes.

Core/shell quantum dots have higher band gap shells around their lower band gap cores, which emit light without any absorption by the shell. The shell passivates surface nonradiative emission from the core thereby enhancing the photoluminescence quantum yield and preventing natural degradation. The shell of type I quantum dots (e.g., CdSe/ZnS) has a higher energy conduction band and a lower energy valance band than that of the core, resulting in confinement of both electron and hole in the core. The conduction and valance bands of the shell of type II quantum dots (e.g., CdTe/CdSe, CdSe/ZnTe) are either both lower or both higher in energy than those of the core. Thus, the motions of the electron and the hole are restricted to one dimension. Radiative recombination of the exciton at the core-shell interface gives rise to the type-II emission. Type II quantum dots behave as indirect semiconductors near band edges and therefore, have an absorption tail into the red and near infrared. Alloyed semiconductor quantum dots (CdSeTe) can also be used, although types I and II are most preferred. The alloy composition and internal structure, which can be varied, permits tuning the optical properties without changing the particles' size.

Particularly preferred quantum dots are selected from the group consisting of CdSe/ZnS core/shell quantum dots, CdTe/CdSe core/shell quantum dots, CdSe/ZnTe core/shell quantum dots, and alloyed semiconductor quantum dots (e.g., CdSeTe). More preferably, the quantum dots are less than about 10 nm in diameter, even more preferably from about 2 nm to about 5.5 nm in diameter, and most preferably from about 1.5 nm to about 4.5 nm in diameter. If different color emission is needed for creating multiple sensors (multiplex detection), this can be achieved by changing the size of the quantum dot core yielding different emission wavelengths. The quantum dots can be stabilized or unstabilized as discussed above regarding particles. Preferred ligands for stabilizing quantum dots are resorcinarenes.

In graphene biosensor of the disclosure advantageously, the graphene core particle acts as a quencher for the detectable moiety's signal, such that there is no need for a co-attached quencher particle to be separately added to the sensor (e.g., directly attached to the carrier particle). Thus, unlike other sensors, the particles (detectable moieties) attached to the graphene core particle interact with the graphene core particle carrier particle, but are typically selected and arranged (e.g., in proximity to one another and the carrier particle) such that they do not interact with one another, and only interact with the graphene core particle in terms of sensing functionality. (see e.g. Characteristic of peptides attached to the graphene particle illustrated and exemplified in the Examples section).

Accordingly in embodiments herein described core particles and biosensors each comprise a graphene core particle in which at least one detectable moiety is attached to pristine graphene nanosheet particulate, via a peptide linkage. In this configuration, the detectable moiety is at a quenching distance with respect to graphene and the detectable signal of the detectable moiety is quenched and either muted or undetectable due to its proximity to the central graphene nanosheet particulate. The peptide linkage comprises a recognition sequence that is specific for a target biomarker, such that the target biomarker, if present in at tested sample, will interact with (and typically cleave or modify the conformation of) the peptide linkage thereby bringing the detectable moiety at an emitting distance where quenching of the graphene particle does not occur (e.g. by releasing the detectable moiety or by modifying the distance by changes of the related conformation). Once released or brought to an emitting distance through changes in conformation, the detectable moiety is no longer quenched by the central graphene nanosheet particulate and its signal (or a change in its signal) can be detected and thereby indicate the presence and/or activity of the target biomarker in the sample.

In most embodiments herein described, in graphene biosensor of the disclosure the diameter of the attached polymer layer plus co-attached consensus sequence does not exceed 20 nm to allow placement of the detectable moiety at a quenching distance with respect to the graphene particles in which the graphene quenches the signal fo the detectable moiety (see Characteristic of Polymers illustrated and exemplified in the Example section).

Accordingly in some embodiments, the coating material in graphene core particle and/or in biosensor of the disclosure has thickness equal to or lower than 18 nm to permit a minimum of 2 nm for the attached peptide sequences that feature targeting abilities.

In some embodiments, the coating material in graphene core particle and/or in biosensor of the disclosure has thickness from 8 to 17 nm, from 2 to 18 nm, or from 5 to 15 nm depending on the size of the detectable component attached or to be possibly attached to the coating material as will be understood by a skilled person upon reading of the present disclosure.

In some embodiments herein described allowable ratio of peptide length (A) and polymer layer thickness (B) in graphene biosensors for protease activity detection can be detected with procedures exemplified in Example 31.

In some embodiments, wherein the target biomarker perform post-translation modification the layer thickness is close to 20 nm before binding to their target or posttranslational modification. Both events elongate the peptide sequence brining the detectable moiety at an emitting distance wherein the graphene particle does not quench the detectable moiety, thus causing fluorescence increase from a tethered fluorophore.

Biosensors of the disclosure have been surprisingly found to have not only a high stability but also a high reproducibility of the related signal detection in particular in embodiments where the graphene layer comprises 2 to 100 sheets of pristine graphene, more preferably fractal pristine graphene, coated with coating material for at least 90% preferably at least 99% and more preferably up to 100% of the graphene particle. In those embodiments target biomarker can be detected with high reproducibility and in particular with a coefficient of variation in detected signal between different manufactured lots or batches of less than 10%, wherein the signal is the amount of fluorescence above the sensor only background for each lot.

In embodiments herein described reproducibility of nanobiosensor is determined by the ability to reproduce a condition of measurement of a defined biological sample which can be expressed in terms of a coefficient of variation.

Accordingly, the high reproducibility of biosensor of the disclosure allows a skilled person to formulate a core particle modified to be chemically stable in an aqueous solution and attached to a varied sensor moiety in accordance with the disclosure, in independent assemblies to produce the same amount of signal from a single biological sample. To have value for measuring biological processes, the amount of signal released by a defined biological sample must be reproducible.

In embodiments of graphene biosensors herein described where the graphene layer comprises 2 to 100 sheets of pristine graphene, coated with coating material for at least 90%, the difference between different manufactured lots or batches of sensor are expected to display a signal with a coefficient of variation of less than 10% for each build.

In particular order to detect reproducibility the quantity of sensor added to a reaction is performed preferably using absorbance rather than being reliant on mass. In particular, the concentration of particle can be determined by absorbance measurements using a standard curve with $R^2$>0.99. Under these conditions, the concentration of particles can be adjusted with a CV %<4%.

In embodiments herein described wherein a suspension of particles in which graphene layer comprises a particle from 10 nm and 5000 nm preferably from 150 to 500 nm on average as determined using scanning electron microscopy and digital light scattering measurements, coated with coating material for at least 90%, the reproducibility can also be detected in terms of stability of an aqueous suspension comprising the sensors, the reproducibility assessed by assessing the colloidal stability at $OD_{650}$ or $OD_{270}$, within a set amount of time. In embodiments where the particle has a dimension of 10 nm to 5000 and preferably from 150 to 500 nm the average decrease in OD650 between measurement is of 24% or less, and in preferred embodiments, typically 10% or less.

In those embodiments, the configuration of the sensor allow a formulation in which the sensor to remain in an evenly suspended state in an aqueous solution. This characteristic allow even distribution of the particles and the subsequent interaction with rare specific biomarker present in a biological sample present a concentration as low as femtomolar. Stability is further supported by modification of the few layer graphene with surface modifications that mask the nonpolar nature of the graphene surface. These modifications introduce charges that allow the particles to remain in suspension in an aqueous environment. Introduction of polar modifications are required to support a preparation of sensor in buffered solution of at least 1 mg/ml. With a stable solution of at least 1 mg/ml, all sensors can be mixed in functional concentrations with the sample between 5 and 500 μg/mL. Preferably, sensor concentration is held at 25, or 30, or 50 or 100, or 200, or 300 μg/mL. The optimal functional concentration can be determined for each sensor based on the specific components and related features. The combined impact of introducing size and charge modifications is to produce a solution that maintains a stable suspension of particles such that the absorbance of the graphene nanobiosensor does not change over a 1 hour period at room temperature. This solution stability is assessed by assessing the colloidal stability at $OD_{650}$ or $OD_{270}$ over a 60 minute interval at room temperature. Graphene sensors show a change in $OD_{650}$ of −20 to −26%. Absorbance of graphene sensors at $OD_{270}$ can show a change of −17% to −21%. Therefore, the colloidal suspension of graphene sensor remains in suspension more efficiently than other particles known in the art as will be understood by a skilled person.

In preferred embodiments, the graphene particle has a size of 900 nm or less, preferably 350 nm or less more preferably 250 nm or less the detection can be performed for target biomarkers present at concentration as low as femtomolar.

Biosensors of the disclosure have been also surprisingly found to have not only a high stability and a high reproducibility of signal detection, but also a high signal to noise ratio in particular in embodiments where the graphene layer comprises 2 to 100 sheets of pristine graphene, more preferably fractal pristine graphene, coated with coating material for at least 90% preferably 100% of the surface of the graphene particle to minimize interference with the fluorescence readouts due to adsorption and quenching of formerly cleaved off detectable moieties (such as fluorescent dyes) at the surface of uncoated graphene.

In particular, biosensors with the above features provide a signal to noise performance (S:N) in aqueous solutions of at least 25 or higher In experiments performed with exemplary biosensor having the above features, the relationship of sample incubated with sensor and serum at time 0 for the biosensor and found the relative fluorescence index (RFI) or sample RFU/Assay control RFU averages 4.3+/−1.9. Furthermore, the biosensors maintained in aqueous solution for up to 90 min shows no significant change in background signal and integrated S:N increases on average from 25 to 46, to 159, to 312 across multiple sensors as different lots of biosensor are measured. Therefore, the integrated S:N, evaluating both the signal to noise ratio at t=0 and t=60 demonstrates an increase of sensitivity for defined stimulus of between 3-fold and 13-fold as the graphene biosensor size and solvent contamination is stabilized (see representative Example 44 and corresponding FIG. 59 and FIG. 60). This S:N performance is dependent on the sensor as will be understood by a skilled person.

In particular, in those experiments performed with exemplary nanobiosensor herein described a 25-fold improvement was measured averaging 4 different sensors (see Example 17, FIG. 20 in Lot 1 formulation, FIG. 59) ranging from 8- to 50- as will be understood by a skilled person. The same 4 sensors had improved to 312 SN average (see Example 40 and Example 43 Lot 4) with a range from 109- to 623-fold S:N. In comparison iron particle sensors had an average SN of 20 (range 6- to 42-) for the same 4 sensors measured with the same buffer and samples at the same time (see Example 44).

In some embodiments, the biosensors can have different lengths and configuration of the sensor within the above configurations. For example in some embodiments, the length of the peptide tether can exceed 50 amino acids. This is possible for example in all cases when back-bending of the peptide chain is envisioned to bring the detectable moiety at an emitting distance.

In some embodiments, the peptide linkage can be attached to the coating layer or to the graphene surface of a graphene core particle of the disclosure and/or to the detectable moiety, indirectly through moieties herein also indicated as spacers or connector. For example, the exemplary peptide linkages of Table 1 can comprise before the N-termini of each sequence the spacer GAG, and the spacer AG is used at the C-termini. Selection of proper spacers in graphene biosensor of the disclosure can be performed in view of the target biomarker to be detected and of the quenching distance and emitting distance of the specific biosensor as will be understood by a skilled person (see Example 9).

In some embodiments, the peptide linkage are oligopeptides comprising a 3 amino acid spacer GAG, and 4+4 amino acid consensus sequence, and a 2-3 amino acid spacer (G)AG, the length is 5±0.5 nm. In some embodiments, the dimension of the layer is 2 nm (functionalized graphene)+12 nm (coating material such as PEI)=14 nm. 14 nm+5 nm peptide linkage comprising a spacer=19 nm<20 nm.

In some embodiments, the graphene-based biosensors are configured for detection methods based upon surface plasmon resonance and FRET between the graphene carrier particle and the detectable moiety. FRET describes energy transfer between two particles. Surface plasmon resonance is used to excite the particles. A donor particle initially in its excited state, can transfer this energy to an acceptor particle in close proximity through nonradiative dipole-dipole coupling. Briefly, while the detectable particle is bound by the oligopeptide in its initial state, a first emission is observed upon excitation of the donor particle. Once the target biomarker binds and/or cleaves its recognition sequence, FRET change is observed, and the emission spectra changes. Typically, once the distance between the two particles is changed by the biomarker (either by cleaving or lengthening the peptide linkage), light is emitted from the detectable particle and a distinct blue-shift in absorption and emission can be observed. This is because the distance between both particles increases. In some embodiments, the signal intensity from the detectable particle increases as the distance between the two particles increases.

In biosensors herein described, in view of the photophysical properties of graphene plasmonic quenching is dominant contrary to other nanomaterials characterized by an overlay of plasmonic excitation and quenching as will be understood by a skilled person.

In general, excitation of the biosensor is directed towards the particle having a higher energy state (e.g., the donor particle). Since the absorption spectrum of graphene (and carboxygraphene) changes only very little between UV and near-IR, this biosensors are capable of working in a broad optical region. Excitation of the detectable particle can advantageously be performed between about 300 nm and about 1500 nm. Excitation is typically performed with an energy source of appropriate wavelength selected from the group consisting of a tungsten lamp, LED, laser, and/or bioluminescence (e.g., luciferase, renilla, green fluorescent protein). The changes in absorption and/or emission of the particles as the peptide binds, cleaves, or chemically modifies the oligopeptide linkages will be observed over a time period of from about 1 minute to about 120 minutes, preferably from about 1 minute to about 60 minutes, and in some cases from about 1 minute to about 30 minutes, depending upon biomarker activity. In practice, the assay can first be calibrated for the particular biosensor using a control sample with and without known concentrations of the target biomarker.

In particular the pristine graphene nanosheet are within a core particle herein described and the attaching is performed by attaching the detectable moiety to the chemically transformed surface of the core particle herein described. In embodiments wherein the core particle comprises a layer of an organic and/or inorganic molecule, the chemically transformed surface is coated with a layer of an organic and/or inorganic molecule and the attachment is performed through binding of the peptide linkage to the layer of an organic and/or inorganic molecule.

In most preferred embodiments, the attaching is preceded by dispersing the pristine graphene nanosheet (e.g. by sonication) and the attaching is performed on the dispersed pristine graphene nanosheet.

In preferred embodiments, dispersion is performed with graphene particle comprising fractal graphene. In those embodiments dispersal can be desirable to decrease the representation of larger fractals in the population of graphene going into manufacturing. In some embodiments wherein detection of target biomarker at femtomolar concentration, the particle population size of the particles is typically between 10 and 5000 nm, optimally between 50 and 500 nm to support a homogenous and stable aqueous solution of particle. The use of sonication introduces energy into the system to disrupt the electrostatic bonds and Van der Walls forces holding fractals together. Once disrupted, the coating reaction (e.g. polymerization) captures the population as represented. Sonication represents one mechanism that introduces energy into the system some of which will be used to break larger fractals. This will continue to an equilibrium depending on the power of the sonication. Introducing between 2 and 40 kJ or between 10 and 20 kJ or more preferably between 12 and 15 kJ using a microtip probe sonicator in a 200 mL solution of few layer graphene in DMF produces a population of suitable particles. Alternatively, the size of the fractal population can be modified by dispersal using a high shear homogenizer. Alternatively, energy is expected to be possibly supplied by microwave to disrupt the larger fractals, or by extrusion under high pressure. These methods use mechanical methods to disperse large fractals to decrease the overall population size. Alternatively size selection is expectedly performed to select a population representing 50-500 nm using size selection techniques such as filtration or size fractionation or sedimentation under centrifugation. The examples included references probe sonication (see Example 22 and related FIG. 27 and FIG. 29). The effective endpoint is determined by determining the size of the end population after treatment for dispersal by any method such as TEM or light scattering methods. Using Absorbance efficiency measured by OD270/mg/ml efficiencies were observed of >1.0, and >2.0 and >3.0 as dispersal steps are included. (see Example 40 and related data in the Table FIG. 55 representative of the efficiencies for the preferred embodiments).

In embodiments herein described, graphene particle of the disclosure are functionalized to present a functional group FGg which is selected to allow attachment of a corresponding functional group of the coating material FGcg, Attachment of the coating material through binding of the groups FGg and FGcg is preferably performed following dispersion of the functionalized graphene particle and results in a core graphene particle presenting a functional group FGcp configured to bind a corresponding functional group FGp presented in the peptide linkage.

In some embodiment, based on the appropriate coupling chemistry as exemplified in Schemes (I) to (IX), the following scheme for the synthesis of a biosensor is described.

Scheme (X)

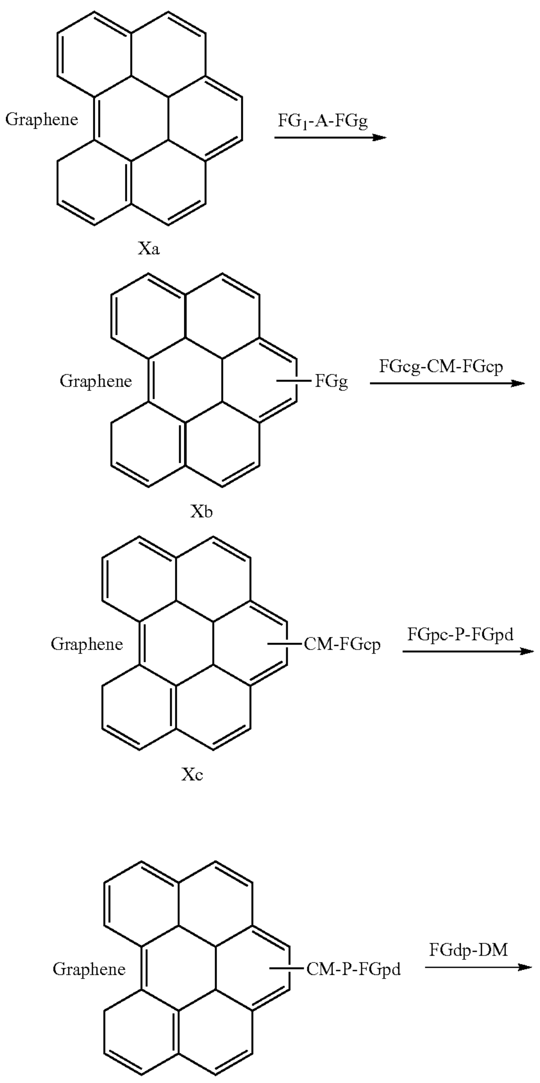

Xa Xb Xc Xd

-continued

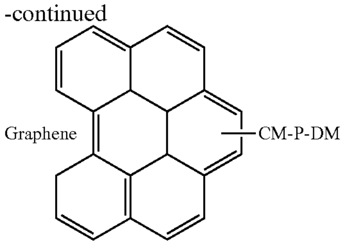

Xe wherein A is a reagents configured to functionalize the graphene, CM a coating material in the sense of the disclosure, P peptide linkage in the sense of the disclosure, and DM a detectable moiety.

As shown in Scheme X, graphene of Formula (Xa) is reacted with reagent FG1-A-FGg wherein FG1 is a reactive functional group that will react or made to react with graphene and FGg is a functional group capable of chemically coupled to a coating material, A is a chemical moiety of C2 to C4, or C5 to C12 substituted or unsubstituted linear or branched alkyl group wherein one to 4 carbon atoms may be replaced by one or more of heteroatoms selected from O, S, or NH. Exemplary FG1 includes but are not limited —N3 (azide) which decompose to nitrene under heating conditions, maleimide which is a dienophile. Exemplary FGg includes —COOH or NH2.

The functionalized graphene of Formula (Xb) reacts with functionalized coating material FGcg-CM-FGcp, wherein FGcg is a functional group capable of reacting with FGg on the functionalized graphene. Thus, when FGg is —COOH, exemplary FGcg can be NH2 to form an amide bond with FGg.

The coated graphene of Formula (Xc) comprises functional group FGcp, wherein the FGcp is a functional group capable of reacting with FGpc on a functionalized peptide FGpc-P-FGpd. Similarly, exemplary FGcp includes —COOH or NH2. Thus, when FGcp is —COOH, exemplary corresponding Fpc can be NH2 to form an amide bond with FGcp.

The peptide derivatized graphene of Formula (Xd) comprises functional group FGpd, wherein the FGpd is a functional group capable of reacting with FGdp on a functionalized detecting moiety FGdp-DM. In a similar fashion, exemplary FGdp includes —COOH or NH2. Thus, when FGdp is —COOH, exemplary corresponding Fpd can be NH2 to form an amide bond with FGdp.

It is to be understood that any of the pair of coupling functional groups herein described can be practiced with any other coupling functional groups, as exemplified in Scheme (I) to Scheme (IX) herein described. Therefore, when one functional group is amine —NH2, the other functional group can be, besides carboxylic acid, NHS (Scheme V), or oxirane (Scheme IX).

In some embodiments herein described the assembly of the coating on the particle preferably dispersed can be performed by attaching a coating layer to the surface of a graphene particle first to provide a coated particle presenting a functional group of the coating layer FGcp such as amide, amine, ester, ether, thioester, or thioester bond and the by attaching the peptide linkage to the functional group FGcp through a corresponding Functional group of the peptide linker FGp. In some embodiments the linker to the polymer first and then attach it to graphene. The attachment can be performed directly or indirectly and can be through covalent or non-covalent binding depending on the corresponding functional group as will be understood by a skilled person.

In some embodiments, peptide linkages of the disclosure can be attached through a spacer configured to attach the graphene directly such as EPLQLKM[27] (targeting the edges of graphene) and HSSYWYAFNNKT[27] (adsorbing on flat graphene surfaces) to anchor any peptide sequence to pristine graphene. [27] (adsorbing on flat graphene surfaces) to anchor any peptide sequence to pristine graphene.

In some embodiments, peptide linkages of the disclosure can be attached a terminal cysteine oxidized to a thiyl radical that attached to graphene.

In some embodiments, Non-natural amino acids can be tethered to the N-terminal end of the peptide sequence to perform the linking (all chemistries as described above).

In some embodiments, coating material can comprise oligoethylene groups of <20 nm, starburst dendrimers with a diameter <20 nm, and block-copolymers: In some embodiments, when coating material can comprise block copolymers are being used, hydrophobic polymers, such as polystyrene, polyisobutylenes, polyvinylchloride, polyethylene, polypropylene and additional polymers identifiable by a skilled person. can be components of block copolymers in combination of hydrophobic and charge attraction when negatively charged polymers, such as polystyrene-sulfonic acid are used in block copolymers of polystyrene. In those embodiments hydrophobic-hydrophilic block copolymers can be be dissolved in a solvent that also disperses graphene well (e.g. dimethylformamide (DMF)). Under continuing sonication, $H_2O$ is added to the mixture, forcing the hydrophobic end of the block-copolymer to bind to graphene. This supramolecular attachment happens spontaneously in the dispersion, due to increasing hydrophobicity decrease due to continuous $H_2O$ addition. Accordingly, as long as this sensor is used in aqueous solvents, this attachment principle is expected to work reliably.

In accordance with the property of graphene biosensors in in the sense of the disclosure in aqueous solution, the graphene biosensor have also been found to be surprisingly stable and capable of providing a highly reproducible detection of target biomarkers in an aqueous sample.

The term “sample” as used herein indicates a limited quantity of something that is indicative of a larger quantity of that something, such as to fluids from a specimen such as biological environment, cultures, tissues, commercial recombinant proteins, synthetic compounds or portions thereof.

The word “specimen” as used herein indicates a portion of matter from an environment for use in testing, examination, or study. The environment can comprise individuals. When referred to as a noun, the term “individual” as used herein in the context of detection, diagnosis and treatment refers to a single biological organism, including but not limited to, animals and in particular higher animals and in particular vertebrates such as mammals and in particular human beings. In these instances, a specimen can include a portion of tissues, organs or other biological material from the living being such as urethra, urine, cervix, vagina, rectum, oropharynges, conjunctiva, or any body fluids.

In particular biological samples can comprise one or more cells of any biological lineage, as being representative of the total population of similar cells in the sampled individual. Exemplary biological samples comprise the following: whole venous and arterial blood, blood plasma, blood serum, dried blood spots, cerebrospinal fluid, lumbar punctures, nasal secretions, sinus washings, tears, corneal scrapings, saliva, sputum or expectorate, bronchoscopy secretions, transtracheal aspirate, endotracheal aspirations, bronchoalveolar lavage, vomit, endoscopic biopsies, colonoscopic biopsies, bile, vaginal fluids and secretions, endometrial fluids and secretions, urethral fluids and secretions, mucosal secretions, synovial fluid, ascitic fluid, peritoneal washes, tympanic membrane aspirate, urine, clean-catch midstream urine, catheterized urine, suprapubic aspirate, kidney stones, prostatic secretions, feces, mucus, pus, wound draining, skin scrapings, skin snips and skin biopsies, hair, nail clippings, cheek tissue, bone marrow biopsy, solid organ biopsies, surgical specimens, solid organ tissue, cadavers, or tumor cells, among others identifiable by a skilled person. Biological samples can be obtained using sterile techniques or non-sterile techniques, as appropriate for the sample type, as identifiable by persons skilled in the art. Some biological samples can be obtained by contacting a swab with a surface on a human body and removing some material from said surface, examples include throat swab, nasal swab, nasopharyngeal swab, oropharyngeal swab, cheek or buccal swab, urethral swab, vaginal swab, cervical swab, genital swab, anal swab, rectal swab, conjunctival swab, skin swab, and any wound swab. Depending on the type of biological sample and the intended analysis, biological samples can be used freshly for sample preparation and analysis, or can be fixed using fixative.

In methods and systems herein described a sample can be split in two or more parts and/or processed through treatment to enrich the target biomarker and/or remove selected materials to increase the quality of the detection. Accordingly, the term sample as used herein comprises samples that are chemically treated or storage, preservation, or further analysis.

Samples used in connection with graphene core particles and related graphene biosensors compositions methods and systems are aqueous samples.

An "aqueous sample" in the sense of the disclosure is a sample in which water is the solvent or main component. In particular, an aqueous solution typically include a buffer component at a concentration capable of maintaining a defined pH in the presence of sensor and sample for the duration of the experiment.

In embodiments, herein described, it has been found that graphene biosensors in the sense of the disclosure having 2 to 100 pristine graphene sheet, preferably fractal graphene, coated with at least 90% coating material preferably are surprisingly stable in an aqueous sample and capable of providing a detection characterized by a high reproducibility and signal to noise ratios in particular when having dimension 10 nm to 5000 and preferably from 150 to 500 nm.

In particular, in some embodiments, the sensors of the disclosure including these feature show an absorbance to replicate sensor concentration (independent batches of a biosensor solution having the same features) with a coefficient of variation CV of <3%. Achievement of this CV obtained by having a solution with sensors that remain evenly distributed in a reaction determined. The preparation of nanosensors prepared with a method comprising a dispersion step (e.g. using sonication) and solvent removal produced solutions of sensors that maintained colloidal stability with less than 15% settling in a 60 min interval. In particular, in embodiments wherein the particles are provided by a method comprising a particle dispersing step and solvent removing step settling was observed from 9% to 10%.

In some embodiments, reproducibility of the sensors of the disclosure can also be detected through a reproducible estimate of both the assay control and the sample as these two values are divided to estimate S:N. Sensors of the disclosure display a CV % between batches of <20%. In this connection, biosensor of the disclosure with the above features combination can provide a batch to batch CV % of between 3% and 10%. Optimally, the CV % between batches will be <10%. This is assessed by preparing independent batches of sensor and comparing the SN (SM/AC) under matched conditions with a standard stimulus. (see Example 22 and related FIG. 27 and Example 44 and related FIG. 59).

In some embodiments, S:N of graphene biosensor of the disclosure can be determined by maintaining a low, stable assay control reading. For example, for biosensors evaluated on a VarioSkan Lux, the AC is between 0.01 and 0.1. The signal is dependent on the sensor and the stimulus. Sample signal for any given sensor using the same stimulus can be improved 15-fold with dispersed, solvent cured sensors. Further, incremental addition of dispersion (6.8-fold average increase in SN) and dispersion and solvent removal (average 15-fold increase in SN) indicates the combined use of the core particle (see Example 44 and related FIG. 59), (1) dispersed using sonication or the equivalent to an Absorbance efficiency of >3.0 $OD_{270}$/mg/ml (see Example 40 and related FIG. 55), and (2) reducing the amount of solvents such that TGA measures a total weight loss of less than 5% (wt %), possibly less than 2%, are associated to this S:N performance (see Example 21 and related FIG. 25).

Figure 57:
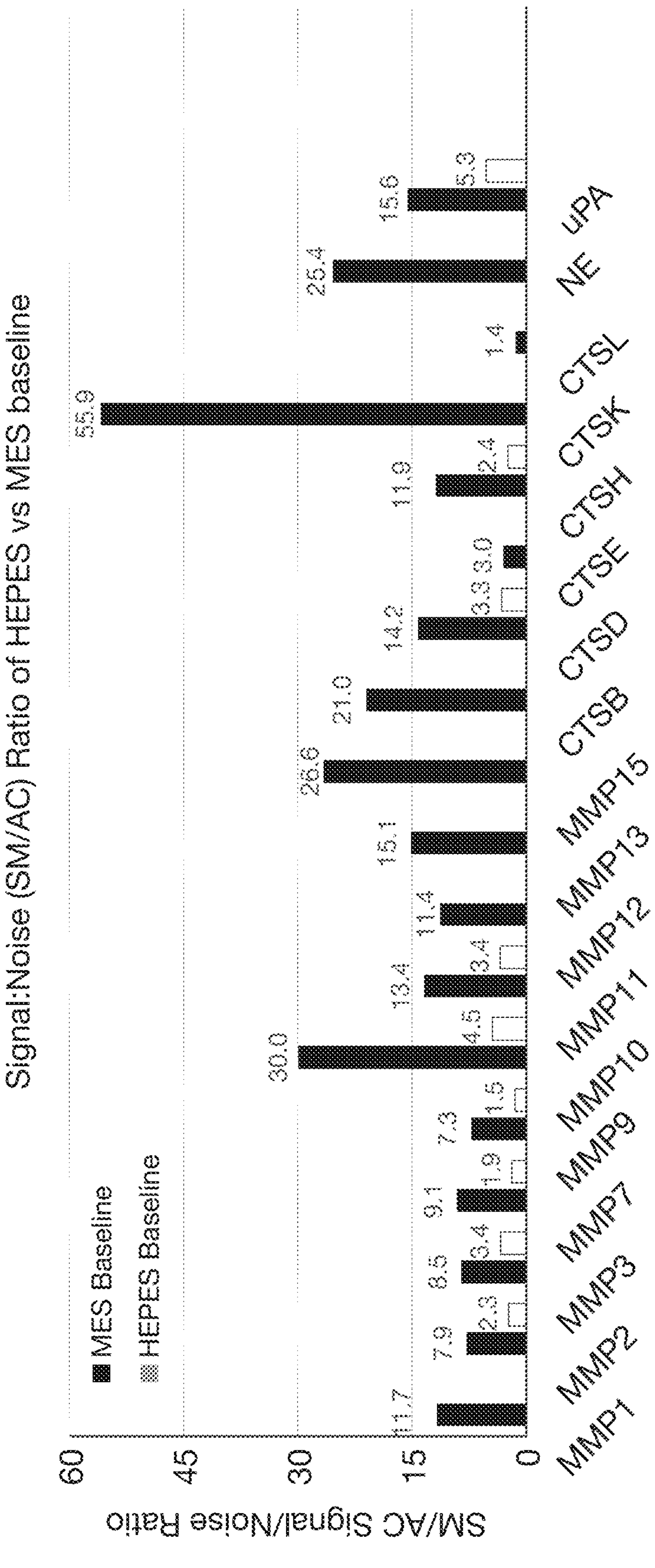
FIG. 57 shows a chart illustrating an exemplary impact of buffer formulation and heat treatment on Signal to Noise performance. Working solutions of gNBS were prepared in HEPES or MES buffer supplemented with 10 μM divalent cations and 155 mM NaCl. Samples were heat treated at 65° C. for 12 min (MES Baseline) or not (HEPES Baseline) and incubated for 90 min at 37° C.

In some embodiments, reproducibility and signal to noise ratio can be increased by performing appropriate buffer selection. Buffer selection can be performed based on a selection from Good's list that reflects the most appropriate pH target for biomarker detection. The addition of monobasic salts increases the S:N performance to an extent dependent on the concentration of salt added as will be understood by a skilled person upon reading of the present disclosure. Monobasic salt decreases the Assay control and relative to the sample producing an increased S:N ratio. Inclusion of monobasic salt decreases the assay control to between 0.01 and 0.1 RFU on a VarioSkan Lux on average. Overall, the impact of buffer across all sensors tested increases the S:N 4-fold on average (range 2.5-fold to 6.7-fold) (see Example 42 and related FIG. 57). Certain protease enzymes require buffer co-factors such as divalent cations. In preferred embodiments for protease detection, the buffer includes 10 μM Calcium, Magnesium and Zinc divalent ions. Formulations tested focused on pH7.2 as a physiologically relevant pH that was used across all sensors. However, the tumor environment and intracellular compartments often reflect pH below 7.0. So the pH does not have to be one condition except when reaction chambers are shared as in a multiplex reaction. Some enzymes require acidic conditions and for any example, pH7.0 and pH6.0 and 6.4 and 6.8 are expected to support enzymes such as cathepsins or enzymes derived from inflammatory environments. Receptor ligand interactions are preferably measured at physiological conditions so 155 mM and pH7.2 is a condition broadly supportive of many sensor formulations as will be understood by a skilled person.

In some embodiments the graphene biosensors of the present disclosure comprise a plurality of detectable components each comprising a detectable moiety and recognition sequence specific for a target biomarker.

In some of those embodiments, the recognitions sequences of the detectable components of the plurality of detectable components configured to specifically recognize different target biomarkers.

Accordingly, in those embodiments the graphene biosensors of the disclosure are configured for multiplex detection, and to simultaneously measure multiple analytes in a single experiment.

In particular the terms multiplexing as used herein indicates embodiments where two or more target biomarkers can be detected in a same reaction, using the same reagent mix.

In the plurality of target specific detectable components of the nanobiosensor, the excitation spectrum of each detectable moieties has a minimized overlap with the emission spectrum of another detectable moiety of the plurality of target specific detectable components. Accordingly, in those embodiments each detectable moiety is assigned to a specific biomarker with minimal to no overlap between the excitation and emission spectra of the detectable moieties of the plurality of detectable components to minimize FRET effects among detectable moieties that will distort the readout.

In graphene sensors configured for multiplex detection in view of the properties and features of the graphene sensors the multiplex ability of sensors having 2 to 100 graphene sheet and coating layer coating at least 90% of the graphene surface, is 5 or higher number of peptide sequences+detectable moiety, possibly up to 10 in the UV/Vis spectrum, and up to 50 for the entire electromagnetic spectrum.

In some embodiments of the graphene biosensor herein described a detectable component comprising a peptide and a detectable moiety (e.g. a fluorophore) can be comprised in multiplex biosensor a concentration up to $1.0\pm0.25\times10^{-3}$ moles per gram. In some embodiments, wherein the fastest signal increase over the concentration range from femtomolar to micromolar of a target biomarkers (e.g. a protease) is desired, the concentration of detectable component can be $1.6\pm0.2\times10^{-5}$ moles per gram of graphene-nanobiosensor as will be understood by a skilled person upon reading of the disclosure.

Accordingly, in some of those embodiments where the biosensor are multiplex biosensor in view of the, the concentration of detectable component (peptide sequences+detectable moiety of $1.0\pm0.25\times10^{-3}$ moles per gram of nanobiosensor is to be divided by the number of peptide sequences+detectable moiety that are being used for the purpose of multiplexing. If unequal concentrations of each detectable component are being used, the sum of all partial concentrations for each peptide sequence+detectable moiety has to be equal to $1.0\pm0.25\times10^{-3}$ moles per gram of nanobiosensor, as will be understood by a skilled person.

Additionally, in some of those embodiments where the biosensor are multiplex biosensor, in view of the preferred concentration of tethered peptide sequences+detectable moiety is $1.6\pm0.2\times10^{-5}$ moles per gram of nanobiosensor to obtain the fastest signal increase over the concentration range from femtomolar to micromolar of a target biomarker (e.g. a protease), this concentration is to be divided by the number of detectable components that are being used for the purpose of multiplexing. If unequal concentrations are being used, the sum of all partial concentrations for each peptide sequence+fluorophore has to be equal to $1.6\pm0.2\times10^{-5}$ moles per gram of nanobiosensor, as will be understood by a skilled person upon reading of the present disclosure.

Accordingly, in some preferred embodiments of multiplexing nanobiosensors herein described, the concentration of the sum of all utilized peptides+fluorophores can range from $1.0\pm0.25\times10^{-3}$ moles per gram to $1.0\pm0.25\times10^{-7}$ moles per gram, preferably from $1.0\pm0.25\times10^{-4}$ moles per gram to $1.0\pm0.25\times10^{-6}$ moles per gram, and even more preferably from $1.0\pm0.25\times10^{-5}$ moles per gram to $2.0\pm0.25\times10^{-5}$ moles per gram, as will be as will be understood by a skilled person upon reading of the present disclosure.

A similar multiplex ability can be achieved by using composition comprising a plurality of biosensors of the disclosure each presenting a detectable component specific for different target biomarker. In those embodiments, the differently assembled sensors can be mixed such that as a fraction of the reaction, each sensor can still produce a signal that is greater than background signal defined as sensor only. In this context, the biosensor specific for a target biomarker can be mixed with 1, or 2, or 3, or 4, or 5, or 6, or 7, or 10 or 20 different sensors and still produce a signal greater than background. At a 1:20 representation, a multiplexed sensor is detectable at 5-7% of the expected value. Therefore multiplexed sensors can be detected at 1 of 20, or 10 or 4 or 2 multiplexed sensors.

In some embodiments, multiplex detection of target biomarker can be performed in connection with detection of a condition associated with a plurality of target biomarkers. For example sensors of the disclosure can be used for multiplex detection of MMP-9, CTS-K, MMP-2 and ARG for presence and absence of lung cancer. In another example. sensors of the disclosure can be used for multiplex detection of arginase IL-13, for detection of anti-inflammatory events and conditions and of. IL-6, GCSF, MIP-1, MCP-1, for detection and diagnosis of pro-inflammatory events and conditions in an individual.

Exemplary Process for Making Multiplex

In some embodiments, one or more graphene core particle, graphene biosensor herein described are comprised in a composition together with a suitable auxiliary agent. The term "auxiliary agent" as used herein indicates any of various media acting usually as solvents, carriers, binders or diluents for the graphene biosensor herein described that are comprised in the composition as an active ingredient. In particular, the composition including the one or more oximes can be used in one of the methods or systems herein described.

In particular, in some embodiments, for storage and/or use, the biosensors would typically be dispersed into a pharmaceutically acceptable solvent system, which could be any type of suitable diluent, excipient, vehicle or the like. As used herein, the term "pharmaceutically acceptable" means not biologically or otherwise undesirable, in that it can be administered to a subject without excessive toxicity, irritation, or allergic response, and does not cause unacceptable biological effects or interact in a deleterious manner with any of the other components of the composition in which it is contained.

In some embodiments, a pharmaceutically-acceptable carrier can be selected to minimize any degradation of the biosensor components as would be well known to one of skill in the art and to minimize any adverse side effects in the subject (for in vivo administration), as would be well known to one of skill in the art. Exemplary carriers include non-aqueous solutions, such as diethyl ether, DMF, DMSO, and the like. The biosensors are shelf-stable at room temperature conditions, even up to elevated temperatures up to 100° C. without deterioration, and can be stored and shipped without special handling requirements (e.g., without refrigeration).

Pharmaceutically-acceptable ingredients include those acceptable for veterinary use as well as human pharmaceutical use, and will depend on the route of administration. For example, compositions suitable for administration via injection are typically solutions in sterile isotonic aqueous buffer. Exemplary carriers include aqueous solutions such as normal (n.) saline (~0.9% NaCl), phosphate buffered saline (PBS), sterile water/distilled autoclaved water (DAW), or other acceptable vehicles as will be understood by a skilled person.

The graphene carrier particles are stable, for an indefinite amount of time based on the data of the present disclosure. The peptide linkages are also stable for long periods of time (years). It will be appreciated that the particular compound selected for the detectable moiety may reduce the shelf stability of the overall biosensors, and the particular sensors could be stored under more careful conditions (e.g., under argon) to preserve delicate detectable moieties for longer periods of time, if desired.

It will also be appreciated that the biosensors can be fabricated in sequential stages where graphene carrier particles can be stored until use, at which time the peptide linkages and detectable moieties are added (e.g., directly before shipping to the end user or added by the ender user). Likewise, the graphene carrier particles can be pre-conjugated with selected peptide linkages and stored without attached detectable moieties, which can be added at a later time closer to use. Notably, the graphene carrier particles have a higher tolerance for mis-labeling, where a detectable moiety that is accidentally attached directly to the graphene particle itself (and not via a linkage) should not interfere with other correctly attached detectable moieties. That is, the signal of the incorrectly attached carrier particle will simply be permanently quenched due to its proximity of the carrier particle. Accordingly, the biosensors have higher tolerance thresholds during manufacturing further contributing to their advantages.

In embodiments, herein described the composition can comprise components additional to the graphene core particle and/or biosensors of the disclosure in suitable concentrations as will be understood by a skilled person. in particular, compositions in the sense of the disclosure can typically comprise a salt and buffer (A substance that is capable of maintaining the pH of a solution in which it is dissolved) selected to maintain the pH of the solution in which it is dissolved at a controlled pH. In an exemplary preferred embodiments, the composition can comprise 5 mM MES with 10 μM divalent cations and 155 mM NaCl as well as additional combinations of salts and buffers identifiable by a skilled person upon reading of the present disclosure.

In one or more embodiments, the biosensors can be pre-distributed into microplate wells and stored/distributed for use. Black chimney well microplates are particularly suited for this purpose. Opaque microplate configurations are preferred for the assay to reduce ambient light interference and noise. Methods for noninvasive detection and quantification of various biological markers are also described herein. These methods utilize biosensors described herein and can be carried out in health care facilities as an integral part of point of care resources, at home or in the field for assessing biological markers indicative of a variety of conditions and diseases. Such biological marker-based diagnostics could have numerous applications in precision medicine, particularly for airway diseases, for example in the differentiation of lung cancer from other lung conditions.

In preferred embodiments the composition can be in lyuphilized forms. Auxiliary reagents in support of lyophilization can include Trehelose, Dextrose, Sucrose, Glycine, Magnesium Stearate, Microcrystalline Cellulose, Starch (corn), Silicone/Titanuin Dioxide, Stearic Acid, Sodium Starch Glycolate, Gelatin, Talc, Sucrose, Calcium Stearate, Povidone, Pregelantinized Starch, HPMC, OPA products, Croscarmellose, Hydroxypropyl Cellulose, Ethylcellulose, Calcium Phosphate, or Crospovidone.

In some embodiments, graphene biosensors herein described can be use in a method of detecting the activity of a biomarker in an aqueous sample comprising contacting a biological sample with any biosensor according to the present disclosure to create a reaction solution; and detecting a change in the reaction solution.

In preferred embodiments the aqueous sample is a biological sample from an individual In those embodiments, a biological sample can be provided by collecting the sample from an individual and process the sample for analysis. In those embodiments, the processing of the sample typically results in a processed aqueous sample configured to be used in combination with detection reagents. In particular the biosensors in a reaction solution can be contacted with the processed biological sample for a period of time sufficient for the target biomarker (if present in the sample) to interact with the recognition sequence in the biosensors. Biological samples include, without limitation, blood, urine, saliva, tears, sputum, bronchoalveolar lavage fluid, nasal swab, breath condensate, milk, feces, rectal fluid, vaginal fluid, and the like. In one aspect, a biological sample is collected from a subject and prepared for analysis. The sample can be collected and prepared manually, which includes, for example, manual pipetting or mixing/diluting of the sample, manual protein spot cutting, manual biopsy collection, manual blood draw, and manual microwell loading. Alternatively, and automated process can be used, which includes, for example, use of automated liquid handlers, automated protein spot cutters, automated biopsy collection, automated blood draws, and automated microwell loading. It will be appreciated that the biological sample may contain the biomarker of interest, including various enzymes described herein, which can be used as biological markers indicative of the health status of the subject. Before, during, or after adding the sample to the reaction solution, a pharmaceutically acceptable buffer can be added to adjust the pH to optimal levels depending upon the biomarker of interest as well as the particular detectable moieties used. For example, slightly alkaline buffers such as HEPES can be used to adjust the pH of the reaction mixture within desired ranges. Moreover, the pH can be adjusted to fine-tune the reaction. For example, certain enzymes, such as MMPs and cathepsins, when taken from cancerous samples are more active under slightly acidic pH (lower limit ~6.6) as compared to non-cancerous samples. Thus, the pH is a parameter that can be optimized within the scope of the disclosure to further enhance the output of the assay. The reaction solution can also be spiked with cofactors such as Mg(II), Ca(II), or Zn(II) to further enhance the enzymatic activity for detection.

When the target biomarker is present in the sample, the detectable moieties generate a detectable signal (e.g., optical or spectroscopic), such as fluorescence or color change, which can be perceived visually or measured with an appropriate instrument. A plate reader can be used to detect the results of the assay. As explained when tethered, the central graphene particle quenches the emission of the detectable moiety. In the presence of the protease or other target biomarker, it cleaves the linkage separating the detectable moiety from the central particle, or modifies the linkage extending the detectable moiety outside the quenching proximity. The detectable particle generates a detectable signal that changes depending upon its proximity to the carrier particle, which can be detected and correlated with activity of the target protein. For example, the maximum absorption of the TCPP is near 420 nm, so an inexpensive 420 nm LED or any other kind of laser diode can be used for excitation of biosensors using TCPP as the detectable moiety. It will be appreciated that the biosensors are not limited to the TCPP-graphene FRET pair exemplified in the examples. Any FRET sensing pair can be used. If other FRET pairs are used, then the excitation wavelength and detection device can be modified accordingly.

In some embodiments FRET can be performed over the entire range of the electromagnetic spectrum In some embodiments photoacoustic detection (the photoacoustic response of various fluorophores can be distinguished.

In some embodiments radioisotopes could be released from the graphene cores and then filtered off.

In some embodiments, MRI probes can be released from graphene coated with a ferromagnetic material (iron oxide) or high-spin d- and f-block metal complex.

In some embodiments EPR probes can be released from graphene coated with a ferromagnetic material (iron oxide) or high-spin d- and f-block metal complex.

Assays using the biosensors can detect biomarkers down to the sub-femtomolar level (<$10^{-15}$ moles per liter), which is at least two orders of magnitude more sensitive to competing technologies, such as immunoassays. In fact, as demonstrated in the working examples using a non-optimized biosensor, $10^{-16}$ limits of detection (LOD) for proteases are possible. A unique advantage of this technology is that different biomarkers (e.g., several proteases, cytokines and kinases) can be measured in one liquid biopsy. That is, the technology permits simultaneous detection of different classes of biomarkers in a single platform. Thus, in multiplexing embodiments, a plurality of different types of detectable moieties are preferably used so that the assays can analyze a plurality of different types of target biomarkers in a single biological sample. Looking at multiple biomarkers permits the differentiation between related diseases (e.g., lung cancer vs. other disease) and the detection of diseases in very early states. The latter is, for instance, important for lung cancer detection, because cancer survival significantly increases when it is detected at stages 0 or 1, compared to 3 or 4.

In particular, in multiplexing biosensor herein described the detectable components are selected so that the excitation and emission spectra of the co-attached detectable moiety (e.g. fluorophores) minimize overlapping. More particular, selection of detectable component in multiplexing embodiments of the biosensors herein described is performed to minimize occurrence of FRET between detectable moieties such as fluorophores. In this respect, for example selection of datable moiety such as BODIPY dyes appear to be well suited, because they show both, narrow excitation and emission spectra as will be understood by a skilled person.

In preferred embodiments, the aqueous sample can be heath treated before performing the contacting and/or during the contacting of the sample with one or more of the graphene biosensors herein described.

In particular in some embodiments a sample in absence of a biosensor as described herein can be heat treated at a temperature ranging from 40° C. to 75° C. for 0.5 to 3 hours. Preferably, the sample or serum can be heat treated at a temperature ranging from 50° C. to 60° C. for 0.5 to 2 hours. In some embodiments, the sample or serum can be heat treated at a temperature of 55° C. for 1 hour.

In some embodiments of the methods for detection of a target biomarker the detecting is preceded by a heating of the testing solution in the presence of a biosensor as described herein. A assay sample or serum in presence of a biosensor as described herein can be heat treated at a temperature ranging from 40° C. to 75° C. for 0.5 to 3 hours. Preferably, the assay sample or serum can be heat treated in presence of a biosensor at a temperature ranging from 50° C. to 60° C. for 0.5 to 2 hours. In some embodiments, the assay sample or serum can be heat treated in presence of a biosensor at a temperature of 55° C. for 1 hour.

In some embodiments, the heating treatment can be performed according to ae protocol for heat treatment of sample exampled in Example 21. Heat treatment can be applied to the sample before the assay or during the assay or both. The impact of heat treatment is to specifically increase the Sample reading while having no effect on the Assay Control. SN therefore increases because of the increased specific signal. Temperatures between room temperature and 75° C. are effective. Preferably, a sample can be pretreated at 65° C. for 5 to 12 minutes or the assay is conducted at 41 or 45° C. for the duration of incubation.

In some preferred embodiments, the heating is performed on a solution comprising monobasic salt, and/or incubation in buffer solutions holding a pH=7.2. In some preferred embodiments, the incubation can be performed at 45° C.

In some embodiments, the biosensor and/or related combination therefore can be configured to detect target biomarkers associated with a target condition in an individual as will be understood by a skilled person.

For example, in one or more embodiments, the nanosensors can be configured for rapid diagnosis of lung conditions based upon protease activity profiling of two or more proteases (e.g., in a panel). The consensus sequences experience either proteolytic cleavage by their respective proteases, or the chemical constitution of the posttranslational modification sequence is changed. For instance, arginases I+II convert arginine to ornithine without proteolytic cleavage of the oligopeptide. Thus, methods described herein can also be adapted for use with other nanosensors, such as those described in WO 2016/149637 for detection of enzymatic posttranslational modification as will be understood by a skilled person. The nanobiosensors and methods can be used to detect target biomarkers and thereby diagnose numerous lung conditions, including lung diseases, cancers, and infections.

In one aspect, nanobiosensors for chronic inflammatory lung disorders (asthma, COPD, fibrosis) target the proteases reported in Table 4 together with corresponding consensus sequences for peptide linkage:

TABLE 4

Target proteases and consensus sequence for peptide linkage

| Host Protease | Consensus Sequence* | SEQ ID NO: |
|---|---|---|
| Proteinase 3 (PR3) | **LYYV-SLSP** | 95 |
| Cathepsin G (CTG) | **NVLH-SWAV** | 82 |

*except where noted, sequences further include N-terminal GAG and C-terminal AG spacers.

In some embodiments, nanobiosensors for pulmonary hypertension (PAH) can be configured to target the proteases reported in Table 5 together with corresponding consensus sequences for peptide linkage:

TABLE 5

| Target proteases and consensus sequence for peptide linkage | | |
|---|---|---|
| Host Protease | Consensus Sequence* | SEQ ID NO: |
| MMP-2 (Matrix Metalloproteinase-2) | **IPVS-LRSG** | 51 |
| MMP-9 | **VPLS-LYSG** | 55 |
| MMP-14 | **LPQG-LRTE** | 93 |

*except where noted, sequences further include N-terminal GAG and C-terminal AG spacers.

PAH can lead to secondary complications, such as COPD (Chronic obstructive pulmonary disease), asthma, chronic bronchitis, and others. The activity of three MMPs is enhanced in PAH, MMP-2, -9, and -14 (MT1-MMP-1). MMP-2, and MMP-9 are capable of cleaving basement membrane-associated collagen IV, which accelerates the remodeling of the pulmonary vasculature. Although MMP-14 is membrane-bound, it can be detected in Liquid Biopsies (serum, BALF, and potentially EBC) in the state of disease.

In some embodiments, nanobiosensors can be designed for the detection of influenza virus infection target the protease reported in Table 6 together with corresponding consensus sequences for peptide linkages.

TABLE 6

| Target proteases and consensus sequence for peptide linkage | | |
|---|---|---|
| Host Protease | Consensus Sequence* | SEQ ID NO: |
| TMPRSS2 (Epitheliasin, transmembrane protease, serine 2) | **RQSR-IVFG** | 86 |
| Human airway trypsin-like peptidase (HAT) | **RSAR-GLKG** | 85 |
| Granzyme B | **VEPN-SLEE** A | 49 |

*except where noted, sequences further include N-terminal GAG and C-terminal AG spacers.

In some embodiments, biosensor of the disclosure can be configured for detection of other proteases in the lung, such as TMPRSS2 (epitheliasin) and Human airway trypsin-like peptidase (HAT) which facilitate influenza virus infections H1N1 (A/Memphis/14/96), H2N9 (A/Mallard/Alberta/205/98), and H3N2 (A/Texas/6/96) upon cleavage of haemagglutinin (HA) in those conditions, the viral pathogens are able to stimulate protease expression in an "Influenza-cytokine-protease cycle." The enzymes are expressed as zymogens are then activated by the network of proteases in the lung. Granzymes are also known to activate H1N1. Therefore, we have included granzyme B into this panel. The advantage of the latter is that it can be detected in EBC as will be understood by a skilled person.

In some embodiments, nanobiosensors can be configured for the detection of viral infections target the activity of kallikreins in the lung. Kallikreins (KLK's) are a family of proteases consisting of 15 closely related, secreted serine proteases with either trypsin-like or chymotrypsin-like specificity. KLK-2, KLK-3, KLK-4, KLK-5, KLK-6, KLK-12, and KLK-15 are poorly expressed in the lung in healthy individuals. This expression pattern changes in response to viral infections. In case of an influenza infection, the expression of KLK-1, KLK-2 and KLK-5 increases, whereas the expression of KLK-13 and KLK-14 decreases. KLK-13 is increased in virtually all coronavirus (SARS and MERS types) infections. An exemplary kallikreins and related corresponding exemplary consensus sequences for the peptide linkages are reported in Table 7.

TABLE 7

| Target proteases and consensus sequence for peptide linkage | | |
|---|---|---|
| Host Protease | Consensus Sequence* | SEQ ID NO: |
| KLK-1 | **EAFR-STGA**** | 98 |
| KLK-2 | **GTSR-SAGG***** | 99 |
| KLK-5 | **YRFR-ILGG** | 100 |
| KLK-12 | **IESK-INGG** | 101 |
| KLK-13 | **VRSR-IVKG** | 102 |
| KLK-14 | **TQPR-IVGG** | 103 |
| KLK-15 | **ALGR-KLVG** | 104 |

*except where noted, sequences further include N-terminal GAG and C-terminal AG spacers.

**includes N-terminal GAG spacer and C-terminal GA spacer

***includes N-terminal GAA spacer and C-terminal AG spacer.

In some embodiments, biosensors can be configured for the detection of *Streptococcus pneumococcus* infection target bacterial protease can: An exemplary protease which is target biomarker for *Streptococcus pneumococcus* and related corresponding exemplary consensus sequences for the peptide linkages are reported in Table 8.

TABLE 8

| Target proteases and consensus sequence for peptide linkage | | |
|---|---|---|
| Bacterial Protease | Consensus Sequence | SEQ ID NO: |
| *Streptococcus pneumoniae* IgA1 protease | **STPP-TPSP**** | 105 |

**includes N-terminal GAG spacer and C-terminal GA spacer

*S. pneumococcus* is the most prevalent bacterial infection in the lung and the vast majority if not totality of streptococci express *Streptococcus pneumoniae* IgA1 protease as will be understood by a skilled person. Accordingly This protease is among the most active proteases know and only present in case of a *Streptococcus* infection. It will permit a rapid test (<10 min.) for a bacterial lung infection.

In one aspect, nanobiosensors for the detection of *Mycobacterium tuberculosis* infection target the following proteases. An exemplary protease which is target biomarker for *Mycobacterium tuberculosis* and related corresponding exemplary consensus sequences for the peptide linkages are reported in Table 9.

TABLE 9

| Target proteases and consensus sequence for peptide linkage | | |
|---|---|---|
| Bacterial Protease | Consensus Sequence | SEQ ID NO: |
| Mycosin Protease MycP1 | **VKAA-SLGK**** | 106 |
| Rv2869c (*Mycobacterium tuberculosis*)-like peptidase (RIP-1) | **TCCA-TCAT-CC**** | 107 |

**includes N-terminal GAG spacer and C-terminal GA spacer

Additional secreted *Mycobacterium tuberculosis* proteases which can be used as target biomarker are MycP1 and Rv2869c (*Mycobacterium tuberculosis*)-like peptidase (RIP-1), which are both specific for MtB as will be understood by a skilled person.

In some embodiments, nanobiosensors of the disclosure can be configured for the detection of Chronic obstructive pulmonary disease (COPD). An exemplary protease which is target biomarker for COPD and related corresponding exemplary consensus sequences for the peptide linkages are reported in Table 10.

TABLE 10

| Target proteases and consensus sequence for peptide linkage | | |
|---|---|---|
| Host Protease | Consensus Sequence | SEQ ID NO: |
| Neutrophil elastase (NE) | **GEPV-SGLP** | 87 |
| MMP-7 (matrilysin) | **VPLS-LTMG** | 53 |
| MMP-8 | **EPYH-LMAL****** | 89 |
| MMP-12 | **GPAN-LVAP******* | 92 |
| Cathepsin G | **NVLH-SWAV** | 82 |
| Proteinase-3 (myeloblastin) | **SYYV-SLSP** | 96 |

*except where noted, sequences further include N-terminal GAG and C-terminal AG spacers.
****includes N-terminal GAP spacer and C-terminal AG spacer.
*****includes N-terminal GAA spacer and C-terminal EG spacer Additional target biomarker for COPD can be identified and selected based on the fact that endogenous serine protease inhibitors are responsible for pulmonary tissue protection against serine proteases in healthy human subjects. Inherited inhibitor deficiencies are considered the most important reason for the development of COPD, followed by smoking. In the absence of effective inhibitors, uncontrolled proteolysis and, subsequently, lung damage are observed. The most important proteases for COPD detection are neutrophil elastase, neutrophil-derived MMP-8, macrophage-derived MMP-12, cathepsin G and proteinase 3. These proteases are capable of damaging ECM components, such as collagen, laminin, fibrillin, and elastin. Especially the cleavage of lung elastin causes emphysema, which is a driver for COPD pathophysiology. MMP-7 degrades the extracellular proteoglycan decorin, which leads to the subsequent release of decorin-bound transforming growth factor-O (TGF-0). Therefore, the co-activation of all six proteases (NE, MMP-7, -8, -12, CTSG, and proteinase 3) permits the detection of COPD.

In some embodiments, nanobiosensors can be configured for the detection of lung cancer and the differentiation between Small Cell Lung Cancer (SCLC) and Non-Small Cell Lung Cancer (NSCLC) target using a panel of proteases: An exemplary protease which is target biomarker for SCLC and NSCLC and related corresponding exemplary consensus sequences for the peptide linkages are reported in Table 11.

TABLE 11

| Target proteases and consensus sequence for peptide linkage | | |
|---|---|---|
| Host Protease | Consensus Sequence | SEQ ID NO: |
| MMP-1 | **VPMS-MRGG** | 88 |
| MMP-2 | **IPVS-LRSG** | 51 |
| MMP-10 | **RPLS-LQTG** | 90 |
| MMP-12 | **GPKN-LKAP******** | 91 |
| MMP-15 | **LPQK-SQHG** | 94 |
| Cathepsin B | **SLLKSR-MVPNFN** | 43 |
| Cathepsin H | **ALQA-RPGP** | 83 |

TABLE 11-continued

| Target proteases and consensus sequence for peptide linkage | | |
|---|---|---|
| Host Protease | Consensus Sequence | SEQ ID NO: |
| Cathepsin L | **SGVVIA-TVIVIT** | 84 |
| Arginase II | **RRRRRRR** | 97 |
| Neutrophil Elastase | **GEPV-SGLP** | 87 |

*except where noted, sequences further include N-terminal GAG and C-terminal AG spacers.
******includes N-terminal GAA spacer and C-terminal AG spacer.

In some embodiments, the relevant datasets for the selection of proteases for the detection of SCLC and NSCLC vs. non-cancerous health conditions, as well as the differentiation between SCLC and NSCLC can be obtained from the NCBI GEO database (see the website www.ncbi.nlm.nih-.gov/geo/ at the filing date of the present disclosure) as will be understood by a skilled person. Datasets included in the analysis were taken from human cancers with datasets that contained both primary tumor samples and healthy human tissue. Exemplary calculated p-values for SCLC and NSCLC is reported in Table 12 below.

TABLE 12

Calculated p-values from NCBI GEO ID's

| ID | P-Value | logFC | Gene Symbol | Gene Description |
|---|---|---|---|---|
| Both, SCLC and NSCLC vs. Tumor Control | | | | |
| NM_002421_at | 2.04E−04 | 0.960344 | MMP1 | matrix metallopeptidase 1 (interstitial collagenase) |
| NM_002425_at | 1.14E−03 | 0.921643 | MMP10 | matrix metallopeptidase 10 (stromelysin 2) |
| NM_002426_at | 3.64E−21 | 3.321265 | MMP12 | matrix metallopeptidase 12 (macrophage elastase) |
| NM_002428_at | 5.58E−22 | −0.75712 | MMP15 | matrix metallopeptidase 15 (membrane-inserted) |
| NM_004530_at | 1.41E−20 | −1.9972 | MMP2 | matrix metallopeptidase 2 (gelatinase A, 72 kDa gelatinase, 72 kDa type IV collagenase) |
| NM_147783_at | 1.33E−06 | −0.75068 | CTSB | cathepsin B |
| NM_004390_at | 2.96E−27 | −2.71018 | CTSH | cathepsin H |
| NM_001333_at | 1.59E−12 | 1.221857 | CTSL2 | cathepsin L2 |
| NM_001172_at | 7.34E−18 | 1.582521 | ARG2 | arginase, type II |
| NM_001972_at | 2.26E−11 | −0.41571 | ELA2 | elastase 2, neutrophil |
| NSCLC vs. SCLC | | | | |
| 204475_at | 9.96E−01 | −3.84E−03 | MMP1 | matrix metallopeptidase 1 |
| 205680_at | 7.62E−04 | 2.16 | MMP10 | matrix metallopeptidase 10 |
| 204580_at | 4.87E−02 | 1.04 | MMP12 | matrix metallopeptidase 12 |
| 203365_s_at | 2.19E−01 | −1.58E−01 | MMP15 | matrix metallopeptidase 15 |
| 201069_at | 7.13E−02 | −5.65E−01 | MMP2 | matrix metallopeptidase 2 |
| 200839_s_at | 1.27E−02 | −6.27E−01 | CTSB | cathepsin B |
| 202295_s_at | 4.80E−05 | −1.19 | CTSH | cathepsin H |
| 202087_s_at | 7.48E−02 | −4.50E−01 | CTSL | cathepsin L |
| 203945_at | 9.67E−01 | −5.25E−03 | ARG2 | arginase 2 |
| 206871_at | 2.71E−01 | −7.17E−02 | ELANE | Elastase 2, neutrophil |

Based on these gene expression data, the selected panel of enzymes should be able to differentiate between SCLC and NSCLC.

Differentiation between SCLC and NSCLC is important, because of different treatment approaches to each type of cancers. The main subtypes of NSCLC are adenocarcinoma, squamous cell carcinoma, and large cell carcinoma. These subtypes, which start from different types of lung cells are grouped together as NSCLC because their treatment and prognoses (outlook) are often similar. A smaller subset of all lung cancers are SCLC. This subset is more sensitive to chemotherapy and radiation treatment, although their overall mortality is higher.

Furthermore, in analogy to pancreatic cancer, detection of NSCLC at stages 0 and 1 by means of Liquid Biopsies will be possible because of distinctly changing protease signatures during the transition from non-cancerous to cancerous. Principally, the same selection of proteases/arginase can differentiate between SCLC and healthy tissue, Based on the gene expression differences, MMP10 and Cathepsin H can be selected as suitable proteases to distinguish between SCLC and NSCLC.

Similar gene expression analysis can be used to determine the proteases that are overexpressed in other solid tumors, such as pancreatic cancer, including using databases, such as NCBI GEO, Entrez Gene ID, Unigene ID and Gene Symbol. This strategy is able to select enzyme candidates that have a high probability of being proximal biomarkers for pancreatic cancer from the human genome.

These target panel sequences and detection platforms can be configured into a number of sensors of the disclosure, including solution-based assays, microfluidics assays, microwell assays, high throughput assays, and the like, including in those described in U.S. Pat. Nos. 8,969,027; 9,682,155; 9,731,034; and 9,216,154, incorporated by reference herein, as well as in co-pending WO 2017/165800 (US 2020/0300849), filed Mar. 24, 2017.

In a further preferred embodiment, inflammatory biological markers can be detected along with detection of specific viral, bacterial, or mold infections. For example, nanosensors could be prepared using a peptide aptamer against Capsid B (AISGSGGSTYYANSVLG (SEQ ID NO:71), recognition sequence for detecting *Haemophilus influenzae* B, or recognition sequences for *Haemophilus influenzae* NT (TNLGILHSMVARAVGNNTQG (SEQ ID NO:72)), or *Moraxella catarrhalis* (GIITYALSGGEIKILAG (SEQ ID NO:73)). Likewise, nanosensors for viral infections can be prepared using protease consensus sequences for HIV detection (SAVL-LEAT (SEQ ID NO:74), or SQNY-PIVQ (SEQ ID NO:75)).

It will be appreciated that each of the foregoing sensors described above can be designed in an alternative configuration where the graphene core particle is attached via a modifiable recognition sequence, a protease consensus sequence, a post-translationally modifiable sequence nt bond that interacts with the target biomarker. In such embodiments, while the detectable particle remains relatively stationary and affixed to the carrier particle, the quencher particle is instead either cleaved or moved away from the detectable particle and carrier particle, to effect the change in distance between the particles, as described above. As noted, the increase in distance between the graphene core particle and the detectable particle (from cleavage or elongation of the quencher particle tether) results in a detectable change in the signal from the nanosensor.

In one or more embodiments, sensors in accordance with the disclosure can be used to diagnose lower respiratory tract infections by detecting markers associated with infected lower airway epithelial cell infection. These markers include CCL20, TSLP, and CCL3-L1. As noted herein, exosome contents can be used to determine whether the exosomes originated from the upper or lower airway, and further assist in localization of where the infection or other condition may originate from in the subject's body. The sensors can also be used for environmental risk assessment in patients with chronic lung disease. Exposure to air pollutants, ozone, particulates, acetaldehydes, acroleine, formaldehyde, tobacco smoke and other compounds triggers inflammation of the respiratory tract. Detection of markers such as cytokines, proteases, and/or kinases can be used to identify the stage at which lower respiratory tract inflammation is manifest, allowing for personalized environmental assessment. The nanosensors can also be used for measurement of lower respiratory tract inflammation in the real-time management of inflammation in asthma. Details regarding biological markers and understanding of protein expression patterns associated with severe asthma are described in U.S. Pat. No. 8,053,199, incorporated by references herein. Currently anti-inflammatory (corticosteroids, IL-13 antibodies and others) are given and monitored on the basis of symptoms and exacerbations. By testing for lower airway markers such as cytokines, proteases, and/or kinases patients and caregivers can track inflammation in real time and adjust treatments accordingly. Similarly, the nanosensors can be used for measurement of lower airway remodeling in severe asthma and chronic obstructive lung disease (COPD). Remodeling refers to the process of fibrosis of the respiratory tract, a process linked to progressive decline in lung function in a subset of patients with severe asthma and COPD. There is no treatment or diagnostic currently available. New therapies directed towards epigenetic remodeling are currently being developed. Our method will enable the development and approval of remodeling inhibitors for clinical use by detecting and measuring the presence of fibronectin, IL6, or vimentin, as indicative of progressive airway remodeling.

In some embodiments the sensors of the disclosure can be used in connection with detection of opportunistic infections. Opportunistic infections are also a significant complication in patients being treated for cancer, immunosuppressed through treatment of rheumatoid arthritis or inflammatory bowel disease, or those with HIV. *Pneumocystis* pneumonia (PCP) is the most common infection of HIV patients, and can only be diagnosed currently by invasive bronchoscopy. Invasive aspergillosis is also an opportunistic lung infection occurring in patients undergoing chemotherapy for leukemia. The nanosensors can be used to indicate the presence of distinct host response proteins when the fungus invades the airway in patients immunosuppressed from their leukemia treatment.

In some embodiments, the sensors of the disclosure can also be used for monitoring for transplant rejections or host versus graft disease in lung transplants. Lung transplant patients are treated with intensive immunosuppressive therapy and their physicians treat a fine line between too much immunosuppression (get opportunistic infections), or too little, where they would reject the organ. If a transplant patient could monitor their immune profiles in a real time basis, this would make management of the transplant much easier. It will also be appreciated that the nanosensors can be used for monitoring for response to lung cancer treatment. Mobile biosensing would detect cancer signatures, such as cytokines, proteases, and/or kinases (e.g., MMPs, EMT, etc.), in the airway or circulating in the blood. This would include free proteins and those contained within microparticles (exosomes).

In some embodiments, sensors of the disclosure can be used in conjunction with protein sample collection, processing, profiling, and detection, embodiments described herein can also be utilized in conjunction with traditional PCR/RT-PCR, real-time quantitative PCR/RT-PCR, and isothermal PCR/RT-PCR methodologies to assess bacterial, viral, and mold infections that are associated with increased or decrease protein level expression. Thus, assays according to the invention can be used as a stand-alone technology, and/or in conjunction with traditional approaches, especially in risk groups that have been pre-identified as being at-risk by genetic testing.

In general, detection performed by sensors of the disclosure involves contacting the prepared sample with the nanosensor (and generally a plurality of nanosensors) to create a reaction mixture. The nanosensors can then be probed or excited using the appropriate energy source. The wavelength used will depend upon the particles used in the nanosensors. The changes in absorption and/or emission of the particles are then detected over a period of time as the target biomarker interacts with the nanosensors (e.g., such as through binding and extension of the recognition sequence).

Embodiments described herein also rely on nanosensors integrated with microfluidic and smart device platforms, which in turn, can be read by a simple-but-robust fluorescence or optical reader. "Microfluidic" refers to techniques manipulating, controlling, and/or analyzing small volumes of (fluid) samples, generally ranging from microliters ($10^{-6}$) to picoliters ($10^{-12}$). In one aspect, microfluidic technology is employed to introduce rapid, high-throughput sample collection, sample processing, sample profiling and target detection. In a further preferred embodiment, the microfluidic device will interface with a mobile computing device such as, but not limited to, a smart phone or smart tablet. Mobile computing devices including tablets, smart phones, hand held computers, laptops, etc. that are capable of optically scanning a sample and transmitting the information to other computing devices. This integrated platform will revolutionize the current "traditional" protocols, which use multiple instruments with tedious, manual sample-handling steps. In a further preferred embodiment, a stand-alone, battery-powered diagnostic platform with rapid analysis times and multiplexing capabilities will achieve statistical significance of measured quantities, with minimum consumption of human fluids (<5 μl per sampling) using a hand-held smartphone-based system that can be used as a diagnostic tool by patients and medical professionals.

In some embodiments assays performed with biosensors of the disclosure can utilize a combination of two or more of the various sensors discussed above. Importantly, nanosensors utilized in accordance with the disclosure can be designed to include a supramolecular recognition sequence, a protease consensus sequence, a post-translationally modifiable sequence, that gives rise to a specific interaction with a biological marker. As used herein, references to "specific interactions" is intended to differentiate the interaction between recognition sequences of the sensors from non-specific binding or reactions between molecules, and means that the set of specific target analytes for which the oligopeptide sequence can interact is limited, and in some cases even exclusive, such that neither binding nor enzymatic cleavage occurs at an appreciable rate with any other molecule.

Methods of the present disclosure can be performed with corresponding systems comprising various combinations of layered graphene, organic and/or inorganic molecule, detectable moieties, peptide linkage, detectable components, biosensors, reagents to perform chemical reactions herein described as well as additional components identifiable by a skilled person.

Exemplary optical detection techniques are described. However, it should be understood that other methods of analyzing the assay can be employed. In general, the methods involve exposing the reaction solution (e.g., in the microwell) to an appropriate energy source. The wavelength used will depend upon the detectable labels used in the biosensors. Both the position/presence and concentration/intensity of the signal from the detectable moiety can then be sensed or detected with the appropriate sensing or detecting instrument for both quantitative and qualitative assessment of the detectable moiety.

The systems herein disclosed can be provided in the form of kits of parts. In kit of parts for performing any one of the methods herein described to make the biosensors, the graphene particles can be included in the kit alone or in the presence of one or more buffers as well as reagents to perform chemical transformation of the graphene particles. In kit for detection of the biomarker one or more biosensors herein described can be included in the kit alone or in the presence of one or more buffers as well as of reagents to perform detection of one or more biomarkers. Additional components identifiable by a skilled person can also be included.

In a kit of parts, the graphene particles, biosensors and the reagents are comprised in the kit independently possibly included in a composition together with suitable vehicle carrier or auxiliary agents. For example, one or more biosensors can be included in one or more compositions together with reagents for detection also in one or more suitable compositions. Additional components can include labels, reference standards, and additional components identifiable by a skilled person upon reading of the present disclosure.

In embodiments herein described, the components of the kit can be provided, with suitable instructions and other necessary reagents, in order to perform the methods here disclosed. The kit will normally contain the compositions in separate containers. Instructions, for example written or audio instructions, on paper or electronic support such as tapes, CD-ROMs, flash drives, or by indication of a Uniform Resource Locator (URL), which contains a pdf copy of the instructions for carrying out the assay, will usually be included in the kit. The kit can also contain, depending on the particular method used, other packaged reagents and materials (i.e. wash buffers and the like).

Further details concerning the identification of the suitable auxiliary agent of the compositions, and generally manufacturing and packaging of the kit, can be identified by the person skilled in the art upon reading of the present disclosure.

EXAMPLES

The following examples set forth methods in accordance with the instant disclosure. It is to be understood, however, that these examples are provided by way of illustration and nothing therein should be taken as a limitation upon the overall scope of the disclosure.

Example 1: Graphene and Metal Photochemical Properties

Graphene contains at least 98% carbon and shows minimal reaction with water or aqueous buffers as well as with thiols functional groups (e.g. presented on proteins and glutathione) in aerated aqueous buffers, These properties are opposite to the ones of metal/metal oxide material, Graphene UV/V's absorption in the Ultra Violet (UV), visible and near-Infra Red (IR) region exceeds the absorption of graphite. [28] In particular Stacked graphene features light absorption over the entire wavelength range from far UV to mid-IR (100 to 1500 nm).[6]

Although direct excitation occurs at deep/far ultraviolet, surface plasmons of graphene in the visible range are of very intensity and not capable of effectively exciting attached organic fluorescent dyes or nanoparticles.[6]

In contrast, many nanoparticles (especially Au, Ag, but also Fe in Fe/$Fe_3O_4$) show strong plasmons in the visible range of the electromagnetic spectrum, which contribute to both, fluorophore excitation and quenching.[29, 30] In graphene, plasmon excitation in the visible range of the spectrum can occur by means of energy transfer from nearby attached fluorescent organic dyes and is expected from metal nanostructures and quantum dots as well.[31]

Because of the photophysical properties of graphene, there is no need for a FRET acceptor per fluorophore to be integrated in the design. This permits multitasking and avoids overcrowding at the surface of the nanobiosensor, which would kinetically slow down the nanobiosensors significantly.

Because of the photophysical properties of graphene, when using graphene within a FRET pair, there is no need for a FRET acceptor to be integrated in the design to complement a FRET donor (such as a fluorophore). These graphene's properties permit allow a user to minimize overcrowding at the surface of the nanobiosensor, which would kinetically slow down the nanobiosensors significantly as will be understood by a skilled person.

In addition to the above, some forms of graphene such as explosion graphene and some fractions from flash graphene possess a super-aggregate fractal morphology which can be ascertain by light scattering methods such as SEM (Scanning Electron Microscopy) and Light Scattering.[18, 19]

Exemplary SEM (Scanning Electron Microscopy) images of fractal graphene comprising 7 layers are reported in FIG. 1. [8]

As can be seen in the illustration of FIG. 1, stacked layers of graphene feature fractal dimensions between Df=2.5±0.3 (upper bound) and Df=1.8±0.4 (lower bound). In general, any fractal dimensions between Df=2.9±0.09 and Df=2.1±0.09 can be attained, depending on the size and surface modification of explosion-graphene.

The fractal geometry of explosion graphene causes enhanced light absorption, because light gets "trapped" within the structure. Whereas in flat graphene sheets light passes through graphene only once, light reflection and diffraction from within the fractal morphology causes multiple absorption events as will be understood by a skilled person.

Example 2: Overview Biosensors and Method of Making

Figure 2A:
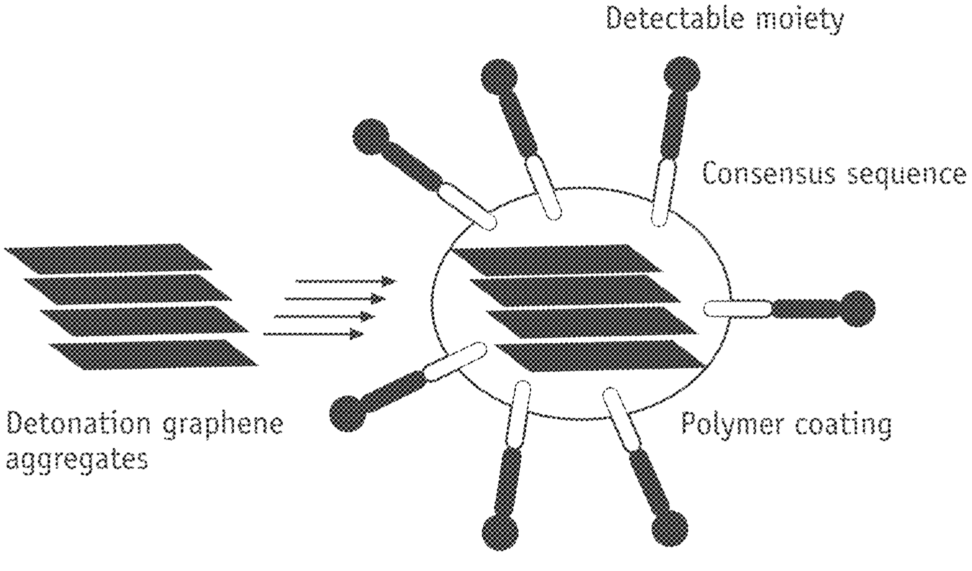
FIG. 2A shows a schematic representation of an exemplary graphene-based biosensors for protease detection of the present disclosure.

A schematic representation of the main components of biosensors herein described is provided in FIG. 2A related to exemplary embodiments where the graphene is provided by detonation graphene and the coating of the core particle is provided by a polymer coating.

In the exemplary configuration schematically illustrated in FIG. 2A, nanosheet of detonation graphene aggregates are used to provide the graphene component of a core particle coated by a monolayer of a polymer coating. Detection components formed by a peptide linkage comprising a consensus sequence and a detectable moiety are further attached to the core particle through attachment to the polymer coating.

Figure 2B:
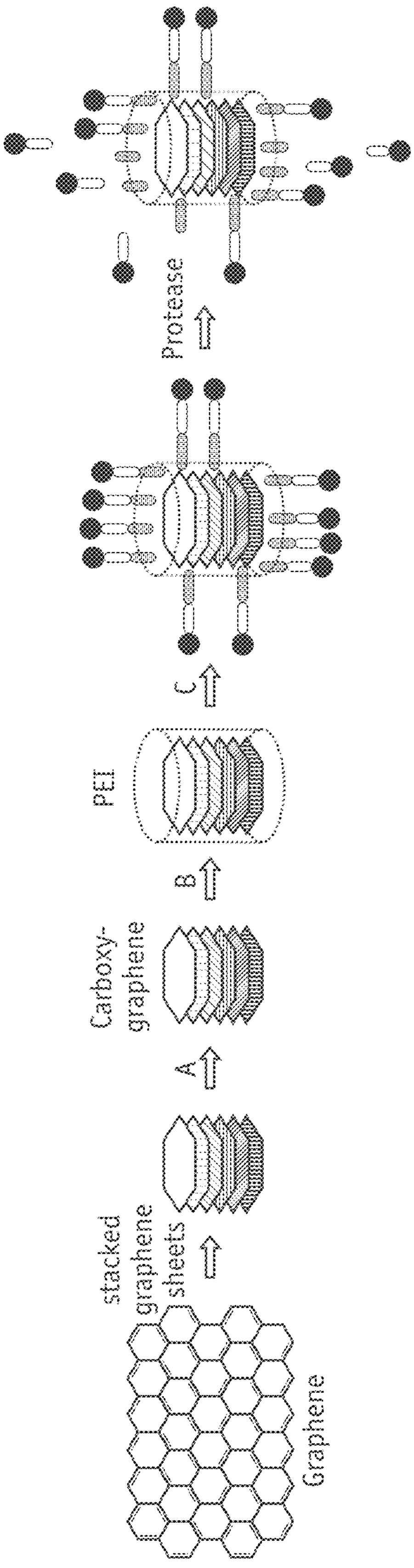
FIG. 2B shows a schematic representation of an exemplary process to provide biosensors according to the disclosure: A: synthesis of Carboxygraphene; B: Chemical attachment of Polyethylene imine via amide bonds; C: Attachment of consensus sequence (oligopeptide) and fluorescent dye, such as tetra carboxy-phenyl-porphyrin (TCPP).

The biosensors with the structure schematically illustrated in FIG. 2A can be provided with an exemplary process schematically shown in FIG. 2B. In the schematic illustration of FIG. 2B, the graphene surface is functionalized with, e.g., a plurality of carboxylic acid groups and/or coated with a thin polymer monolayer. In the exemplary illustration of FIG. 2B, a plurality of detectable moieties can be attached to the same carrier particle via respective oligopeptide linkages. For example, two or more different detectable moieties can be attached to the same carrier particle via respective oligopeptide linkages with specificity for respective target biomarkers as schematically shown in FIG. 2B.

In particular, the schematic illustration of FIG. 2B show the design of novel biosensors: A: synthesis of Carboxygraphene; B: Chemical attachment of Polyethylene imine via amide bonds; C: Attachment of consensus sequence (oligopeptide) and fluorescent dye (TCPP). TCPP is attached to the N-terminal end of the oligopeptide while on resin. After cleavage from the resin and HPLC-purification (if necessary), the consensus sequence+TCPP is attached by means of its C-terminal end to the polyethylene imine. Due to kinetic reasons, consensus sequences+TCPP are attached via the C-terminal end of the oligopeptide. In the presence of the correct protease, the consensus sequence is proteolytically cleaved and the fluorescent dye TCPP+covalently attached half of the consensus sequence is released (light switch effect).

Figure 2C:
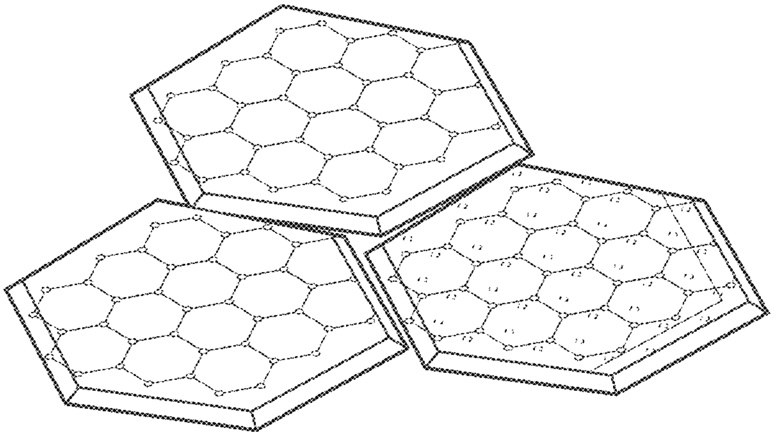
FIG. 2C shows a schematic representation illustrating thin monolayers of graphene entangled with each other with overlapped edges, or more ordered stacking of nanosheets comprising or consisting of two to three layers.

A further schematic illustration of thin monolayers of graphene entangled with each other with overlapped edges, or more ordered stacking of nanosheets comprising or consisting of two to three layers is reported in FIG. 2C.

Figure 2D:
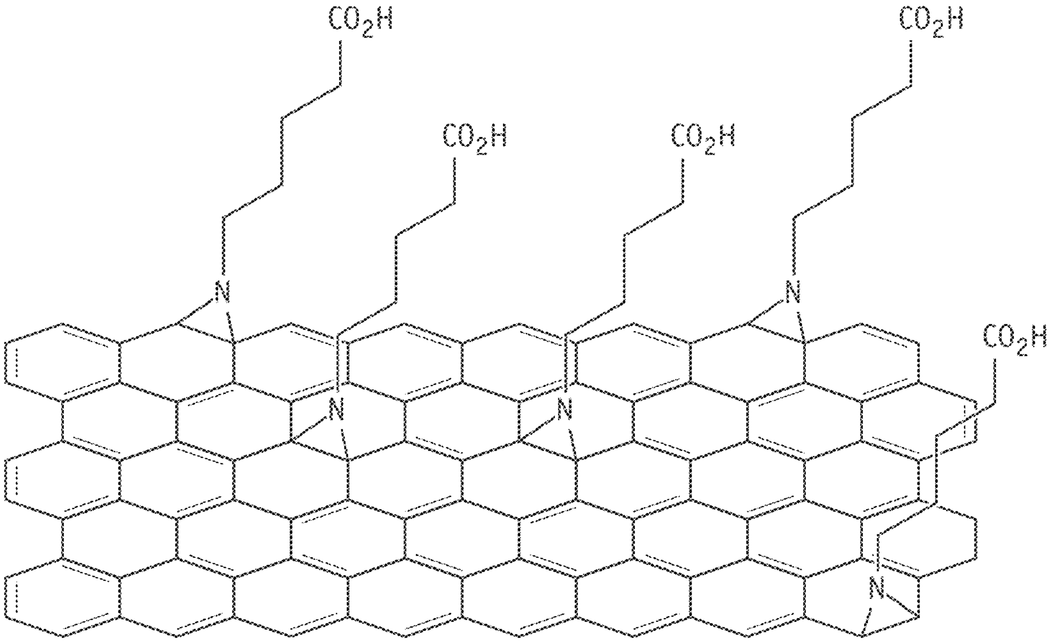
FIG. 2D shows a schematic representation of a high density of carboxylic acid groups added across the surface of a graphene nanosheet particulate.

A schematic illustration of a high density of carboxylic acid groups added across the surface of a graphene nanosheet particulate is reported in FIG. 2D.

Additional details concerning process for carboxylation of graphene and attachment of detectable components through PEI polymer coating are reported in Example 3 to Example 9.

Example 3: Synthesis of Carboxygraphene—General Process

To synthesize a graphene derivative referred to herein as "carboxygraphene," detonation graphene (0.2-0.5) nanoparticulates (nanosheet particulates) are dispersed in anhydrous dimethylformamide (DMF) at room temperature.

After the dispersion is complete, a carboxylic acid with a primary or secondary halogen is added, followed by the addition of anhydrous sodium azide ($NaN_3$). The temperature will then be slowly increased (1° C./minute) to 80° C. Between 20° C. and 40° C. a nucleophilic substitution reaction ($S_N$) occurs, in which an organic azide and DMF-soluble sodium halogenide are formed. The organic azide releases dinitrogen ($N_2$) and forms a nitrene intermediate at temperatures >50° C. Nitrenes feature 6 instead of 8 electrons in the outer shell of nitrogen. This reactive intermediate undergoes a cycloaddition with a 1-H double bond at the surface of graphene to form a stable azirane anchor.

The azirane-cycloaddition offers the opportunity to add a tailored amount of carboxylic acids to the surface of graphene without compromising the optical and electrical properties of graphene.

An exemplary reaction scheme and protocol are outlined in Example 4.

Example 4: Graphene Derivatization (Carboxygraphene (CG))

Figure 3A:
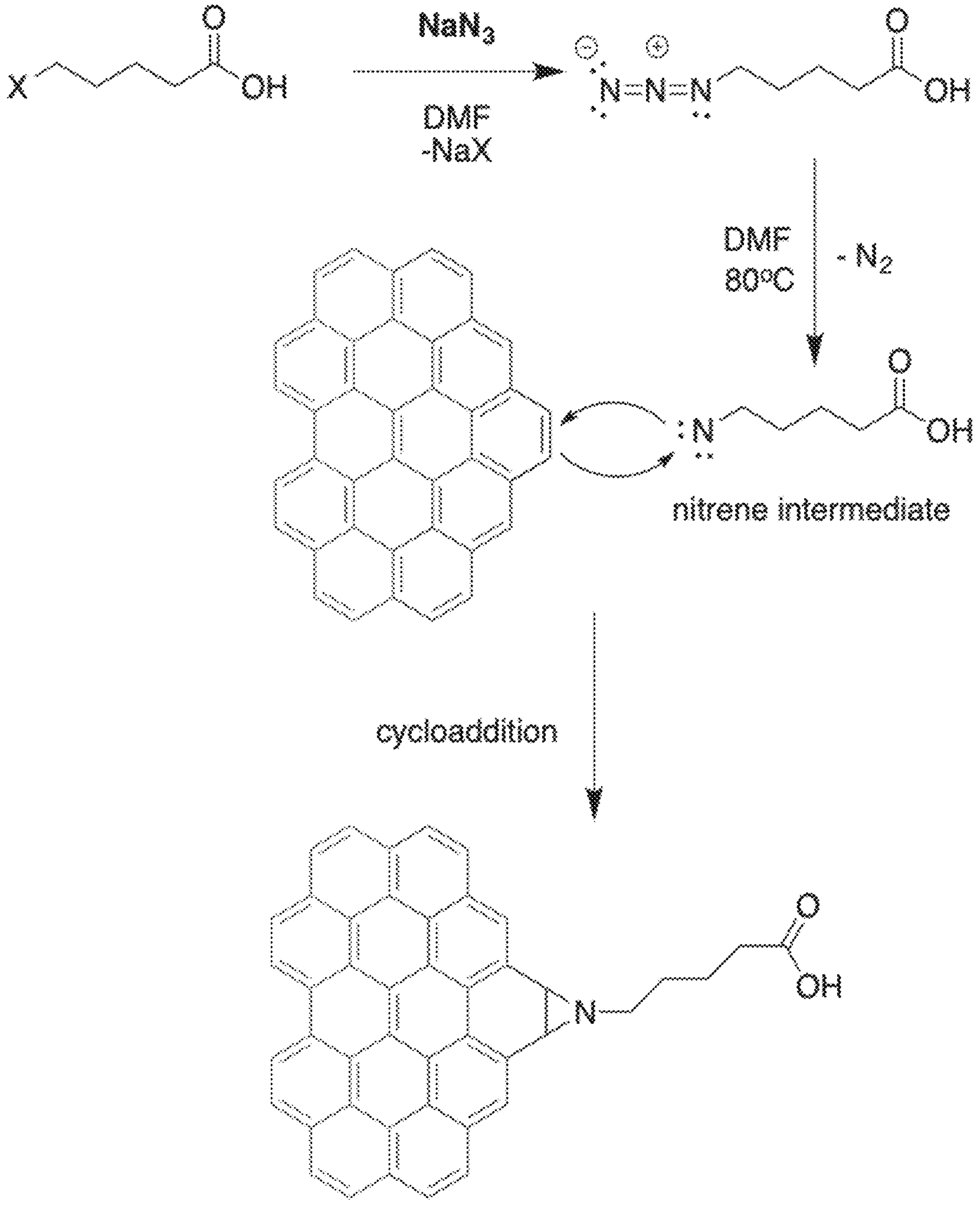
FIG. 3A shows a reaction scheme for azirane-cycloaddition to add a tailored amount of carboxylic acids to the surface of graphene.

An example reaction scheme for synthesis of carboxygraphene from detonation graphene in a one-pot reaction is shown in FIG. 3A.

The protocol starts with detonation-synthesized graphene (0.40) nanosheet particulates having an elementary composition of: 98.9% C, 0.08% H, and 1.02% O. The material is then reacted with bromovaleric acid and sodium azide to yield carboxygraphene (CG) as follows.

1.0 g of graphene nanosheet (GN) particulates were suspended in 20 mL DMF at 20° C. in a 250-mL three-necked round bottom flask. Next, at 40° C., 0.50 g of 5-bromovaleric acid (0.0028 mol) were added to the GN suspension, as well as 0.18 g $NaN_3$ crystals. After $NaN_3$ was dissolved, the suspension was slowly heated up to 80° C. (about 1° C./min.) and stirred for 1 hr. The release of $N_2$ was observed. Finally, after 1 hour, the suspension was cooled down to room temperature, and derivatized GN was collected via centrifugation (5 min @ 7,000 rpm) and washed 5 times with DMF and then 3 times with anhydrous diethyl ether. The resulting CG was dried for characterization at 50° C. for 1 h and then stored under argon. Yield: 82% (by weight, assuming total reaction). Elementary analysis of carboxygraphene is 94.22% C, 1.79% H, 1.17% N, and 2.82% O. The incorporation of N indicates that the addition reaction was successful.

A schematic structure of Carboxygraphene in which only a single graphene nanosheet is shown is reported in FIG. 3B, while a Side-view illustration of Carboxygraphene top layer showing high density distribution of carboxylic acid groups across the surface is reported in FIG. 3C.

As shown in FIG. 3D, Differential Thermogravimetry (DTA) indicates a weight loss of 4.5±0.5 percent by weight when heated beyond 100° C. At temperatures beyond 100° C. the material is virtually stable, as this can be expected from graphene. The initial weight loss arises from the partial loss of attached valeric acid units in the outer shell of carboxygraphene.

Example 5: Titration of Carboxygraphene (CG)

100 mg of Carboxygraphene (CG) were suspended in 20 mL of 0.100 M NaOH. After stirring the suspension for 5 min at 300K, 0.100 M HCl solution was added in incremental steps. At each step the pH of the solution was recorded using a pH meter after making sure equilibrium had been reached (1-5 min.), before addition of next amount of HCl. The same procedure was used with the same volume of NaOH but without the addition of Carboxygraphene.

Figure 4:
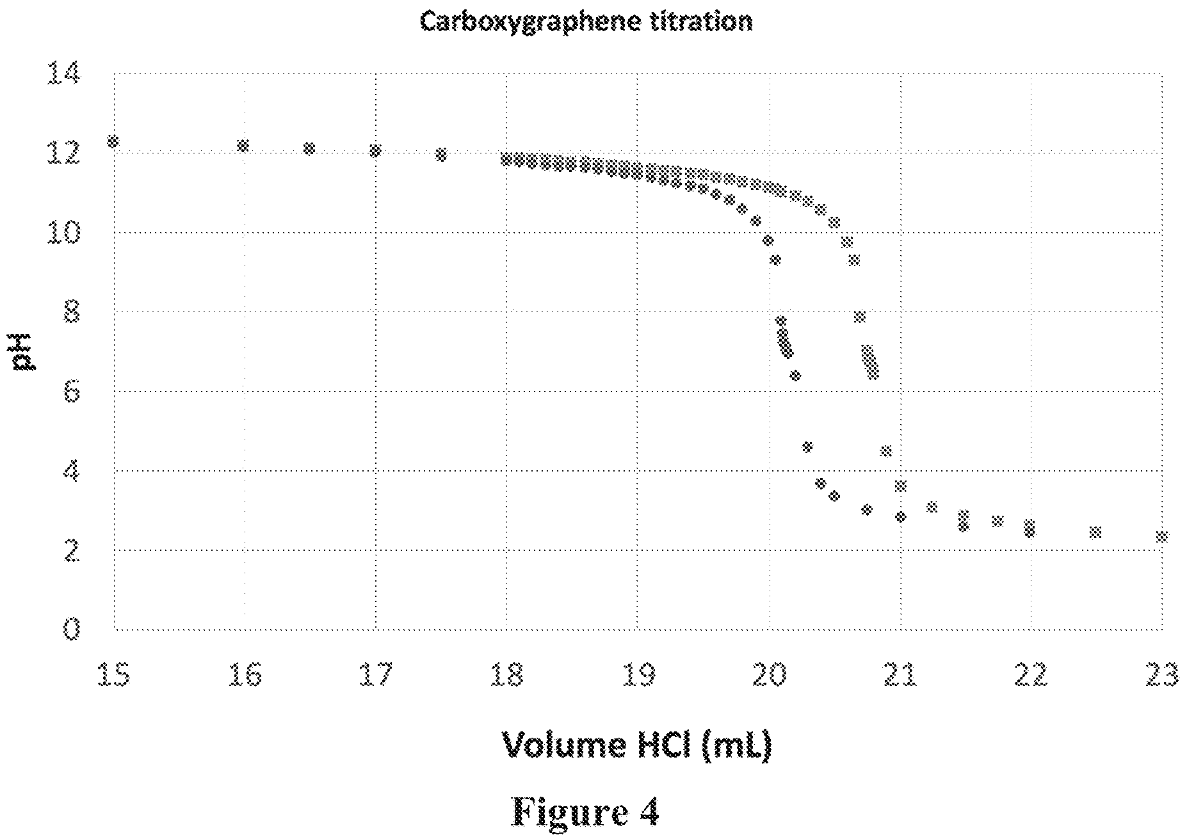
FIG. 4 shows titration curves (pH vs. volume 0.100 M HCl) starting with adding 20 mL of 0.100 M NaOH to 100 mg of carboxygraphene. round dots: titration of carboxygraphene; square dots: reference curve (no GO added).

The difference in the volumes of HCl in the two titration curves for the same value of pH of ~7.00 gives the concentration of the ionized groups (carboxyl groups) per weight increment of Carboxygraphene, as shown in FIG. 4. This titration curve indicates that we have a $6.1*10^{-4}$ mol/g of acidic groups (—COOH) (i.e., surface density of 4-COOH groups per $nm^2$). For comparison, this is 4 times higher compared to our Fenton-oxidized graphene oxide which possesses $1.7*10^{-4}$ mol/g (i.e., surface density of 1-COOH group per $nm^2$). This density of —COOH groups at the surface of carboxygraphene corresponds to an average space per —COOH group of 0.27 $nm^2$ in the synthesized carboxygraphene. This corresponds to a very high labeling density with surface —COOH groups, contributing to a much higher water dispersibility for these carboxygraphene nanosheet particulates.

It will be appreciated that the synthesis of carboxygraphene is even further simplified as compared to Fenton-oxidized graphene oxide, with faster reaction times. The process also does not involve addition of an iron salt, which would somewhat interfere with the photophysical properties of the attached fluorophore in biosensors described herein.

Example 6: Carboxygraphene-Polyethylenimine (G-PEI)

An exemplary synthetic procedure for tethering polyethylenimine to carboxygraphene to produce polyethylenimine-derivatized carboxygraphene is described below.

100 mg of carboxygraphene synthesized above was suspended in 20 mL anhydrous DMF in a 50 mL round bottom flask at room temperature. Next, 50 mg of polyethylenimine, branched, molecular weight 10,000 (PEI), 25 mg of 1-Ethyl-3-(3-dimethylaminopropyl) carbodiimide (EDC), and 25 mg of 4-Dimethylaminopyridine (DMAP) were added to the carboxygraphene solution. The reaction was stirred at room temperature overnight. Afterwards, carboxygraphene-polyethylenimine (G-PEI) was collected via centrifugation (5 min @ 7000 rpm) and washed twice with DMF and three times with diethyl ether. Material was collected via centrifugation after each washing step. Yield: 65% (by weight, assuming total reaction).

Figure 5A:
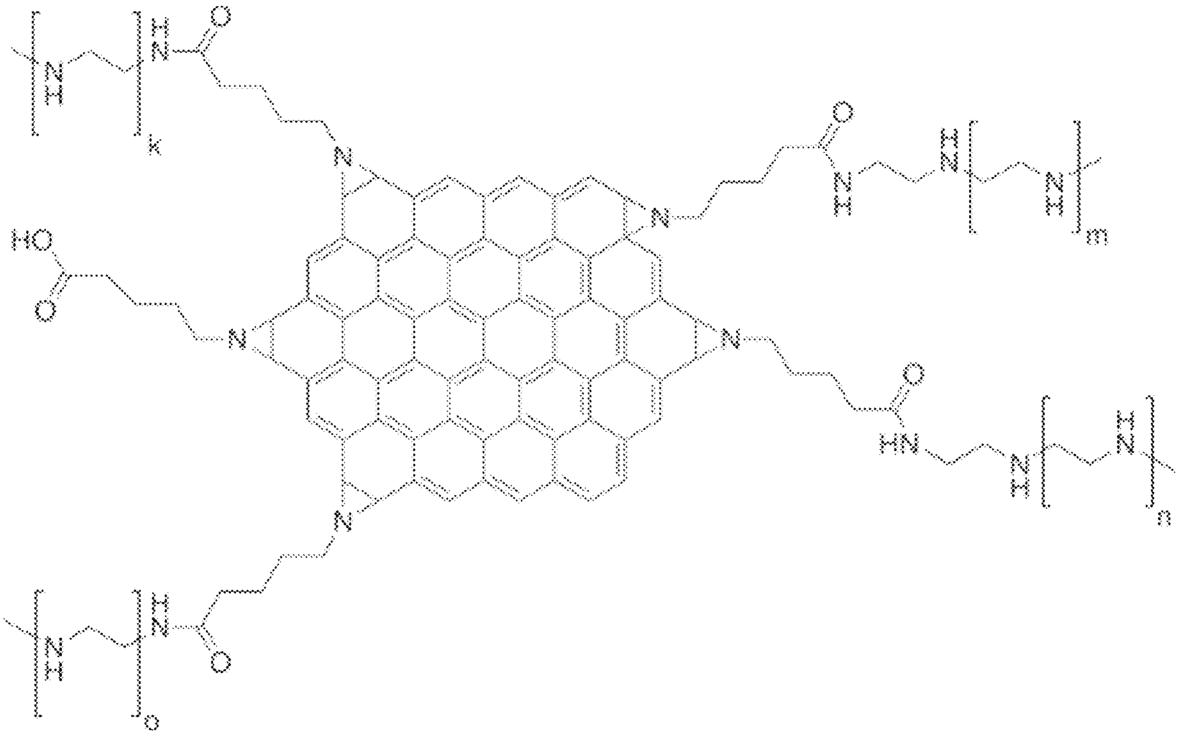
FIG. 5A shows a structure of carboxygraphene-polyethylenimine, only a single sheet is shown for reference.

A schematic representation of the structure of resulting carboxygraphene-polyethylenimine, is shown in FIG. 5A where only a single sheet is shown for reference. The Elementary analysis of the resulting carboxygraphene-PEI: 82.58% C, 4.65% H, 10.65% N, and 2.12% O. The significant increase in N content indicates that the addition reaction of PEI was successful. Based on the N-content we estimate that the resulting carboxygraphene-PEI contains 27±2% PEI.

Figure 5B:
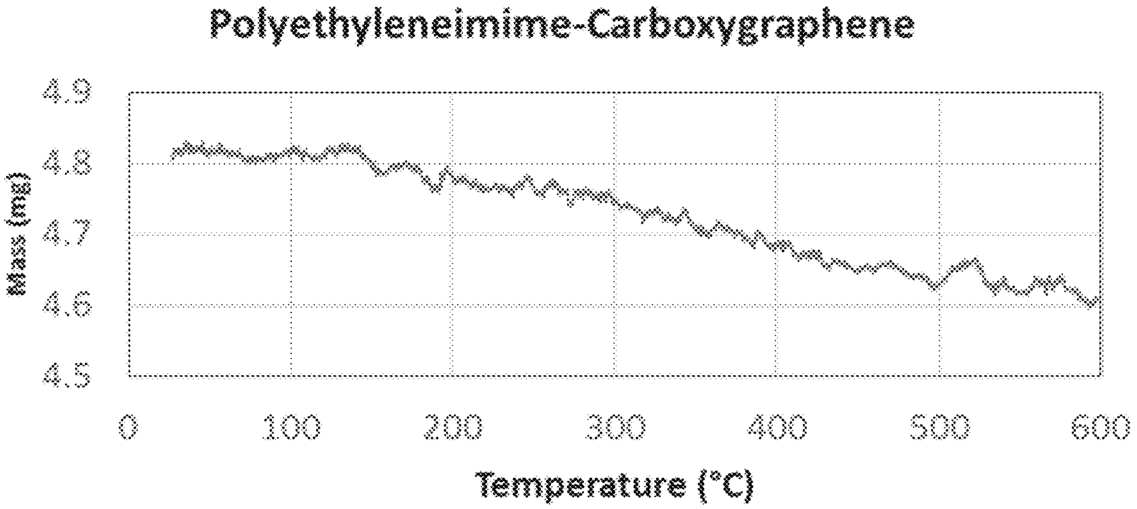
FIG. 5B shows chart reporting the results of Differential Thermogravimetry Analysis (DTA) of exemplary synthesized carboxygraphene-polyethylenimine (G-PEI) under $N_2$.

A Differential Thermogravimetry Snalysis (DTA) shown in shown in FIG. 5B, indicates a weight loss of 4.5±0.5 percent by weight starting at 150° C. and extending through the entire temperature range. This behavior is clearly different from carboxygraphene and consistent with the stabilization of the graphene nanosheets by the linkage of polyethylenimine.

Example 7: Synthesis of PEI Coated Explosion Graphene-Based Biosensors

A detectable component formed by Tetra(4-carboxyphenyl)porphyrin (TCPP) and a peptide cleavage sequence for MMP-1 (GAGVPMS-MRGGAG) was attached to a PEI coated graphene based biosensor according to the following protocol.

50 mg of carboxygraphene-PEI synthesized above was suspended in ~8.1 mL DMF in a small glass vial. Next, 5 mg DMAP and 5 mg EDC were added to the vial along with ~3.5 mg of TCPP pre-conjugated with a peptide cleavage sequence for MMP-1 (GAGVPMS-MRGGAG). The sample was sonicated for 5 min. to ensure everything was suspended in DMF. The reaction was then stirred overnight at room temperature.

Figure 6A:
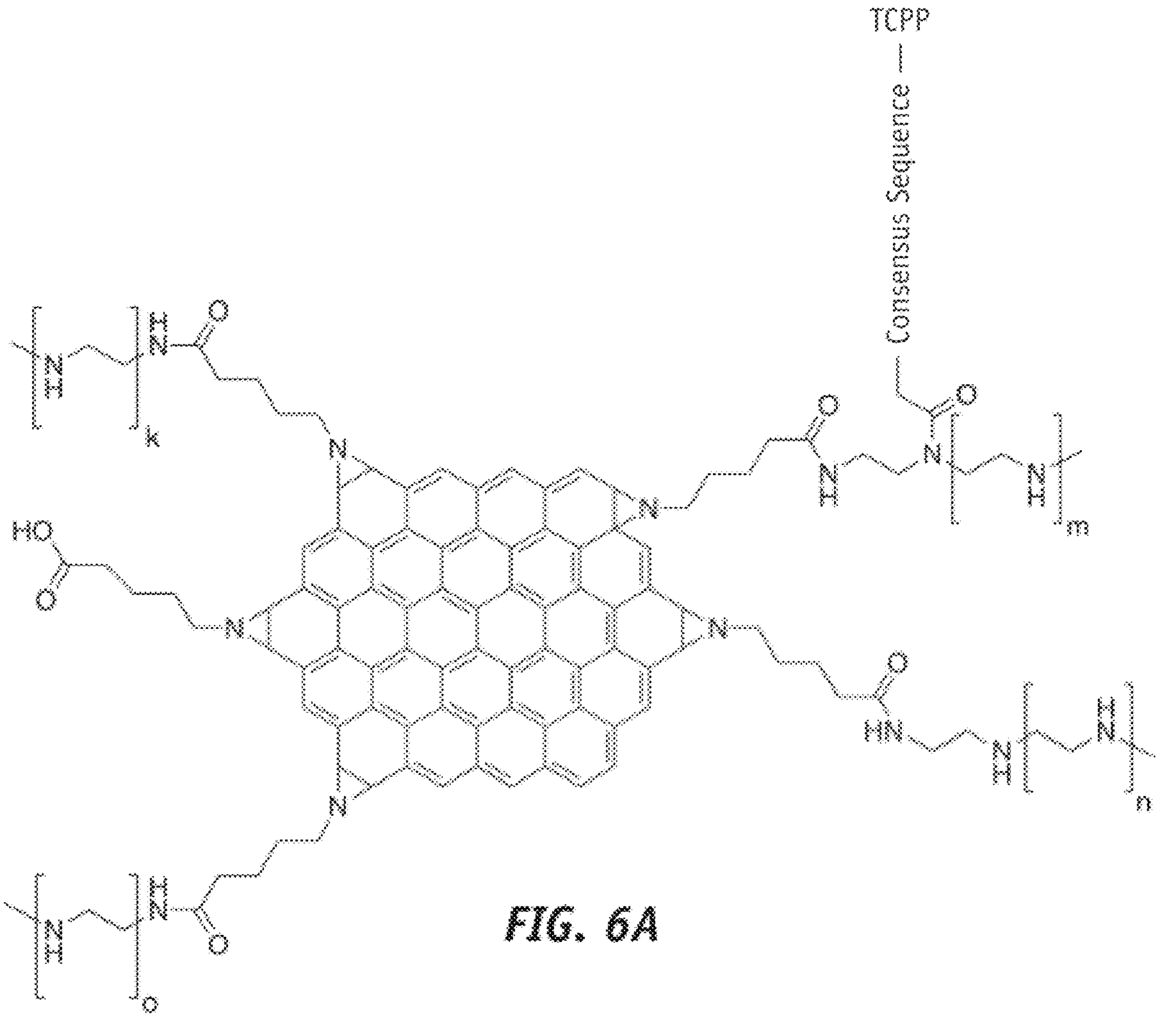
FIG. 6A shows a structure of an exemplary carboxygraphene-polyethylenimine-based biosensor, in which only a single sheet is shown for reference.

The biosensor was collected via centrifugation (5 min @ 7000 rpm) and washed with DMF and three times with diethyl ether. FIG. 6A shows structure of carboxygraphene-polyethylenimine-based biosensor, only a single sheet is shown for reference.

Figure 6B:
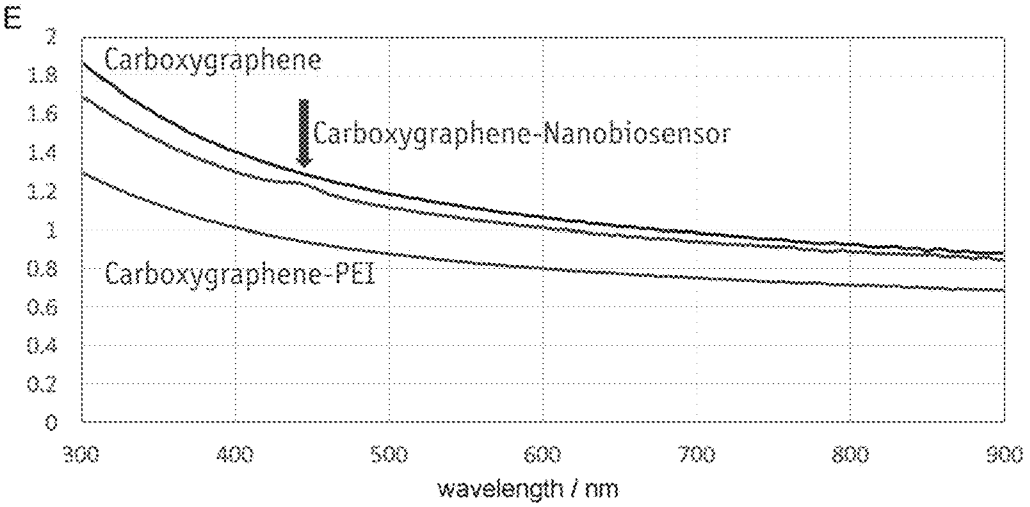
FIG. 6B shows UV/Vis Spectra of Carboxygraphene (top curve), Carboxygraphene-PEI (bottom curve), and the Carboxygraphene-Biosensor (middle curve) for MMP-1 in water.

The synthesized materials were analyzed via spectroscopy. As shown in FIG. 6B, the UV/Vis Spectra of carboxygraphene, carboxygraphene-PEI, and the carboxygraphene-biosensor for MMP-1 in water were analyzed. The Soret band of the TCPP detectable label is clearly discernible at ~420 nm. TCPP is tethered to the polyethylenimine layer via the peptide containing the consensus sequence for MMP-1. Based on an estimated absorption coefficient of 135,000 $M^{-1}$ $cm^{-1}$, the TCPP concentration is $1.63\times10^{-5}$ moles per gram carboxygraphene.

Additional exemplary detectable moiety that can be added with the process schematically shown above are reported in FIG. 6C which shows BODIPY dyes with no or only a minimal overlap between the excitation and absorption spectra, including BODIPY FL, BODIPY TR, BODIPY 530550, and BODIPY 630650.

Example 8: Additional Functionalization of Graphene Surface

In the previous examples, functionalization of graphene surface was performed to tether carboxylic acid groups to the surfaces of the graphene. Polyethyleneimine (or, principally, other polymers) were then bound via stable amide bonds to the carboxylic acid functions.

Additional functional groups can be presented on the surface of graphene for example through modification of the carboxylic group. A skilled person will be able to perform such a functionalization using the whole toolbox of Organic Chemistry[32] for carboxylic acid reactions which is applicable to tether polymers or monomers to the surface of graphene. Reference is made for instance to the following exemplary reactions:

- Conversion of carboxylic acids into alcohols and formation stable ethers
- Conversion of carboxylic acids into esters
- Conversion of carboxylic acids into aldehydes and then into double bonds (Wittig-type reactions)
- conversion of carboxylic acids into carbon centers with effective leaving groups, followed by nuclear substitution reactions.

Additional reactions can be used on graphene with or without previous functionalization to present a functional group configured to bind a corresponding functional group on an organic or inorganic compound, or directly on a peptide linkage as will be understood by a skilled person. These reactions comprise:

- Click reactions[33, 34] (especially Diels-Alder reactions [35, 36]). These can be performed directly with the surface of graphene or to connect a peptide sequence and a tether that is already linked to the surface.
- Additions of radicals (e.g. carbon, nitrogen, oxygen, and sulfur-centered) to the surface of graphene[37, 38]
- Additions of electrophiles (e.g. carbon, nitrogen, oxygen, and sulfur-centered) to the surface of graphene[38]

In embodiments where functionalization is performed to provide carboxygraphene according to titration experiments of carboxygraphene and molecular modelling, the highest possible packing density of linear molecules attached to the surface of graphene is: $6.0\pm0.5\times10^{-4}$ mol/g. The lower bound at which water dispersibility still can observed is $2.40\pm0.05\times10^{-5}$ mol/g.

Additional maximum and minimum packing density can be identified for different functionalization as will be understood by a skilled person. In case of synthesizing asymmetrical nanobiosensors featuring a surface region of unsubstituted (pristine) graphene, this region is not be larger than 10 relative percent to minimize interference of with the fluorescence readouts of the particle due to adsorption and quenching of formerly cleaved off fluorescent dyes at the surface of graphene.

Example 9: Direct and Indirect Attachment of Peptides to Carboxylated Graphene

In an alternative attachment process for detectable component, instead of utilizing polyethylenimine or other water-soluble polymers, the peptide sequences that are linked to the fluorescent dye can also be directly linked to carboxyl groups of carboxygraphene.

In some instances, in addition or in place of direct attachment to the graphene surface a peptide linkage can be indirectly attached through a spacer or connector presenting an amine group for binding to the carboxy For that purpose, lysine, ornithine, or any non-natural amino acid featuring a spacer and an accessible extra primary amine can be utilized to facilitate attachment as shown by the schematic illustration of FIG. 7.

Spacers can be used by a skilled person in combination with a desired peptide linkage while controlling the particle dimensions to obtain a desired distance between particles and detectable moiety.

A special class of "connectors" between a central graphene-based nanostructure and detectable component of the biosensors herein described (e.g. consensus sequences with attached fluorophore) are supramolecular systems. A plethora of supramolecular host-guest systems are published in the literature. [39] [40] The following host-guest systems are noteworthy:

a) Biotin/streptavidin [41]
b) Cyclodextrines and a variety of hosts [42]
c) Stoddart-cyclophanes and hydrophilic hosts [43]
d) Cucurbiturils and tailored hosts [44]
e) (structurally modified) DNA assemblies [45]
f) Nucleic Acid/Peptide Hybrids [46]
g) Supramolecular binding of designer peptides [47]

Figure 8:
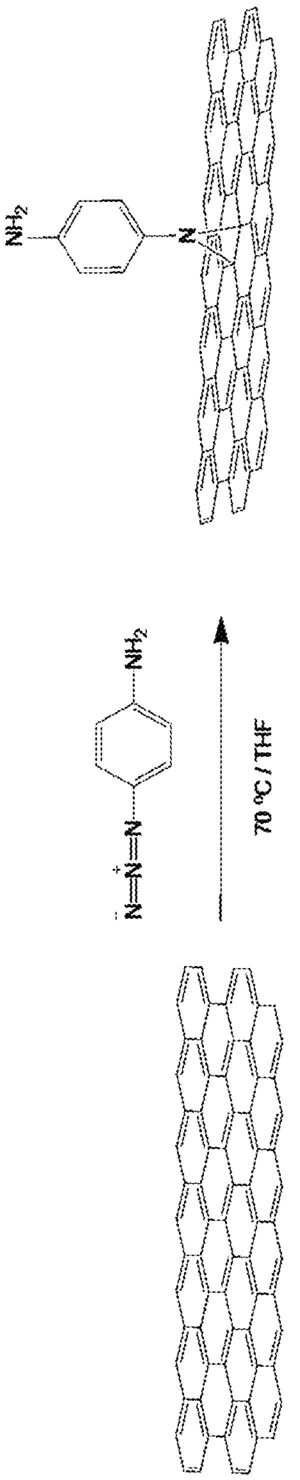
FIG. 8 shows a schematic representation illustrating an aromatic substituted nitrene reaction for chemical amination of a graphene surface.

Example 10: Chemical Amination of Graphene Surfaces and Attachment of Peptide Linkage An exemplary additional chemical amination of the graphene surfaces such as an aromatic substituted nitrene reaction for chemical amination of a graphene surface [20] is schematically illustrated in FIG. 8.

According to an exemplary protocol 1.0 g of graphene nanosheet (GN) particulates were suspended in 20 mL DMF at 20° C. in a 250-mL three-necked round bottom flask. Next, at 40° C., 0.50 g of 1-amino-4-bromo-butane (0.0033 mol) were added to the GN suspension, as well as 0.20 g $NaN_3$ crystals. After $NaN_3$ was dissolved, the suspension was slowly heated up to 80° C. (about 1° C./min.) and stirred for 1 hr. The release of $N_2$ was observed. Finally, after 1 hour, the suspension was cooled down to room temperature, and derivatized GN was collected via centrifugation (5 min at 7,000 rpm) and washed 5 times with DMF and then 3 times with anhydrous diethyl ether. The resulting grapheneamine (GA) was dried for characterization at 50° C. for 1 h and then stored under argon. Yield: 80% (by weight, assuming total reaction). Elementary analysis of carboxygraphene is 95.48% C, 1.86% H, 2.38% N, and 0.28% O. The incorporation of N indicates that the addition reaction was successful.

In order to add a detectable component TCPP-GAG RPFS-MIMG AEG 1.00 g of GA was dispersed in 30 mL DMF in a flask with a stir bar. 0.54 g EDC and 0.53 g DMAP were added and stirred until dissolved at room temperature. 0.20 g TCPP-GAG RPFS-MIMG AEG was added and the reaction stirred for 21 hours. The CGP particles were washed 4-times with DMF using centrifugation as above, and 3-times with ethyl-ether. The GA-consensus sequence for MMP 3-TCPP labeled particles were dried by flushing with Argon and holding at room temp for 48 hours loosely covered. This reaction can be performed with every peptide that designed and configured to be as peptide linkage in the sense of the disclosure (consensus sequence, posttranslational modification and supramolecular binding).

Example 11: Reaction of Graphene-Embedded Carbocations with Secondary Amine Groups of PEI Additional attachment reaction of PEI can be performed through binding of secondary amine groups with carbocations in explosion graphene.

In explosion graphene 0.3 numerous "holes" (carbocations) are embedded in the structure, thus causing a zeta potential of +60 mV. [8] Holes near the surface can react with polyethylene imine, as shown above. It is noteworthy that a nucleophilic addition reaction can occur between explosion graphene and virtually all (polymeric, monomeric, and small molecule) alcohols, thiols, amines, phosphines, and—potentially—carboxylic acids.

Figure 9:
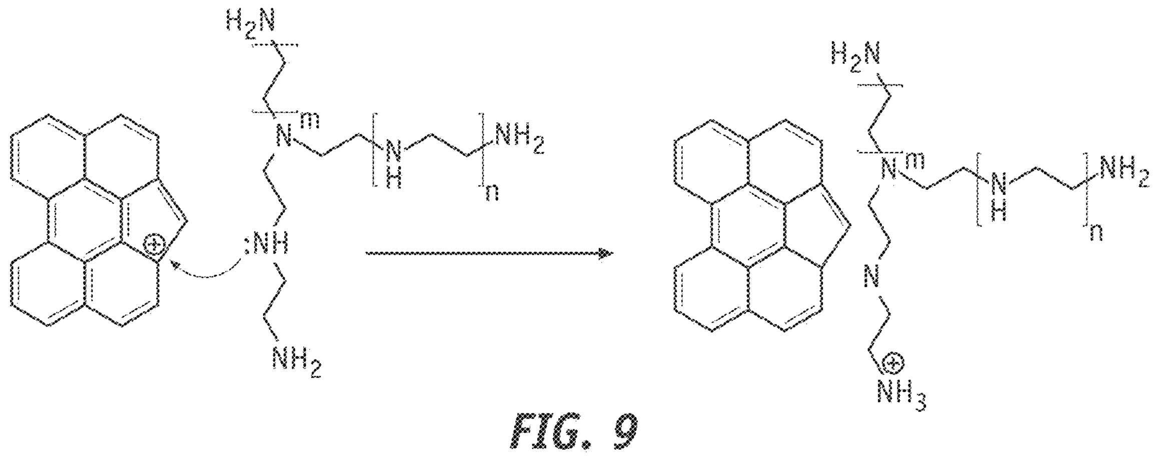
FIG. 9 shows a reaction scheme of graphene-embedded carbocations with secondary amine groups of PEI, leading to the chemical attachment of PEI at the surface of graphene. It is noted that primary amine groups can react as well.

In conventional few-layer graphene, hydroxyl groups and oxirene functions can react with PEI. Hydroxyl groups form carbocations after elimination, which then react according to the scheme in FIG. 9. Oxirene (oxygen-containing three-membered rings) react with amines under nucleophilic addition. These reactions will covalently attached PEI to the graphene layers. Another possibility of directly attaching PEI to graphene presents itself if defects (carbocations) are present in graphene. This permits a direct nucleophilic attachment of PEI to graphene surfaces.

Example 12: Electrostatic Attraction at the Surface of Graphene

Making use of the strongly positive charge of explosion graphene, anionic polymers featuring sulfonic acids, aminosulfonic acids, and organic sulfates can be adsorbed at the surface of graphene. The driving force is the electrostatic attraction. Note that when block copolymers are being used, hydrophobic polymers, such as polystyrene, polyisobutylenes, polyvinylchloride, polyethylene, polypropylene etc. can be components of block copolymers. They will be adsorbed on the surface of pristine graphene, whereas their hydrophilic component will mediate water-dispersibility. Note that the surface charge of explosion-graphene is positive (zeta potential=+60 mV). [8] This permits the combination of hydrophobic and charge attraction when negatively charged polymers, such as polystyrene-sulfonic acid are used in block copolymers of polystyrene etc.

Example 13: "Click Chemistry" of Graphene

A further reaction allowing attachment of molecule on the surface of graphene nanosheets of the core particles herein described can be performed by click chemistry.

Figure 10:
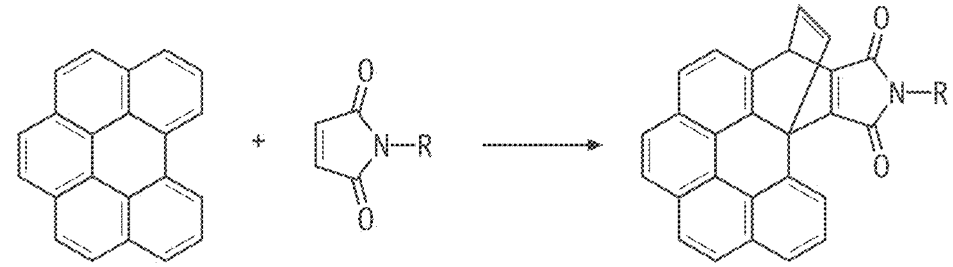
FIG. 10 shows Diels-Alder reaction between a maleimide-derivative and graphene.

"Click Chemistry" can be performed at the surface of explosion (and few layer) graphene. A typical reaction is the Diels-Alder reaction, because it does not require a copper-catalyst. FIG. 10 depicts a scheme of Diels-Alder reaction between a maleimide-derivative and graphenes. However, principally any click reaction, including the addition of thiols on the surface can be conducted as described for example in Li et al. 2016 [48], Namvari et al. 2014 and Farivar et al 2021 [50] as well with additions of radicals (e.g. carbon, nitrogen, oxygen, and sulfur-centered) to the surface of graphene[37, 38], additions of electrophiles (e.g. carbon, nitrogen, oxygen, and sulfur-centered) to the surface of graphene[38] and other methods identifiable by a skilled person (see also Example 8).

Example 14: Use of Biosensors and Related Functional Principles

Figure 11:
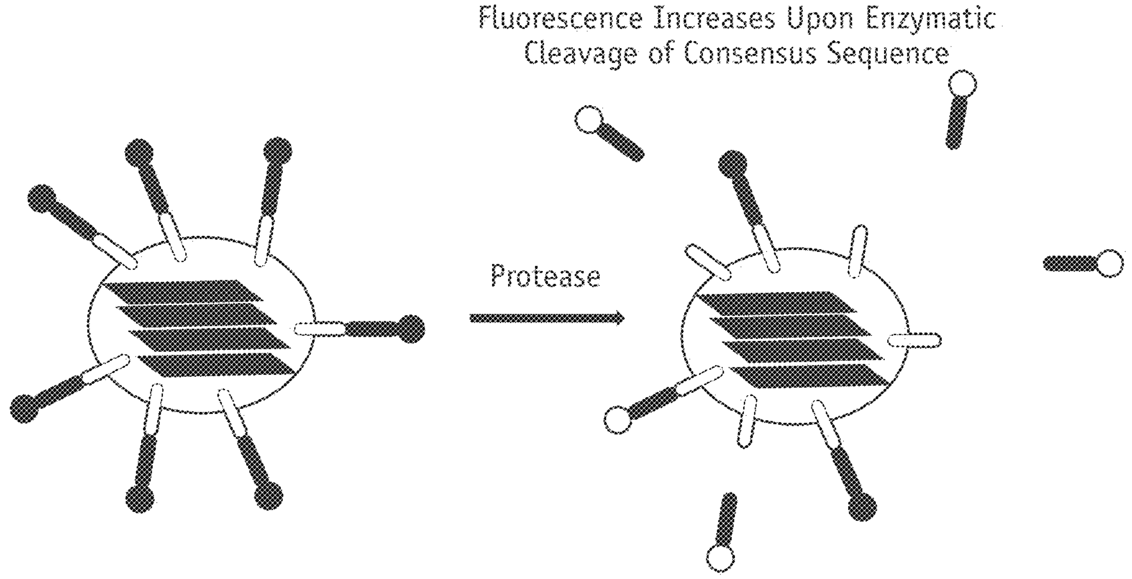
FIG. 11 shows a schematic representation of functional principles of graphene-based biosensors of the disclosure used for protease detection.

The functional principle of the biosensor here described for the related use is schematically illustrated in FIG. 11.

In the schematic illustration of FIG. 11 it is shown that upon interaction with a biological sample containing the target biomarker, the peptide linkage is changed (e.g., cleaved or elongated) resulting in a characteristic change in a detectable signal of the detectable moiety used in the sensor, such as a change in the fluorescence spectrum. The observable change in fluorescence (increase, decrease, shift, etc. depending on the detectable moiety) is a function of biomarker presence and/or activity.

In the exemplary embodiment schematically shown in FIG. 11, upon proteolytic cleavage of the consensus sequence (oligopeptide), the attached fluorophore is released and escapes the quenching by the graphene core of the biosensor. Fluorescence increase and intensity is observed that is a function of protease activity. Instead of particle-based biosensors, the biosensors can be constructed using similar components, except that the graphene is first immobilized on a solid support (e.g., planar substrate), onto which the other elements, e.g., peptide linkage, and then detectable moieties, are attached to create a planar sensor, e.g., lateral flow type sensor or stationery microwell sensor. The sensor would otherwise operate the same, where the sample is added to the solid support, and binding or cleavage by the target biomarker in the sample would yield a detectable change in the assay on the solid support as would be understood by a skilled person upon reading of the disclosure.

Example 15: Multiplex Biosensors

Whereas the classic biosensor design permits the use of only one protease-cleavable fluorescent dye or quantum dot per particle, the broad UV/Vis absorption spectrum of graphene and derivatives permits the attachment of several biosensors for different proteases.

Figure 12:
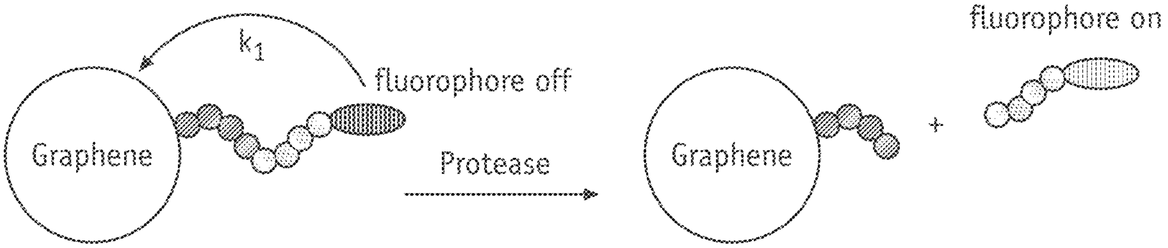
FIG. 12 shows a schematic representation of working principle for an exemplary a graphene-based biosensors configured to detect for protease activity.

FIG. 12 shows a Working Example of a Detonation-graphene based Biosensor for Matrix-Metalloproteinase-1. The working principle for graphene-based biosensors for protease activity is shown herein.

As shown in FIG. 12, the protease (if present in the tested sample) cleaves its consensus (cleavage) sequence and releases the fluorophore. The latter escapes the quenching of the graphene, resulting in a measurable increase in fluorescence ("fluorophore on"). The prototype biosensor for MMP1 was tested in a sample with increasing concentration of enzyme.

Figure 13A:
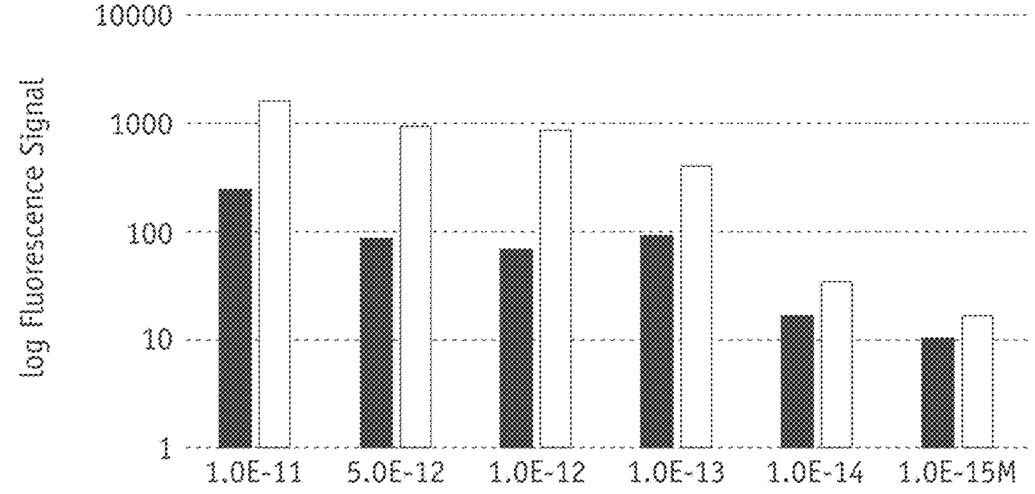
FIG. 13A shows an estimation of limit of detection (LOD) as indicated by log signal vs. enzymeconcentration in an exemplary biosensor of the disclosure; In particular.
Figures 13B, 14:
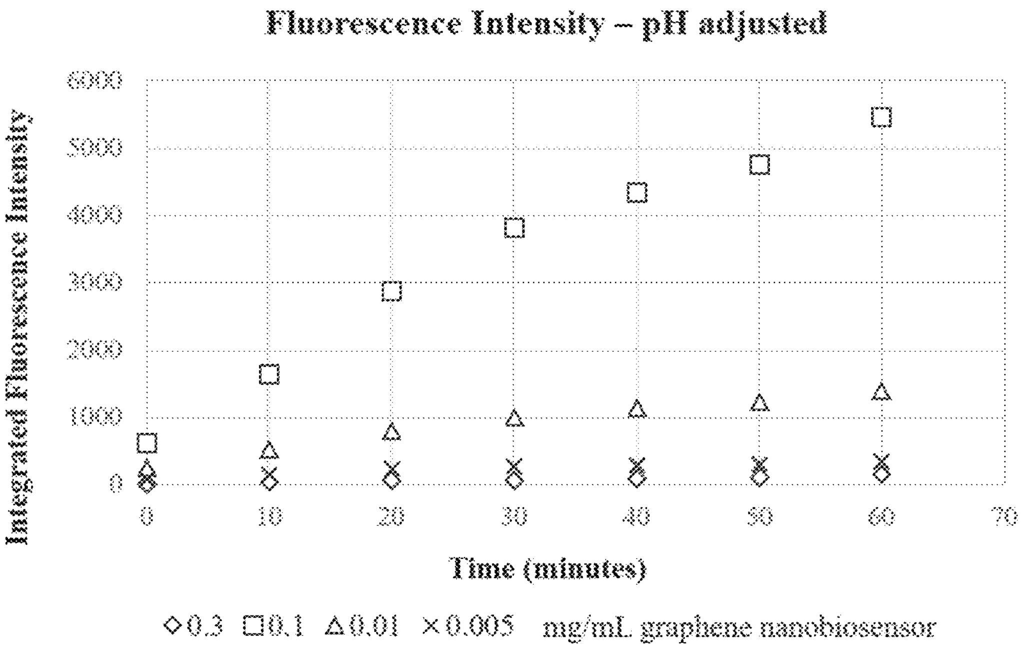
FIG. 13B shows a chart illustrating the fluorescence signal vs incubation time for different exemplary biosensor concentrations tested. Four different concentration of graphene biosensor solutions were incubated with serum and measured over 60 min. incubation at 37° C., each concentration is represented with a symbol, indicating that optimal signal quantified were for biosensor concentrations between 0.01 and 0.1 mg/mL.
FIG. 14 shows a table reporting 11 exemplary buffer formulations for pan gNBS buffering.

It can be seen that the intensity of the detected signal is proportional to concentration of enzyme, as shown in FIGS. 13A and 13B. The estimated limit of detection (LOD) for this prototype biosensor under even non-optimal experimental design still show that femtomolar protease activities can be detected. When TCPP is bound, it shows virtually no fluorescence due to strong carboxygraphene quenching. It is then released during 60 min. and its fluorescence is detectable.

Example 16: Buffering and a Standard Reaction

Protease enzymes are protein digesting enzymes that operate in physiological conditions. The Matrix Metalloproteinase family involve a complexed divalent cation while Cathepsin proteases are primarily activated in an acidic lysosomal environment. The operation of the Fe—NBS protocol as originally designed was prepared in a 25 pM HEPES buffer with 10 μM of divalent cations.

This system was altered to achieve more robust signal though improved pH control, by including isotonic conditions to support the protease activity while also supporting the divalent cation needs. It was also sought to demonstrate it was possible to build a buffer compatible with multiple different gNBS sensors at once to allow for future multiplexing.

To this end, a series of buffers was designed that all included 10 μM final concentrations of $MgCl_2$, $CaCl_2$ and $ZnCl_2$. HEPES buffer was evaluated as well as MES, TRIS and phosphate buffered saline (Table in FIG. 14).

Solutions of uPA gNBS and CTSD gNBS were prepared at 10× working concentration of 300 μg/ml in water. They were sonicated for 10 minutes in a sonicating water bath. The gNBS were diluted 1:10 in each of the different buffer formulations reported in FIG. 14.

Figure 15:
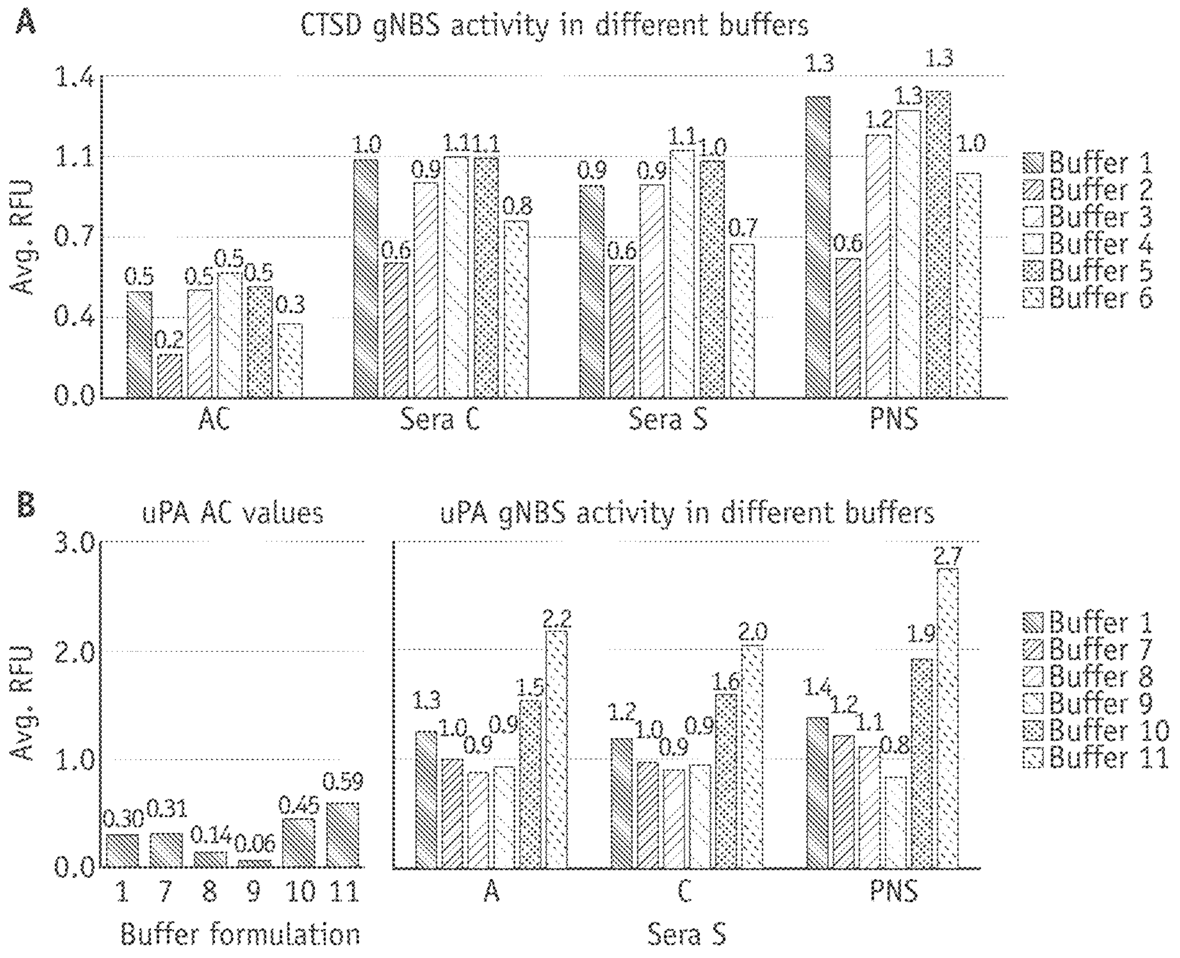
FIG. 15 shows charts reporting results illustrating the performance of Cathepsin D (CTSD gNBS (Panel A) and urokinase (uPA) gNBS (Panel B) in the buffers of FIG. 17. CTSD and uPA gNBS were suspended at 30 μg/ml final concentration in buffers 1-11 of FIG. 17 as indicated. 5 μl of sera A, S or pooled normal sera (PNS) or buffer only (AC) was added in triplicates to the working solution. The fluorescence at 421 nm/650 nm was measured after incubation at 37° C. for 60 minutes.

125 μl gNBS solution was dispensed in replicates in a black 96 well plate. 5 μL serum was added and the plates were incubated at 37° C. for 60 min. Released fluorescence was read on a VarioSkan Lux plate reader with 421 nm excitation and 650 nm emission. The assays included an assay control where 5 μl of the appropriate buffer was added in place of the serum. The gNBS were incubated with two different normal health donor sera samples or a pooled normal sera (PNS). Buffer 1 was the original formulation. Protease activity was observed in all the buffering conditions. The results are reported in FIG. 15 Panel A (CTDS gNBS) and FIG. 15 Panel B (uPA gNBSS).

A much more stable pH was observed in the PBS and MES buffered formulations with the pH holding steady for multiple days. Only DMSO significantly increased the RFU observed under stimulated conditions. However, of note, the buffers that included NaCl significantly lowered both the background and serum signal. Decreasing the AC serves to increase the signal to noise performance of the gNBS. Buffers 2, 3, 6, 8 and 9 all containing NaCl, had significantly reduced AC performance in comparison to the original buffer.

Figure 16:
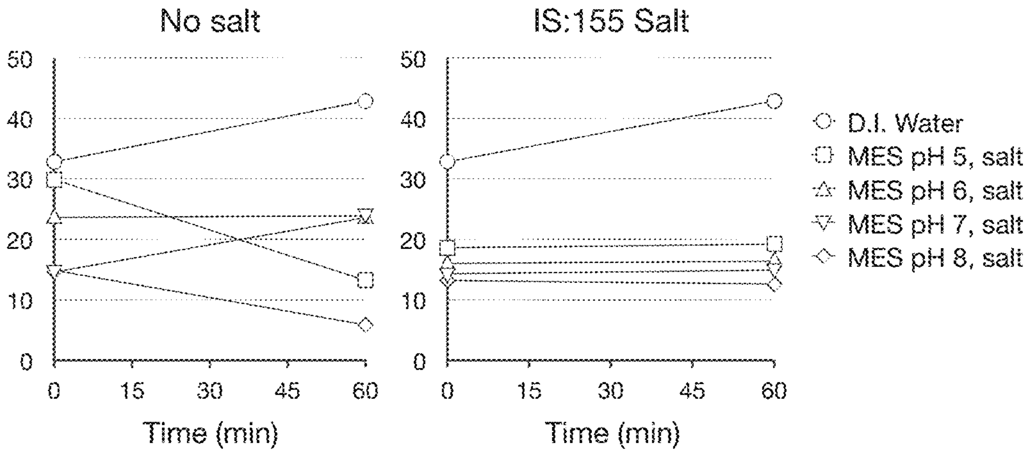
FIG. 16 shows charts reporting results illustrating the impact of salt on Zeta Potential stability. uPA gNBS was assembled in a working solution of 5 mM MES buffer with the indicated pH with (Panel B) or without (Panel A) 155 mM NaCl. A control solution of uPA gNBS was prepared in deionized water.

Buffer 9 was selected as the buffer with the best signal to noise performance. This performance supported the conclusion that the impact of physiological ion concentrations was stabilizing the zeta potential and enabling the natural conformation of the peptide-TCPP construct. Thus the zeta potential stabilization which contributes to the stability of the particle solution, also supports optimal enzyme conditions. The impact of NaCl on zeta potential can be observed in FIG. 16. To confirm these observations, the experiment was repeated on additional gNBS using Buffers 1, 2 and 9.

Figure 17:
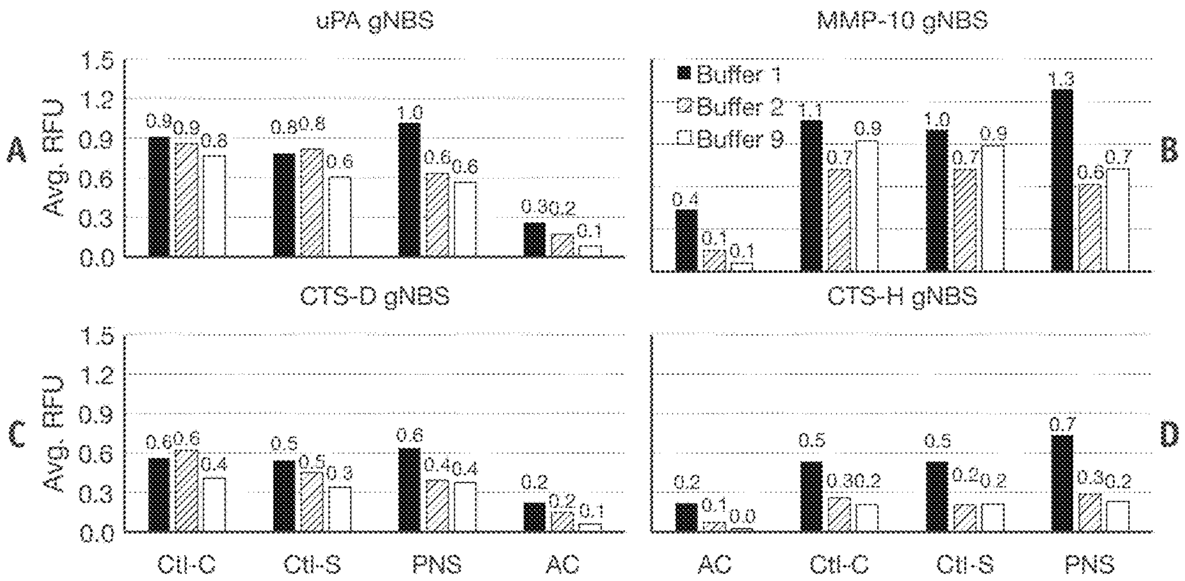
FIG. 17 shows charted reporting results of experiments illustrating the performance of uPA gNBS (Panel A), Matrix Metalloproteinase 10 (MMP10) gNBS (Panel B), CTSD gNBS (Panel C), and Catepsin H (CTSH) gNBS (Panel D) in isotonic salt buffers. CTSD, uPA, MMP10 and CTSH gNBS were suspended at 30 μg/ml final concentration in buffers 1, 2 or 9 as indicated. 5 μl of sera A, S or pooled normal sera (PNS) or buffer only (AC) was added in triplicates to the working solution. The fluorescence at 421 nm/650 nm was measured after incubation at 37° C. for 60 minutes.

Evaluation of gNBS for uPA, CTSD, MMP10, and CTSH all showed decreasing AC signal and highest signal to noise for buffers containing isotonic salt concentration with Buffer 9 outperforming Buffer 2 (FIG. 17).

These experiments have demonstrated the role of ions for the efficient function of a gNBS used to detect protease activity in addition to the features of biosensor of the disclosure.

In particular, the functionality of a sensor of the present disclosure relies on the ability of built repeatedly with the same specifications and allow the measurement of activated proteases or other suitable biomarker in a normal serum sample such that different batches and lots of the sensors can be manufactured to produce the same signal.

In addition, buffer and manufacture conditions can be selected to generate an optimal signal to noise ratio. It is observed in this experiment that the inclusion of monobasic salt ions contributes to a significant reduction in the noise as reflected by a reduced buffer only signal (see AC values FIG. 15 and FIG. 17).

The impact of monobasic salt ions was also noticed to stabilize the zeta potential of the particles across a range of pH from pH5.0 to ph8.0. This range reflects the natural working environments for certain protease family members that are normally expressed in lysosomes or other acidic environments. Protease activity can occur across a range of pH conditions that reflect natural biological environments from pH2.0 to pH10.0. Depending on the pH requirements, MES buffer may be replaced with a buffer whose pKa is better suited to the pH target such as PIPES, MOPS, HEPES, TRIS, Phosphate buffer, Bikini, CHES or other buffers commonly found on Good's list.

Figure 18:
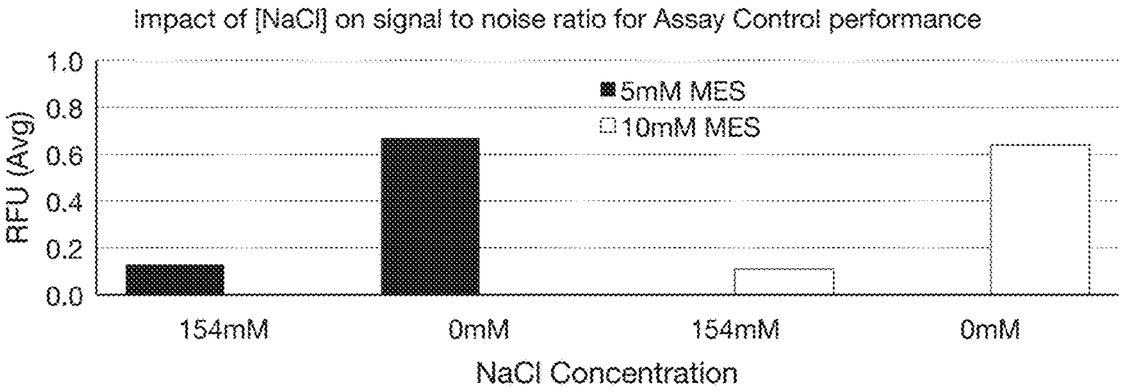
FIG. 18 shows Impact of NaCl concentration on background noise. uPA gNBS were incubated with 5 mM or 10 mM MES buffer containing 10 pM divalent cations or 154 mM NaCl or no salt. The signal obtained (expressed as average RFU) after 90 minutes at 37° C.

The above observations supported the conclusion that the inclusion of salt decreases the AC activity of the sensors. The effective salt concentrations can be observed as a ratio less than 1.0 in comparison with the same sensor in the same buffer but absent any monobasic salt ions (shown in FIG. 18). Monobasic salt ions of between 15.5 mM and 155 mM decrease the ratio of AC of salt/no-salt conditions. Hypertonic salt conditions may similarly increase the signal to noise performance by reducing AC. The salt concentrations in physiological conditions reflecting high salinity environments may be as great as 600 mM, or as high as 1M.

Example 17: Preparation and Performance of Biosensor Prepared with Sonication Step Few layers graphene can be produced in a detonation reaction using gas phase detonation of a hydrocarbon substrate in the presence of a defined ratio of oxygen. The resulting graphene is made up of ramified fractal aggregates that are on average between 50 and 500 nm in size when detonated with a molar oxygen ratio of 0.3.

Figure 19A:
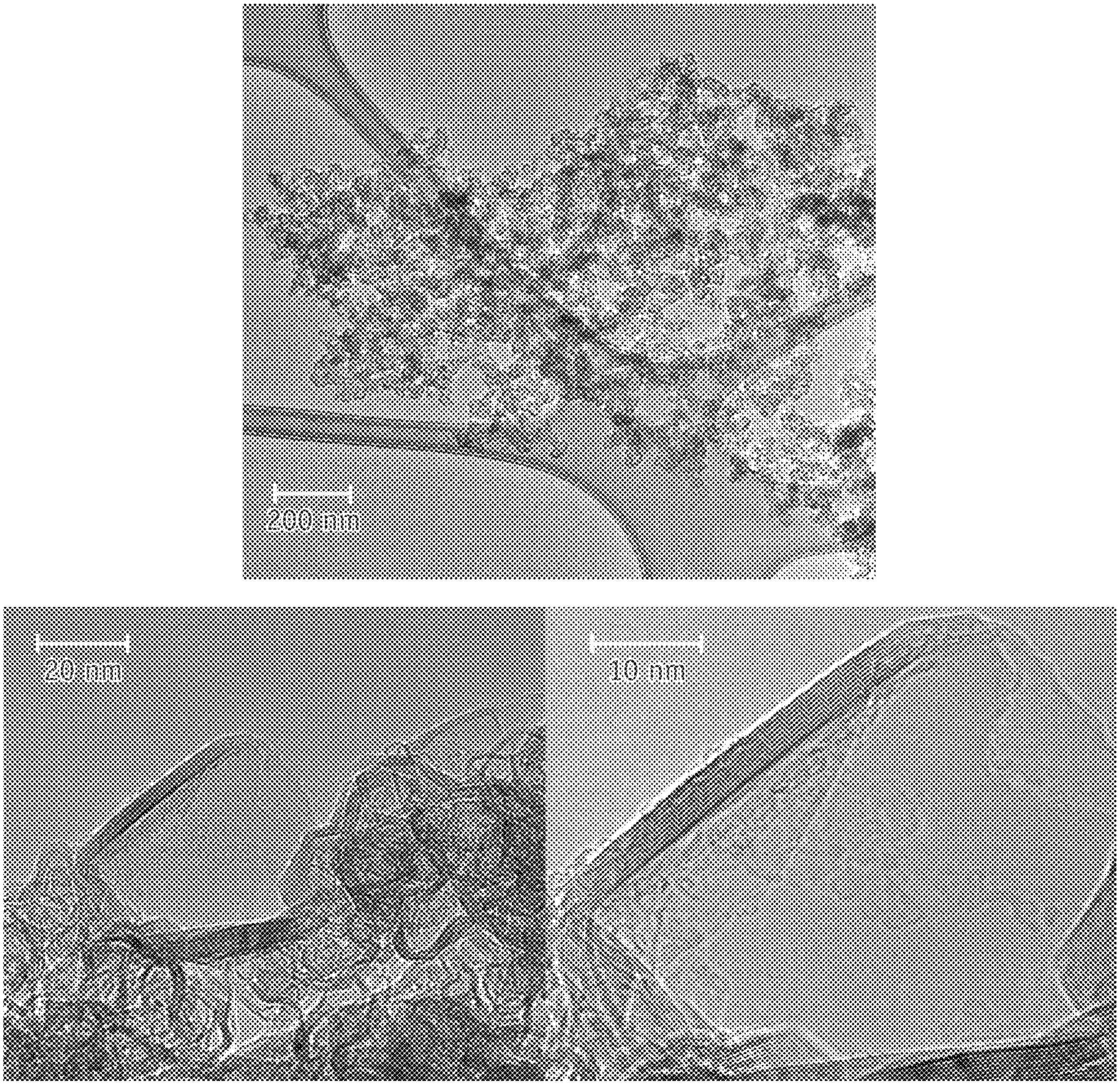
FIG. 19A shows TEM images of pristine detonation graphene at different magnification scales, in particular, 5 nm: magnification 250,000, 10 nm: magnification 120,000, 20 nm: magnification 70,000 200 nm: magnification 10,000.

Electron microscopy of the resulting particles shows graphene aggregates variously composed of chains, sheets, aggregates and individual platelets as illustrated by the exemplary pictures of FIG. 19A.

Figure 19B:
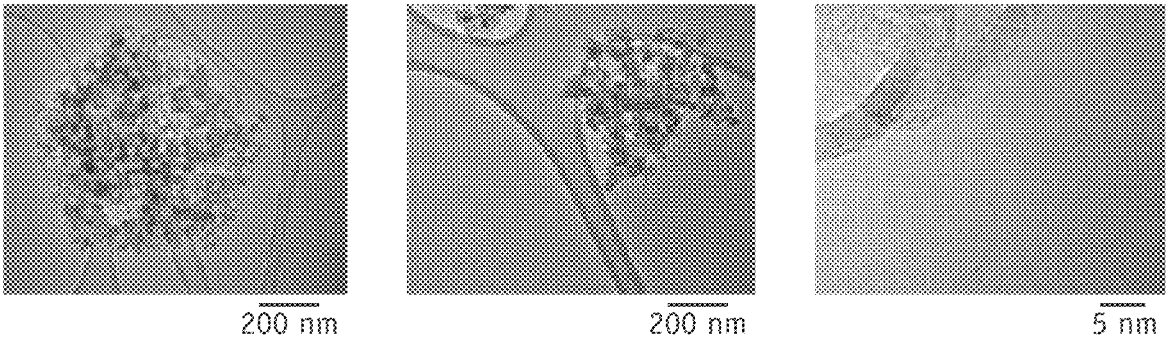
FIG. 19B shows TEM images of graphene biosensor. gNBS were assembled with peptide targets for MMP15. Scanning electron micrographs were collected at 15,000× (left panel) and (middle panel) 300,000× magnification (right panel). Overall size can be seen and the layered structure of the graphene sheets are revealed. Bars indicate 200 nm or 5 nm.

The spectrum of sizes and shapes is evident from analysis of the transmission electron microscopy performed on gNBS (FIG. 19B). The particles imaged in FIG. 19B were prepared as described in the KSU disclosure of 30 Dec. 2020 (Lot 120120). They show irregular shaped particle of many different sizes and the number of layers on higher magnification reflect the expected 5-25 layers of graphene.

As a fractal, there is no defined size or shape for the individual particles. They are made up of aggregates that are formed in the detonation process so are random in size and shape within the spectrum.

Figure 20:
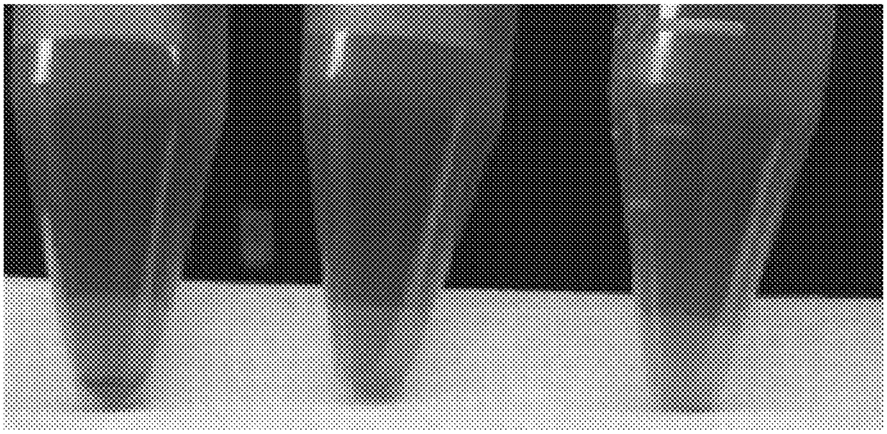
FIG. 20 shows a picture reporting the results of experiment showing the impact of sonication on graphene starting material. The three tubes show samples of KSU Lot 1, HEB100, and HEB101 in order left to right. gNBS were assembled with peptide targets for NE using the original KSU protocol. The only difference was HEB100 was probe sonicated for 10 minutes and HEB 101 was probe sonicated for 60 minutes before assembly of gNBS sensor. After preparation of the gNBS working solution, particles of gNBS can be seen precipitating out of the KSU Lot 1 preparation. A small amount can also be detected in HEB 100. No precipitate is observed in the HEB 101 preparation.

Exemplary SEM (Scanning Electron Microscopy) of explosion graphene are shown in FIG. 1. [8] To prepare a solution of gNBS for an assay, the gNBS is massed out and resuspended in buffer to a defined concentration by mass. This solution is then dispersed in a sonicating water bath. The time in the water bath is not defined in the original disclosure and has the potential to lead to different levels of disruption of the particles. The impact of this variance is seen in FIG. 20. When working solutions of gNBS are generated, the KSU Lot 120120 preparation results in some particles precipitating out of solution. This is due to the absence of efficient dispersion of graphene during the initial manufacturing process leading to an unstable final product. In contrast, when graphene is prepared by probe sonication during manufacturing and before assembly of the gNBS, the particles remain more polydisperse.

To evaluate further the impact of sonication on the distribution of the resulting gNBS population, the dispersion properties of the particles was analyzed on a Malvern Instruments ZetaSizer running v7.02 analysis software. Detonation graphene was either dissolved in DMF directly (no sonication) or actively dispersed by sonicating with a Fisherbrand FB705 Sonic Dismemberator for 1 hour in DMF.

Figure 21:
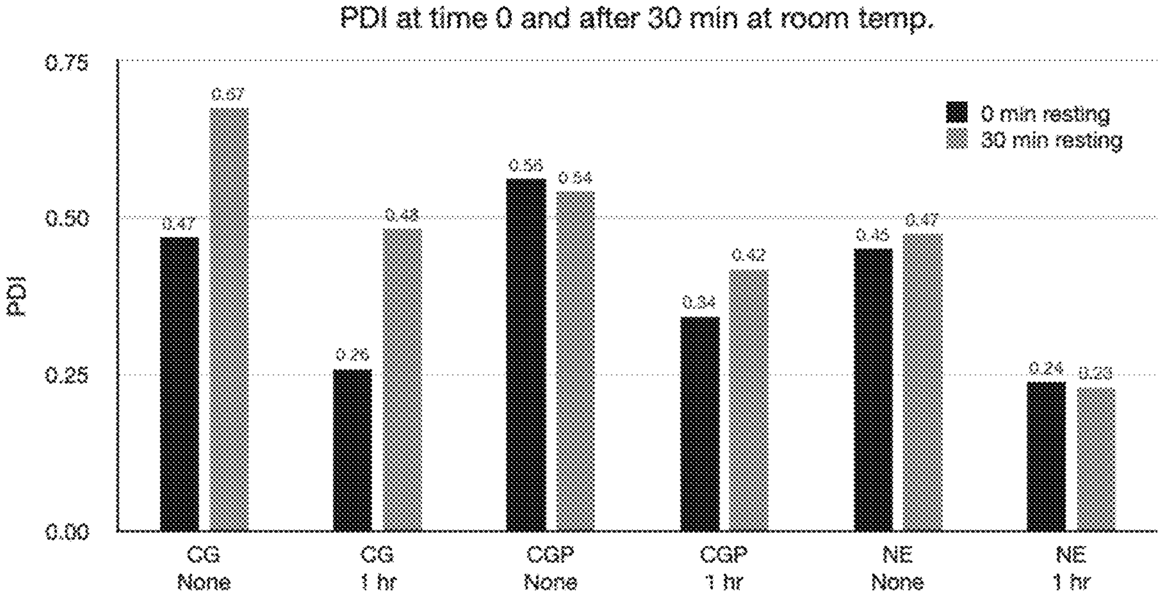
FIG. 21 shows charts reporting the results of experiment showing impact of sonicating starting material on polydispersity. The graph shows the polydispersity index (PDI) for each formulation when the working solution is first made and dispersed in a sonicating water bath (0 min resting) and then after 30 minutes (30 minutes resting). A significant decrease in the PDI was observed at each stage in manufacture for particles made using the sonicated graphene reflecting a greater uniformity of the particles generated at each stage in the process.

The resulting graphene solution was assembled into a gNBS using the standard protocol by first reacting with bromovaleric acid and sodium azide to yield carboxygraphene (CG) (FIG. 21: Panel A). It is further modified by tethering Polyethyleiminine to the carboxygraphene using EDC and DMAP to yield Polyethyleinimine-derivitized carboxygraphene (FIG. 21, Panel B). Finally, peptide-TCPP is added using EDC chemistry with DMAP catalyst to yield the sensor; in this case using a peptide recognized by the protease neutrophil elastase (NE). Solutions of each intermediate, CG, and CG derivatized with polyethyleimine (CGP) were prepared and processed in a sonicating water bath for 10 minutes to disperse the solution for efficient mixing and redistribution of particles and to ensure effective surface modification and water solubility. PDI measurements were taken immediately after sonication and then again after settling for 30 minutes.

The results of the polydispersity index (PDI) measurements are shown in FIG. 21. PDI is a measure of the uniformity of the particles in a solution. The data show the uniformity of the particle sizes is greater (a smaller PDI number) after sonication of the starting graphene material for 1 hour before assembly of the gNBS. This uniformity was apparent for the CG and the CGP intermediate, as well as the NE gNBS final product.

Figures 22, 23:
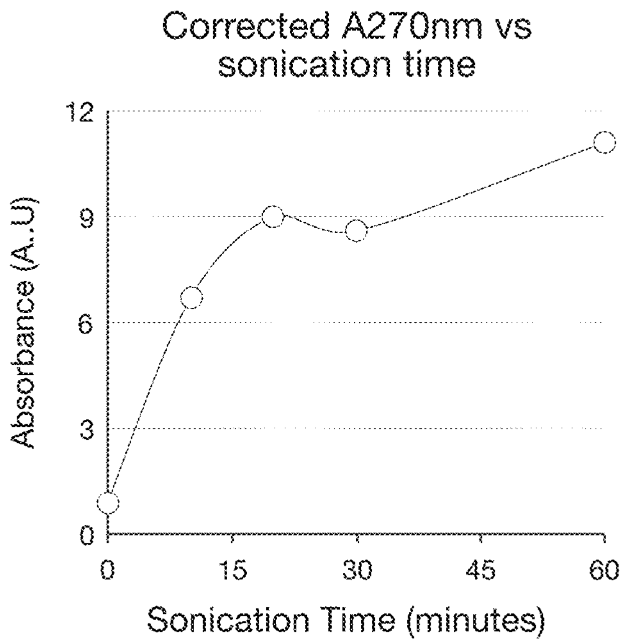
FIG. 22 shows a chart reporting the absorbance at 270 nm for graphene with increasing sonication time. A solution of graphene in DMF was probe sonicated for incremental periods of time. Samples were taken at intervals and the absorbance measured and the related measurement plotted in the chart.
FIG. 23 shows a table reporting the results of Thermogravimetric Analysis (TGA) in terms of total weight loss of original KSU Lot 120120 and CG preparations CG-1, CG-2, CG-3 and CG-4 following different drying protocols.

Further to this, a solution of 1.0 g Graphene 0.3 (0-C Ratio) was dissolved in 20 mL DMF without further processing. The Absorbance at 270 nm was measured on a NanoDrop 1000 C spectrophotometer. The solution was then dispersed using a probe sonicator using 20 s on and 10 s off pulses at 35 intensity level for up to 60 minutes. A sample was collected at intervals and the $ABS_{270\ nm}$ was measured out to 1 hour. As the probe sonication was continued, the slurry of graphene got thicker to the point it had to be diluted to perform an $ABS_{270\ nm}$ reading and the reading corrected for dilution. FIG. 22 shows the increment in absorbance with increasing sonication time. The absorbance increases because the graphene fractals are broken into smaller particles as more energy is applied.

As the number of particles increases from the energy applied during sonication, the overall particle size decreases resulting in Mie or Rayleigh scattering of light which is observed as a decrease in transmission on the UV-vis spectra [51]. Therefore, as the graphene is sonicated, the input mass is decrease into the manufacture process but can maintain the same or more numbers of peptide-TCPP particles attached due to an overall increase in particle surface area.

Proteases are very sensitive to environmental changes such as pH and chemicals in the buffers. It was checked that the chemicals used during washing and manufacture of the biosensors were not remaining on the sensors and contributing to batch to batch variation we observed. It was performed a thermogravimetric analysis (TGA) on 4 preparations of CG. Using a TGA Instrument TGA5500 and incrementing the temperature from room temperature (20° C.) to 1000° C. at 20° C./min in a nitrogen environment.

It was observed an overall decrease in Mass Loss Percentage in lots of manufactured nanosensor that had an effort to completely dry the particles (Table in FIG. 23).

Figure 24:
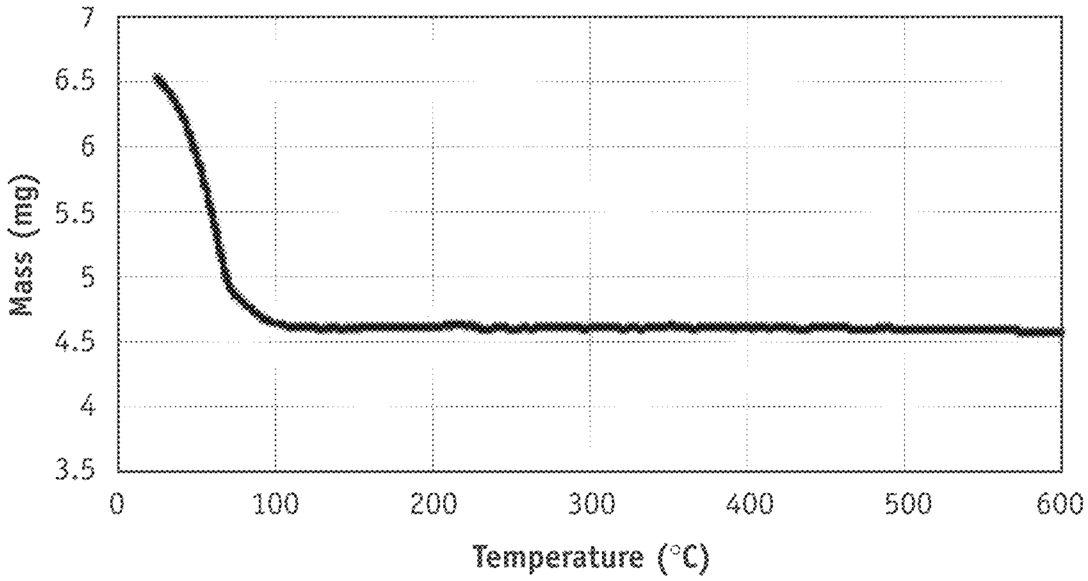
FIG. 24 shows a chart reporting the results of thermogravimetric analysis of a CG preparation featuring $1.6\pm0.1\times10^{-4}$ mol/g of carboxylic acid functions, according to titration. Graph shows change in mass as temperature is increased from RT to 600° C. Graphs indicate the mass that is lost during the increase to 100° C. Change in mass after 400° C. is minimal.
Figure 25:
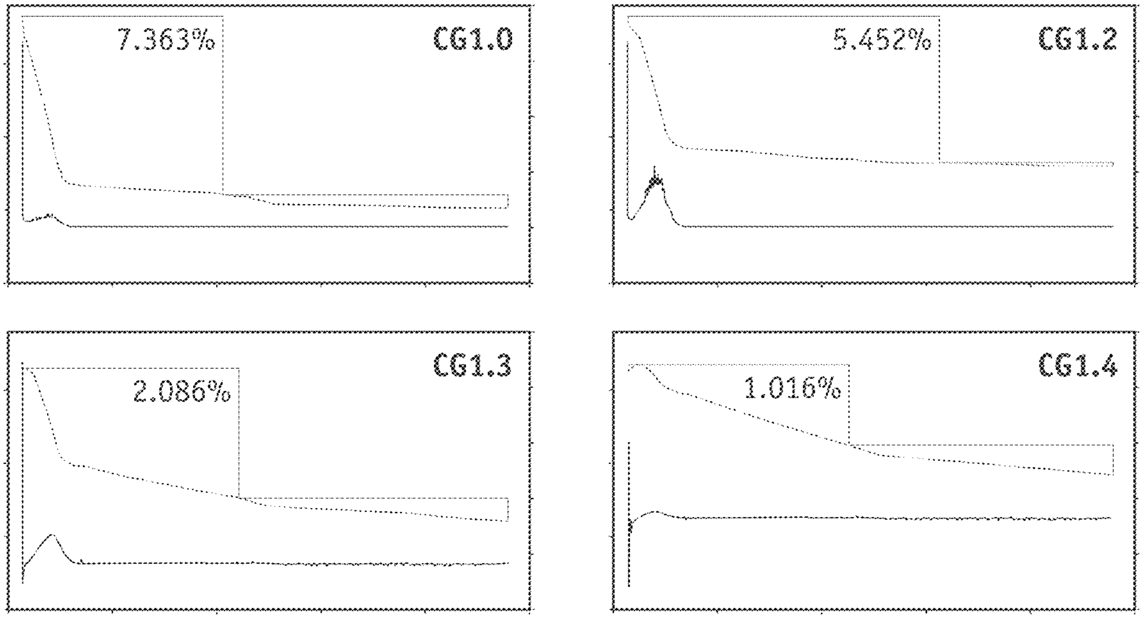
FIG. 25 shows the results of Thermogravimetric analysis of CG preparations CG1.1, CG1.2, CG1.3 and CG1.4 of FIG. 23. Different preparations of CG were subject to TG analysis. Graphs show change in mass as temperature is increased from RT to 1000° C. Graphs indicate the mass that is lost during the increase to 100° C. Change in mass after 400° C. is minimal.

Specifically, the TGA for the original KSU lot (120110) indicated the majority of the mass was lost in the temperature interval up to 100° C., matching the boiling points of the solvents used in manufacturing and indicating residual solvent contamination. As the protocol was modified to include the efforts to dry using temperature and desiccants, the percentage of mass loss decreased (FIG. 24 and FIG. 25).

Figure 26:
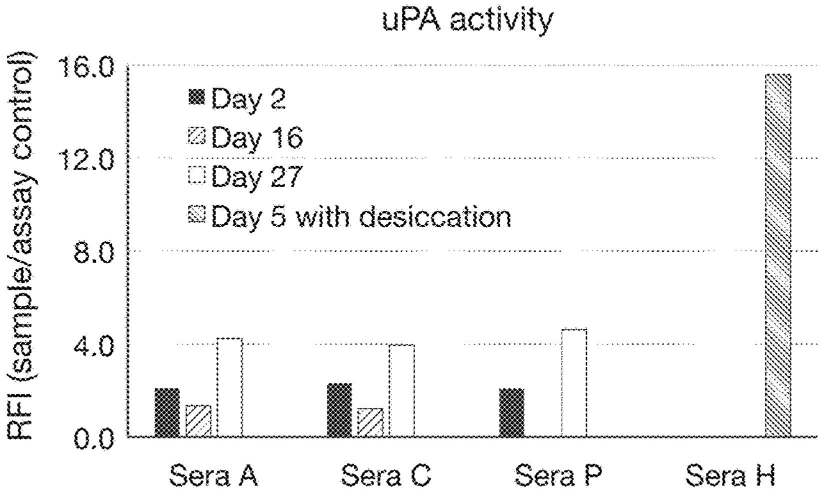
FIG. 26 shows a chart reporting results of experiments showing the impact of removal of solvents on gNBS performance. In particular uPA gNBS were evaluated in triplicate day 2, 16 or 27 after manufacture using the standard protocol. A separate lot of uPA gNBS were manufactured including ambient drying for 30 minutes and overnight in a 37° C. oven. These were evaluated 5 days after manufacture. The chart shows relative fluorescent index calculated by sample/assay control. In the experiments reported in FIG. 26, the uPA sensors used, are based on Carboxygraphene/Polyethylene imine.

It was observed that sensors that do not have solvents removed have to go through a curing period before being fully functional. For the initial lots of nanosensor made by KSU, this period was determined to be 2 weeks where the signal/noise ratio was insufficient to produce significant signal due chiefly to an elevated AC. In contrast, a nanosensor prepared with efforts to remove residual solvents, including a 37° C. overnight drying incubation post manufacture, generated robust signal within 5 days of manufacture (FIG. 26). Desiccation of the final sensor product is considered important to remove residual solvents and reveal optimal activity.

Residual solvents impact the performance of the gNBS by inhibiting optimal activation of the sensors revealed as a reduced signal to noise performance. The removal of manufacturing solvents is therefore characterized using TGA. TGA provides a measurement of the quantity of solvent released as a percentage of total mass. Specifically, the solvents are removed between 20° C. and 200° C. or 20° C. and 400° C. As a contribution to the total mass of the sensor, the preparation of gNBS should result in a contribution of thermally transitioned mass of less than 30%. Optimally the mass loss measured by TGA should be less than 10%, or 5%. Optimally the mass loss as measured by TGA should be less than 1%.

Example 18: Batch to Batch Variation and the Impact of Sonication

The manufacture protocol as defined by the original disclosure was a three-step process.

First graphene was modified to generate Carboxygraphene (CG). This was achieved by dispersing 2.0 g detonation synthesized graphene 0.3 (0-C Ratio) in 40 mL DMF in a 250 mL Erlenmeyer flask suspended in a room temperature silicone oil bath with a magnetic stir bar. After dispersion, the absorbance of the solution was measured on a NanoDrop 2000 C spectrophotometer. The temperature of the reaction was raised to 40° C. and 1.0 g of 5-Bromovaleric acid was added to the graphene suspension followed by slow addition of 0.36 g Sodium Azide crystals. Once all the reagents were dissolved, the temperature was ramped slowly to 80° C. and incubated for 1 hr at 80° C. and then allowed to cool to room temperature. The suspension was washed by centrifugation at 10,000×g for 5 minutes 5-times with DMF and 3-times with ethyl-ether before drying.

Second, for manufacture of the polyethylenimine-derivatized carboxygraphene (CGP) intermediate, Ig of CG was dispersed in 30 mL DMF in a flask with a stir bar. 0.54 g EDC and 0.53 g DMAP were added and stirred until dissolved at room temperature. 1.2 g polyethylenimine was added and the reaction stirred for 21 hours. The CGP particles were washed 4-times with DMF using centrifugation as above, and 3-times with ethyl-ether. The CGP particles were dried by flushing with Argon and holding at room temp for 48 hours loosely covered.

The last step is the conjugation of the sensor peptide-TCPP. 103 mg of CGP was dispersed in 16 mL DMF using a sonicating water bath for 1 minute. 10.5 mg of EDC and 11 mg of DMAP was added to the CGP with stirring at room temperature. 7 mg of TCPP labelled peptide was then added and the reaction stirred for 20 hrs at room temperature. The resulting gNBS was washed 3-times with DMF and 3-times with ethyl-ether before flushing with Argon The final gNBS product was stored at −20° C. This protocol mirrors the original KSU protocol.

Figure 27:
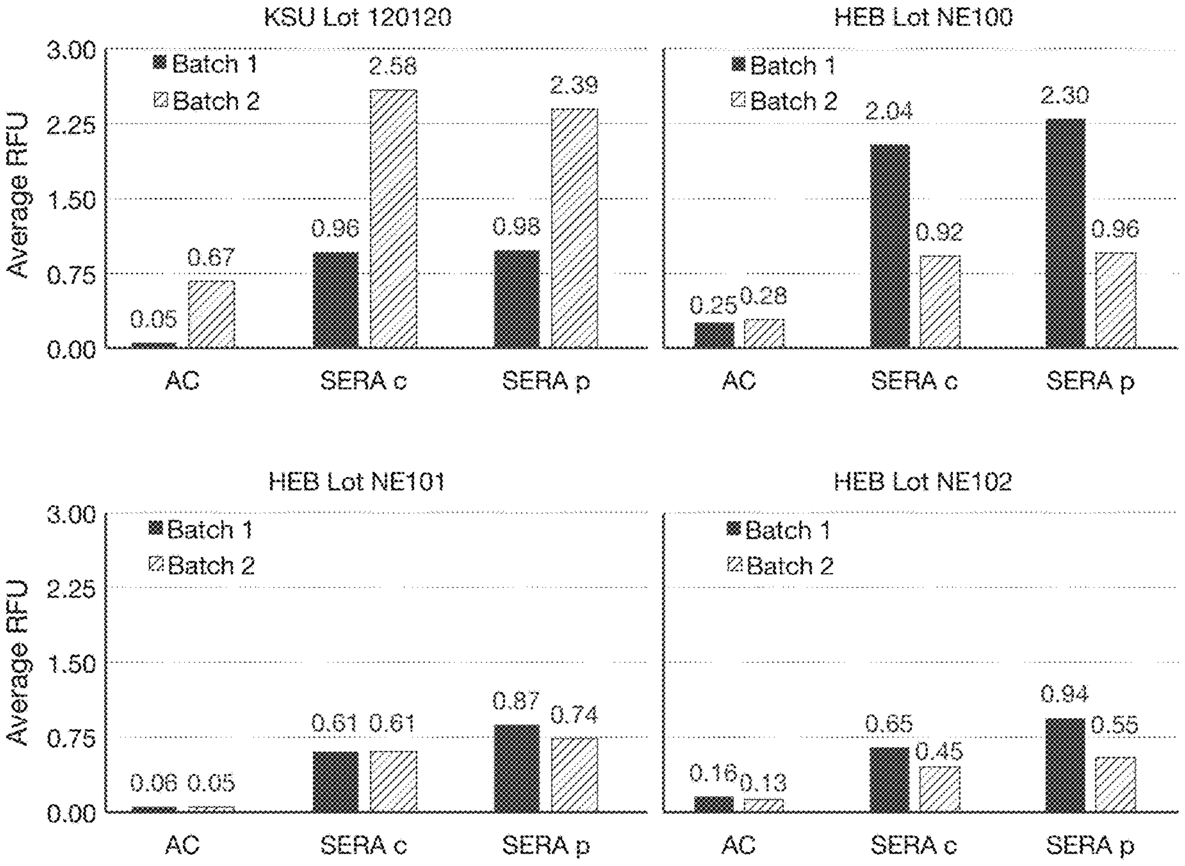
FIG. 27 shows charts reporting the impact of sonicating starting material on the batch-to-batch variation in signal. Three lots of gNBS for Neutrophil Elastase (NE), HEB Lot NE100, HEB Lot NE 101 and HEB Lot NE 102 were manufactured and compared to the original KSU Lot 120120. gNBS were tested under normal condition with sera from 2 different normal human donors.

It was observed that preparations of gNBS made with graphene using the initial protocol presented with large variances in performance between lots, even those batches prepared on the same day (FIG. 27 compare Lots 120120 and NE100 with NE101 and NE102). The possibility was considered that in the preparation of working solution, the dispersal of sensor using a sonicating water bath may generate a different population size and particle number with every sonication. So unless the particle size was optimized before manufacture, the repeated sonication of the gNBS working solutions would regularly alter the result of an analysis.

To determine the impact of sonication on the starting material, the manufacture was modified as outlined in Table in FIG. 28 The starting graphene material was used without sonication as described in the original protocol, being dispersed in DMF with a stir bar only, or the starting material was dispersed with a probe sonicator for 10 or 20 minutes (Table in FIG. 28). After dispersion, the input quantity of graphene was reduced due to the increased numbers of particles and surface area, but the quantity of peptide TCPP input to the conjugation reaction remained the same. One Lot of NE gNBS was manufactured using the KSU protocol and two Lots using 10 and 20 minutes probe sonication of the starting graphene.

All three were compared to the Lot manufactured at KSU (FIG. 26). KSU Lot 120120 and HEB Lot NE100 were manufactured using the same protocol and dispersion procedures. HEB Lots NE101 and NE102 were modified by the inclusion of probe sonication. The gNBS were evaluated under standard conditions using normal human sera compared to the assay control (AC) containing sensor and buffer but no serum. It was observed a 244% average difference between batch 1 and 2 for Lot 120120 and HEB Lot NE100. In contrast the probe sonicated Lots (NE101 and NE102) showed a 132% average difference between batches (FIG. 27). It was concluded that dispersion through sonication before manufacture lead to more consistent particle sizes in the graphene starting material, a smaller and more acceptable PDI (<0.5) (FIG. 21), and produced more repeatable activity in the final gNBS sensor.

To confirm the impact on particle size in the final preparation, we evaluated the impact of sonication in a water bath on the finished particles. A significant ABS increase was observed in NE-gNBS that had undergone no sonication during manufacture with an average increase in ABS of 259% at the ABS wavelength for graphene (265 nm) and TCPP (425 nm).

Figure 29:
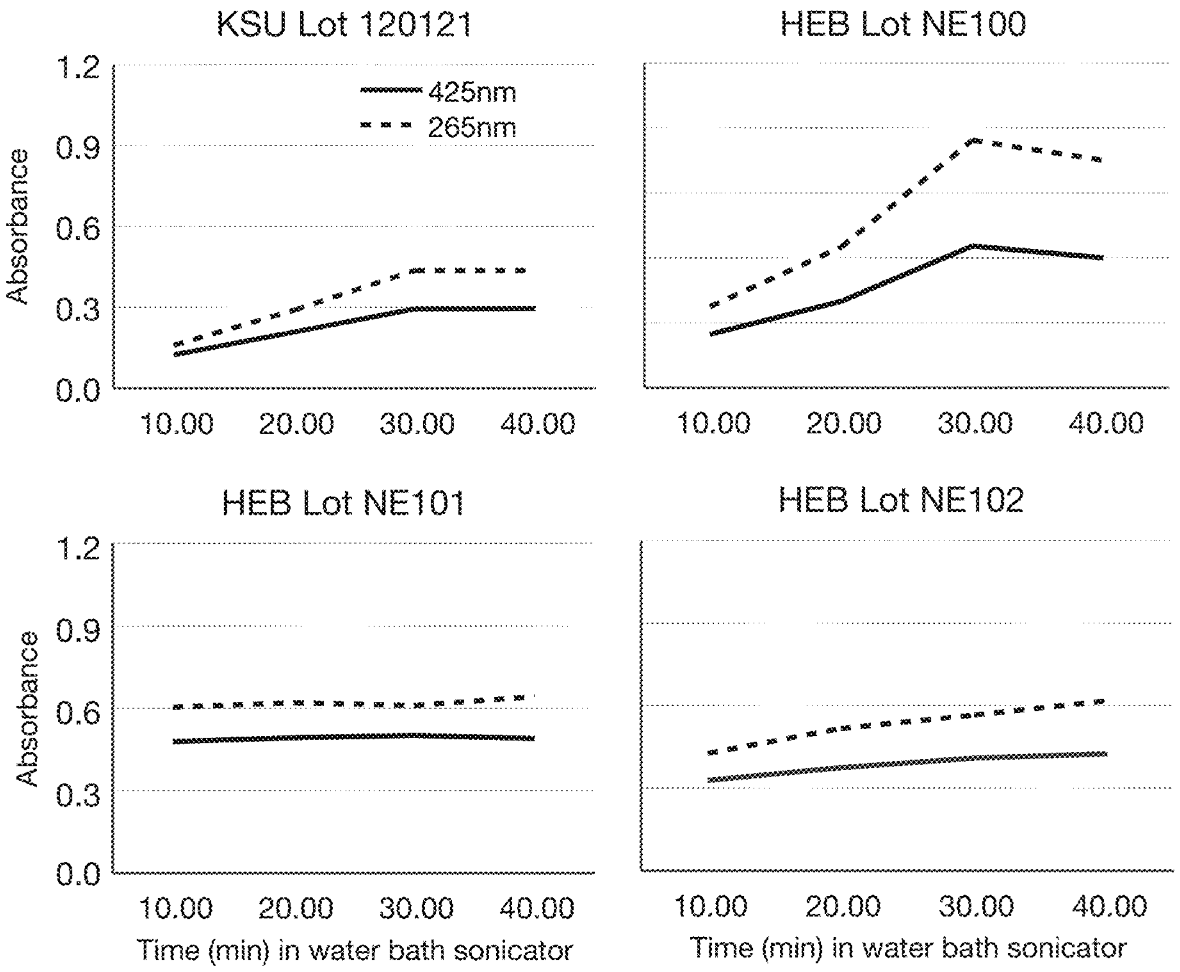
FIG. 29 shows charts reporting results of experiments directed to assess impact of water bath sonication on gNBS absorbance over time. gNBS HEB Lot NE100, HEB Lot NE 101 and HEB Lot NE 102 and KSU Lot 120120 were resuspended in working buffer and suspended in a sonicating water bath for incremental amounts of time. At intervals, a sample was recovered and the Absorbance at 425 nm and 265 nm was measured. 4 different Lots of gNBS for NE are shown.

In contrast, the change in ABS over time for the Lots prepared including sonication showed on average a 121% change in ABS over time at the same wavelengths (FIG. 29). Our conclusion was that preparation of the particles including a probe sonication step produced a more homogenous suspension that was not impacted by the water bath sonication steps used to prepare working solutions.

Example 19: Preparation and Performance of Biosensors

The preferred protocol for assembly of the particles includes adjusting size distribution of particles using sonication or physical disruption. The graphene is derivatized by addition of a carboxyl moiety to the surface using an azirane anchor. The surface is then modified by addition of a polymer such as polyethylenimine (PEI), followed by conjugation of a peptide dye complex.

With the set of experiments reported in the present examples It was sought to find the boundaries of these steps and components by substituting other components to evaluate the modifications that could be considered for alternate manufacturing protocols.

In particular, experiments were repeated to determine the amount of carboxy labelling that occurs during the first step of synthesis. Solutions of 0.5M NaOH and HCl were prepared using hew high purity HPLC grade water. The 0.5M NaOH solution was degassed with Argon for 2 hours before dispersing CG. After degassing, 250 mg of CG was dispersed in 50 mL of 0.05M NaOH. The sample was sonicated for 10 minutes in a water bath and then stirred for 24 hr at room temperature. After 24 hrs, the CG suspension was filtered out to remove the CH< and solutions (CG filtered 0.05M NaOH, 0.05M NaOH, and 0.05M HCl were degassed overnight. Next, 20 mL of 0.05M HCl were added to a 10 mL aliquot of the CG treated and filtered NaOH solution. The pH was recorded after every addition of NaOH once the pH had stabilized and before the next addition. For blank, a 10 mL solution of 0.05M NaOH was prepared the same way by addition of 0.05M HCl and back titration with 0.05M NaOH. Degassing was maintained during titration. Using this protocol, CG preparations required more NaOH than blank for neutralization implying the presence of acidic functional groups. Replicate experiments calculated a concentration of $1.765\times10^{-4}$ and $1.8\times10^{-4}$ mol/g acidic groups. Although lower than the original estimate, it supported the addition of acidic groups to the graphene (FIG. 30 Panel A and Panel B).

Figures 30, 31:
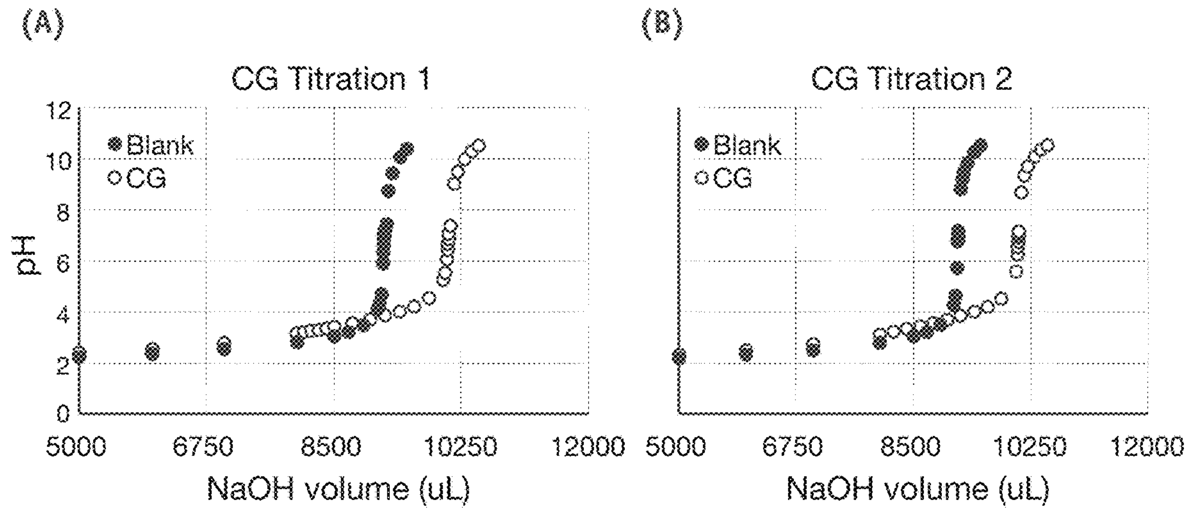
FIG. 30 panel A and FIG. 30 panel B show charts reporting the results of pH Titration of carboxygraphene. Solution of carboxygraphene prepared using the protocol as described herein were prepared in 50 ml of 0.05M NaOH. After incubation and removal of the CG, the resulting solution was treated with 20 mL 0.05M HCl and then neutralized with incremental amounts of 0.05M NaOH and compared to neutralization of a solution of water.
FIG. 31 shows a table reporting results of an Elemental Analysis of different lots of graphene CarboxyGraphene (CG) preparations and CG derivatized with polyethyleimine (CGP) preparations. In particular two different lots of graphene, 6 different preparations of CG and one preparation of CGP as indicated were subjected to elemental analysis for C, H, O and where results cited, N. All results were produced by Galbraith Laboratories other than*data for which were generated by KSU. Results are presented in percent composition. For comparison, CGP102 is PEI derivatized product assembled with CG1.0.

In support of this observation, elemental analysis of unmodified graphene and carboxygraphene showed undetectable levels of oxygen and hydrogen in the starting graphene material (Table in FIG. 31). After carboxylation there were detectable levels of H and O observed between 0.5% and 3.5%. Decreased oxygen content weas noted in comparison to the original KSU protocol (KSU and CG1.0) so conclude some of that oxygen content is derived from solvents. In support of this, preparations CG1.2, CG1.3, and CG1.4 (Refer to Table in FIG. 28) were prepared with sonication and included drying protocols and showed lower resulting percentages of H and O detected. For comparison, CG product that was derivatized with PEI (CGP102) produced significantly higher contributions of H, O and N. CGP102 was assembled using CG1.0 (Table in FIG. 31).

On this basis it was concluded that the original pH titration overestimated the numbers of carboxylic acid groups added to the graphene and was more accurately estimated using Argon degassing and back titration. This was supported by the elemental analysis that showed a lower estimate of oxygen content in CG preparations where efforts were made to eliminate residual solvent than in product generated with original protocols. Despite differences in elemental analysis, all the protocols as described were still able to annotate graphene with H and O and to produce functional biosensors.

To determine the steps for the biosensors assembly, the addition of PEI to graphene was tested in the absence of a previous carboxylation step. In the first instance, control uPA gNBS was assembled using the standard protocol by carboxylation of graphene followed by PEI polymerization. In a second example, 0.3 graphene was substituted for CG with the same addition of 500 mg/g PEI using 243 mg/g EDC and 247 mg/g DMAP as outlined for CGP104 in Table in FIG. 28 (uPA-no GC).

This reaction was incubated with stirring at RT for 90 minutes. In a third instance, 0.3 graphene was dispersed into DMF with the addition of 550 mg/g PEI but no EDC or DMAP catalyst were added. Instead, the reaction was heated to 80° C. for 1 hour (uPA—80° C.). On completion of the addition of PEI, all three preparations were washed at least 5 times with 200 proof Ethanol and resuspended in DMF. All three preparations were then conjugated to Peptide TCPP using the uPA-TCPP sequence. All three constructs were treated with 105 mg/g EDC, 111 mg/g DMAP and 65 mg/g uPA-TCPP with stirring at RT for 90 min. The resulting particles were washed with Ethanol and dried overnight in a 37° C. oven. The sensors were tested by preparing solutions of 200 μg/ml in 10 mM MES, 10 pM $CaCl_2$, $MgCl_2$, $ZnCl_2$, and IS:155. 70 μl of each working solution was incubated with 10 μl of pooled normal sera at 45° C. for 90 minutes.

The fluorescence was measured on a VarioSkan Lux plate reader with 425 nm excitation and 653 nm emission. All three preparations produced assay controls values less than 0.05 and had RFU from pooled normal serum between 19 and 31 (in FIG. 32). All three sensors were insensitive to adjustment of the reaction to 10 mM KOH, a treatment that reveals non-covalently bound TCPP (Data not shown).

It was thus concluded that since the elemental analysis of graphene has a limit of detection for oxygen of 0.5%, as the quantity of oxygen increases to the detectable levels with production of CG the targets for addition of PEI also become detectable. However, given the functional sensors generated by heat based condensation at 80° C. or adding PEI with catalyst directly to graphene, evidence is obtained that 0.3 graphene has some ability to attach the small numbers of PEI molecules necessary to assemble a sensor implying the presence of oxygen in the detonation graphene.

Additional methods of coupling PEI to graphene which might require fewer steps or be more efficient were also evaluated. It was identified surrogates for the bromovaleric acid linker step such as a modified tetra ethylene glycol (TEG), Azidoacetic acid NHS ester, or Azidoacetic Acid. These molecules provide the azido-group and the carboxylate or amine group in place of the Bromovaleric acid+azide.

An experiment was performed where 125 mg graphene was probe sonicated into 22.5 mL DMF and heated to 60° C. PEI was prepared by adding 60 mg 10 k MW PEI to 3 ml DMF and then adding 270 mg Azidoacetic acid NHS Ester.

The mixture was heated to 60° C. and incubated for 30 minutes. The activated PEI solution was then added to the graphene and the temperature ramped over 10 minutes from 60° C. to 80° C. The reaction was continued for 1 hour and purified as using Ethanol washes and desiccation. A second preparation was made the same way but substituting the 10 k MW PEI for 1.2 k MW PEI. Both constructs were subsequently treated with 105 mg/g EDC, 111 mg/g DMAP and 65 mg/g uPA-TCPP with stirring at RT for 90 min. The resulting particles were washed with ethanol and dried overnight in a 37° C. oven. The sensors were tested by preparing solutions of 200 μg/ml in 10 mM MES, 10 μM $CaCl_2$, $MgCl_2$, $ZnCl_2$, and IS:155. 70 μl of each working solution was incubated with 10 μl of buffer, 50 mg/mL acetylated BSA, or pooled normal sera at 45° C. for 90 minutes in a black 384 well plate.

The fluorescence was measured on a VarioSkan Lux plate reader with 425 nm excitation and 653 nm emission (FIG. 33). It was observed similar activation of the uPA sensor made with either PEI preparation. This observation indicates it is possible to manipulate the distance of a peptide and the associated dye from the graphene backbone—by selecting polymers of different molecular weight therefore decreasing the distance between the graphene quencher and fluor. This will likely become necessary as we change to more efficient fluorescent dyes that have shorter Förster radius or are more efficient fluorophores. This experiment also confirms the ability to use anchors other than bromovaleric acid.

Currently, assembly of graphene based biosensors consists of a series of surface modification reactions, which are performed using the following modifications: graphene to carboxygraphene to carboxygraphene-PEI to graphene biosensors. In order to reduce this complex synthetic procedure, it was investigated a single surface modification of graphene prior to the assembly of the biosensor, which is described below.

A small scale reaction was started by dispersing Ig of 0.3 detonation graphene in 50 mL of distilled and degassed N,N-Dimethylformamide (DMF) (Fisher Scientific Cat #: D119-20) in a round bottom flask at room temperature. This dispersion solution was then heated up to 40° C. and 556 μL (0.0028 mol) of Azido-TEG3-amine (BroadPharm Cat #: BP-20580) was added slowly. Then, temperature was increased to 80° C. and reaction solution was stirred for 1 hour. After the 1 hour, reaction was cooled down to room temperature and sample was collected via centrifugation (5 minutes at a speed of 8000 rpm). Finally, the G-TEG3amine product was washed 5 times with DMF and 3 times with anhydrous diethyl ether. Resulting G-TEG3amine was further dried with argon and stored at −20° C.

The next step was to assemble MMP1 biosensor using G-TEG3amine, which was assembled following the same optimized conditions established for G-PEI biosensors. For this, two solutions were prepared: 1) 3.75 mg of TCPP-MMP1 peptide, 5 mg of EDC, and 5 mg of DMAP were dissolved in 2 mL of distilled and degassed DMF and 2) 50 mg of G-TEG3 amine were dispersed in 2 mL of distilled and degassed DMF. Both solutions were sonicated in a sonicating water bath (3 minutes) and vortexed until completely dissolved. Solution 1) and 2) were then mixed, and solutions were further sonicated (3 minutes) to ensure everything remained suspended in DMF. Solution was then stirred overnight at room temperature. After 24 hr, biosensor was collected via centrifugation (8 minutes at 8000 rpm), washed three times with DMF and three times with diethyl ether. Lastly, biosensor was dried with argon and stored and stored at −20° C.

Once biosensors were assembled, dynamic light scattering (DLS) and zeta potential measurements were taken using the NanoBrook 90Plus PALS. For this, a 0.03 mg/mL solution of MMP1 was prepared using highly pure water (HPLC water, Fisher Cat #: W7-4). Average size (DLS), polydispersity index, and zeta potential surface charge are shown (Table in FIG. 34). Results demonstrated that biosensor has a slightly positive charge of 4.36 mV, an average diameter size of 713.30 nm, and PDI of 0.147.

The following experiment was a side-by-side comparison of both biosensor, G-PEI MMP1 vs G-TEG3amine MMP1. For this experiment, a 0.03 mg/mL solution of each MMP1 biosensor was prepared using HEPES Buffer (25 μmol/L HEPES buffer enriched with 10 μmol/L of $Ca^{2+}$, $Mg^{2+}$, $Zn^{2+}$, pH 7.20). After preparing the biosensor solutions, pH increased to 7.40 for G-TEG3amine and 7.52 for G-PEI, therefore, pH was then adjusted to 7.20 for both solutions using a 0.1 M HCl solution.

Three solutions were prepared (as described below) and plated in duplicates in a 96-well plate (Greiner Bio-one, microplate 96 well, PS, F-bottom, Black non-binding; item #: 655900).

Solution 1: Sample control (125 μL of HEPES buffer+5 μL of collected control serum—S, P, or Pooled)

Solution 2: Assay control (125 μL of biosensor solution in HEPES buffer+5 μL of HEPES buffer)

Solution 3: Assay (125 μL of biosensor solution in HEPES buffer+5 μL of collected control serum—S, P, or Pooled).

Figure 35:
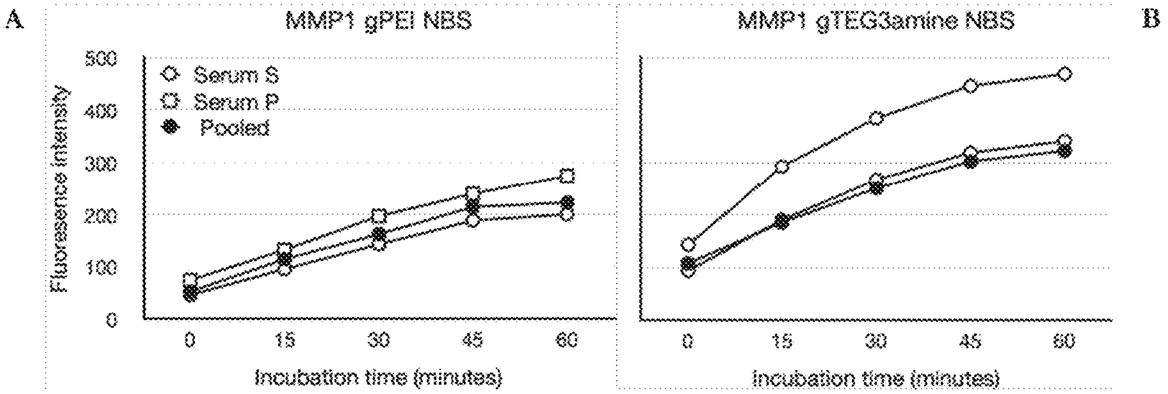
FIG. 35 shows charts reporting results of fluorescence intensity measured for MMP1 G-PEI biosensors (Panel A) vs B) MMP1 G-TEG3amine biosensors (Panel B). Fluorescence intensity was measured every 15 min after incubation at 37° C., and these intensities continue increasing as time passed, following almost a linear trend for both. Comparing both biosensors, G-TEG3amine gave a higher intensity compared after the 60 min incubation compared to G-PEI.

After the solutions were plated, 96-well plate was incubated at 37° C. for 1 hour, and fluorescence intensities were measured every 15 min during the 1 hr incubation. Fluorescence intensity was measured using a BioTek Synergy H1 plate reader ($_{exc}$=425±10 nm, $_{em}$: 650±20 nm). FIG. 35 shows the fluorescence intensities measured every 15 min for MMP1 G-PEI and MMP1 G-TEG3 amine biosensor for each control sera (S, P, and Pooled). The highest intensity measured after 1 hr incubation for G-TEG3amine was higher for all 3 control sera tested compared to G-PEI biosensor.

Figure 36:
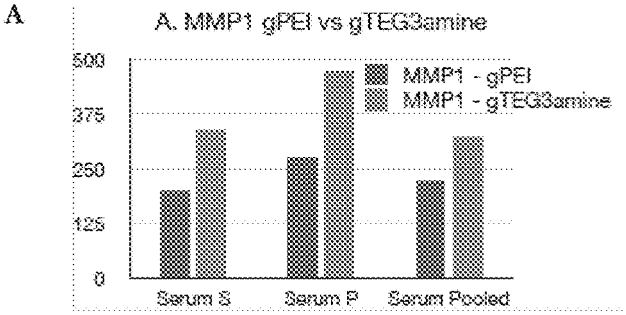
FIG. 36 shows charts reporting results of fluorescence intensity after 60 min incubation for G-PEI vs G-TEG3amine and assay control. After 60 min incubation (Panel A), intensity for G-TEG3amine gave the highest intensity compared to G-PEI. shows that for control serum S and P, intensity for G-TEG3amine was almost twice as higher compared to G-PEI. (Panel B) Fluorescence intensity measured for assay controls for MMP1 G-PEI vs G-TEG3amine biosensors.

Also, intensity increased over time following an almost linear trend for both biosensors tested with all 3 control sera samples. FIG. 36 panel (A) shows the intensity measured after the 1 hr incubation with both biosensors tested with each control sera. Here, the differences in intensities can be noticed comparing G-PEI vs G-TEG3 amine, which was almost twice as high for G-TEG3amine as for control serum S and P compared to G-PEI. It should be also mentioned that intensity for assay controls were lower for G-TEG3amine compared to G-PEI, which are summarized in FIG. 36 panel (B). Overall, G-TEG3amine based biosensor produces improved signal/noise measurements with lower assay control and greater specific signal for serum.

In view of the above experiments, it was concluded that since explosion synthesized graphene is hydrophobic and virtually not dispersible in water or aqueous buffers (and many surfactants interfere with the fluorescence quantum yield of organic dyes), addition of a hydrophilic coating is to be performed to obtain the desired stability.

This can be achieved by attaching carboxylic acid groups to the surface of the graphene stacks via nitrene addition [52]. Alternatively, amine-terminated oligoethylene glycol can be attached to the surface of explosion graphene via nitrene addition.

To this carboxylic acid, polyethylene imine is attached. Alternatively, amine groups can be attached to the surface of explosion graphene, and then a polymer displaying carboxylic groups.

Alternatively, the precursor can be bound for graphene addition bearing an azide group to the polymer, and then anchor the polymer to the graphene surface.

The attached organic coating (polymer, oligoethylene glycol) has the following functions:

Without hydrophilic coating the graphene nanobioensors would not be dispersible in aqueous buffers. The achievable concentration of the biosensor strongly depends on the chemical nature of the coating and the mass ratio of the coating to graphene.

The coating is responsible for the stability of the biosensor when dispersed in aqueous buffers and the graphene cores of the biosensor are extremely stable.

The size and structure of the PEI is responsible for the observed increase of fluorescence upon proteolytic cleavage of the consensus sequence. In general, Förster Resonance Energy Transfer (FRET) is occurring between graphene (acceptor) an attached organic fluorophore. The efficacy of FRET is distance depending. Therefore, the structure of PEI (branched vs. linear) matters. However, graphene (and especially graphene stacks) efficiently absorbs light from the UV into the near infrared region. Theoretical studies by Bian et al. (2016) suggest that the quenching sphere around a graphene monolayer extends approx. 20 nm [53]. Within this "Förster Volume" strong quenching occurs, which very strongly decreases TCPP fluorescence. Upon escape from the Förster Volume, TCPP starts emitting.

Example 20: Multiplex Graphene Biosensor

Figure 37:
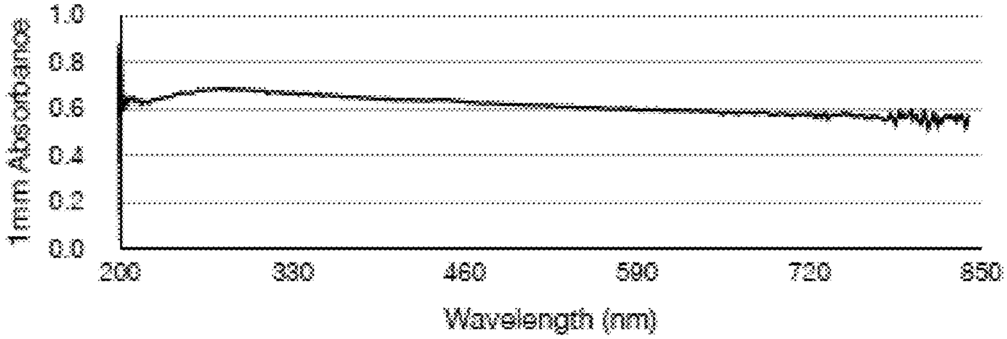
FIG. 37 shows a chart reporting the results of absorbance over the visible spectrum of a solution of Neutrophil Elastase gNBS.

The possibility was considered of running multiple different sensors in the same reaction well. Graphene has a broad spectrum absorbance of light (FIG. 37). Accordingly, multiple different peptide-dye sequences can be assembled on a single graphene particle or multiple sensors each labeled with a different single peptide-dye could be mixed together.

Figure 38:
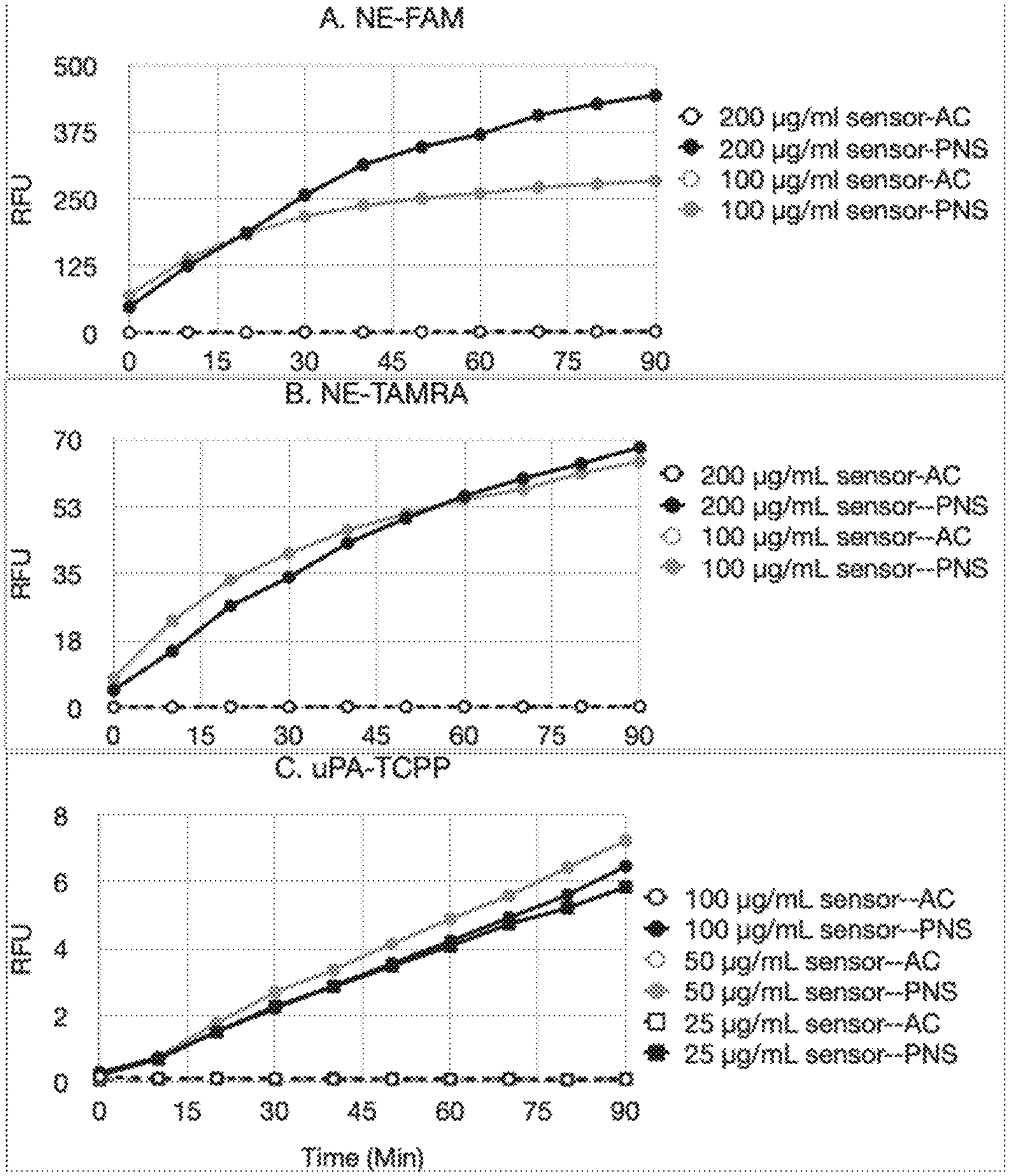
FIG. 38 shows charts reporting the results of experiments showing quenching of multiple different dyes by graphene. gNBS were prepared by coupling NE-FAM (Panel A), NE-TAMRA (Panel B), or uPA-TCPP (Panel C) to sonicated graphene using the standard procedures. Dose responses of each sensor in a 70 μL volume were stimulated in triplicate with buffer alone (AC) or with 10 μl serum in a 384 well plate. The plates were incubated at 45° C. and fluorescence was read at 10 minutes intervals for 90 min.
Figure 39:
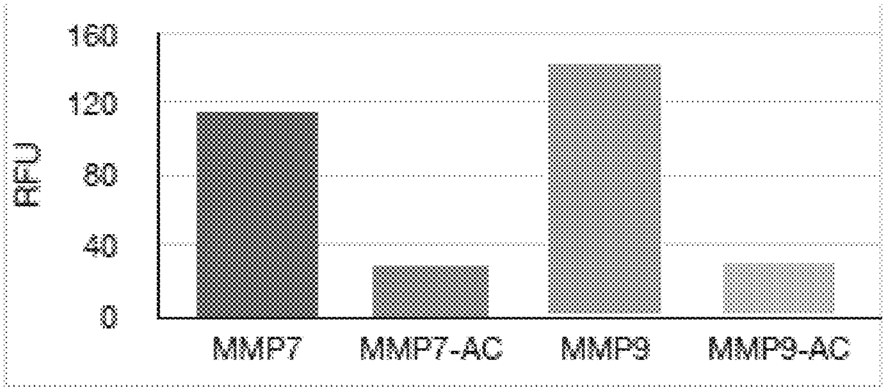
FIG. 39 shows a chart reporting the results of experiments showing quenching of Rhodamine-B by graphene with Rhodamine-B gNBS. MMP7 and MMP9 RhodamineB peptide were coupled to CGP and incubated in the presence of sera or buffer only (AC) for 60 minutes.

The multiplex capability of the biosensor of the disclosure was evaluated using the later system—mixing two independently labelled particles. Peptides for Neutrophil Elastase (NE) and Arginase (ARG) were variously labelled with FAM or TAMRA. Peptide-FAM or Peptide-TAMRA were directly substituted into the manufacture process for the Peptide-TCPP with the only modification being conjugation at half the density due to the increased fluorescent efficiency of these dyes. So the peptides were added at 35 mg/g CGP (Reference Table in FIG. 28). gNBS working solutions were prepared by massing out NE-FAM, NE-TAMRA, or uPA-TCPP gNBS into assay buffer comprised of 10 mM MES, 10 μM $CaCl_2$, $MgCl_2$, $ZnCl_2$, IS:155. 1251 of working solution with incremental quantities of each gNBS were dispensed in black 96 well plates and stimulated in a single well with buffer for the assay control (AC) or in triplicate with 5 μl of pooled normal sera. The plates were incubated in the VarioSkan Lux at 45° C. (FIG. 38 and FIG. 39). Fluorescence was observed for each reaction over 90 minutes using $Ex_{496}/Em_{526}$ for FAM and $Ex_{555}/Em_{556}$. Alternatively, MMP7 and MMP9 peptides were conjugated to Rhodamine-B and conjugated to CGP at 70 mg/g using the KSU manufacture protocol as above. gNBS working solutions were prepared with a final concentration of 30 μg/mL gNBS in 10 mM MES, 10 μM $CaCl_2$, $MgCl_2$, $ZnCl_2$, IS:155 and 125 μL reactions were set up in triplicate in black 96 well plates and incubated with 5 μL sera or buffer only (AC) for 60 min at 37° C. Fluorescence was measured at $Ex_{535}/Em_{570}$ on a BioTek Synergy H1 FL800 plate reader (FIG. 39).

These observations support the model that graphene can act as an effective quencher for multiple different dyes. Having demonstrated that multiple different sensors can be built with different dyes and these dyes can be successfully quenched by the graphene backbone in separate reactions, it was sought to demonstrate that multiple dyes could be observed in the same reaction.

Arg-FAM and NE-TAMRA gNBS was prepared again halving the input peptide dye contribution to 35 mg/g CGP for the gNBS manufacture protocol as above. gNBS working solutions were prepared by massing out 400 μg/ml Arg-FAM or NE-TAMRA gNBS into assay buffer comprised of 10 mM MES, 10 μM $CaCl_2$, $MgCl_2$, $ZnCl_2$, IS:155. 80 μl reactions were set up in 384w black plates with 35 μl single sensor and 35 μl buffer or 35 μl of each sensor mixed for a 200 μg/ml final concentration of either sensor. 10 μl pooled normal sera or buffer was added to each sensor solution.

Figure 40:
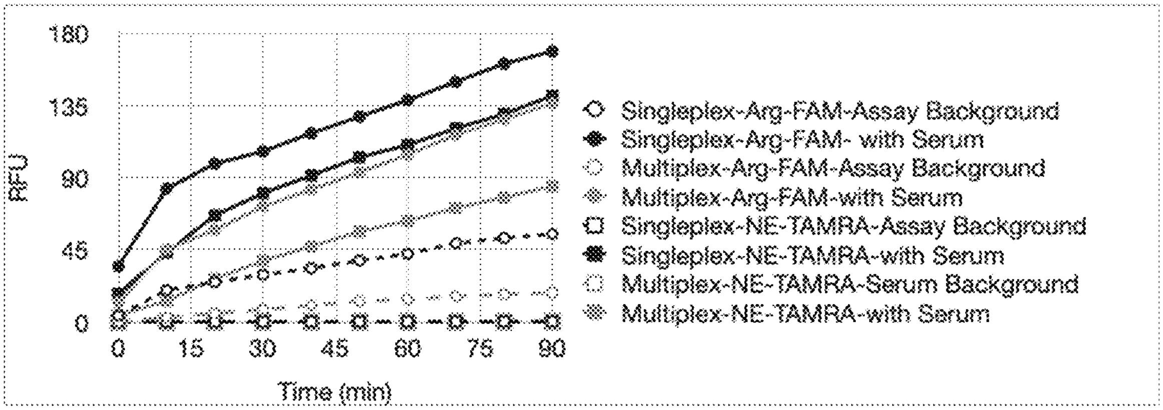
FIG. 40 shows a chart reporting results of experiments with multiplex gNBS. gNBS sensors were prepared by coupling Arg-FAM or NE-TAMRA as indicated to sonicated graphene using the standard procedures. 70 μl working solutions were prepared with 200 μg/ml final concentration of each sensor alone (Singleplex) or both together (Multiplex). Triplicate wells were treated with 10 μl buffer or 10 μl serum and incubated for 90 minutes at 45° C. with measurements taken at 10 minute intervals. Each well was measured at 496/526 (FAM) and 555/586 (TAMRA) (D03-250).
Figure 41:
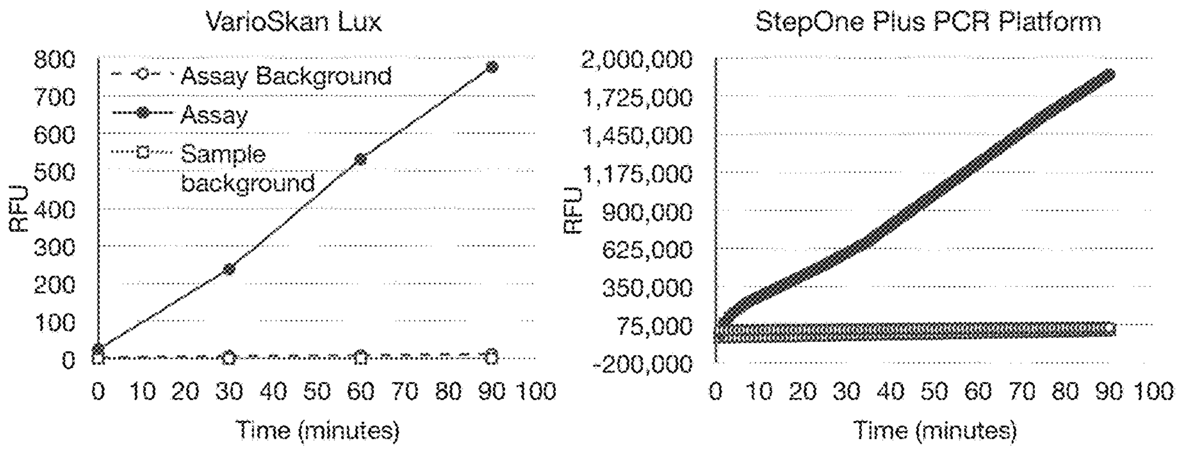
FIG. 41 shows charts reporting results of Nanosensor analysis on multiple different platforms. gNBS sensors were prepared by coupling NE-FAM to sonicated graphene using the standard procedures. 125 μl working solutions were prepared with 200 μg/ml of sensor. Triplicate wells were treated with 5 μl buffer (AC) or 5 μl serum. An additional well diluting 5 μl serum into 125 μl of buffer was also prepared (sample background). Each well was measured at 496/526 (FAM) at 30 minute intervals on the Varioskan and 1 minute intervals on the StepOnePlus.

The sensors were all stimulated in triplicate and incubated for 90 minutes at 45° C. with measurements taken at 10 minute intervals. Each well was measured at 496/526 nm (FAM) and 555/586 nm (TAMRA) (FIG. 40).

It was noted that the individual sensor and the multiplexed sensors can both be detected and there was no detection of signal from one sensor into the other channel although there is evidence for some quenching when both sensors are present (Compare singleplex to multiplex fluorescence in either channel). It was also noted that the Arg-FAM presented with an elevated background in the singleplex and multiplex reactions. It was interpreted this as an indication that the amount of peptide conjugated when high efficiency dyes are being used may exceed the capacity of the graphene backbone to quench.

This noise can be alleviated by titrating down the level of labeling. Alternatively, a shorter linking chemistry between the FAM dye and the graphene would bring the FAM closer to the FRET partner and improve quenching. In this context, it was considered substituting the 10 k MW PEI with the 1.2K MW PEI as described in FIG. 32 as a viable solution.

Using a combination of polymerization as with PEI or direct conjugation as by TEG or Azidoacetic acid NHS ester or equivalent was considered to conjugate dye labelled peptide to a graphene backbone, such that the graphene backbone effectively quenches the attached dye.

Variations on this chemistry are expected to be effective as exampled above so long as the peptide-dye conjugate is maintained within 20 nm of the graphene [53] [54]. So the signal to noise performance is modified by altering the distance between the dye conjugate and the graphene backbone by optimizing the polymerization or conjugation chemistry to optimize the efficient quenching of the dye depending on the quantum efficiency of the dye selected. This conjugation selection must also contribute sufficient charged groups such as carboxylic acid, amino, or alcohol side chains to allow secondary conjugation of the peptide-dye complex and to support solubilization of the graphene particles.

Finally, a NE-FAM gNBS reaction was set up in duplicate with one assay being conducted in a 96w black plate and analyzed in a VarioSkan Lux platform and the other assay using NE-FAM gNBS in a 96 well PCR plate and analyzed in a StepOnePlus PCR platform (FIG. 31). The absence of background signal and the linear relationship between incubation time and fluorescence is apparent on both platforms and raises the possibility that these types of gNBS assays could be run on laboratory equipment even more widely distributed than fluorimeters, such as quantitative PCR platforms.

Example 21: Heat Treatment of Serum

Figure 42:
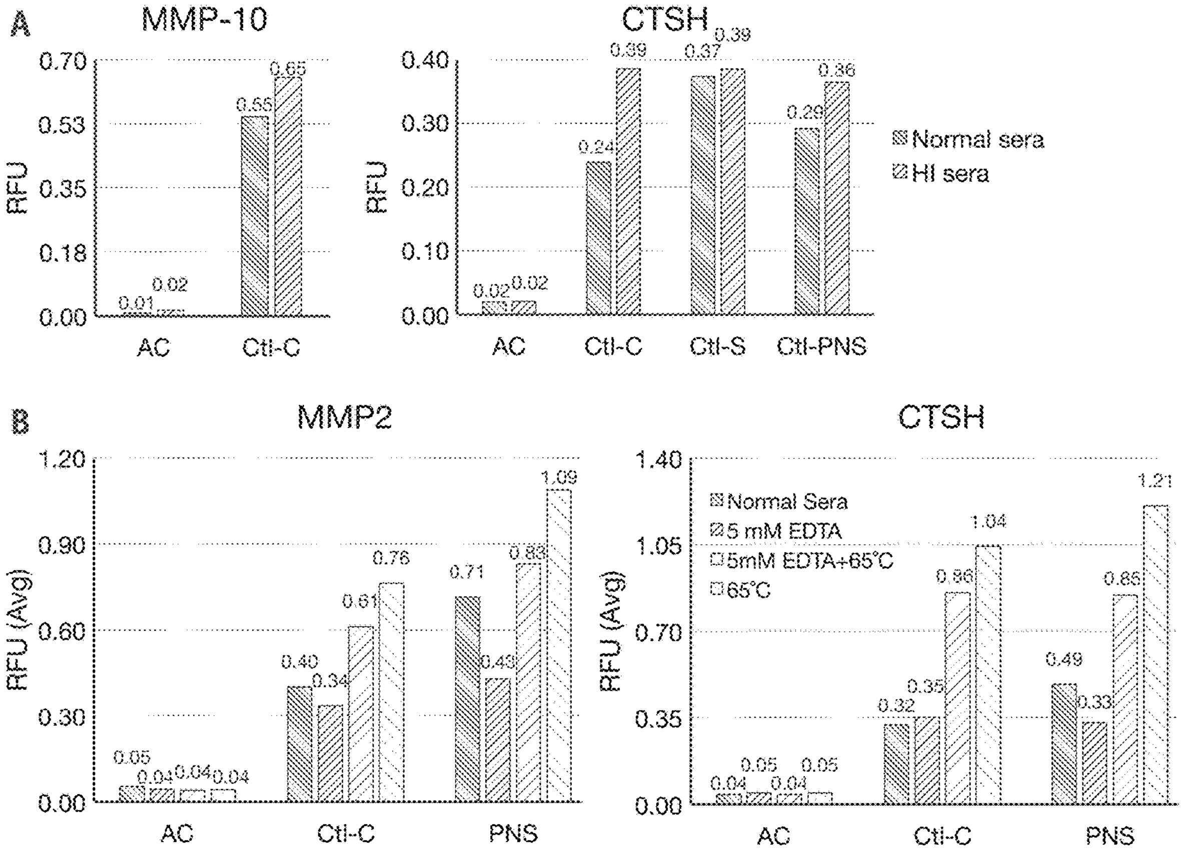
FIG. 42 shows results of experiments directed to detect proteases following heat treatment (Panel A) Control sera and pooled normal control sera were used to stimulate MMP10 gNBS and CTSH gNBS in in 125 μl working solution of 5 mM MES, 10 pM cations and IS:155. An aliquot of each serum was incubated at 55° C. for 60 minutes and used to stimulated replicate reactions. Both sets of reactions were incubated at 37° C. for 1 hour and the fluorescence measured on a Varioskan Lux. (Panel B) MMP2 gNBS and CTSH gNBS were stimulated in 125 μl working solution of 5 mM MES, 10 pM cations and IS:155. They were stimulated with 5 μl buffer (AC) or in triplicated with 5 μl control serum C or pooled normal sera (PNS). Sera were alternatively treated in advance with 65° C. for 10 min, EDTA such that the final concentration was 5 mM or both. The resulting activity reported in RFU are show for each sensor.
Figure 43:
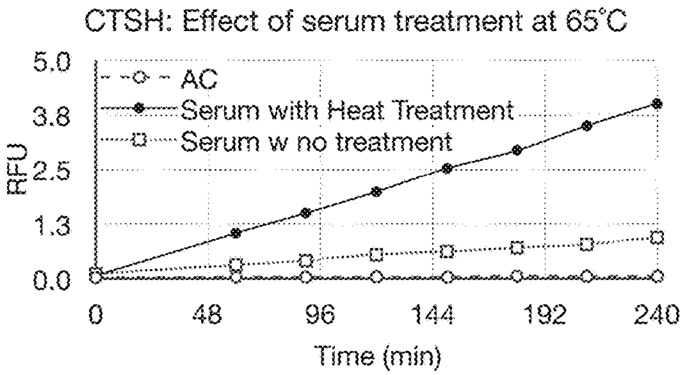
FIG. 43 shows a chart reporting results of experiments including heat pretreatment of sera. CTSH gNBS were stimulated in 125 μl working solution of 5 mM MES, 10 pM cations and IS:155. They were stimulated with 5 μl buffer (AC) or in triplicated with 5 μl PNS that was either previously heat treated at 65° C. or not. The activity of CTSH gNBS was monitored in a 37° C. incubation at 30 minutes intervals for 6 hours. The chart shows that heath pretreatment results in linear activity.

An experiment was designed to demonstrate the specificity of these reactions by heat inactivating the protease enzymes. To this end, samples of two different control sera were heat treated at 55° C. for 1 hour. The heat treated sera and the untreated sera were incubated with MMP10 and CTSH gNBS using the standard conditions. With both sera and for both sensors, a modest elevation in the RFU was unexpectedly observed. (FIG. 42 Panel A). The experiment was repeated with treatment of the two control sera at 65° C. for 10 minutes (any longer interval caused precipitation of the sera). In addition, we treated the sera with EDTA such that the final EDTA concentration in the sensor reaction was 5 mM. We also substituted MMP2 for MMP10 gNBS to see how generalizable this observation was (FIG. 42 Panel B). Treatment of sera with EDTA produced a modest decrease in activity consistent with other reports [55]. In contrast, heat treating the sera at 65° C. gave a significant increase in activity in both sera and both sensors. The addition of EDTA modestly decreased the elevated activity as it did for the untreated sera and this affect was more pronounced for the MMP2 sensor. Therefore, surprisingly treatment of sera at elevated temperatures reveals additional protease activity that can increase the gNBS signal. To determine if this change is the result of additional activation events occurring as zymogens become activated, we stimulated CTSH gNBS with pooled normal sera or replicate sample that was heat treated to 65° C. for 10 minutes. The reaction was measured at 30 minute intervals after the first hour for over 240 minutes. The activity of the untreated sera and heat treated sera were both maintained as linear reactions for the duration (FIG. 43). If additional zymogens were being activated, an increase in kinetics would be expected over time. However, no evidence were seen of a change in kinetics.

Figure 44:
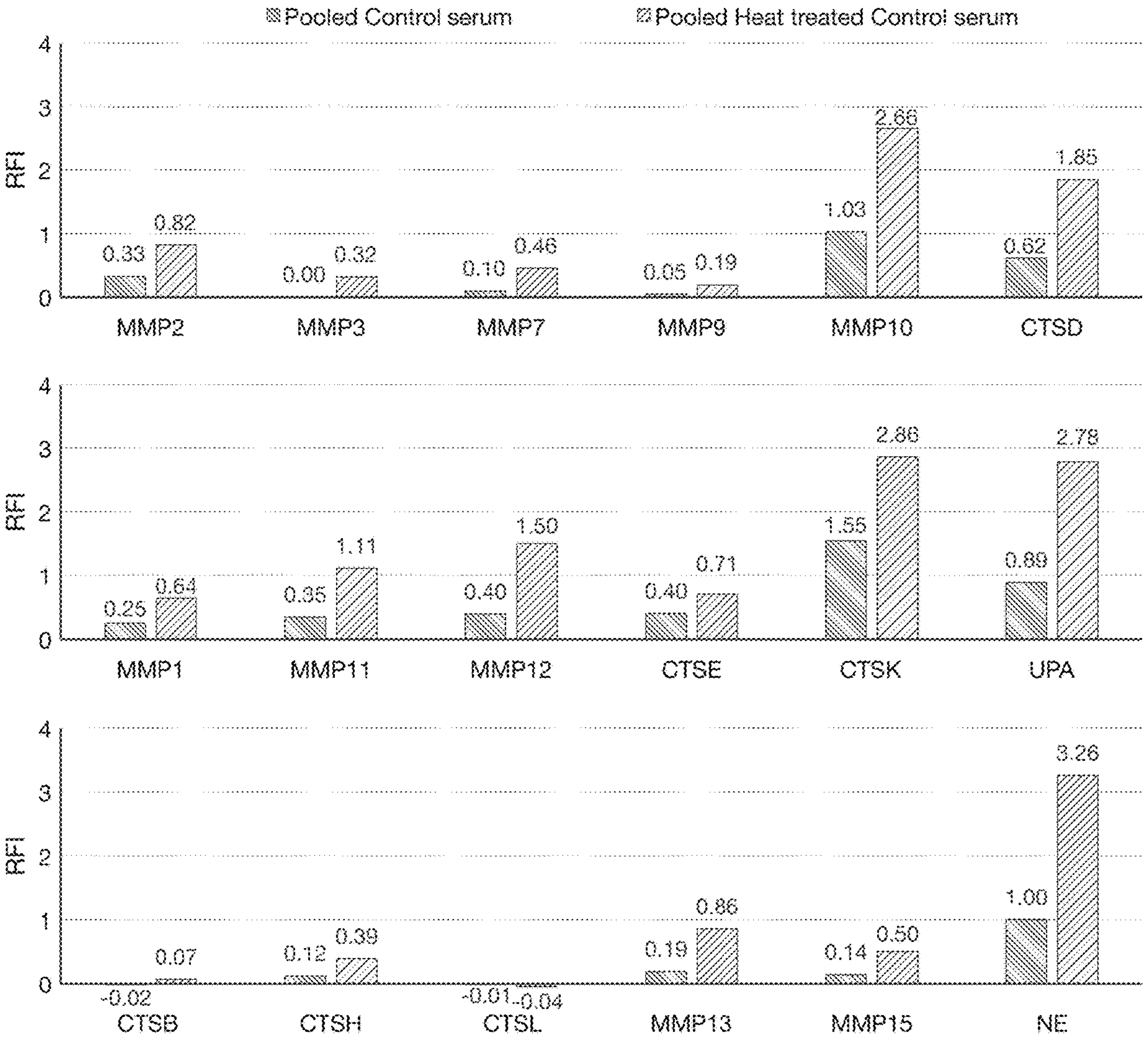
FIG. 44 shows a chart reporting results of experiments including heat pretreatment of sera. Eighteen gNBS were prepared in 125 μl working solution of 5 mM MES, 10 μM cations and IS:155. They were stimulated with 5 μl buffer (AC) or in triplicated with 5 μl PNS that was either previously heat treated at 65° C. or not. The activity of gNBS was measured after 37° C. incubation for 90 minutes. Results are presented as RFI where the sample RFU is divided by the assay control (RFI=SM−(AC+SC). The chart shows that heat pretreatment results in increased activity across the sensor panel.

In support of this conclusion, the impact of heat treatment on pooled normal sera sensor activity was evaluated in 18 protease biosensors (FIG. 44). Every sensor that has a signal significantly above the assay control (RFI >0.05) demonstrated an increase in activity of on average 3.2-fold when 65° C. heat treated sera was used.

Lastly, MMP12 and CTSD gNBS were prepared in 125 μl working solution of 5 mM MES, 10 μM cations and IS:155. They were stimulated with 5 μl buffer (Assay background) or in triplicate with 5 μl PNS. Replicate plates were assembled and each replicate was incubated at 37°, 410 or 45° C. in the VarioSkan Lux. Fluorescence was measured at 10 minute intervals for the duration of the incubation. Sample background measurements showed the results from wells that were incubated with 125 μL of buffer (no sensor) with 5 μL of sera added. In this arm of the experiment, the serum was not heat treated prior to the measurement. Instead, the reactions were carried out at incremental temperatures.

Figure 45:
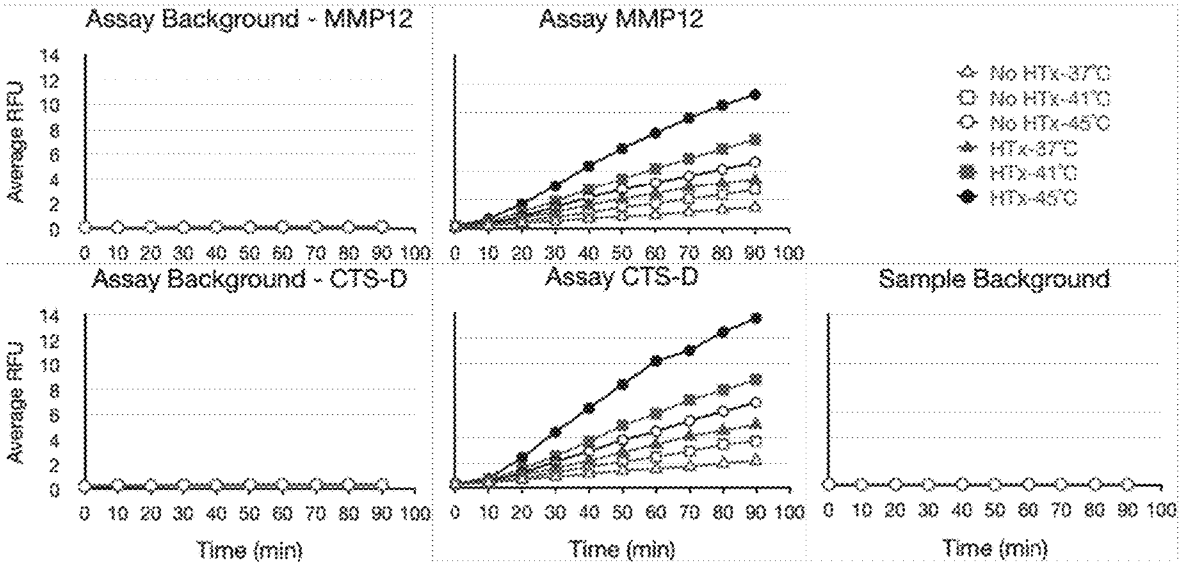
FIG. 45 shows charts reporting results of assays performed at different temperatures. 125 μL MMP12 and CTSD gNBS were stimulated with 5 μl buffer (Assay background graphs) or in triplicate with 5 μl PNS and the assay was incubated at 37, 41 or 45° C. (open symbols) in the VarioSkan Lux. Alternatively, serum was heat treated at 65° C. for 12 minutes and then 5 μL was added in triplicate to 125 μL MMP12 or CTSD gNBS in standard MES buffer. Fluorescence was measured at 10 minutes intervals for the duration of the incubation. Sample background measurements showed the results from wells that were incubated with 125 μL of buffer with no sensor but with 5 μL of sera added. The charts show that elevated temperature of incubation mimics heat treatment of serum.

Each temperature increment revealed additional activity so for both MMP12 and CTSD gNBS, the 41° C. incubation produced more fluorescence than 37° C. and 45° C. more than 41° C. (FIG. 45). For MMP12 and CTSD, in serum that was not previously heat treated, increasing the assay temperature to 41° C. nearly doubled the RFU (1.7× and 1.9× respectively). Increasing the assay temperature to 45° C. tripled the RFU (3.1×). There was no elevation in the background signal of the sensors or the sample background under these conditions. For comparison, we also pretreated sera at 65° C. of 5 minutes and compared the impact on signal to noise when both pretreatment with 65° C. and elevated assay temperature were applied (compare open and closed symbols in FIG. 45).

Pretreating sera at 65° C. increases the signal 2.3-fold over heat-treated sera. It also 2.3× and 2.0× signal for assays subsequently run at 41° C. and 45° C. respectively. Therefore, pretreating sera and running the protease assay at elevated temperature improve signal to noise using separate and additive mechanisms.

With respect to thermal stability of protease enzymes, active MMP2 enzyme has been reported to have two irreversible unfolding temperatures at 70° C. and 78° C.; substantially above the temperatures used herein [56]. The possibility was considered that the family of inhibitors designed to regulate protease activity express greater temperature sensitivity and operating these reactions at higher temperatures reduces their inhibitor impact. The impact of elevated temperature was concluded to alter multiple aspects of the assay that together contribute to significant improvements in signal:noise ratio.

Figure 46:
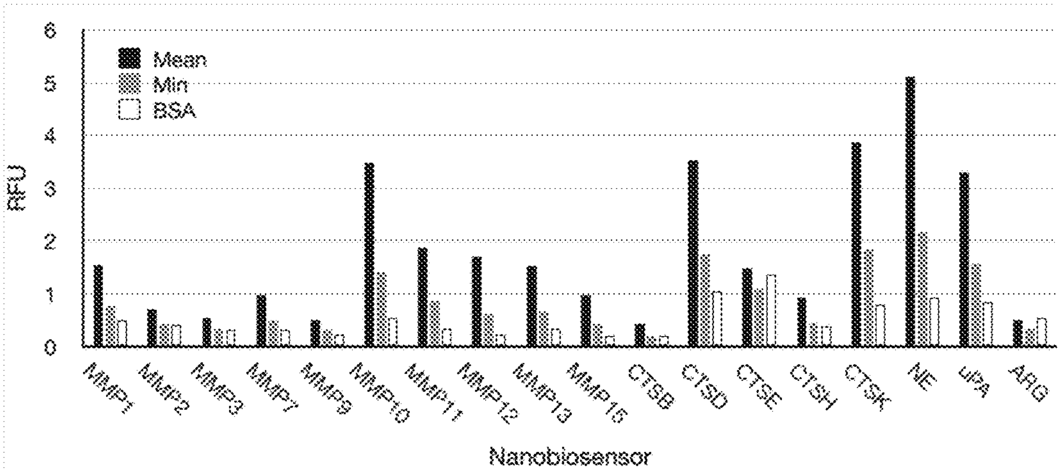
FIG. 46 shows a chart reporting detection of the protein corona of gBNS specific for 18 different target proteases as indicated in the chart. The mean and minimum signal observed across 175 human samples was compared to a 20 mg/ml acetylated BSA solution. The graph shows the mean and minimum fluorescent readouts for 175 samples across all 18 sensors.

It is expected that the stability of protease enzymes and the relative instability of inhibitor proteins to temperature increases will alter the ratio of activity to inhibited enzymes. Elevated temperature will result in elevated enzyme kinetics at elevated temperature offer improved detection of protease activity. Furthermore, it is expected that increased temperature to modify the protein corona observed around particles and described herein (FIG. 46).

A gradient of temperature dependence was expected that balances improvements to protease activity with temperatures that will denature other proteins in serum before causing precipitation. Incubating sera before the assay or during the assay are both effective at increasing the signal to noise ratio. It has been considered 41° C., or 45° C. or 50° C. or 55° C. or 60° C. or 65° C. or 70° C. or 75° C. or intervals between these targets to be effective for the desired impact.

Example 22: Negative Controls

There is well described literature describing the corona formed when proteins aggregate around particles [57]. It was wanted to test whether a solution of protein devoid of any activity could be shown to generate and contribute to background signal. Recall that the majority of these sensors require a protease specific cleavage.

Arginase is the exception as an enzyme that post-translationally modified targets. In the gNBS system, Arginase will convert arginine to ornithine and urea. This modification alters the structure and causes the peptide to position the terminal TCPP dye outside the Förster radius of graphene. So a contribution of general protein corona to background performance is important to understand. In order to understand the signal-to-noise using protein as a negative control, it was evaluated 175 human sera samples on 18 gNBS. Each gNBS was massed out in a MES Assay buffer (10 mM MES, 10 μM Cations, 155 mM NaCl, pH 7.2). 125 μL of each gNBS working solution was added to three wells. 5 μL sera was added to duplicate wells and 5 μL buffer to the third well.

A sample-only control was also included with 5 μL of sera added to 125 μL of buffer with no sensor. In addition, each set of sensors was also stimulated with 5 μl of a solution of 20 mg/mL acetylated BSA. The plates were loosely covered and incubated at 45° C. for 90 minutes before fluorescence was measured at Ex/Em 425/653 nm for 500 ms on a VarioSkan Lux plate reader (FIG. 24). With a single exception (Arg gNBS), the mean fluorescence obtained by all the gNBS was significantly greater than the BSA reaction. Only one sensor had serum samples with signal that was at or below the BSA control. The BSA control was significantly greater that the assay control which has been used to measure the amount of fluorescence presented by the sensor in buffer only. We interpret this negative control as a much more valuable reflection of non-specific performance of the gNBS. The impact of temperature on the activity of the Arg gNBS may prove optimal temperatures for this sensor are lower than 45° C.

Example 23: Lyophilization

Maintaining a performance that is repeatable and reproducible is central to maintaining an effective signal to noise. Preparations of uPA, CTSE, CTSK, and NE gNBS in MES working buffer were provided and lyophilized plates were prepared using three different excipient formulations. The plates were tested on different days using the same lot of normal sera and compared to the wet chemistry batch added to the same plate.

Figures 47, 48:
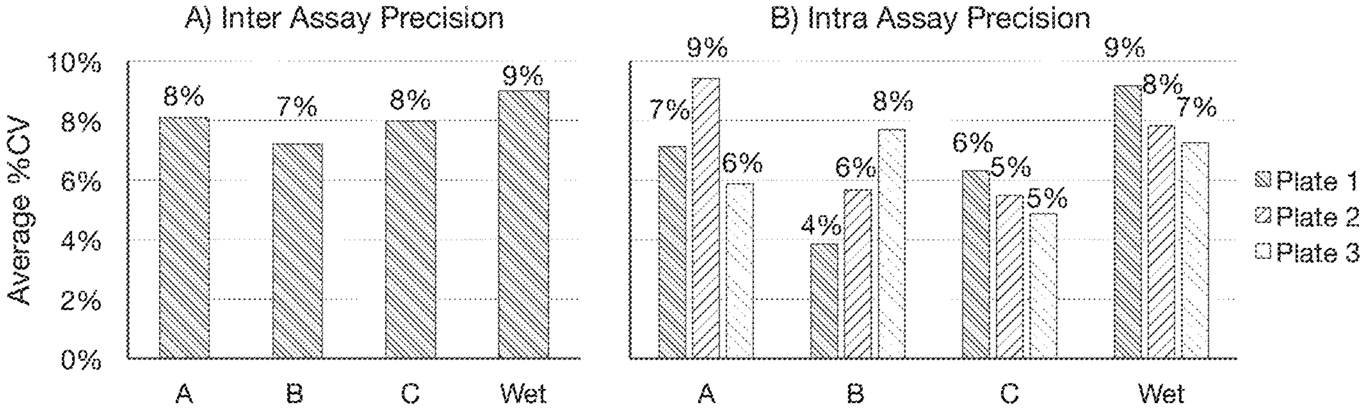
FIG. 47 shows charts reporting results of experiments directed to detect precision of lyophilized gNBS reagents. A selection of gNBS were lyophilized in 384 well plates in one of three different excipient formulations: A, B, or C. Each formulation was compared to the wet reagents prepared from the same batch but not lyophilized. (Panel A) Inter Assay Precision: 3 384-well plates tested over 3 separate days, 256 total serum samples and 4 NBS per plate. 64 serum samples tested per excipient on each plate. % CV measured by averaging the quotient of the sample standard deviation of means and the mean of means for each excipient. (Panel B) Intra Assay Precision: 64 serum samples and 4 NBS tested per excipient. Precision measured from the average % CV of each excipient within a 384-well plate run.
FIG. 48 shows tables reporting the average RFU for each NBS assessed on 256 or 175 patients separated into lung cancer and non-lung cancer groups. Two studies referred to as EU 351 and US SST-18 which interrogated 207 and 175 total patients respectively are presented. The numbers indicated the mean RFU produced by each gNBS for the indicated groups. Subjects in each group are separated into pathologically confirmed lung cancer cases or clinically confirmed negative lung cancer cases. All cases are untreated patients.

An improvement in inter assay and intra assay precision was observed when compared to wet reagents as measured by decreased coefficients of variation in both settings (FIG. 47). Thus, maintaining greater precision allows measurements of protease activity to produce a more repeatable signal across different measurements. This precision is necessary to maintain a constant signal to noise performance in an assay setting. With consistent, repeatable and reproducible measurements of protease activity, a relationship between protease activity across a panel of protease targets can be assembled to distinguish sera derived from normal patients from patients with a spectrum of different inflammatory conditions.

Example 24: Clinical Performance of Graphene Biosensors

The performance of gNBS was evaluated on clinical samples. In the first cohort, 256 subjects were accumulated from European sites and classified as lung cancer (n=89) or non-lung cancer (n=167). The serum samples were heat treated for 12 minutes at 65° C. in a thermal cycler and cooled to 15° C. MES Assay Buffer (5 mM MES, 10 pM cations, pH 7.20, 154 mM NaCl) was used to make a working solution with each gNBS adjusted to a final $ABS_{425m}$ of 0.1-0.15 depending on the sensor. This preparation was sonicated for in a water bath for 10 minutes and 125 μL dispensed in replicate wells. 5 μl heat treated sera was added to duplicate wells and a single sera only control. A sensor only assay control was included for each plate.

The plates were covered with loose foil and placed in a 37° C. incubator for 90 minutes. Fluorescence was read on the VarioSkan Lux taking readings at Ex/Em 425/653 nm. The mean fluorescence observed for the LC and non-LC subjects was reported (Table in FIG. 48). A general diminishment of protease activity is recorded in lung cancer patients vs non-lung cancer patients. The stage of patients and sub-type of disease did not impact this observation. Similarly, non-LC subjects included 9 patients with breast cancer, colorectal cancer and hematologic malignancies that did not confound the non-LC analysis although those subjects are not included in this analysis. A second cohort of 175 subjects were recruited as part of the "US SST-18" cohort.

In this experiment, all the non-LC control were age matched donors with >20 pack year smoking habits, a case controlled group for the LC cohort. In the LC cohort, the majority of the LC samples were from untreated Stage I subjects. In this experiment, we tested a second Lot of sensors, a different VarioSkan Lux fluorimeter, samples derived from the US rather than the EU. gNBS were massed out and solutions adjusted to a final $ABS_{425m}$ of 0.1-0.15 depending on the sensor in MES Assay Buffer (10 mM MES, 10 pM cations, pH 7.20, 155 mM NaCl). 125 μl of Assay Buffer or Assay buffer containing each gNBS were loaded into a 96w black plate.

The plates were covered with loose foil and incubated at 45° C. for 90 minutes. The fluorescence was read on the VarioSkan Lux using a one-time endpoint at Ex/Em 425/653 nm (500 ms). It was observed the same striking decrease in overall protease activity in the LC samples (Table in FIG. 48). It was calculated the Student's two-tailed heteroscedastic t-test comparing the RFU of lung cancer with the varied non-lung cancer cohorts. The present calculations gave p-values between 2.6e-6 and 2.6e-27 across both cohorts and all sensors. The impact of this observation is the possibility that these sensors could be configured in many different arrangements to achieve a diagnostic potential with very powerful ability to detect the presence of disease.

Figures 49, 50:
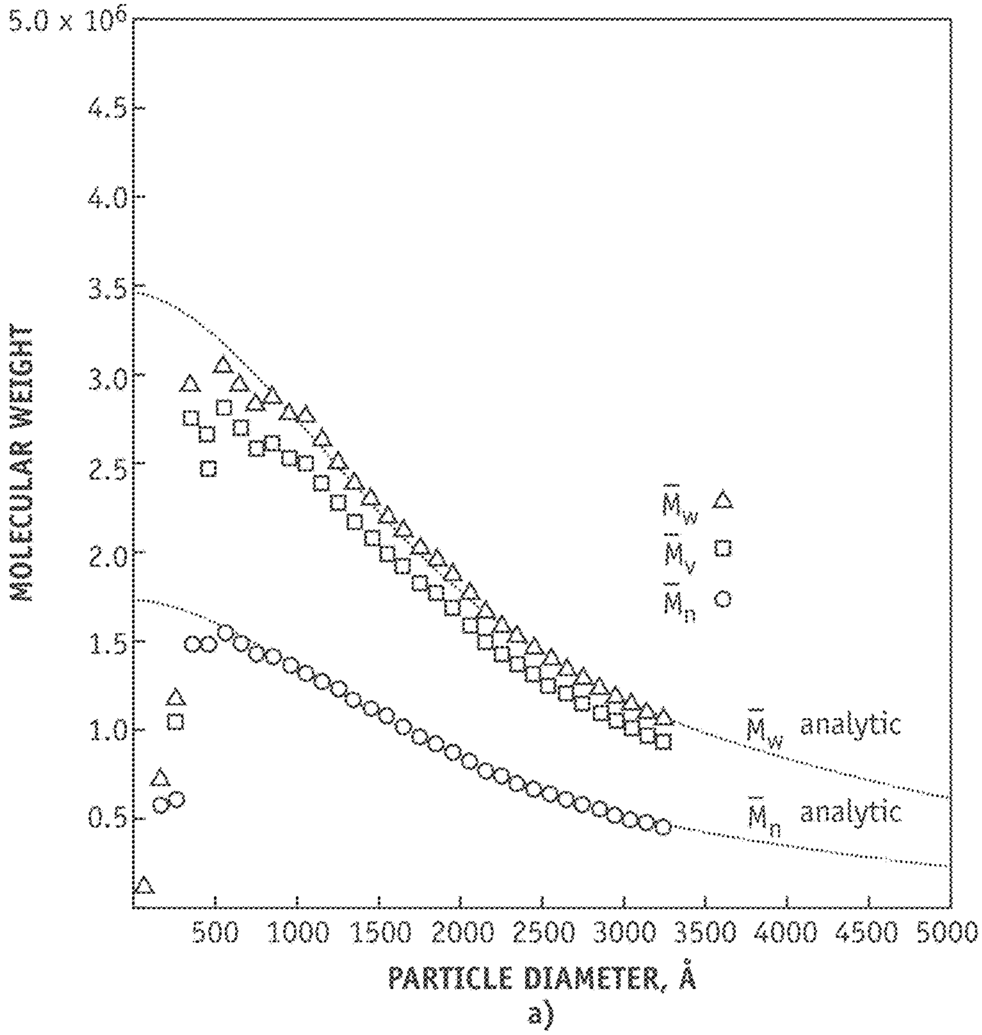
FIG. 49 shows a table of p-values for student's two-tailed, heteroscedastic t-Test comparing RFU of Lung Cancer and non-Lung Cancer samples.
FIG. 50 shows a plot of molecular weight (Da) vs. particle diameter (Ångström). $M_n$: number averaged macromolecular weight, $M_w$: weight averaged macromolecular weight, $M_v$: average macromolecular mass (corresponding to FIG. 1 of Loebach 1975 [2]).

FIG. 49 shows a table of p-values for student's two-tailed, heteroscedastic t-Test comparing RFU of Lung Cancer and non-Lung Cancer samples.

Example 25: Exemplary Method and System to Make a Biosensors

Exemplary methods for assembling a particle can comprise the following steps

1) Dispersing a mass of few layered graphene in Dimethyl Formamide (DMF) to obtain a solution
2) Sonicating the solution for up to 1 hr using a probe sonicator using 10-15 kJ per g of graphene over 1 hour
3) Functionalizing the graphene surface to derive carboxylated surface by using a nucleophilic substitution reaction with sodium azide and bromovaleric acid as described herein to obtain a carboxylated graphene (CG)
4) Washing the CG with DMF or Ethanol to remove reactants
5) For core particle assembled with PEI, resuspending the CG in DMF to obtain a CG/DMF solution
6) Distributing the CG/DMF using sonication
7) In case of exemplary Polyethylenimine (PEI) conjugating the PEI using 1-ethyl-3-(-3-dimethylaminopropyl) carbodiimide hydrochloride, (EDC) and 4-Dimethylaminoyridine (DMAP) at a defined ratio for 1-2 hours at RT.
8) washing the product extensively with Ethanol to obtained a core particle
9) Drying the core particle at ambient temperature for 30 min. and further drying the core particle for 24-48 hours at 37° C.

A corresponding system can comprise a) Layered graphene;
b) Reagents for modification of the graphene, attachment of the polymer and subsequently the sensor;
c) Devices for Sonication, probe sonication, physical dispersal using a high shear mixer, dispersal (e.g. a microwave);

d) A tool for measuring absorbance to standardize the concentration of graphene used in assembly (e.g. e a Nanodrop spectrophotometer); and/or e) Devices for sensor manufacture to dry the sensor (e.g. ovens complemented in some cases by vacuum or desiccation chambers).

Example 26: Exemplary System to Detect a Biomarker with Biosensors of the Disclosure Methods to detect one or more target biomarkers according to the disclosure can be performed with systems comprising the following components 1) The nanosensor. This can be a single sensor or multiple sensors. The sensors can be provided as a solution and adjusted to a working concentration using defined absorbance for the working solution for each sensor. Or the sensors can be provided previously lyophilized in an opaque 96 or 384 well plate.

2) A buffer: the sensor activity is supported by an optimal buffer. This buffer may be provided as a solution or as a lyophilized cake in a multi well plate. The buffer includes a component to stabilize the solution at a defined pH. In the current configuration this pH is 7.2. The optimal pH can vary depending on the sensors present and the optimal pH required to support enzyme health and activity.

Preferably, the buffer will also contain monobasic ions. Monobasic solutions support enzyme health and provide ion buffering for the particles to support dispersion. Also, peptide configuration will be impacted by the mono basic salt concentration.

In general, a buffer will contain necessary ions for enzyme activity. In the example of proteases enzymes, MMP are divalent cation requiring enzymes so buffers are supplemented with a selection of divalent cations.

Additional components comprise for example

3) A standard curve comprised of the included dyes at a range of concentrations. These standard curves would be used to convert a relative fluorescent unit (which is dependent on the fluorimeter used) to a concentration of dye. The standard curve could contain multiple different dyes for a multiplexed reaction. Therefore, a standard curve allows the kit to be used on many different platforms. Alternatively, the relative fluorescence may be used.

In addition or in the alternative the system can also comprise

4) Controls to demonstrate the presence of functional sensors. These controls might include serum samples with known and demonstrated activity. They might be purified enzymes with known activity. They might be chemistries designed to hydrolyze a peptide thus releasing the dye non-enzymatically.

The system can further comprise

5) An incubator capable of maintaining the multi-well plate at constant temperature for the duration of the experiment. For some fluorimeters, this incubation capability is included. The plates need to be maintained at 25° C. or 37° C. or 41° C. or 45° C. or 50° C. or 55° C. or 60° C. or 65° C. for the duration of the experiment or for up to 5 minutes.

6) A fluorimeter to determine the amount of fluorescence released during the reaction. This fluorescence is typically measured as an endpoint but may also be measured kinetically such that the rate of change is measured at intervals of 1 min or 5 min or 15 min or 30 min or 60 min.

7) An algorithm specific for a defined application. The integration of sensor activities to describe a diagnostic status will require an algorithm to interpret the defined activities and assign a classification to the sample. This algorithm will be application and sensor specific.

In particular components 1 to 4 and 7) can be included in kit of parts as will be understood by a skilled person.

For multiplex detection, additional considerations are: Dye selection, combinations of sensor with multiple dyes are calibrated to ensure there is no FRET between dyes. In addition, depending on whether the sensors are attached to a single particle or attached to separate particles and mixed, the final concentration of particles has to be optimized such that there are sufficient particles to interact with reactants and drive the reaction but not so much graphene particles that they quench released signal. Furthermore, for mixed sensors, there should be a buffer that compromises for the optimal activity of both enzyme targets. The reproducibility of the signal is dependent on reproducing the environment for every reaction. So providing a buffer with stable pH and defined salt concentrations as well as spectrophotometrically defined concentration of sensor will duplicate the environment and support batch to batch stability (see FIG. 27).

Example 27: Stability, Reproducibility Signal to Noise Ratio and Multiplex Capability of the Biosensors in a Testing Solution During the manufacture of gNBS sensors, few layered graphene is covalently bound to the sensor reagents. The graphene particles being covalently assembled are not subject to disassembly in aqueous solutions. As a result, the particles are observed not to cause pH drift in an aqueous solution and as described herein, they are dispersible in aqueous solutions.

A second aspect of the structural advantage of a graphene based sensor is reflected in the signal to noise performance of each family of nanosensors in aqueous solutions in the presence of serum. At time 0, one would not expect significant release of any fluorescent signal as at t=0 there has been no time for the enzyme to cleave and release any fluorescence. Moreover, upon addition of serum, the increase in signal is dependent on both the sensitivity of the system and a consistently low noise so that the signal can be distinguished. The relationship of sample incubated with sensor and serum at t=0 for both FeNBS and gNBS was evaluated and two differences found.

The Assay Control, that is sensor in the presence of buffer only, shows a slight increase in signal over a 60 min period depending on the sensor for FeNBS. This increase is on the order of 2-fold. In contrast, the gNBS maintained in aqueous solution for up to 90 min shows no significant change in background signal. However, the S:N performance of gNBS that is neither prepared with sonication nor has solvents removed, while the S:N is reduced at t=0, also generate a lower signal over time. SO the performance of the gNBS sensors is dependent on better S:N at t=0 and improved S:N detection on incubation with stimulus.

More significantly, when the signal:noise for graphene NBS at t=0 is calculated, a low signal to noise is observed as measured by dividing sample fluorescence by Assay Control fluorescence. The gNBS sensors present smaller difference between Assay Control and Sample at t=0. The S:N at t=0 is 4.1+/−1.6 (1 S.D) for multiple different graphene sensors in Lots that were not manufactured using probe sonication or extensive drying (in these examples, CTSB, uPA, CTSK, CTSD, CTSE, MMP12, MMP13, MMP15, NE, MMP3, MMP9).

In contrast, as sonication and desiccation are included, the S:N at t=0 increases to 6.9-7.6; not significantly different from FeNBS. However, after stimulation for 60 min with serum, for an example FeNBS sensor CTSB, the S:N at t=60 was 2.0. For CTSB made with CG KSU Lot 120120, the SN at t=60 was 9.8. For HEB CTSB100, the SN was 12.0, for HEB CTSB101 SN=18.5 and CTSB102, SN=27. Thus, as solvent removal and sonication are included in the manufacturing, the amount of enzyme activity revealed with a single sample of sera increase from 2.0 to 27 in this example.

The S:N performance difference is manifest in both the t=0 performance and the relative signal generated over time for a given sample. So S:N does not rely on the different performance of any individual sensor. Rather it is generalizable to the backbone and not to any particular enzyme activity. FeNBS to gNBS were compared in a single experiment with different lots of gNBS reflecting the inclusion of solvent removal and sonication. The S:N performance of the gNBS increments with each iteration of the manufacture protocol in reflecting solvent removal and sonication.

In defining the testing solution, the optimal formulation coordinates the best S:N performance being a measure of the stability of the sensor, with the best kinetic increase in activity over time, which reflects the provision of a healthy environment for enzyme activity.

This balance has been observed to be optimized with a pH environment of 7.2 using MES. Inclusion of monobasic salts has maintained a physiological environment for enzyme activity when included at 155 mM. However, a range of monobasic salt concentrations from 0 mM to 1M also impact he S:N of the sensor. As demonstrated by the results reporting in FIG. 14 increasing mono basic salt concentration reduce the assay control signal at 60 min. Thus the “noise” ascribed to the particle only is lower as the concentration of salt increases. 155 mM was used as a concentration that both reduces the particle noise and supports enzyme activity at physiological conditions.

Example 28: Stability, Reproducibility Signal to Noise Ratio and Multiplex Capability of the Biosensors in a Testing Solution, in Embodiments where there is a Heating Step An impact of heat treatment has been observed when applied to serum in advance of incubation or when the assay is carried out at temperatures elevated above 37° C. For a typical sensor, in this example MMP10, heat treatment in advance of the assay by incubation at 65° C. for 5 min, the SM/AC S:N is 1.2 without heat treatment and 1.3 with heat treatment. Thus the low signal to noise is not increased by heat treatment. After incubation in the presence of serum, the signal of untreated serum increased to 14.1 SM/AC after 90 minutes. In contrast, the heat treated sample SM/AC increased to 26.8, a 190% increase in signal strength. So the impact of heat treatment is not manifest for the t=0 signal, rather both heat treatment (FIG. 44) and increased assay temperature (FIG. 45) provide more enzyme activity which results in greater signal over the kinetic interval measured. Enzyme activity is increased on average 3.2 fold when pretreated with increased temperature (65° C.). Similarly, the signal was increased 3.1-fold on average when the assay was incubated at 45° C. and 1.7- to 1.9-fold when incubated at 41° C. Such changes were observed for all sensors and the increase in activity measured was dependent on temperature. So 41° C. revealed more activity than 37° C. 45° C. revealed more activity than 41° C.

The temperature was established and maintained in an oven or in a fluorimeter that had a temperature regulating function. Elevated temperature will result in elevated enzyme kinetics at elevated temperature offer improved detection of protease activity. Furthermore, it is expected that increased temperature will modify the protein corona observed around particles and described herein (FIG. 46).

A gradient of temperature dependence that balances improvements to protease activity with temperatures is expected, that will denature other proteins in serum before causing precipitation. Incubating sera before the assay or during the assay are both effective at increasing the signal to noise ratio. Temperatures of 41° C., or 45° C. or 50° C. or 55° C. or 60° C. or 65° C. or 70° C. or 75° C. or intervals between these targets were considered to be effective for the desired impact.

Example 29: Explosion Graphene PEI Core Particle

The exemplary experimental procedures below are discussed using explosion graphene [12] [58]. However, virtually any few layer graphene can be used for the synthesis of biosensors biomarker detection. in this connection, the utilized graphene sheets or aggregates are of a size that is dispersible in water (<1 micrometer in diameter).

Explosion graphene typically consists of 5-7 layers of stacked graphene. The approximate diameter of each layer is 150 nm. [8] The surface reaction forming carboxygraphene is only targeting the two outer surfaces of the graphene stack and potentially some of the edges.

Polyethylene imine can be covalently bound to the carboxylic acid groups at the surface of carboxygraphene (density of carboxylic acid groups: $1.76\pm0.6\times10^{-4}$ moles —COOH groups per gram, according to pH titrations).

Example 30: Characterizing Features of the Polymer or Other Organic or Inorganic Structures Attached to the Graphene Particle Polyethylene imine is very hydrophilic (Consensus log P=−1.94, solubility in water $>1.2\times10^5$ grams per liter $H_2O$, which is required to disperse the graphene particles in aqueous buffers. [59]

Principally, all polymers of the correct size can be attached that feature a consensus log P<0, or a solubility in water of $>1.0\times10^3$ grams per liter $H_2O$. [23] The photophysical properties of graphene [53] permit the quenching of attached organic fluorophores, metal particles, and quantum dots over a distance of up to 20 nm, which is again larger than any other known energy transfer distance (Förster Resonance Energy Transfer (FRET) and plasmonic quenching. [53]

Consequently, the diameter of the attached polymer layer plus co-attached consensus sequence does not exceed 20 nm. Otherwise, the fluorescence of the attached fluorophore will not increase upon enzymatic release. According to the plot of molecular weight vs. particle diameter (Loebach (1975), FIG. 1 [60]) for emulsion polymers herein reported as FIG. 50, which is applicable for this estimation, the allowable mass range of polymers featuring a diameter of up to 20 nm is from 0.5 to $1.7\times10^6$ ($M_n$) and 0.5 to $3.0\times10^6$ ($M_w$). However, smaller polymers may be used since their diameters can add up to 20 nm.

Example 31: Attachment of Peptides

Depending on their size, peptides may be classified as oligopeptides (2-20 residues) and polypeptides (>20 residues). Proteins consist of polypeptide chains exceeding 50 residues in length. [61] The average lengths of peptides can be estimated to 0.35 to 0.40 nm per aminoacid, depending on the 2D structure of the peptide (alpha-helix or amorphous). [61] Note that peptides forming beta-sheets are not suitable for the design of biosensors, because their release kinetics upon enzymatic cleavage is very slow. A peptide of 50 amino acids has a length of 17.5 to 20 nm, depending on its 2D structure. It should also be noted that non-natural amino acids can be used in these peptides, either for anchoring the peptide to the surface of graphene or graphene-attached organic or inorganic shells, or for the attachment of the fluorophore (organic dye or nanostructure).

Figure 51:
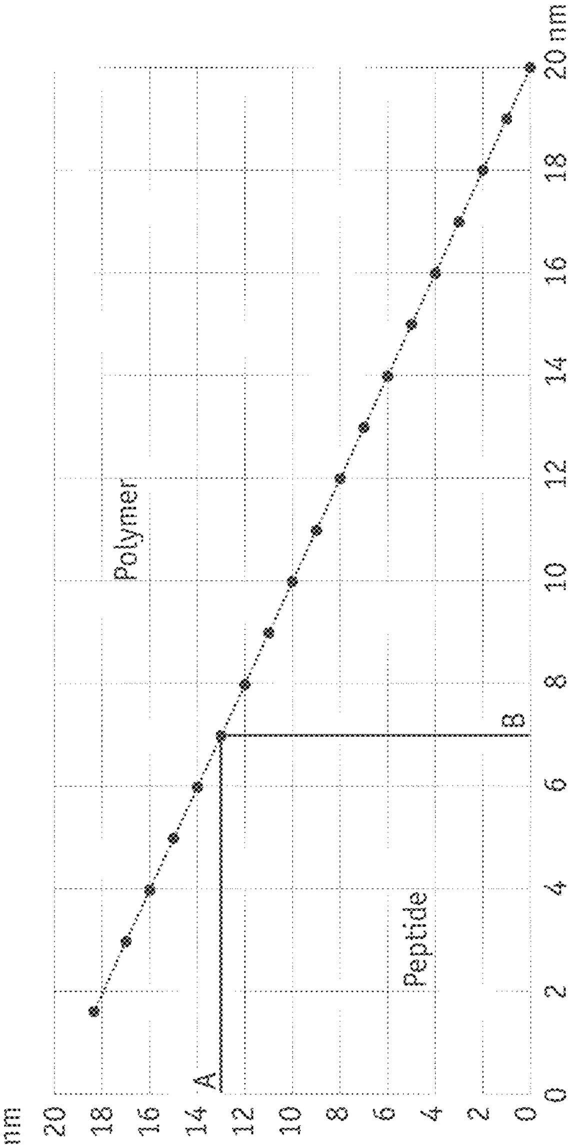
FIG. 51 shows allowable ratio of peptide length (A) and polymer layer thickness (B) in graphene biosensors for protease activity detection.

FIG. 51 shows allowable ratio of peptide length (A) and polymer layer thickness (B) in graphene biosensors for protease activity detection. The maximal layer thickness (peptide+polymer) cannot exceed 20 nm. In graphene biosensors for cytokine/chemokine and arginase detection, the layer thickness is close to 20 nm before binding to their target or posttranslational modification. Both events elongate the peptide sequence, thus causing fluorescence increase from a tethered fluorophore.

Principally, the graphene particles can be surrounded with an inorganic water-soluble shell (for instance a mesoporous silica nanolayer). [62] In that case, the thickness requirements for organic and inorganic nanolayers are the same: the maximal diameter of mesoporous silica shell+peptide sequence has to be smaller or equal 20 nm.

Example 32: Attachment Organic Molecule

Organic and inorganic compounds presenting a functional group can be attached to a graphene surface chemically modified to present one or more corresponding functional group.

For example, a monolayer of water-soluble organic molecules, for instance oligoethylene glycols presenting an OH functional group, can be tethered to the surface of graphene modified by adding a nitrene group to obtain modified graphene and presenting an NH2 functional group.

Figure 52:
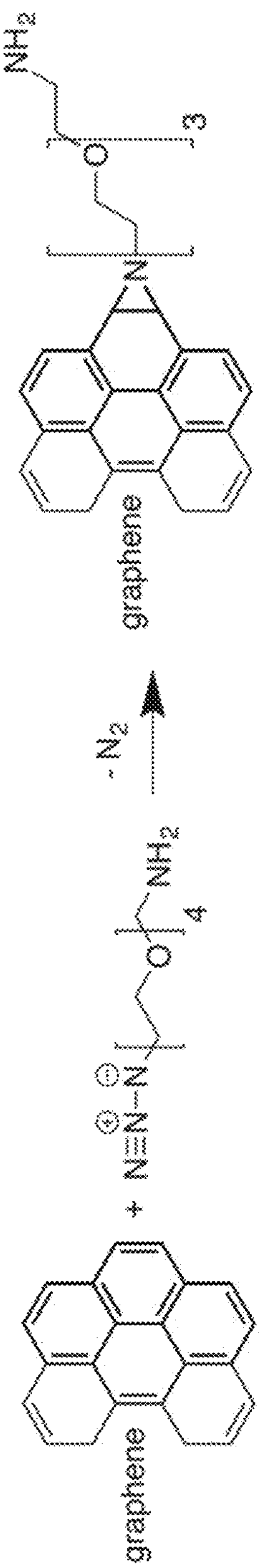
FIG. 52 shows an exemplary monolayer of water-soluble organic molecules of oligoethylene glycols and the related reaction scheme for related attachment to the surface of graphene

Instead of a polymer, a monolayer of water-soluble organic molecules, for instance oligoethylene glycols, can be tethered to the surface of graphene as shown in FIG. 52. Principally, the requirements for log P and water solubility are the same as for organic polymers.

Note that the greatest diameter of Amino-tetraethylene glycol azide ($NH_2$-TEG-$N_3$) is 1.5 nm, according to molecular modelling (Chemdraw 3D). Accordingly, in those exemplary embodiments the size of a tetraethylene glycol unit is 1.4 nm. Therefore, the number of glycol units (—O—$CH_2$—$CH_2$—) is less than 58, not to exceed a total length of 20 nm.

When coating a graphene particle to configure a sensor, the length of the oligopeptide will have to be subtracted from the length of the oligoethylene oxide tether.

Note that, principally, any linear or branched molecule that can be attached to the surface of graphene and that complies with the required solubility in water (log P<0 or solubility in water >$1.0\times10^3$ grams per liter $H_2O$ [23] can be used, as long as it complies with the 20 nm energy transfer quenching distance requirement.

A skilled person will be able to modify the above example for a different organic or inorganic material presenting functional groups corresponding to functional groups of the graphene surface. In particular, a skilled person will understand that any linear or branched molecule that can be attached to the surface of graphene and that achieves target dispersibility in aqueous solvents (>0.1 mg per mL), and the related graphene core particle can be used to provide a biosensor of the disclosure as long as the configuration of the coating material and peptide linkage complies with the 20 nm energy transfer quenching distance requirement Example 33: Titration of Carboxygraphene (CG)

250 mg of Carboxygraphene (CG) were dispersed in 50 mL of 0.05 M NaOH (NaOH solution prepared using HPLC water and degassed with argon for 2 hours). Carboxygraphene suspension was sonicated for 10 minutes and stirred for 24 hours at 300K. After the 24-hour stirring, suspension was filtered to remove the carboxygraphene, and all solutions (carboxygraphene filtered solution, 0.05 M HCl, and 0.05 M NaOH) were degassed with argon overnight. Before titrations were started the following day, pH meter was calibrated with standard pH solutions. 20 mL of 0.05 M HCl were added to a 10 mL aliquot from the carboxygraphene filtered solution and back-titrated with 0.05 M NaOH (added in incremental steps). The pH was recorded after each addition of NaOH after the pH meter had stabilized before the next addition of NaOH. For the blank titration, a 10 mL of 0.05 M NaOH was prepared in the same way as carboxygraphene, adding 20 mL of 0.05 M HCl and back-titrate with 0.05 M NaOH.

Figure 53:
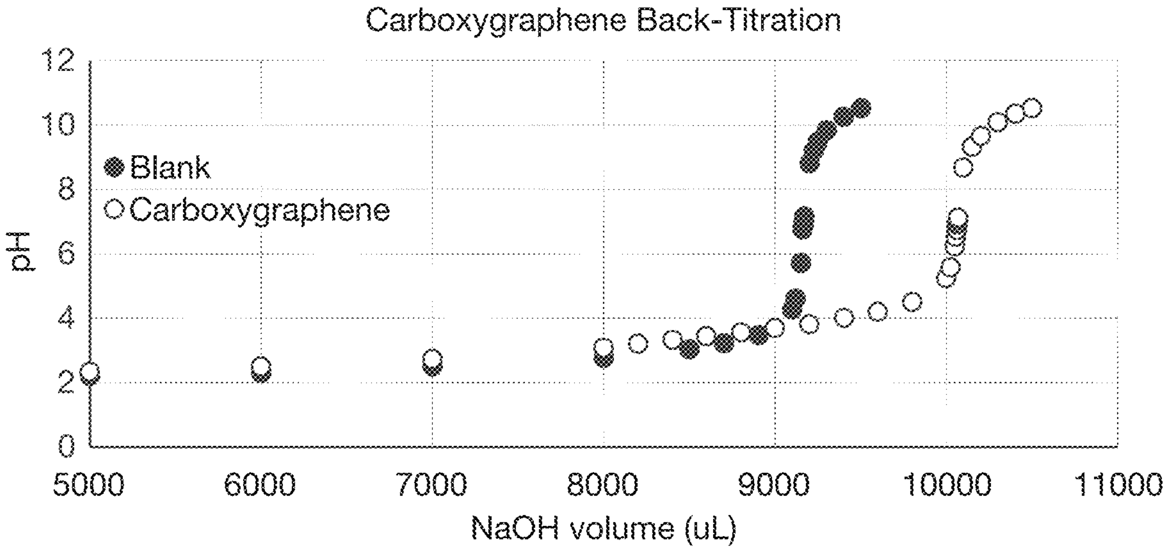
FIG. 53 shows a pH Titration of carboxygraphene in which difference in the volumes of NaOH in the two titration curves for the same value of pH of ~7.00 gives the concentration of the ionized groups (carboxyl groups) per weight increment of Carboxygraphene.

The difference in the volumes of NaOH in the two titration curves for the same value of pH of ~7.00 gives the concentration of the ionized groups (carboxyl groups) per weight increment of Carboxygraphene, as shown in FIG. 53.

It should be mentioned that degassing with argon was maintained during titration for both the carboxygraphene filtered solution and blank.

The difference in the volumes of HCl in the two titration curves for the same value of pH of ~7.00 gives the concentration of the ionized groups (carboxyl groups) per weight increment of carboxygraphene. This titration curve indicates that we have a be $1.765\times10^{-4}$ and 1.8x10−4 mol/g of acidic groups (—COOH) (i.e., surface density of 4-COOH groups per $nm^2$).

Example 34: Signal to Noise Ratio

Structural features responsible for increasing the signal-to-noise ratio comprise, configuring the biosensor to include fractal graphene and a coating and peptide linkage configured to maintain a distance of less than 20 nm from the graphene surface of the tethered detectable moiety fluorescent dye (TCPP, as well as other dyes with higher fluorescence quantum yields).

The majority of the consensus sequences feature 13 amino acid residues, which results in 5±1 nm in length. The thickness of the covalently attached PEI layer is 10 nm. Consequently, the average position of the TCPP fluorophores is well below the threshold of 20 nm.

Additional examples of signal to noise ratios achievable with the biosensors herein described are illustrated in Example 19 (see FIG. 33, and FIG. 35 and related portions of the specification) Example 28 (see FIG. 46 and related portions of the specification) and Example 46 (see FIG. 54 and related portions of the specification) These examples show the operability that all embodiments that maintain a distance between graphene surface and tethered fluorophore of <20 nm as will be understood by a skilled person.

Example 35: Method of Making a Core Graphene Particle for Biosensor

An exemplary procedure for making a core particle according to the disclosure:

Step 1: selecting detonation graphene or few layer graphene to secure the required UV/Vis absorption behavior (strong emission from UV to mid-IR (100 to 1500 nm).

Step 2: Performing a chemical transformation of the graphene surface e.g. by including an organic or inorganic shell, to make the graphene particle dispersible in aqueous buffers.

The resulting organic or inorganic shell has a size of less than 20 nm in diameter due to the quenching properties of graphene.

The main characterization steps of the resulting particle are:

Step 1: UV/Vis absorption spectroscopy, range 200 to 1500 nm in chloroform; RAMAN and XRD to confirm that the material is graphene, elemental analysis to confirm that the material is 98++ carbon, TEM to ascertain the size distribution of the graphene nanoflakes, SEM to ascertain the fractal nature of graphene.

Step 2: FTIR to characterize functional groups of the organic or inorganic shell around graphene, RAMAN and XRD to confirm that the material is graphene, elemental analysis to confirm the chemical composition of the graphene core+shell, TEM to ascertain the size distribution of the graphene nanoflakes, SEM to ascertain the fractal nature of graphene. Solid state NMR shows the chemical makeup of the shell alone when cross-polarization is utilized, because there are no hydrogen atoms within graphene. [63]

Example 36: Method of Making a Biosensor of the Disclosure

An exemplary procedure to make a biosensor of the disclosure comprises the following steps Step 1: selecting detonation graphene or few layer graphene to secure the required UV/Vis absorption behavior (strong emission from UV to mid-IR (100 to 1500 nm).

Step 2: Performing a chemical transformation of the graphene surface to make it dispersible in aqueous buffers by including an organic and/inorganic shell. The resulting organic or inorganic shell should be less than 20 nm in diameter due to the quenching properties of graphene.

Step 3: Synthesizing the required peptide sequences and add a fluorophore to the N-terminal end of the peptide sequence. This is followed by cleavage of the peptide+fluorophore from the resin.

Step 4: attaching the peptide+fluorophore to the organic or inorganic shell.

Example 37: Method of Detecting a Biomarker with a Biosensor of the Disclosure

An exemplary method to detect a biomarker according to methods of the disclosure comprises 1) Selecting the optimal range of attached fluorophore to graphene. The optimal concentration of peptide+TCPP was 7.3 mg for 100 mg of carboxy graphene. This results in $1.6\pm0.2\times10^{-5}$ moles peptide+TCPP (fluorophore) per gram carboxygraphene-PEI. At loading higher than that, the biosensors react significantly slower due to steric interference with the enzyme kinetics. The upper bound (when activity in the presence of $1\times10^{-10}$ moles $L^{-1}$ of active protease is not detectable within an hour) is $1.0\pm0.25\times10^{-3}$ moles peptide+TCPP (fluorophore) per gram carboxygraphene-PEI. The lower bound (disappearance of signal) is $1.0\pm0.25\times10^{-7}$ moles peptide+TCPP (fluorophore) per gram carboxygraphene-PEI.

2) Dispersing of the biosensor in the defined aqueous buffer. The optimal concentration range of the biosensor solution is from 0.1 to 0.03 mg per mL, having 0.3 mg per mL yielding the highest fluorescence intensity.

3) Adding the Liquid Biopsy (blood, plasma, serum, saliva, Bronchoalveolar lavage, exhaled breath condensate) in defined buffer. The concentration of the targeted enzyme or protein should be in the range of sub-femtomolar ($10^{-16}$ moles $L^{-1}$) to micromolar ($10^{-6}$ moles $L^{-1}$)

4) Incubating of the dispersed biosensor+liquid biopsy at defined temperature for defined time or recording of the increase in fluorescence over time at a defined temperature or temperature interval.

All biosensors for proteolytic activity measurements feature a highly selective consensus sequence. The biosensor for arginase measurements relies on post translational modification (post synthetic modification: arginine to ornithine), which elongates the peptide. Binding of targeting peptides to protein receptors elongates the former as well. All distance increase between fluorophore and graphene leads to an increase in fluorescence (and subsequent detection of activity) if the distance of 20 nm from graphene is exceeded. Otherwise, fluorescence quenching will be dominant.

Example 38: Method of Multiplex Detecting a Biomarker with a Biosensor of the Disclosure Principally, the concentration ranges of dispersed biosensors and the preparation of the Liquid Biopsy are the same for the detection of one or multiple species. Due to kinetic aspects (the enzyme has to reach the peptide sequence), we cannot increase the maximal density of peptide+fluorophore at the surface of graphene.

As discussed above, the highest possible concentration of peptide+TCPP (fluorophore) is $1.0\pm0.25\times10^{-3}$ moles per gram, the optimal concentration (fastest signal increase over the concentration range from femtomolar to micromolar protease act) is in $1.6\pm0.2\times10^{-5}$ moles peptide+TCPP (fluorophore) per gram carboxygraphene-PEI. When several peptide sequences+different fluorophores are used to achieve multitasking, their fractions have to add up to $1.6\pm0.2\times10^{-5}$ moles peptide+TCPP (fluorophore) per gram carboxygraphene-PEI to ensure optimal reaction kinetics. For slower sensors, the total concentration (all fractions) of peptides+different fluorophores can reach is $1.0\pm0.25\times10^{-3}$ moles per gram.

Methods of attaching more than peptide+fluorophore to the shell around graphene comprise: 1) stepwise addition, 2) addition of all peptides+fluorophors in parallel. For either approach, the chemical addition conditions have to be optimized.

After chemically attaching several peptides+fluorophors and several washing procedures (three times redispersion in DMF, followed by centrifugation, followed by three times redispersion in diethyl ether plus centrifugation, followed by drying under argon at 40° C. for 24 h). The multitasking biosensor is dispersed in the buffer used for analysis and the concentrations of attached fluorophores is measured by means of UV/Vis absorption spectroscopy using calibration curves of the same dyes in the analytical buffer.

Moreover, additional modifications can be carried out to decrease the surface charge of the graphene making it suitable for binding cationic polymers in lieu of or in addition to the functionalizations described above.

Example 39: Features of Graphene Particles and Additional Components of Biosensors Any surface reaction that makes graphene water-dispersible and/or permits the anchoring or either organic ligands or polymers of sufficient water-solubility (consensus log P<0, or a solubility in water of >$1.0\times10^3$ grams per liter $H_2O$. [23]) is suitable. Alternative, inorganic shells, such as mesoporous silica, can be used to disperse graphene as well.

The most important factors for organic or inorganic coating are water solubility, the presence of functional groups to attach the peptide+detectable moiety component, and the requirement of less than 20 nm thickness around graphene to facilitate quenching of the fluorophore when attached.

With respect to the peptide linkage, the specificity arises from the peptide sequences used. Different fluorophores are attached to the N-terminal position of the peptide while on resin. Alternatively, the fluorophores could also be attached to the C-terminal end, but this approach is more complicated and expensive (but doable).

Multiplexing is achieved by the interaction of the enzymes and proteins in the Liquid Biopsy with each co-attached peptide, because cleavage and subsequent fluorescence increase occurs much faster if there's a match with protease and its respective consensus sequence. The same is true for successful binding events of targeting peptide sequences and their respective protein targets.

In addition to the fluorescence from attached dyes, additional detectable signals comprise:

1) Phosphorescence from attached nanostructures and dyes
2) Principally, excitation could be achieved by multiphoton excitation
3) Photoacoustic signatures from attached nanostructures and dyes
4) Radioisotopes that will be cleaved off a graphene surface and analyzed.
5) Stable radicals (EPR probes) that will be released from graphene that is covered with an oxide possessing a high-spin d- or f-block metal, or co-tethered to another stable radical.
6) MRI probes that will be released from graphene that is covered with an oxide possessing a high-spin d- or f-block metal cation, or a supramolecularly bound high-spin d- or f-block metal cation.

Example 40: Impact of Dispersal and Solvent Removal on Absorbance Efficiency of Graphene Biosensors Solutions of graphene biosensors reflecting lots 1, 2, 3 and 4 of nanosensor reflecting the KSU protocol, the HEB replication of the KSU protocol, a sonicated protocol (Lot 3) and a sonicated protocol that eliminates solvent contamination (Lot 4) respectively were prepared as working solutions in 5 mM MES pH7.4 containing 155 mM NaCl. The sensors were prepared at concentrations of 25 μg/mL. The working solutions were prepared and sonicated in a water bath for 1 min per mL of solution. Samples were vortexed once immediately before sampling 2 μL three times, The absorbance was established by measuring the absorbance across 250 nm to 650 on a Nanodrop. The samples were then allowed to sit for 1 hour without any agitation. After 60 min, 2 μL samples were taken with a pipette tip submerged to 50% depth in the sensor solution. The absorbance spectrum was repeated on this t=60 sample. The graphs show the absorbance spectrum for each of 4 Lots of NE and MMP15 biosensor. The absorbance efficiency is displayed on the table calculated as absorbance at 260 nm per mg/ml of biosensor. The analysis shows the increasing absorbance of sensor as it is sonicated during preparation and dried to remove solvents. This observation is not dependent on the biosensor measured. (see FIG. 55).

Figure 56:
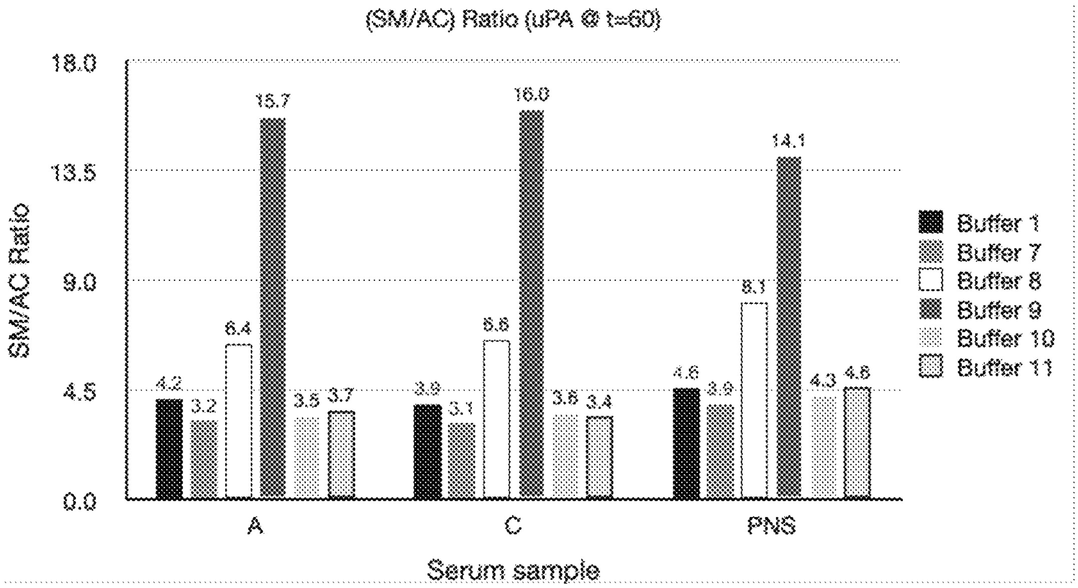
FIG. 56 shows the Impact of buffer formulation on Signal to Noise performance. Working solutions of gNBS were prepared in buffers as detailed in FIG. 14. Signal to noise was calculated based on the ratio of fluorescence observed in samples/assay control (RFI). Buffer 7 containing MES only performed similarly to Buffer 1 (Hepes). Addition of 30 mM NaCl (Buffer 8) or 155 mM NaCl (Buffer 9) increases RFI.

Example 41: Impact of Buffer Formulation on Signal to Noise Performance of Graphene Biosensor Solutions of uPA nanosensor were prepared at 10× working concentration of 300 μg/ml in water. They were sonicated for 10 minutes in a sonicating water bath. The nanosensor was diluted 1:10 in each of the different buffer formulations reported in FIG. 14. 125 μl biosensor solution was dispensed in replicates in a black 96 well plate. 5 μL serum was added and the plates were incubated at 37° C. for 60 min. Released fluorescence was read on a VarioSkan Lux plate reader with 421 nm excitation and 650 nm emission. The assays included an assay control where 5 μl of the appropriate buffer was added in place of the serum. The biosensor was incubated with two different normal health donor sera samples or a pooled normal sera (PNS). Buffer 1 was the original formulation. Protease activity was observed in all the buffering conditions. The S:N are reported in FIG. 56 (uPA biosensor) showing the SM/AC ratio as an estimate of S:N. It was noted the buffers that included NaCl significantly lowered both the background and serum signal. Decreasing the AC serves to increase the signal to noise performance of the gNBS. Buffers 7 and 8 containing NaCl, had significantly reduced AC performance in comparison to the original buffer. This yielded an increased SN performance.

Example 42: Impact of Buffer Formulation and Heat Treatment on Signal to Noise Performance of Graphene Biosensors Working solutions of 18 different biosensors were prepared in HEPES or MES buffer supplemented with 10 μM divalent cations and 155 mM NaCl. Samples were heat treated at 65° C. for 12 min (MES Baseline) or not (HEPES Baseline) and incubated for 90 min at 37° C. After 90 minutes, fluorescence released was evaluated on a VarioSkan Lux and the S:N performance was calculated according by SM/AC. The impact of protocol changes to add monobasic salt ions, more robust pH control with MES buffer demonstrated an average reduction of AC on the VarioSkan platform to 0.10 RFU or lower. The more stable pH control in addition to the lower AC produced a S:N calculation that was on average 4-fold increased over the HEPES baseline (see FIG. 57).

Example 43: Colloidal Stability of Graphene Biosensors

Solutions of NE or MMP15 graphene biosensors reflecting lots 1, 2, 3 and 4 of the KSU protocol, the HEB replication of the KSU protocol, a sonicated protocol (Lot 3) and a sonicated protocol that eliminates solvent contamination (Lot 4) respectively were prepared as working solutions in 5 mM MES pH7.4 containing 155 mM NaCl. The sensors were prepared at working concentrations of 25 μg/mL. As a comparator, a preparation of Fe biosensor was also prepared at a working concentration of 300 μg/mL using the same buffer. The working solutions were prepared and sonicated in a waterbath for 1 min per mL of solution. Samples were vortexed once immediately before sampling 2 μL three times. The absorbance was established by measuring the absorbance across 250 nm to 650 on a Nanodrop. The samples were then allowed to sit for 1 hour without any agitation. After 60 min, 2 μL samples were taken with a pipette tip submerged to 50% depth in the sensor solution. The absorbance spectrum was repeated on this t=60 sample. The performance is displayed as a percentage change in absorbance efficiency at $OD_{270}$ or $OD_{650}$.

The analysis shows the increasing stability of sensor as it is sonicated during preparation and dried to remove solvents reflected in the decreasing change in absorbance over 60 minutes with each Lot preparation. This observation is not dependent on the biosensor measured. (FIG. 58).

Example 44: Evaluation of Signal to Noise Across Different Manufacturing Protocols for Graphene Biosensors Solutions of NE, CTSB or MMP12 graphene biosensors reflecting lots 1, 2, 3 and 4 of the KSU protocol, the HEB replication of the KSU protocol, a sonicated protocol (Lot 3) and a sonicated protocol that eliminates solvent contamination (Lot 4) respectively were prepared as working solutions in 5 mM MES pH7.4 containing 155 mM NaCl. and 10 μM divalent cations. The sensors were prepared at working concentrations of 25 μg/mL. As a comparator, a preparation of Fe biosensor was also prepared at a working concentration of 300 μg/mL using the same buffer. Biosensors were stimulated with the same sera on the same day (panel A, B and C, FIG. 59, and Panel D, FIG. 59).

Figure 59:
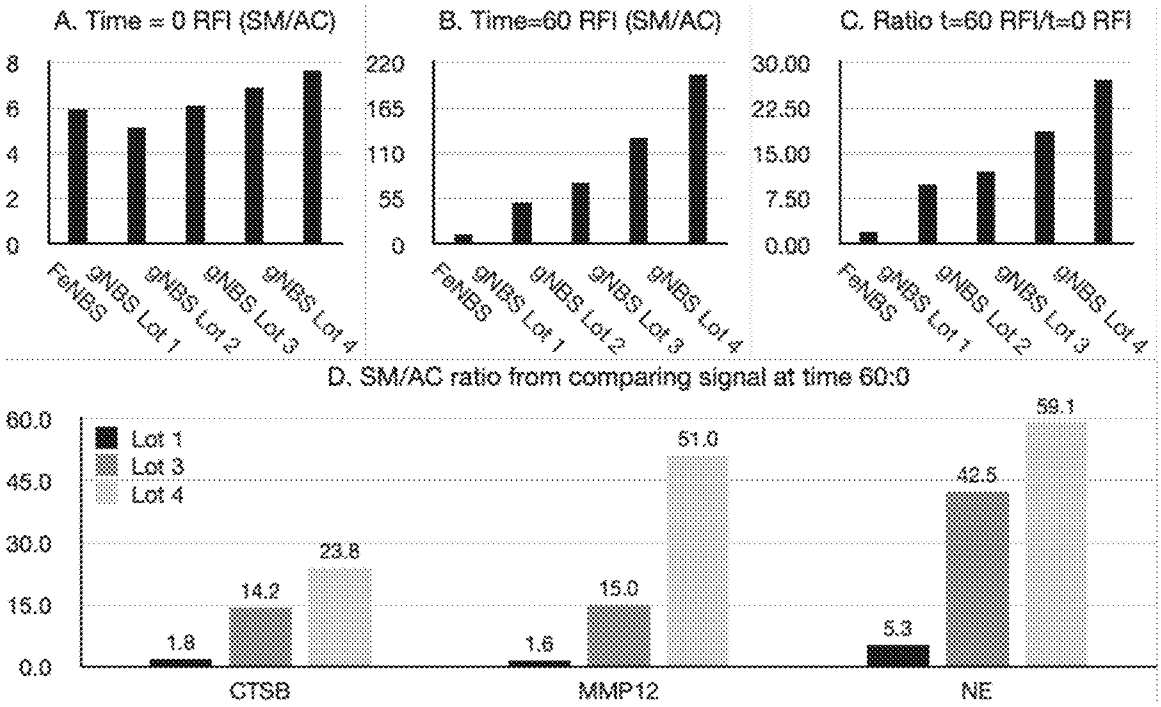
FIG. 59 shows charts illustrating an exemplary evaluation of signal to noise across different manufacturing protocols for gNBS. CTSB was manufactured using the original Iron backbone (FeNBS), using a graphene backbone and the original KSU protocol (gNBS Lot 1), a replicate of the KSU protocol using extended drying procedures (gNBS Lot 2), using probe sonicated gNBS backbone (gNBS Lot 3), and probe sonicated gNBS backbone thoroughly desiccated for solvent removal on manufacture (gNBS Lot 4). The graphs show Signal:Noise as measured by RFI (SM/AC) at time 0 (A), Signal:Noise after 60 min incubation with pooled normal serum (B.) and the Signal:Noise expressed as a ratio of RFI 60/RFI 0 (C). Similar observations were made for CTSB, MMP12 and NE in separate experiments (D).
Figure 61:
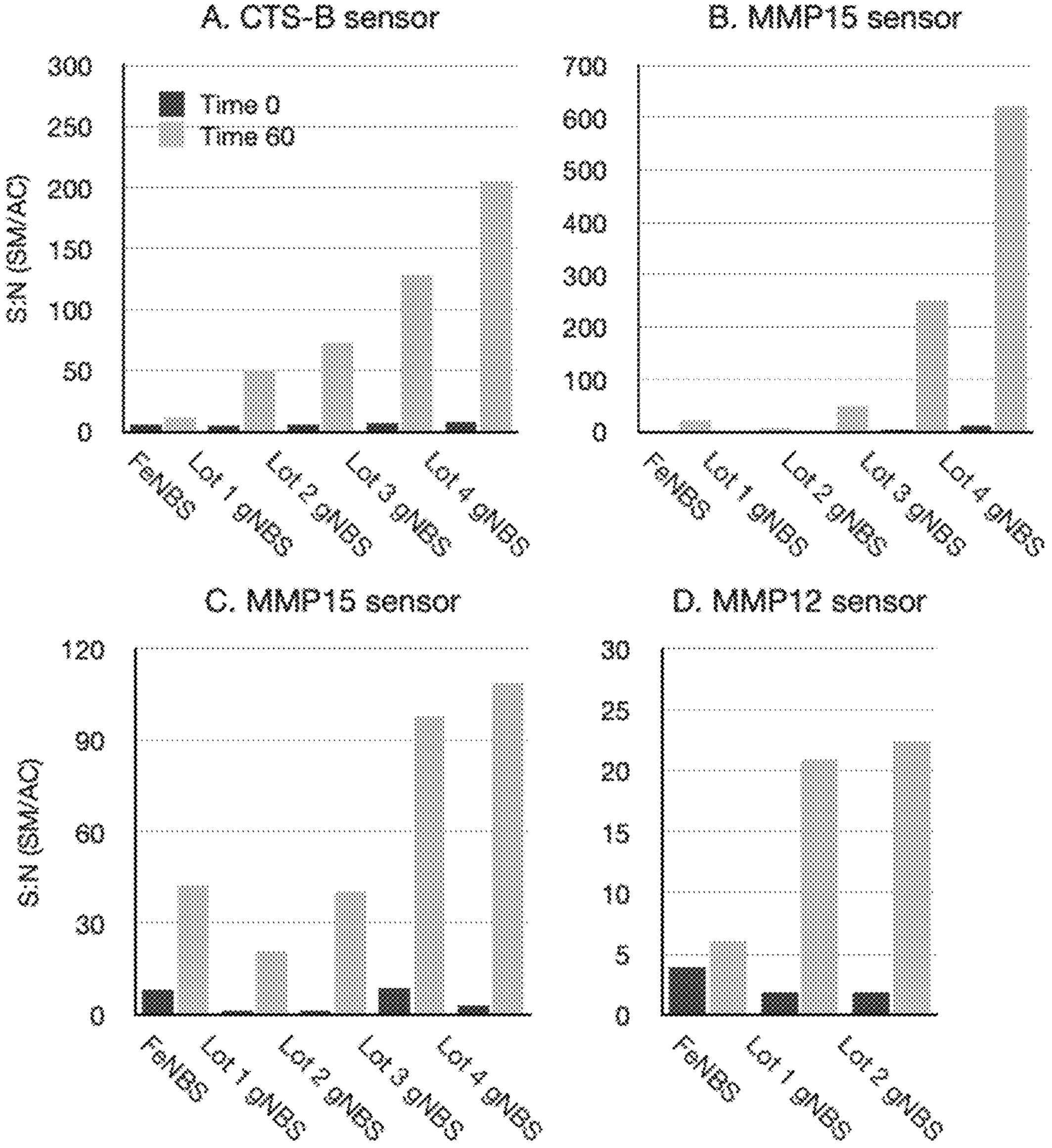
FIG. 61 shows charts illustrating an exemplary evaluation of signal to noise across different manufacturing protocols for Fe and graphene biosensor. Biosensor was manufactured using the original Iron backbone (FeNBS), using a graphene backbone and the original KSU protocol (gNBS Lot 1), a replicate of the KSU protocol using extended drying procedures (gNBS Lot 2), using probe sonicated gNBS backbone (gNBS Lot 3), and probe sonicated gNBS backbone thoroughly desiccated for solvent removal on manufacture (gNBS Lot 4). The graphs show Signal:Noise as measured by RFI (SM/AC) at time 0 and after 60 min incubation with two different normal human sera averaged. Four exemplary biosensors are displayed.

The fluorescence released after 60 min at 45° C. was measured on a VarioSkan Lux. Across four biosensors on different days, the impact of sonication (Lots 3 & 4) and solvent removal (Lot 4) clearly demonstrate and increase t=60 S:N. (See t=60 RFI (FIG. 59, Panel B and FIG. 61). To capture the stability of unstimulated graphene nanosensor vs Fe nanosensor, we also calculated the ratio of S:N at time 0 and time 60. For three different biosensors on three different measurements, the t=60/0 S:N ratio was significantly increased for Lot 3 and Lot 4 (FIG. 59, Panel C and D). All the arrangements were noted to produce stronger S:N performance than Fe biosensor. (FIG. 61)

Example 45: Evaluation of Signal to Noise Across Different Manufacturing Protocols for Graphene Biosensors Solutions of graphene biosensors for CTS-K labelled with TCPP and NE labelled with the fluorescent dye FAM were made up at 50 μg/ml each in 10 mM MES solution with 10 pM divalent cations and 155 mM NaCl, pH 7.25. A solution of CTSK-TCPP biosensor was mixed in volume ratios to produce mixtures of 5% NE-FAM, 10%, 25%, 50%, 75%, 90% or 100% NE-FAM biosensor. 70 μL of each mixture was stimulated on a 384 well plate in triplicate with 10 μL pooled normal serum and incubated at 45° C. for 90 minutes before fluorescence at 422/650 and 496/526 nm was measured to detect TCPP and FAM respectively.

Figure 60:
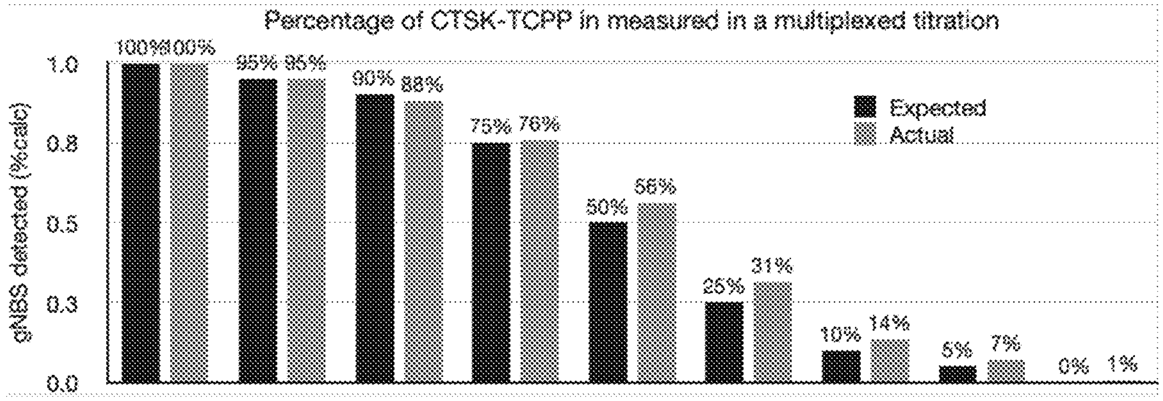
FIG. 60 shows a chart illustrating the results of detection of gNBS in multiplexed setting. Signal is presented as a percentage of the signal obtained at 100%.

The data were analyzed to determine what percentage of signal was detectable at each dilution of sensor based on the known mixture of sensors. The graph shows the expected signal and the observed signal for TCPP (FIG. 60).

A very efficient detection of signal from TCPP or FAM labelled sensors was observed, even when the sensors were diluted 1:20 in a competing sensor that was independently generating a separate signal for a different sensor.

These results support the conclusion that one can reliably detect sensors present as 1:20 mixtures in multiplexed reactions as it will be understood by a skilled person.

Example 46: Synthesis of Graphene-Based Biosensors: G-PEI and G-TEG3Amine

Two different cleavable peptide sequences were labeled with two different dyes, MMP-9 (GAGVPLS-LYSGAG) (SEQ ID NO: 132) was labeled with TCPP and a second MMP-9 (GCDDHAAG-LLGLDG) (SEQ ID NO: 132) was labeled with rhodamine B. These were attached to graphene-based biosensors, G-PEI and G-TEG3amine according to the following protocol.

25 mg of carboxygraphene-PEI or graphene-TEG3amine were sonicated and suspended in 4 mL of DMF in a small glass vial. Then, for each vial 2.5 mg of DMAP, 2.5 mg of EDC, and ~1.75 mg of TCPP and rhodamine B labeled peptides were added. Sample was sonicated for 5 minutes and reaction was stirred overnight at room temperature.

The next day, each biosensor was collected via centrifugation (5 min @ 7000 rpm) and washed twice with DMF and three times with diethyl ether.

Each biosensor was incubated with 3 different control serum sample to measure fluorescence intensity for both TCPP (425 nm excitation and 650 nm emission) and rhodamine B (535 nm excitation and 570 nm emission) over 60 min. incubation at 37° C.

Figure 54:
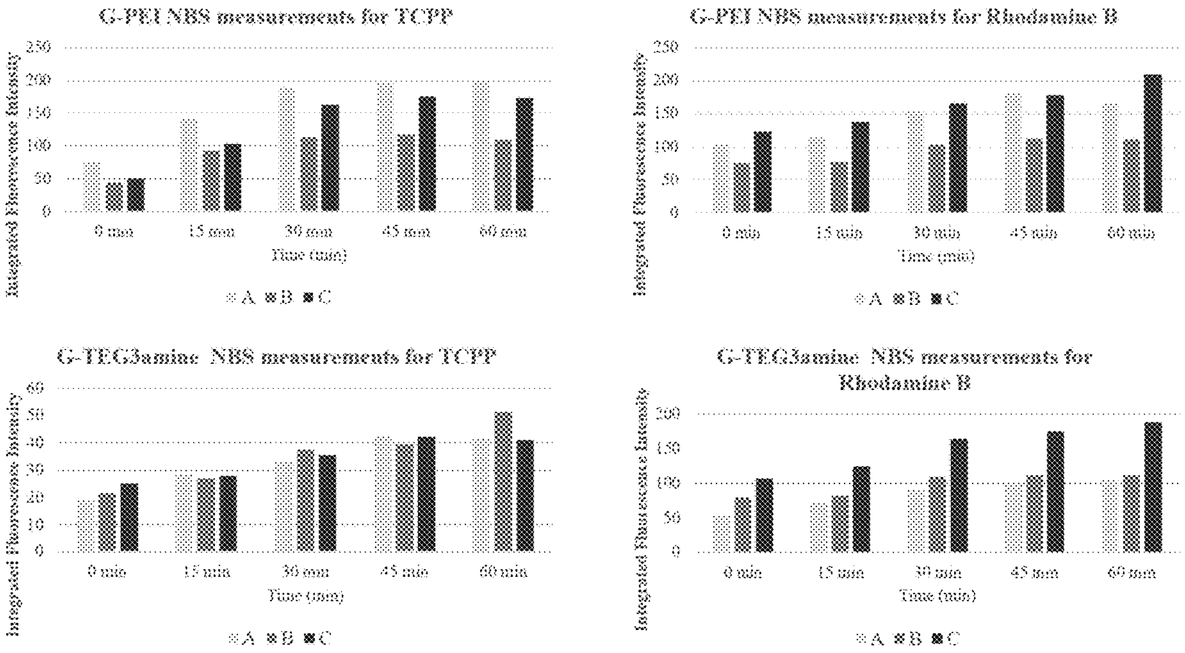
FIG. 54 shows charts illustrating the results of experiments showing detection of target biomarker MMP-9 in 3 different control serum samples with core particle G-PEI and G-TEG3amine presenting different cleavable peptide sequences labeled with two different dyes, in particular MMP-9 (GAGVPLS-LYSGAG)(SEQ ID NO: 132) labeled with TCPP and a MMP-9 (GCDDHAAG-LLGLDG) (SEQ ID NO: 133) labeled with rhodamine B. The fluorescent intensity was measured over time as indicated in the three control samples (marked as A B and C in each chart).

FIG. 54 shows the fluorescence intensity measured every 15 min. for both biosensors within the 60 min incubation period. Results demonstrated that fluorescence intensity increased for both corresponding fluorophores as the incubation time increased, reaching the highest intensity at 60 min. for both G-PEI and G-TEG3amine biosensors incubated with each control serum sample. These results demonstrated successful assembly of both biosensors using 2 different fluorophores.

Example 47: Method of Making Multiplex Sensor

Multiplex graphene biosensors can be prepare by stepwise addition or competitive synthesis.

The maximal number in the UV/Vis/Near IR range is 10, due to the requirement of virtual non-overlapping excitation and emission spectra.

The optimal density of oligopeptides tethered to the shell surrounding graphene is $1.6\pm0.2\times10^{-5}$ moles peptide+fluorophore per gram of biosensor. At loading higher than that, the biosensors react significantly slower due to steric interference with the enzyme kinetics. The upper bound (when activity in the presence of $1\times10^{-10}$ moles $L^{-1}$ of active protease is not detectable within an hour) is $1.0\pm0.25\times10^{-3}$ moles peptide+fluorophore per gram biosensor. The lower bound (disappearance of signal) is $1.0\pm0.25\times10^{-7}$ moles peptide+fluorophore per gram of biosensor.

The synthesis of a multitasking sensor can be achieved as follows:

1) Competitive binding of up to 10 different peptides+fluorophores to the shell around graphene. The bonds form during the same time interval. The resulting distribution of peptides+fluorophores is statistical.
2) Each of the peptide+fluorophore is added separately, followed by purification.

Both approaches can be optimized in terms of the concentrations of added reagents and reaction time. Competitive synthesis is less time-consuming.

Example 48: General Protocol to Identify a Peptide Linkage Specific for a Target Biomarker The original information about consensus sequences for proteases is obtained from the data base MEROPS [64]. For all proteases, up to 25 different candidates for consensus sequences are built. By using CAPS-dock, a computational service provided by the Kolinski research group at the University of Warsaw, Poland, we were able to select the consensus sequences that are excellent fits for the active centers of the human proteases [65]. [00608]. CABS-dock performs docking searches and determination of preferred binding sites allowing for full flexibility of the peptide and small fluctuations of the receptor backbone. CABS-dock simulations are carried out using a coarse-grained protein model, which is reverted to Protein Data Bank (PDB)-compatible coordinates once the optimization is completed.

For kinases, the relevant peptide sequences in the vicinity of the phosphorylation site are available from UNIPROT. For cytokines/chemokines, the structures of cytokine/chemokine receptors are available from UNIPROT. Docking experiments with CAPS-dock are able to guide point mutations of the relevant amino acids in these receptors for finding stronger binding oligopeptides. All in-silico derived oligopeptides are tested in biosensors.

In summary, provided herein are graphene biosensors and related core particles, compositions methods and systems in which more than one pristine graphene sheet is coated with a coating layer of an organic or inorganic material to provide a core graphene particle, to which detectable components comprising a detectable moiety and a peptide linkage are attached through binding of the peptide linkage.

The examples set forth above are provided to give those of ordinary skill in the art a disclosure and description of how to make and use embodiments of the biosensors, core particles, materials, compositions, methods and systems of the disclosure, and are not intended to limit the scope of what the inventors regard as their disclosure. Those skilled in the art will recognize how to adapt the features of the exemplified biosensors, core particles, materials, compositions, methods and systems based on the target compound removing agents, nucleic acid removing agents, solid matrices, and devices according to various embodiments and scope of the claims.

All patents and publications mentioned in the instant specification inclusive of Background, Summary, Brief description of the Drawings, Detailed Description and Examples are indicative of the levels of skill of those skilled in the art to which the disclosure pertains.

The entire disclosure of each document cited (including webpages patents, patent applications, journal articles, abstracts, laboratory manuals, books, or other disclosures) in the instant disclosure inclusive of Background, Summary, Brief description of the Drawings, Detailed Description and Examples is hereby incorporated herein by reference. All references cited in this disclosure inclusive of Background, Summary, Brief description of the Drawings, Detailed Description and Examples are incorporated by reference to the same extent as if each reference had been incorporated by reference in its entirety individually. However, if any inconsistency arises between a cited reference and the present disclosure, the present disclosure takes precedence.

The terms and expressions which have been employed in the instant disclosure are used as terms of description and not of limitation, and there is no intention in the use of such terms and expressions of excluding any equivalents of the features shown and described or portions thereof, but it is recognized that various modifications are possible within the scope of the materials, compositions, systems and methods of the disclosure claimed. Thus, it should be understood that although the biosensors, core particles, materials, compositions, methods and systems of the disclosure have been specifically described by embodiments, exemplary embodiments and optional features, modification and variation of the concepts herein described can be resorted to by those skilled in the art, and that such modifications and variations are considered to be within the scope of this disclosure in the instant disclosure as defined by the appended claims.

It is also to be understood that the terminology used herein is for the purpose of describing particular embodiments only and is not intended to be limiting. As used in this specification and the appended claims, the singular forms "a," "an," and "the" include plural referents unless the content clearly dictates otherwise. The term "plurality" includes two or more referents unless the content clearly dictates otherwise. Unless defined otherwise, all technical and scientific terms used herein have the same meaning as commonly understood by one of ordinary skill in the art to which the disclosure pertains.

When a Markush group or other grouping is used in the instant disclosure, all individual members of the group and all combinations and possible subcombinations of the group are intended to be individually included in the disclosure. Every combination of components or materials described or exemplified herein can be used to practice the materials, compositions, systems and methods of the disclosure, unless otherwise stated. One of ordinary skill in the art will appreciate that methods, device elements, and materials other than those specifically exemplified can be employed in the practice of the materials, compositions, systems and methods of the disclosure without resort to undue experimentation. All art-known functional equivalents, of any such methods, device elements, and materials are intended to be included in the instant disclosure.

The present description also uses numerical ranges to quantify certain parameters relating to various embodiments of the present disclosure. Whenever a range is given in the specification, for example, a temperature range, a frequency range, a time range, or a composition range, all intermediate ranges and all subranges, as well as, all individual values included in the ranges given are intended to be included in the disclosure. In particular. It should be understood that when numerical ranges are provided, such ranges are to be construed as providing literal support for claim limitations that only recite the lower value of the range as well as claim limitations that only recite the upper value of the range. For example, a disclosed numerical range of about 10 to about 100 provides literal support for a claim reciting "greater than about 10" (with no upper bounds) and a claim reciting "less than about 100" (with no lower bounds).

Any one or more individual members of a range or group disclosed herein can be excluded from a claim of this disclosure. The disclosure illustratively described herein suitably can be practiced in the absence of any element or elements, limitation or limitations, which is not specifically disclosed herein.

As used herein, the phrase "and/or," when used in a list of two or more items, means that any one of the listed items can be employed by itself or any combination of two or more of the listed items can be employed. For example, if a composition is described as containing or excluding components A, B, and/or C, the composition can contain or exclude A alone; B alone; C alone; A and B in combination; A and C in combination; B and C in combination; or A, B, and C in combination.

"Optional" or "optionally" in the instant disclosure means that the subsequently described circumstance may or may not occur, so that the description includes instances where the circumstance occurs and instances where it does not according to the guidance provided in the present disclosure. For example, the phrase "optionally substituted" means that a non-hydrogen substituent may or may not be present on a given atom, and, thus, the description includes structures wherein a non-hydrogen substituent is present and structures wherein a non-hydrogen substituent is not present. It will be appreciated that the phrase "optionally substituted" is used interchangeably with the phrase "substituted or unsubstituted." Unless otherwise indicated, an optionally substituted group may have a substituent at each substitutable position of the group, and when more than one position in any given structure may be substituted with more than one substituent selected from a specified group, the substituent may be either the same or different at every position. Combinations of substituents envisioned can be identified in view of the desired features of the compound in view of the present disclosure, and in view of the features that result in the formation of stable or chemically feasible compounds. The term "stable", as used herein, refers to compounds that are not substantially altered when subjected to conditions to allow for their production, detection, and, in certain embodiments, their recovery, purification, and use for one or more of the purposes disclosed herein.

A number of embodiments of materials, compositions, systems and methods of the disclosure have been described. The specific embodiments provided herein are examples of useful embodiments of the materials, compositions, systems and methods of the disclosure and it will be apparent to one skilled in the art that the materials, compositions, systems and methods of the disclosure can be carried out using a large number of variations of the devices, device components, methods steps set forth in the present in the instant disclosure. As will be obvious to one of skill in the art, methods and devices useful for the present methods can include a large number of optional composition and processing elements and steps.

In particular, it will be understood that various modifications may be made without departing from the spirit and scope of the present in the instant disclosure. Accordingly, other embodiments are within the scope of the following claims.

REFERENCES

1. Wright, J. P., et al., *Synthesis of nanoscale graphene via chamber detonation of oxygen/acetylene mixtures*. Materials Chemistry and Physics, 2021. electronic preprints.
2. Loebach, D. V., *The relationship between particle size and molecular weight in emulsion polymerization, in Chemical Engineering*. 1975, Iowa State University: Ames, IA. p. 129.
3. Wikipedia. Graphene. 2021 [cited 2021 Dec. 19]; Available from: https://en.wikipedia.org/wiki/Graphene #cite_note-geini2007-2.
4. De Nicola, F., et al., *Wetting properties of graphene aerogels*. Scientific reports, 2020. 10(1): p. 1916.
5. Güler, O., et al., *Production of graphene layer by liquid-phase exfoliation with low sonication power and sonication time from synthesized expanded graphite*. Fullerenes, Nanotubes and Carbon Nanostructures, 2016. 24(2): p. 123-127.
6. Cui, L., J. Wang, and M. Sun, *Graphene Plasmon for Optoelectronics*. Reviews in Physics, 2021. 6: p. 100054.
7. Nuvoli, D., et al., *The production of concentrated dispersions of few-layer graphene by the direct exfoliation of graphite in organosilanes*. Nanoscale research letters, 2012. 7(1): p. 1-7.
8. Wright J P, S. S., Corkill S, Covarrubias J, LeBan L, Nepal A, Li J, Bossmann S H, Sorensen C M, *Synthesis of nanoscale graphene via chamber detonation of oxygen/acetylene mixtures*. Materials Chemistry and Physics, 2021. electronic preprints.
9. Backes, C., et al., *Production and processing of graphene and related materials*. 2D Mater., 2020. 7(2): p. 022001.
10. Luong, D. X., et al., *Gram-scale bottom-up flash graphene synthesis*. Nature (London, U. K.), 2020. 577 (7792): p. 647-651.
11. Stanford, M. G., et al., *Flash Graphene Morphologies*. ACS Nano, 2020. 14(10): p. 13691-13699.
12. Nepal, A., et al., *One-step synthesis of graphene via catalyst-free gas-phase hydrocarbon detonation*. Nanotechnology, 2013. 24(24): p. 245602.
13. Luong, D. X., et al., *Gram-scale bottom-up flash graphene synthesis*. Nature, 2020. 577(7792): p. 647-651.
14. Sorensen, C., A. Nepal, and G. P. Singh. U.S. Pat. No. 9,440,857.
15. Dhaubhadel, R., et al., *Aerosol gelation: Synthesis of a novel, lightweight, high specific surface area material*. Aerosol science and technology, 2007. 41(8): p. 804-810.
16. Sorensen, C. M., et al. U.S. Pat. No. 7,691,909
17. Daniel, D. *Fractal Dimension*. 2011; Available from: http://soft-matter.seas.harvard.edu/index.php/Fractal_Dimension.
18. Sorensen, C., *Light scattering by fractal aggregates: a review*. Aerosol Science & Technology, 2001. 35(2): p. 648-687.
19. Sorensen, C. M., *Light Scattering by Fractal Aggregates: A Review*. Aerosol Science and Technology, 2001. 35(2): p. 648-687.
20. Qin, H., et al., *Chemical amination via cycloaddition of graphene for use in a glucose sensor*. Journal of nanoscience and nanotechnology, 2016. 16(5): p. 5034-5037.
21. Ma, M., et al., *Rational design, synthesis, and application of silica/graphene-based nanocomposite: A review*. Mater. Des., 2021. 198: p. 109367.
22. Wikipedia. Polymer. 2021 [cited 2021 Dec. 20]; Available from: https://en.wikipedia.org/wiki/Polymer.
23. Daina, A., O. Michielin, and V. Zoete, *iLOGP: a simple, robust, and efficient description of n-octanol/water partition coefficient for drug design using the GB/SA approach*. Journal of chemical information and modeling, 2014. 54(12): p. 3284-3301.

24. Covarrubias, J. J., *Rational Chemical Applications of Explosion-Graphene, in Chemistry.* 2021, Kansas State University: Manhattan, KS, USA. p. 110.
25. Ainavarapu, S. R. K., et al., *Contour Length and Refolding Rate of a Small Protein Controlled by Engineered Disulfide Bonds*. Biophysical journal, 2007. 92: p. 225-33.
26. Puente, X. S., et al., *Human and mouse proteases: a comparative genomic approach*. Nature Reviews Genetics, 2003. 4(7): p. 544-558.
27. Kim, S. N., et al., *Preferential Binding of Peptides to Graphene Edges and Planes*. J. Am. Chem. Soc., 2011. 133(37): p. 14480-14483.
28. Guler, O., et al., *Production of graphene layer by liquid-phase exfoliation with low sonication power and sonication time from synthesized expanded graphite*. Fullerenes, Nanotubes, Carbon Nanostruct., 2016. 24(2): p. 123-127.
29. Wu, Y., G. Li, and J. P. Camden, *Probing Nanoparticle Plasmons with Electron Energy Loss Spectroscopy*. Chemical Reviews, 2018. 118(6): p. 2994-3031.
30. Zhang, B., et al., *Preparation of aramid nanofiber and its application in polymer reinforcement: A review*. Eur. Polym. J., 2020. 139: p. 109996.
31. Lange, P., et al., *Evidence for graphene plasmons in the visible spectral range probed by molecules*. arXiv: 1404.6518 Condensed Matter>Nanoscale Physics, 2014. arXiv:1404.6518.
32. Wade, L. and J. Simek, *Organic Chemistry* (*Mastering Chemistry*) *9th Edition.* 2017, Essex CM20 2JE England: Pearson.
33. Castelaín, M., et al., *Effect of Click-Chemistry Approaches for Graphene Modification on the Electrical, Thermal, and Mechanical Properties of Polyethylene/Graphene Nanocomposites*. Macromolecules, 2013. 46(22): p. 8980-8987.
34. Li, W., Y. Li, and K. Xu, *Azidated graphene: direct azidation from monolayers, click chemistry, and bulk production from graphite*. Nano letters, 2020. 20(1): p. 534-539.
35. Sarkar, S., et al., *Diels-Alder Chemistry of Graphite and Graphene: Graphene as Diene and Dienophile*. Journal of the American Chemical Society, 2011. 133(10): p. 3324-3327.
36. Sarkar, S., E. Bekyarova, and R. C. Haddon, *Chemistry at the Dirac Point: Diels-Alder Reactivity of Graphene*. Accounts of Chemical Research, 2012. 45(4): p. 673-682.
37. Salavagione, H. J., *Modification of graphene with polymers via addition chemistry, in Graphene Science Handbook: Mechanical and Chemical Properties*, M. Aliofkhazraei, Editor. 2016, Institute of Polymer Science and Technology (CSIS) Madrid, Spain: Department of Polymer Physics, Elastomers, and Energy Applications
38. Park, J. and M. Yan, *Covalent functionalization of graphene with reactive intermediates*. Accounts of chemical research, 2013. 46(1): p. 181-189.
39. Atwood, J. L. and J. W. Steed, *Encyclopedia of Supramolecular Chemistry,* 2004, Boca Raton, FL: Taylor & Francis, 1639.
40. Huang, B., et al., *Recent advances and perspectives on supramolecular radical cages*. Chemical Science, 2021. 12(41): p. 13648-13663.
41. Knoll, W., et al., *Streptavidin arrays as supramolecular architectures in surface-plasmon optical sensor formats*. Colloids and Surfaces A: Physicochemical and Engineering Aspects, 2000. 161(1): p. 115-137.
42. Biedermann, F., W. M. Nau, and H. J. Schneider, *The Hydrophobic Effect Revisited—Studies with Supramolecular Complexes Imply High-Energy Water as a Noncovalent Driving Force*. Angewandte Chemie International Edition, 2014. 53(42): p. 11158-11171.
43. Liu, Z., S. K. M. Nalluri, and J. F. Stoddart, *Surveying macrocyclic chemistry: from flexible crown ethers to rigid cyclophanes*. Chemical Society Reviews, 2017. 46(9): p. 2459-2478.
44. Shetty, D., et al., *Can we beat the biotin-avidin pair?: cucurbit* [7] *uril-based ultrahigh affinity host-guest complexes and their applications*. Chemical Society Reviews, 2015. 44(23): p. 8747-8761.
45. McLaughlin, C. K., G. D. Hamblin, and H. F. Sleiman, *Supramolecular DNA assembly*. Chemical Society Reviews, 2011. 40(12): p. 5647-5656.
46. Higashi, S. L., et al., *Supramolecular architectures of nucleic acid/peptide hybrids*. International Journal of Molecular Sciences, 2020. 21(24): p. 9458.
47. Zhu, H., et al., *Supramolecular peptide constructed by molecular Lego allowing programmable self-assembly for photodynamic therapy*. Nature communications, 2019. 10(1): p. 2412.
48. Li, J., et al., *Click and patterned functionalization of graphene by Diels-Alder reaction*. Journal of the American Chemical Society, 2016. 138(24): p. 7448-7451.
49. Namvari, M. and H. Namazi, *Sweet graphene I: toward hydrophilic graphene nanosheets via click grafting alkyne-saccharides onto azide-functionalized graphene oxide*. Carbohydrate research, 2014. 396: p. 1-8.
50. Farivar, F., et al., *Highly Water Dispersible Functionalized Graphene by Thermal Thiol-Ene Click Chemistry*. Materials, 2021. 14(11): p. 2830.
51. Sandhya, M., et al., *Ultrasonication an intensifying tool for preparation of stable nanofluids and study the time influence on distinct properties of graphene nanofluids—A systematic overview*. Ultrasonics sonochemistry, 2021. 73: p. 105479.
52. Strom, T. A., et al., *Nitrene addition to exfoliated graphene: a one-step route to highly functionalized graphene*. Chemical communications, 2010. 46(23): p. 4097-4099.
53. Bian, T., R. Chang, and P. T. Leung, *Förster resonance energy transfer between molecules in the vicinity of graphene-coated nanoparticles*. Plasmonics, 2016. 11(5): p. 1239-1246.
54. Zhou, J., et al., *Two-dimensional nanomaterials for Förster resonance energy transfer-based sensing applications*. Nanophotonics, 2020. 9(7): p. 1855-1875.
55. Gendron, R., et al., *Inhibition of the activities of matrix metalloproteinases* 2, 8, *and* 9 *by chlorhexidine*. Clinical Diagnostic Laboratory Immunology, 1999. 6(3): p. 437-439.
56. Meraz-Cruz, N., et al., *Thermal stability of human matrix metalloproteinases*. Heliyon, 2020. 6(5): p. e03865.
57. Blume, J. E., et al., *Rapid, deep and precise profiling of the plasma proteome with multi-nanoparticle protein corona*. Nature communications, 2020. 11(1): p. 3662
58. Sorensen C, N. A., Singh G P, inventors; Kansas State University Research Foundation, USA.assignee., Process for high-yield production of graphene via detonation of carbon-containing material U.S. Patent PGPub No. US20140335010A1, 2014.
59. Daina A, M. O., Zoete V., *SwissADME: a free web tool to evaluate pharmacokinetics, drug-likeness and medicinal chemistry friendliness of small molecules*. Sci Rep. 2017; 7:42717. Epub 20170303. doi: 10.1038/srep42717. PubMed PMID: 28256516; PMCID: PMC5335600, 2017.

60. Loebach, D. V., *THE RELATIONSHIP BETWEEN PARTICLE SIZE AND MOLECULAR WEIGHT IN EMULSION POLYMERIZATION*. 1975: Iowa State University.
61. Ainavarapu, S. R. K., et al., *Contour length and refolding rate of a small protein controlled by engineered disulfide bonds*. Biophysical journal, 2007. 92(1): p. 225-233.
62. Liu, J., et al., *Advances in Multicompartment Mesoporous Silica Micro/Nanoparticles for Theranostic Applications*. Annual Review of Chemical and Biomolecular Engineering, 2018.9: p. 389-411.
63. Mollica, G., et al., *Structural Investigations of Polymer Materials by Dynamic Nuclear Polarisation Solid-state NMR*. NMR Methods for Characterization of Synthetic and Natural Polymers, 2019: p. 533-554.
64. EBI. *MEROPS*. 2021; Available from: https://www.ebi-.ac.uk/merops/.
65. Kolinski, A. *Multiscale molecular modeling*. 2021; Available from: http://biocomp.chem.uw.edu.pl/.

The invention claimed is:

1. A graphene biosensor configured to detect a target biomarker, the graphene biosensor comprising:

a graphene core particle and a detectable moiety capable of emitting a fluorescent signal, the detectable moiety is covalently bonded to the graphene core particle through a peptide linkage comprising a recognition sequence specific for the target biomarker, wherein the graphene core particle comprises at least two pristine graphene nanosheets having a pristine graphene nanosheet surface stacked over one another to form a pristine graphene aggregate, and a coating layer covering at least 50% of a pristine graphene nanosheet surface, said coating layer comprising an organic and/or inorganic compound, wherein the organic and/or inorganic compound has a solubility in water of at least 10 grams per liter $H_2O$ at 25 degrees C. and is able to be covalently linked to, or in water electrostatically stably attached to, pristine graphene, wherein the organic and/or inorganic compound is attached to a pristine graphene nanosheet to form said coating layer, wherein the pristine graphene of the at least two pristine graphene nanosheets has a carbon content of at least 99%, an oxygen content of less than 1% and is pure, such that the pristine graphene is free of foreign substances and impurities, wherein the pristine graphene nanosheet and/or the organic and/or inorganic compound of the coating layer is configured to present a functional group capable of binding a corresponding functional group in an aqueous solution, wherein, the coating layer and the peptide linkage are configured to set a quenching distance between the graphene nanosheets and the detectable moiety in which the graphene nanosheets quench the fluorescent signal of the detectable moiety, wherein the peptide linkage is further configured to set, upon recognition by the target biomarker of the recognition sequence, an emitting distance between the graphene nanosheets and the detectable moiety wherein the graphene nanosheets do not quench the fluorescent signal of the detectable moiety, and wherein the target biomarker specific peptide linkage and the detectable moiety thus form a target specific detectable component configured to emit a detectable fluorescent signal upon modification of the peptide linkage by the target biomarker.

2. The graphene biosensor of claim 1, wherein said recognition sequence is specific for a biomarker selected from the group consisting of proteases, kinases, arginases, cytokines/chemokines, dioxygenases, esterases, and combinations thereof.

3. The graphene biosensor of claim 2, wherein said protease is selected from the group consisting of serine, aspartyl, cysteine, metalloprotease, caspase, urokinase, cathepsin, caspase, and combinations thereof.

4. The graphene biosensor of claim 1, wherein said biomarker is indicative of a condition selected from the group consisting of cancerous or precancerous cellular activity, bacterial activity, infection, inflammation, and combinations thereof.

5. The graphene biosensor of claim 1, wherein said detectable moiety is a chromophore/luminophore selected from the group consisting of organic dyes, inorganic dyes, fluorophores, phosphophores, luminophores, light absorbing particles, quantum dots, combinations thereof, and the metalated complexes thereof.

6. The graphene biosensor of claim 5, wherein said chromophore/luminophore is an organic dye selected from the group consisting of coumarins, pyrene, cyanines, BODIPY dyes, benzenes, N-methylcarbazole, erythrosin B, N-acetyl-L-tryptophanamide, 2,5-diphenyloxazole, rubrene, and N-(3-sulfopropyl) acridinium.

7. The graphene biosensor of claim 5, wherein said chromophore/luminophore is an inorganic dye selected from the group consisting of porphyrins, phthalocyanines, chlorins, and metalated chromophores.

8. The graphene biosensor of claim 7, wherein said porphyrins are selected from the group consisting of tetra carboxy-phenyl-porphyrin (TCPP) and Zn-TCPP.

9. The graphene biosensor of claim 5, wherein said chromophore/luminophore is a fluorophore or phosphor selected from the group consisting of phosphorescent dyes, fluoresceines, rhodamines, and anthracenes.

10. The graphene biosensor of claim 5, wherein said quantum dot is selected from the group consisting of CdSe/ZnS core/shell quantum dots, CdTe/CdSe core/shell quantum dots, CdSe/ZnTe core/shell quantum dots, and alloyed semiconductor quantum dots.

11. The graphene biosensor of claim 1, wherein said coating layer comprises a polymer monolayer selected from the group consisting of polyethyleneimine, polycaprolactone, polyvinyl alcohol, polyvinylpyrrolidone, (meth)acrylate- and (meth)acrylamide polymers, polystyrene-carboxylic acid, polystyrene-amine, dextran, pullulan, chitosan, alginate, cellulose, and hyaluronic acid, and mixtures or co-polymers thereof.

12. The graphene biosensor of claim 1, wherein the graphene core particle has a size of from about 50 nm to about 500 nm.

13. The graphene biosensor of claim 1, comprising a plurality of detectable components attached to the graphene core particle via respective peptide linkages.

14. The graphene biosensor of claim 1, comprising at least two different detectable moieties attached to said central carrier the graphene core particle via respective peptide linkages that each have a recognition sequence specific for different target biomarkers.

15. A composition comprising one or more graphene biosensors of claim 1, in combination with a suitable auxiliary agent.

16. The composition of claim 15, wherein the composition is a pharmaceutical composition and the auxiliary agent is a pharmaceutically acceptable auxiliary agent.

17. A method of detecting the activity of a biomarker in a biological sample comprising:

contacting a biological sample with the graphene biosensor of claim 1 to create a reaction solution; and detecting a change in said reaction solution.

18. The method of claim 17 further comprising:

exposing said reaction solution to an excitation light source; and detecting a change in an absorption or emission spectrum of the detectable moiety as a function of activity of said biomarker in said sample.

19. The method of claim 17, wherein said change comprises a blue-shift in the absorption or emission maximum of said detectable moiety after said contacting relative to the absorption or emission spectrum prior to said contacting.

20. The method of claim 17, wherein said change comprises the appearance of a new visible color or luminescence band relative to the absorption or emission spectrum of said detectable moiety prior to said contacting.

21. The method of claim 17, wherein said contacting comprises incubating said sample with said biosensor for a period of time of less than 90 minutes, preferably less than 60 minutes.

22. The method of claim 17, wherein said contacting comprises providing a microplate comprising a plurality of microwells therein, one or more of said microwells comprising a plurality of said biosensors distributed therein, and adding said biological sample to said microwells to create respective reaction solutions in each of said microwells.

23. The method of claim 17, wherein the detecting is preceded by a heating of the sample and/or of the testing solution.

24. A system for detecting the activity of a biomarker in a biological sample, the system comprising a biosensor of claim 1 and reagents for simultaneous combined or sequential use in a method of detection of the activity of a biomarker in a biological sample, the method comprising:

contacting a biological sample with the graphene biosensor of claim 1 to create a reaction solution; and detecting a change in said reaction solution.

25. A method for making a biosensor of claim 1, the method comprising providing a graphene core particle comprising:

at least two pristine graphene nanosheets having a pristine graphene nanosheet surface stacked over one another to form a pristine graphene aggregate, and a coating layer covering at least 50% of a pristine graphene nanosheet surface, said coating layer comprising an organic and/or inorganic compound, wherein the organic and/or inorganic compound has a solubility in water of at least 10 grams per liter $H_2O$ at 25 degrees C. and is able to be covalently linked to, or in water electrostatically stably attached to, pristine graphene, wherein the organic and/or inorganic compound is attached to a pristine graphene nanosheet to form said coating layer, wherein the pristine graphene of the at least two pristine graphene nanosheets has a carbon content of at least 99%, an oxygen content of less than 1% and is pure, such that the pristine graphene is free of foreign substances and impurities, wherein the pristine graphene nanosheet and/or the organic and/or inorganic compound of the coating layer is configured to present a functional group capable of binding a corresponding functional group in an aqueous solution, the method further comprising attaching to the graphene surface a detectable moiety through a peptide linkage.

26. The method of claim 25, wherein the attaching is preceded by dispersing the graphene core particle, and the attaching is performed by contacting the dispersed graphene core particle with the detectable component comprising the detectable moiety attached to the peptide linkage.

27. A multiplex graphene biosensor, comprising: a graphene core particle and a plurality of target specific detectable components attached to the graphene core particle, wherein the graphene core particle comprises at least two pristine graphene nanosheets having a pristine graphene nanosheet surface stacked over one another to form a pristine graphene aggregate, and a coating layer covering at least 50% of a pristine graphene nanosheet surface, said coating layer comprising an organic and/or inorganic compound, wherein the organic and/or inorganic compound has a solubility in water of at least 10 grams per liter $H_2O$ at 25 degrees C. and is able to be covalently linked to, or in water electrostatically stably attached to, pristine graphene, wherein the organic and/or inorganic compound is attached to a pristine graphene nanosheet to form said coating layer, wherein the pristine graphene of the at least two pristine graphene nanosheets has a carbon content of at least 99%, an oxygen content of less than 1% and is pure, such that the pristine graphene is free of foreign substances and impurities, wherein the pristine graphene nanosheet and/or the organic and/or inorganic compound of the coating layer is configured to present a functional group capable of binding a corresponding functional group in an aqueous solution;

wherein each target specific detectable component is formed by a detectable moiety capable of emitting a fluorescent signal, the detectable moiety attached to a peptide linkage comprising a recognition sequence specific for a target biomarker, wherein in each target specific detectable component the peptide linkage is configured to provide in combination with the coating layer of the graphene core particle, a quenching distance between the detectable moiety and the graphene core particle, wherein the graphene nanosheet quenches the fluorescent signal of the detectable moiety, and wherein the recognition sequence for the target biomarker of each detectable component is configured to specifically detect a target biomarker and the plurality of detectable components is selected to specifically detect a plurality of different target biomarkers.

28. The multiplex graphene biosensor of claim 27, comprising up to 10 target specific detectable components, each detectable component presenting a detectable moiety, detectable over the whole range of the UV/Vis/NIR spectrum.

29. The multiplex graphene biosensor of claim 27, comprising target specific detectable components oligopeptides at a density of $1.6\pm0.2\times10^{-5}$ moles per gram of biosensor.

30. A system for multiplexed detection of the activity of a plurality of biomarkers in a biological sample, the system comprising a multiplex graphene biosensor and/or a graphene biosensor each comprising a graphene core particle presenting a peptide linkage specific for one biomarker of the plurality of the biomarkers wherein the graphene core particle comprises at least two pristine graphene nanosheets having a pristine graphene nanosheet surface stacked over one another to form a pristine graphene aggregate, and a coating layer covering at least 50% of a pristine graphene nanosheet surface, said coating layer comprising an organic and/or inorganic compound, wherein in the graphene core particle (i) the organic and/or inorganic compound has a solubility in water of at least 10 grams per liter $H_2O$ at 25 degrees centigrade and is able to be covalently linked to or in water electrostatically stably attached to pristine graphene, (ii) the organic and/or inorganic compound is attached to a pristine graphene nanosheet to form said coating layer, (iii) the pristine graphene of the at least two pristine graphene nanosheets has a carbon content of at least 99%, an oxygen content of less than 1% and is pure, such that the pristine graphene is free of foreign substances and impurities, and (iv) the pristine graphene nanosheet and/or the organic and/or inorganic compound of the coating layer is configured to present a functional group capable of binding a corresponding functional group in an aqueous solution, wherein the graphene multiple biosensors further comprise a plurality of target specific detectable components attached to the graphene core particle, in which each target specific detectable component is formed by a detectable moiety capable of emitting a fluorescent signal, the detectable moiety attached to a peptide linkage comprising a recognition sequence specific for a target biomarker, the peptide linkage of each target specific detectable component is configured to provide in combination with the coating layer of the graphene core particle, a quenching distance between the detectable moiety and the graphene core particle, wherein the graphene nanosheet quenches the fluorescent signal of the detectable moiety, and the recognition sequence for the target biomarker of each detectable component is configured to specifically detect a target biomarker and the plurality of detectable components is selected to specifically detect a plurality of different target biomarkers, and wherein each graphene biosensor further comprises:

a detectable moiety capable of emitting a fluorescent signal, the detectable moiety covalently bonded to the graphene core particle through a peptide linkage comprising a recognition sequence specific for the target biomarker, in which the coating layer and the peptide linkage are configured to set a quenching distance between the graphene nanosheets and the detectable moiety in which the graphene nanosheets quench the fluorescent signal of the detectable moiety, the peptide linkage is further configured to set, upon recognition by the target biomarker of the recognition sequence, an emitting distance between the graphene nanosheets and the detectable moiety wherein the graphene nanosheets do not quench the fluorescent signal of the detectable moiety, and the peptide linkage and the detectable moiety thus form a target specific detectable component configured to emit a detectable fluorescent signal upon modification of the peptide linkage by the target biomarker.

* * * * *